(12) United States Patent
Fujisawa et al.

(10) Patent No.: US 7,060,791 B2
(45) Date of Patent: Jun. 13, 2006

(54) MELTRINS

(75) Inventors: Atsuko Fujisawa, Bunkyo-ku (JP);
Toru Yamakawa, Shinjuku-ku (JP);
Kamon Shirakawa, Shinjuku-ku (JP);
Chitose Orii, Shinjuku-ku (JP); Naoki Ogawa, Shinjuku-ku (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 443 days.

(21) Appl. No.: 09/983,531

(22) Filed: Oct. 24, 2001

(65) Prior Publication Data

US 2002/0147132 A1 Oct. 10, 2002

Related U.S. Application Data

(63) Continuation of application No. 09/138,675, filed on Aug. 24, 1998, now abandoned, which is a continuation of application No. PCT/JP96/03017, filed on Oct. 17, 1996.

(30) Foreign Application Priority Data

Feb. 23, 1996 (JP) ................................. 8-061756

(51) Int. Cl.
*A61K 38/04* (2006.01)
(52) U.S. Cl. ..................................... 530/324
(58) Field of Classification Search ............... 530/395, 530/324
See application file for complete search history.

(56) References Cited

U.S. PATENT DOCUMENTS 5,883,241 A 3/1999 Docherty et al.
6,191,113 B1 * 2/2001 Nakahara et al.

FOREIGN PATENT DOCUMENTS

WO WO 97/31109 8/1997
WO WO 97/40072 10/1997

OTHER PUBLICATIONS

EMBL Database Accession No. D50411, Sequence Identity MMMAB, Nov. 6, 1995, "Mouse mRNA for Meltrin Alpha", S. Fujisawa, XP002151067.
EMBL Database Accession No. D50410, Sequence Identity MMMBA, Nov. 6, 1995, "Mouse mRNA for Meltrin Beta", S. Fujisawa, XP002151068.
EMBL Database Accession No. D50412, Sequence Identity MMMGC, Nov. 6, 1995, "Mouse mRNA for Meltrin Gamma", S. Fujisawa, XP002151069.
"MDC9, A Widely Expressed Cellular Disintegrin Containing Cytoplasmic SH3 Ligand Domains" G. Weskamp et al., The Journal of Cell Biology, vol. 132, No. 4, Feb. 1, 1996, 717-726, XP000644308, Rockefeller University Press.

"Prediction of the Coding Sequences of Unidentified Human Genes . . . " N. Nomura et al., DNA Research, JP, Universal Academy Press, vol. 1, No. 1, 1994, 27-35, XP002049267.
EMBL Database Accession No. D14665, Sequence Identity HSORF09, Mar. 31, 1993, "Prediction of New Human Genes . . . ", N. Nomura et al., XP002151070.
Swissprot Database Accession No. Q13443, Nov. 1, 1996, "Cellular Disintegrin-Related Protein Precursor", XP002151071.
Yagami-Hiromasa et al, NATURE 377, 652-656, 1995.
Mizushima et al. Nucleic Acid Res. 18, 5322, 1990.
Knudsen et al. Exp. Cell. Res., 188, 175-184, 1990.
Mege et al J. Cell Sci., 103, 897-906, 1992.
Donalies et al. Pro. Natl. Acad. Sci., 88, 8024-8028, 1991.
Rosen el al. Cell, 69, 1107-1119, 1992.
Smith, Donald B. et al, "Single-step purification of polypeptides expressed in *Escherichia coli* as fusions with glutathione S-transferase", Gene, 67 (1988) pp. 31-40.
Morrison, T.G., "Structure, function, and introcellular processing of paramyxovirus membrane proteins", Virus Research, 10 (1988) pp. 113-136.
Blobel, Carl P. et al, "A potential fusion peptide and an integrin ligand domain in a protein active in sperm-egg fusion", Nature, vol. 356, Mar. 19, 1992, pp. 248-252.
Yagami-Hiromasa et al Cell Structure and Function, vol. 20, No. 6, 1995, p. 585.
Endo, Takeshi Biochemistry, vol. 68, No. 8, Aug. 1996, pp. 1453-1458.
Cho, Chunghee et al, "Chromosomal Assignment of Four Testis-Expressed Mouse Genes from a New Family of Transmembrane Proteins (ADAMs) Involved in Cell-Cell Adhesion and Fusion", Genomics, 34, Apr. 10, 1996, pp. 413-417.

* cited by examiner

*Primary Examiner*—Christina Chan
*Assistant Examiner*—Maher Haddad
(74) *Attorney, Agent, or Firm*—Griffin & Szipl, P.C.

(57) ABSTRACT

The purpose of the present invention is to provide a novel protein involved in adhesion and fusion between myoblasts in the course of the formation of byotube. The present invention relates to Meltrins, which a membrane protein having fusion, adhesion and aggregation activity of cells, especially myoblast; and to polypeptides of their domains, DNAs encoding them, antisense RNA for these DNAs, various antibodies to Meltrins and the polypeptides of their domains, expression vectors containing these DNAs, and transformants by these vectors; as well as to the process for producing Meltrins and the polypeptides of their domains using those transformants and medical compositions comprising Meltrins or antagonist against them as an effective ingredient.

2 Claims, 90 Drawing Sheets

Fig. 1a

```
Ma    HGRGVCMNRK NCHCEAHWAE PEDKFEFEG STDSGPIRCA DNQGLTVGIL VSILCLIAG FVVYKRKTL MRLSTHKKT.TMEKLRCVHQ SRTPSGPHLG  762
MS2   NH-SVCMHKR ECHCHKCQRE ENFVQ----R LADVSDEQAA STSLPVSVVV ILVILVAMV APRQIQRRSV APKPIS---                     707
Fa    NEMGICMNLG HCHLGDGFAE ENLKECGTSG SIDSGPPPS QTTKASSENL ALIGIILVI LLALVICAI CLGIPAEEND PPPEEEAGE            783

Ma    QAHHTPGKGL LMMRAPHFNT PKDRHSLKCQ NMDISRFLDA RAVPQLQSPQ RVLLPLHQTF RAPSGPARGI PASPAVRQAQ GIRKGSPCK PIPADPLSRT 862
MS2   ---GLSNPLF YTRDSSL-PA KNRPPDPSET VSTNQPPRPI AKPKRP---- ------PPAP PGAVSSS--GI GVPVYAPKIP NQFRDQPTK PIPELKPKQV 792
Fa    LEEEPEPEPE PEEEEAAEEE D                                                                                   804

Ma    SRLTSALVRT PGQQEPGHRP APIRPPRPKHQ VPRPSHNAYI K                                                             903
MS2   KPTFAPPTPP VKRGTGGTVF GATQGAGGPK VALKVPIQK- R                                                             832
```

```
         190       200       210       220       230       240
CGCGGGGCCCGAAGCAGCTGCACGCCAGGCCGGCGACAATGGCAGAGGCCGGGGCG                      7
                                    M  E  R  P  A  R 250       260       270       280       290       300
GCGCGGCCCCCGCGCCCTCCTGCTGGGCCCTGGGGCCCTGCTGGCGCCCCG                          27
 R  A  P  P  A  R  A  L  L  L  A  L  A  G  A  L  L  A  P  R 310       320       330       340       350       360
TGCAGCCCGAGGGATGAGTTTGTGGGACCAGAGAGGAGCTTACGAAGTGGCCAGAGCCTC                 47
 A  A  R  G  M  S  L  W  D  Q  R  G  A  Y  E  V  A  R  A  S 370       380       390       400       410       420
CCTTCTGAGCAAGGACCCTGGGATCCCAGGACAGAGCATCCCAGCCAAGGATCATCCAGA                 67
 L  L  S  K  D  P  G  I  P  G  Q  S  I  P  A  K  D  H  P  D 430       440       450       460       470       480
CGTGCTGACTGTGCAACTGCAGCTGGAGAGCCGAGACCTGATCCTCAGCCTGGAAAGGAA                 87
 V  L  T  V  Q  L  Q  L  E  S  R  D  L  I  L  S  L  E  R  N
```

Fig. 2b

```
         490       500       510       520       530       540
TGAGGGACTCATTGCCAATGGCTTCACGGAGACCCATTATCTGCAAGATGGTACTGATGT   107
 E  G  L  I  A  N  G  F  T  E  T  H  Y  L  Q  D  G  T  D  V 550       560       570       580       590       600
CTCTCTCACTCGAAATCACACGGATCATTGTTACTACCATGGACATGTGCAAGGAGATGC   127
 S  L  T  R  N  H  T  D  H  C  Y  Y  H  G  H  V  Q  G  D  A 610       620       630       640       650       660
TGCATCAGTGGTCAGCCTCAGTACTTGCTCTGATCTCCGGGGACTTATCATGTTTGAAAA   147
 A  S  V  V  S  L  S  T  C  S  D  L  R  G  L  I  M  F  E  N 670       680       690       700       710       720
TAAAACGTACAGCTTAGAGCCAATGAAAAACACCACTGACAGCTACAAACTCGTCCCAGC   167
 K  T  Y  S  L  E  P  M  K  N  T  T  D  S  Y  K  L  V  P  A 730       740       750       760       770       780
TGAGAGCATGACGAACATCCAAGGGCTGTGTGGGTCACAGCATAACAAGTCCAACCTCAC   187
 E  S  M  T  N  I  Q  G  L  C  G  S  Q  H  N  K  S  N  L  T
```

Fig. 2c

```
            790       800       810       820       830       840
CATGGAAGATGTCTCCCCTGGAACCTCTCAAATGCGGGCAAGAAGGCATAAGAGAGAGAC        207
  M  E  D  V  S  P  G  T  S  Q  M  R  A  R  R  H  K  R  E  T 850       860       870       880       890       900
CCTTAAGATGACCAAGTACGTAGAGCTGGTTATTGTGGCAGACAACAGAGAGTTTCAGAG        227
  L  K  M  T  K  Y  V  E  L  V  I  V  A  D  N  R  E  F  Q  R 910       920       930       940       950       960
GCAAGGAAAAGACCTGGAGAAAGTTAAGCAGCGATTAATAGAGATCGCCAATCACGTTGA        247
  Q  G  K  D  L  E  K  V  K  Q  R  L  I  E  I  A  N  H  V  D 970       980       990      1000      1010      1020
CAAGTTTTACAGACCCTATAAGCCACTGAACATCCGGATCGTGCTGGTAGGAGTGGAAGTGTGGAATGA    267
  K  F  Y  R  P  L  N  I  R  I  V  L  V  G  V  E  V  W  N  D 1030      1040      1050      1060      1070      1080
CATCGACAAATGCTCTATAAGCCAGGACCCATTCACCAGGCTCCATGAGTTTCTAGACTG        287
  I  D  K  C  S  I  S  Q  D  P  F  T  R  L  H  E  F  L  D  W
```

Fig. 2d

```
      1090       1100       1110       1120       1130       1140
GAGAAAGATAAAGCTTCTACCTCGAAAATCCCACGACAATGCTCAGCTTATCAGTGGGGT        307
 R  K  I  K  L  L  P  R  K  S  H  D  N  A  Q  L  I  S  G  V 1150       1160       1170       1180       1190       1200
TTATTCCAAGGAACCACCATCGGCATGGCACCCATCATGAGCATGTGCACTGCAGAACA        327
 Y  F  Q  G  T  T  I  G  M  A  P  I  M  S  M  C  T  A  E  Q 1210       1220       1230       1240       1250       1260
GTCTGGAGGAGTTGTCATGGACCATTCAGACAGCCCCTTGGTGCCGCAGTGACCTTGGC        347
 S  G  G  V  V  M  D  H  S  D  S  P  L  G  A  A  V  T  L  A 1270       1280       1290       1300       1310       1320
ACATGAGCTGGGCCACAACTTCGGGATGAACCATGACACACTGGAGAGGGGCTGCAGCTG        367
 H  E  L  G  H  N  F  G  M  N  H  D  T  L  E  R  G  C  S  C 1330       1340       1350       1360       1370       1380
CAGAATGGCCGCAGAGAAAAGGAGGCTGCATCATGAACCCGTCCACGGGGTTCCCATTCCC        387
 R  M  A  A  E  K  G  G  C  I  M  N  P  S  T  G  F  P  F  P
```

Fig. 2e

```
      1390      1400      1410      1420      1430      1440
CATGGTGTTCAGCAGCTGCAGCAGGAAGGACCTGGAGGCTAGCCTGGAGAAGGGCATGGG      407
 M  V  F  S  S  C  S  R  K  D  L  E  A  S  L  E  K  G  M  G 1450      1460      1470      1480      1490      1500
GATGTGCCTCTTCAACCTACCAGAGGTCAAGCAGGCCTTTGGGGGCCGGAAGTGTGGAAAA      427
 M  C  L  F  N  L  P  E  V  K  Q  A  F  G  G  R  K  C  G  N 1510      1520      1530      1540      1550      1560
TGGCTATGTGGAAGAGGGAGAAGAGTGTGACTGCGGAGAACCGGAGGAATGCACGAATCG      447
 G  Y  V  E  E  G  E  E  C  D  C  G  E  P  E  E  C  T  N  R 1570      1580      1590      1600      1610      1620
CTGCTGTAACGCTACCACCTGTACTCTGAAGCCAGATGCTGTGCGCGCCACGGGCAGTG      467
 C  C  N  A  T  T  C  T  L  K  P  D  A  V  C  A  H  G  Q  C 1630      1640      1650      1660      1670      1680
CTGTGAAGACTGTCAGCTGAAGCCTCCAGGAACTGCATGCAGGGGCTCCAGCAACTCCTG      487
 C  E  D  C  Q  L  K  P  P  G  T  A  C  R  G  S  S  N  S  C
```

Fig. 2f

```
        1690      1700      1710      1720      1730      1740
TGACCTCCCAGAATTCTGCACAGGGACTGCCCCTCACTGTCCAGCCAATGTGTACCTACA   507
 D  L  P  E  F  C  T  G  T  A  P  H  C  P  A  N  V  Y  L  H 1750      1760      1770      1780      1790      1800
TGATGGCCACCCGTGTCAGGGCGTGGATGGTTACTGCTACAACGGCATCTGCCAGACCCA   527
 D  G  H  P  C  Q  G  V  D  G  Y  C  Y  N  G  I  C  Q  T  H 1810      1820      1830      1840      1850      1860
TGAGCAGCAGTGTGTCACGCTCTGGGGACCAGGTGCTAAACCGGCTCCTGGCATCTGCTT   547
 E  Q  Q  C  V  T  L  W  G  P  G  A  K  P  A  P  G  I  C  F 1870      1880      1890      1900      1910      1920
TGAGGGAGTCAACTCTGCAGGAGATCCTTATGGTAACTGTGGCAAAGACTCCAAGAGCGC   567
 E  R  V  N  S  A  G  D  P  Y  G  N  C  G  K  D  S  K  S  A 1930      1940      1950      1960      1970      1980
CTTCGCCAAATGTGAGCTGAGAGATGCCAAGTGTGGGAAAATCCAGTGTCAAGGTGGTGC   587
 F  A  K  C  E  L  R  D  A  K  C  G  K  I  Q  C  Q  G  G  A
```

Fig. 2g

```
      1990       2000       2010       2020       2030       2040
AAGCCCGACCTGTCATTGGTACCAATGCTGTTTCCATAGAAACAAATATCCCACAGCAGGA                607
  S   R   P   D   L   S   L   V   P   M   L   F   P   *   K   Q   I   S   H   S   R
(annotation row as shown: S R P V I G T N A V S I E T N I P Q Q E)

2050       2060       2070       2080       2090       2100
AGGAGGTCGGATTCTGTGCCGGGGGACCCATGTGTACTTGGGTGATGACATGCCAGACCC                627
 G   G   R   I   L   C   R   G   T   H   V   V   L   G   D   D   M   P   D   P 2110       2120       2130       2140       2150       2160
AGGGCTTGTGCTTGCAGGAACAAAGTGTGCAGAAGGAAAAATCTGCCTCAATCGTCGATG                647
 G   L   V   L   A   G   T   K   C   A   E   G   K   I   C   L   N   R   R   C 2170       2180       2190       2200       2210       2220
TCAGAATATCAGTGTCTTCGGGGTTCACAAGTGCCATGCCAGTGCCACGGCCGAGGGGT                 667
 Q   N   I   S   V   F   G   V   H   K   C   A   M   Q   C   H   G   R   G   V 2230       2240       2250       2260       2270       2280
ATGTAACAACAGGAAGAATTGCCACTGTGAAGCCCACTGGGCTCCACCCTTCTGTGACAA                687
 C   N   N   R   K   N   C   H   C   E   A   H   W   A   P   P   F   C   D   K
```

Fig. 2h

```
      2290       2300       2310       2320       2330       2340
GTTGGCTTTGGAGGAAGCACAGACAGTGGTCCCATCAGGCAAGCAGATAACCAGGGCTT      707
 F  G  F  G  G  S  T  D  S  G  P  I  R  Q  A  D  N  Q  G  L 2350       2360       2370       2380       2390       2400
GACTGTAGGAATCCTGGTGAGCATCCTGTGTCTGCTTGCTGCTGGATTTGTGGTGTATCT      727
 T  V  G  I  L  V  S  I  L  C  L  L  A  A  G  F  V  V  Y  L 2410       2420       2430       2440       2450       2460
CAAAAGGAAGACGTTGATGGGCTGTTCACACATAAAAAACCACCATGGAAAAGCT          747
 K  R  K  T  L  M  R  L  L  F  T  H  K  K  T  T  M  E  K  L 2470       2480       2490       2500       2510       2520
AAGGTGTGTGCACCCTTCCCGGACACCCAGTGGCCCTCACCTTGCCAGGCTCACCACAC      767
 R  C  V  H  P  S  R  T  P  S  G  P  H  L  G  Q  A  H  H  T 2530       2540       2550       2560       2570       2580
CCCCGGGAAAGGCCCTGCTGATGAACCGGGCACCCACATTTCAATACCCCAAGGACAGGCA    787
 P  G  K  G  L  L  M  N  R  A  P  H  F  N  T  P  K  D  R  H
```

Fig. 2i

```
      2590       2600       2610       2620       2630       2640
CTCGCTGCTGAAATGCCAGAACATGGACATCAGCAGGCCCCTGGACGCTCGAGCCGTCCCACA    807
  S  L  K  C  Q  N  M  D  I  S  R  P  L  D  A  R  A  V  P  Q 2650       2660       2670       2680       2690       2700
GCTTCAGTCACCTGCAGGCGAGTGCTCCTGCCTCTCCACCAGACCCCAGTGCACCCAGTGG    827
  L  Q  S  P  Q  R  V  L  L  P  L  H  Q  T  P  R  A  P  S  G 2710       2720       2730       2740       2750       2760
CCCTGCCAGGCCCCTGCCCGCCAGTCCTGCAGTCAGGCAGGCCCAGGGCATTGAAAACC    847
  P  A  R  P  L  P  A  S  P  A  V  R  Q  A  Q  G  I  R  K  P 2770       2780       2790       2800       2810       2820
CAGTCCTCCTCAGAAGCCTCTGCCTGATCCACTGAGCAGGAGGACTTCTCGGCTCACTAG    867
  S  P  P  Q  K  P  L  P  A  D  P  L  S  R  T  S  R  L  T  S 2830       2840       2850       2860       2870       2880
TGCCTTGGTGAGGACCCCAGGGCAGCAGGAACCTGGGCACCGGCCCCAGCCCCATCAGACC    887
  A  L  V  R  T  P  G  Q  Q  E  P  G  H  R  P  A  P  I  R  P
```

Fig. 2j

```
      2890       2900       2910       2920       2930       2940
TGCCCCTAAGCATCAAGTACCCAGACCTTCCCACAATGCCTATATCAAGTGAGAAGCCAG
 A  P  K  H  Q  V  P  R  P  S  H  N  A  Y  I  K  ***  903
```

Fig. 3a

```
         70        80        90        100       110       120
TCATGCCCGGGGCGGCGGGGCGTCCGCCCGGTTCTGCTTGCTCTGCTTCTGCTCAGCTAC
  M  P  G  R  A  G  V  A  R  F  C  L  L  A  L  Q  L  H 130       140       150       160       170       180
ATTGGCCGCTGGGCGTGGAGCCGGATGGACCACAAGAGGAAGCCAAGAAGGTAGCC
  W  P  L  A  A  C  E  P  G  W  T  T  R  G  S  Q  E  G  S  P 190       200       210       220       230       240
CTCCGGCTACAGCATGAACTCATAATACCTCAGTGGCGGGACTTCAGAAAGCCCTGGGAGAG
  L  Q  H  E  L  I  I  P  Q  W  R  T  S  E  S  P  G  R  G 250       260       270       280       290       300
GAAAGCATCCACTCAGAGCAGAGCTCAGGGTCATGGCTGAAGGGCGAGAGCTGATCCTAG
  K  H  P  L  R  A  E  L  R  V  M  A  E  G  R  E  L  I  L  D 310       320       330       340       350       360
ACCTGGAGAAGAACGAGCACCTTTTTGCTCCAGCCTACACAGAAACCTGTACACTGCAA
  L  E  K  N  E  H  L  F  A  P  A  Y  T  E  T  C  Y  T  A  S
```

```
      370         380         390         400         410         420
GTGGCAATCCTCAAACCAGCACGCTGAAGTCTGAGGATCACTGCTTTTACCACGGGACTG   120
  G  N  P  Q  T  S  T  L  K  S  E  D  H  C  F  Y  H  G  T  V 430         440         450         460         470         480
TGAGGGACGTGGATGAGTCCAGTGTCCAGCACCTCAGCACCTGCCGGGGGAATTAGAGGACTGA   140
  R  D  V  D  E  S  S  V  T  L  S  T  C  R  G  I  R  G  L  I 490         500         510         520         530         540
TTATAGTGAGAAGTAACCTCAGCTACATCATCGAGCCCGTCCCTAACAGCGACAGCCAAC   160
  I  V  R  S  N  L  S  Y  I  I  E  P  V  P  N  S  D  S  Q  H 550         560         570         580         590         600
ACCGTATTTACAGATCCGAACATCTCACGCTGCCCCCGGGAACTGTGGGTTCGAGCACT   180
  R  I  Y  R  S  E  H  L  T  L  P  P  G  N  C  G  F  E  H  S 610         620         630         640         650         660
CCGGGCCCACCTCGAAGGACTGGGCCCTTCAGTTTACACATCAGACCAAAAGCAACCTC   200
  G  P  T  S  K  D  W  A  L  Q  F  T  H  Q  T  K  K  Q  P  R
```

Fig. 3c

```
       670       680       690       700       710       720
GCAGAATGAAACGGGAAGATCTACACTCTATGAAGTACGTGGAGCTTTACCTGGTGGCTG       220
 R  M  K  R  E  D  L  H  S  M  K  Y  V  E  L  Y  L  V  A  D 730       740       750       760       770       780
ATTATGCAGAGTTTCAGAAGAATCGACATGACCAGGATGCCACCAAACGCAAGCTCATGG       240
 Y  A  E  F  Q  K  N  R  H  D  Q  D  A  T  K  R  K  L  M  E 790       800       810       820       830       840
AGATTGCCAACTATGTTGATAAGTTTTACCGCTCCCTGAACATCCGAATTGCACTTGTCG       260
 I  A  N  Y  V  D  K  F  Y  R  S  L  N  I  R  I  A  L  V  G 850       860       870       880       890       900
GCTTGGAGGTGTGGACGCATGGGGATAAGTGTGAAGTTTCAGAGAATCCCTACTCTACCC       280
 L  E  V  W  T  H  G  D  K  C  E  V  S  E  N  P  Y  S  T  L 910       920       930       940       950       960
TCTGGTCCTTCTTAGTTGGAGGCGCAAGCTGCTTGCTCAGAAGAGCCATGACAATGCTC       300
 W  S  F  L  S  W  R  R  K  L  L  A  Q  K  S  H  D  N  A  Q
```

Fig. 3d

```
          970       980       990      1000      1010      1020
AGCTAATCAGGGGCAGTCCTTCCAAGGCACCACCATTGGCCTGGCCCCCCTCATGGCCA
  L  I  T  G  R  S  F  Q  G  T  T  I  G  L  A  P  L  M  A  M   320

1030      1040      1050      1060      1070      1080
TGTGCTCCGTGTACCAGTCTGGAGGAGTTAGCATGGACCACTCCGAGAATGCCATTGGTG
  C  S  V  Y  Q  S  G  G  V  S  M  D  H  S  E  N  A  I  G  V   340

1090      1100      1110      1120      1130      1140
TAGCCTCCACTGTGGCCCATGAGATTGGCCACAACTTTGGCATGAGCCATGATTCTGCAC
  A  S  T  V  A  H  E  I  G  H  N  F  G  M  S  H  D  S  A  H   360

1150      1160      1170      1180      1190      1200
ACTGTGTTCTGCCAGTGCAGCCGATGGGCTGCATCATGGCCCGCCACCGGGCACC
  C  C  S  A  S  A  A  D  G  G  C  I  M  A  A  A  T  G  H  P   380

1210      1220      1230      1240      1250      1260
CTTTCCCCAAAGTGTTCAGTTGGTGTAACAGGAAGCTGGACAGGTATCTGCAGACAG
  F  P  K  V  F  S  W  C  N  R  K  E  L  D  R  Y  L  Q  T  G   400
```

Fig. 3e

```
           1270      1280      1290      1300      1310      1320
GAGGAGGGATGTGTCTCTCCAACATGCCGGACACTAGGACGCTGTATGGAGGCCGGAGGT    420
 G  G  M  C  L  S  N  M  P  D  T  R  T  L  Y  G  G  R  R  C 1330      1340      1350      1360      1370      1380
GTGGCAACGGGTACCTGGAAGACGGTGAAGAATGTGACTGTGGAGAAGAGGAGGAATGTA    440
 G  N  G  Y  L  E  D  G  E  E  C  D  C  G  E  E  E  E  C  K 1390      1400      1410      1420      1430      1440
AGAACCCTGCTGCCAATGCCTCCAACTGCACTCTGAAGGAAGGGGCAGAGTGTGCCCATG    460
 N  P  C  C  N  A  S  N  C  T  L  K  E  G  A  E  C  A  H  G 1450      1460      1470      1480      1490      1500
GTTCCTGCTGCCACCAGTGCAAGCTGGTGGCTCCTGGAACCCAGTGTGCGGGAGCAGGTTC    480
 S  C  C  H  Q  C  K  L  V  A  P  G  T  Q  C  R  E  Q  V  R 1510      1520      1530      1540      1550      1560
GGCAATGTGACCTCCCCGAGTTCTGCACCGGCAAGTCTCCCCACTGCCCACCAACTATT    500
 Q  C  D  L  P  E  F  C  T  G  K  S  P  H  C  P  T  N  Y  Y
```

Fig. 3f

```
          1570         1580         1590         1600         1610         1620
ATCAGATGGATGGCACCCCTGCGAGGTGGCCAGGCCTACTGCTACAACGGCATGTGCC
 Q   M   D   G   T   P   C   E   G   G   Q   A   Y   C   Y   N   G   M   C   L     520

1630         1640         1650         1660         1670         1680
TCACTTACCAGGAACAGTGCCAGCAGCTGTGGGGACCTGGAGCCCGGCCCTGCCCTCGATC
 T   Y   Q   E   Q   C   Q   Q   L   W   G   P   G   A   R   P   A   L   D   L     540

1690         1700         1710         1720         1730         1740
TTGCTTTGAGAGGGTGAATGCTGCTGGTGACACCTATGGAAACTGTGGCAAGGGCTTGA
 C   F   E   R   V   N   A   A   G   D   T   Y   G   N   C   G   K   G   L   N     560

1750         1760         1770         1780         1790         1800
ATGCCAATACAGGAAGTGCCAGTCCCAGGGATGCCAAGTGTGGSAAGATTCAGTGCCAGA
 G   Q   Y   R   K   C   S   P   R   D   A   K   C   G   K   I   Q   C   Q   S     580

1810         1820         1830         1840         1850         1860
GCACCCAGGCCCGGCCCCTGGAATCCAACGCAGTATCTATTGACACCACCATCACCTTGA
 T   Q   A   R   P   L   E   S   N   A   V   S   I   D   T   T   I   T   L   N     600
```

Fig. 3g

```
         1870       1880       1890       1900       1910       1920
ACGGGAGGGGGATCCACTGTCGGGGCACCCACGTCTACCGGGTCCTGAGGAGGAGGAAG
  G  R  R  I  H  C  R  G  T  H  V  Y  R  G  P  E  E  E  E  G        620

1930       1940       1950       1960       1970       1980
GGGAAGGTGACATGCTGGACCCAGGGCTGGTGATGACTGGAACCAAGTGTGGCCACAACC
  E  G  D  M  L  D  P  G  L  V  M  T  G  T  K  C  G  H  N  H        640

1990       2000       2010       2020       2030       2040
ATATTTGCTTCGAGGGGCAGTGCAGGAACACCTCCTTCTTTGAGACGGAAGGCTGTGGGA
  I  C  F  E  G  Q  C  R  N  T  S  F  F  E  T  E  G  C  G  K        660

2050       2060       2070       2080       2090       2100
AAAAGTGCAATGGCCACGGGGTCTGCAACAACAAGAACTGTCATTGCTTCCCTGGCT
  K  C  N  G  H  G  V  C  N  N  K  N  C  H  C  F  P  G  W        680

2110       2120       2130       2140       2150       2160
GGTCTCCACCTTTCTGTAACACCCCGGGAGATGGTGGCAGCGTCGACAGTGGTCCTTGC
  S  P  P  F  C  N  T  P  G  D  G  G  S  V  D  S  G  P  L  P        700
```

Fig. 3h

```
     2170      2180      2190      2200      2210      2220
CCCCTAAGAGTGTGGGGTCCCGTGATCGCTGGGGTGTTTCAGCTCTCTTCGTGTTGGCAG      720
  P  K  S  V  G  P  V  I  A  G  V  F  S  A  L  F  V  L  A  V 2230      2240      2250      2260      2270      2280
TTCTGGTGCTACTGTGTCACTGCTACAGACAGAGCCACAAACTGGGCAAACCCTCGGCTC      740
  L  V  L  L  C  H  C  Y  R  Q  S  H  K  L  G  K  P  S  A  L 2290      2300      2310      2320      2330      2340
TCCCTTTCAAGCTGCGGCATCAGTTCAGTTGTCCCTTCAGGTATCTCAGAGTGGTGGAA      760
  P  F  K  L  R  H  Q  F  S  C  P  F  R  V  S  Q  S  G  G  T 2350      2360      2370      2380      2390      2400
CTGGCCATGCCAACCCAACTTTCAAGTTGCAGACCCCAGGGCAAGGCGAAAGGTGACTA      780
  G  H  A  N  P  T  F  K  L  Q  T  P  Q  G  K  R  K  V  T  N 2410      2420      2430      2440      2450      2460
ACACCCCTGAATCCCTCTCCGGAAGCCGTCCCACCCCCCTCCGGCCCCTCCAGACTACC      800
  T  P  E  S  L  R  K  P  S  H  P  P  L  R  P  P  P  D  Y  L
```

Fig. 3i

```
        2470       2480       2490       2500       2510       2520
TGGCGGCGTTGAATCGCCACCTGCACCATTGTCGGCACATCTGAACAGGGCTGCTGGGAGCT        820
  R  V  E  S  P  P  A  P  L  S  A  H  L  N  R  A  A  G  S  S 2530       2540       2550       2560       2570       2580
CCCCAGAAGCTGGGGCTCGAATAGAAAGAAAGGAGTCAGGCCAGGAGCCTCCCCAAGCC
  P  E  A  G  A  R  I  E  R  K  E  S  A  R  R  P  P  P  S  R         840

2590       2600       2610       2620       2630       2640
GACCCATGCCCCCTGCACCTAACTGCCTACTGTCCCAGGACTTCTCCAGGCCTCGACCAC
  P  M  P  P  A  P  N  C  L  L  S  Q  D  F  S  R  P  P  P        860

2650       2660       2670       2680       2690       2700
CTCAGAAGGCACTCCCAGCCAATCCGGTGCCAGGCCAAAGGACCGGTTCCCAGGTCAGGAG
  Q  K  A  L  P  A  N  P  V  P  G  Q  R  T  G  P  R  S  G  G        880

2710       2720       2730       2740       2750       2760
GCACCTCCCCTGTTCAGCCCCCTACTTCTGTCCTCAGCCCCCAGGCCTCCAGCCAGTGC
  T  S  L  L  Q  P  P  T  S  G  P  P  Q  P  P  R  P  P  A  V  P        900
```

Fig. 3j

```
        2770      2780      2790      2800      2810      2820
CTGTTCCAAAGCTACCCGAGTACCGATCACAGAGGGTTGGAGCAATAATTAGCTCCAAGA
 V  P  K  L  P  E  Y  R  S  Q  R  V  G  A  I  I  S  S  K  I 2830      2840      2850      2860      2870      2880
TCTAGAAGTGTCGAGAAGTTTCTTGTTCCGATGGAAGACTCCGATGCCATGGAAGGTCC
```

```
         70         80         90        100        110        120
CCCTCGGCTATGGGGCCGCGGCGCCCTGCCCCTTGCTCTCTGCCTGACTAAGGTGGCTGC    18
            M  G  P  R  A  L  S  P  L  A  S  L  R  L  R  W  L  L 130        140        150        160        170        180
TGGCGTGTGGCTTGCTGGGCCCAGTCCTCGAGGCCGGGACCAGACTTGAACAGACTG        38
 A  C  G  L  L  G  P  V  L  E  A  G  R  P  D  L  E  Q  T  V 190        200        210        220        230        240
TCCATCTTCTTTCTTATGAAATTATTACTCCTTGGAGATTAACTAGAGAAAGAAGGGAAG    58
 H  L  S  S  Y  E  I  I  T  P  W  R  L  T  R  E  R  R  E  A 250        260        270        280        290        300
CTCTGGGCCCAGTTCACAGCAGATCTCTTACGTCATCCAGGCCCAAGGAAAACAGCATA    78
 L  G  P  S  S  Q  Q  I  S  Y  V  I  Q  A  Q  G  K  Q  H  I 310        320        330        340        350        360
TTATTCACTTGGAAAGAAACACAGACCTTTACCTAATGATTTGTAGTTTACACCTACG      98
 I  H  L  E  R  N  T  D  L  L  P  N  D  F  V  V  Y  T  Y  D
```

Fig. 4b

```
      370       380       390       400       410       420
ACAAGGAAGGCTCCCTACTCTCTGACCATCCCAAGTACAGAGCCATTGTCACTATCGAG        118
 K  E  G  S  L  L  S  D  H  P  N  V  Q  S  H  C  H  Y  R  G 430       440       450       460       470       480
GCTATGTGGAGGGAGTGCAGAATTCCGGGTTGCTGTGAGCGCCTGCTTTGGACTCAGAG        138
 Y  V  E  G  V  Q  N  S  A  V  A  V  S  A  C  F  G  L  R  G 490       500       510       520       530       540
GCTTGCTGCATTTGGAGAATGCCAGTTTTGGAATTGAACCCTCTGCACAACAGCTCACACT     158
 L  L  H  L  E  N  A  S  F  G  I  E  P  L  H  N  S  S  H  F 550       560       570       580       590       600
TTGAGCACATATTTTACCCCATGGATGGCATCCACCAGGAGCCCTCTGAGATGTGGAGTCT     178
 E  H  I  F  Y  P  M  D  G  I  H  Q  E  P  L  R  C  G  V  S 610       620       630       640       650       660
CTAACAGGGACACAGAGAAGGAAGGCACACAGGGGGATGAGGAGGAGCATCCGAGTGTCA     198
 N  R  D  T  E  K  E  G  T  Q  G  D  E  E  E  H  P  S  V  T
```

Fig. 4c

```
            670       680       690       700       710       720
CTCAGCTGCTGCGGCAGAAGAAGAGAGCTGTGTTCTACCACAGACCCGCTATGTGGAGCTGTTCA      218
 Q  L  L  R  R  R  R  A  V  L  P  Q  T  R  Y  V  E  L  F  I 730       740       750       760       770       780
TTGTGTAGACAAGGAAAGGTACGACATGATGGGACGGAACCAGACTGCTGTGAGAGAAG            238
 V  V  D  K  E  R  Y  D  M  M  G  R  N  Q  T  A  V  R  E  E 790       800       810       820       830       840
AGATGATTCGCTTAGCAAACTACCTGGATAGCATGTACATCATGTTAAACATTCGAATTG          258
 M  I  R  L  A  N  Y  L  D  S  M  Y  I  M  L  N  I  R  I  V 850       860       870       880       890       900
TGCTGGTTGGACTAGAAATTTGGACAGACAGAAATCCTATCAATATAATTGGAGGAGCTG          278
 L  V  G  L  E  I  W  T  D  R  N  P  I  N  I  I  G  G  A  G 910       920       930       940       950       960
GAGATGTGCTGGGCAACTTTGTTCAGTGGGGGAAAAAGTTCCTTATAACTCGTCGGAGAC          298
 D  V  L  G  N  F  V  Q  W  R  E  K  F  L  I  T  R  R  R  H
```

Fig. 4d

```
       970        980        990       1000       1010       1020
ACGACAGTGCACAGTTGGTTTGAAGAAAGGCTTTGGTGGAACTGCAGGAATGGCGTTTG        318
 D  S  A  Q  L  V  L  K  K  G  F  G  G  T  A  G  M  A  F  V 1030       1040       1050       1060       1070       1080
TAGGAACAGTATGTTCAAGGAGCCACGGCCAGGTGGGATCAATGTGTTTGGGCAAATCACTG    338
 G  T  V  C  S  R  S  H  A  G  G  I  N  V  F  G  Q  I  T  V 1090       1100       1110       1120       1130       1140
TGGAGACATTGCATCCATTGTTGCTCATGAATTGGGGCATAACCTTGGAATGAATCATG      358
 E  T  F  A  S  I  V  A  H  E  L  G  H  N  L  G  M  N  H  D 1150       1160       1170       1180       1190       1200
ATGATGGGAGAGAGTGTTTCTGTGGAGCAAAGAGCTGTATCATGAATTCAGGAGCATCCG     378
 D  G  R  E  C  F  C  G  A  K  S  C  I  M  N  S  G  A  S  G 1210       1220       1230       1240       1250       1260
GGTCCAGAAACTTTAGCAGTTGCAGTGCGGAGGACTTGAGAAGTTAACGTTGAATAAGG      398
 S  R  N  F  S  S  C  S  A  E  D  F  E  K  L  T  L  N  K  G
```

Fig. 4e

```
      1270       1280       1290       1300       1310       1320
GAGGAAGCTGCCTGCTTAACATCCCGAAGCCTGACGAAGCCTACAGCGCGGCCCTCCTGTG         418
 G  S  C  L  L  N  I  P  K  P  D  E  A  Y  S  A  P  S  C  G 1330       1340       1350       1360       1370       1380
GTAATAAGCTGGTGGACCCTGGAGAGGAGTGTGACTGCGGCACAGCGAAGGAGTGTGAGG         438
 N  K  L  V  D  P  G  E  E  C  D  C  G  T  A  K  E  C  E  V 1390       1400       1410       1420       1430       1440
TGGACCCATGCTGTGAAGGAAGCACTTGTAAGCTCAAGTCATTTGCTGAGTGTGCATATG         458
 D  P  C  C  E  G  S  T  C  K  L  K  S  F  A  E  C  A  Y  G 1450       1460       1470       1480       1490       1500
GCGACTGTTGTAAAGATTGCCAGTTCCTTCCAGGAGGCTCCATGTGCAGAGGGAAGACCA         478
 D  C  C  K  D  C  Q  F  L  P  G  G  S  M  C  R  G  K  T  S 1510       1520       1530       1540       1550       1560
GTGAGTGTGATGTTCCTGAGTACTGCAACGGTTCCTCTCAGTTCTGCCCGCCAGATGTCT         498
 E  C  D  V  P  E  Y  C  N  G  S  S  Q  F  C  P  P  D  V  F
```

Fig. 4f

```
      1570      1580      1590      1600      1610      1620
TCATTCAGAATGGATATCCTTGCCAGAACAGCAAAGCCTACTGCTACAATGGCATGTGCC       518
  I   Q   N   G   Y   P   C   Q   N   S   K   A   Y   C   Y   N   G   M   C   Q 1630      1640      1650      1660      1670      1680
AATATTATGACGGCAGTGTCAGGTCATCTTTGGTTCAAAGGCTAAGGCTGCCCCAAGAG       538
  Y   Y   D   A   Q   C   Q   V   I   F   G   S   K   A   K   A   A   P   R   D 1690      1700      1710      1720      1730      1740
ATTGCTTCATTGAAGTCAATTCTAAAGGTGACAGATTTGGCAACTGTGGTTTCTCCGGCA       558
  C   F   I   E   V   N   S   K   G   D   R   F   G   N   C   G   F   S   G   S 1750      1760      1770      1780      1790      1800
GTGAGTACAAGAAGTGTGCCACTGGGAACGCGCTGTGTGGAAAGCTTCAATGCGAGAATG       578
  E   Y   K   K   C   A   T   G   N   A   L   C   G   K   L   Q   C   E   N   V 1810      1820      1830      1840      1850      1860
TACAGGACATGCCGGTGTTTGGAATAGTACCAGCTATCATTCAGACACCCAGTCGAGGCA       598
  Q   D   M   P   V   F   G   I   V   P   A   I   I   Q   T   P   S   R   G   T
```

Fig. 4g

```
      1870      1880      1890      1900      1910      1920
CCAAATGCTGGGGTGTGGATTTCCAGCTTGGTTCCGACGTTCCAGACCAGGATGGTGA      618
 K  C  W  G  V  D  F  Q  L  G  S  D  V  P  D  P  G  M  V  N 1930      1940      1950      1960      1970      1980
ATGAAGGCACCAAATGTGATGCTGGCAAGATTTGCAGGAATTTCAGTGTGTAAATGCTT      638
 E  G  T  K  C  D  A  G  K  I  C  R  N  F  Q  C  V  N  A  S 1990      2000      2010      2020      2030      2040
CTGTCCTGAATTATGACTGTGACATTCAGGGAAAAATGTCATGGCCATGGGTATGTAACA      658
 V  L  N  Y  D  C  D  I  Q  G  K  C  H  G  H  G  V  C  N  S 2050      2060      2070      2080      2090      2100
GCAATAAGAATTGTCACTGTGAAGATGGCTGGGCTCCCCCACACTGTGACACCAAAGGAT      678
 N  K  N  C  H  C  E  D  G  W  A  P  P  H  C  D  T  K  G  Y 2110      2120      2130      2140      2150      2160
ATGGAGGAAGCGTGGACAGCGGCCCGACGTATAATGCAAAGAGCACAGCACTGAGGGACG      698
 G  G  S  V  D  S  G  P  T  Y  N  A  K  S  T  A  L  R  D  G
```

Fig. 4h

```
         2170       2180       2190       2200       2210       2220
GGCTTCTGGTCTTCTTCTTCCTAATCGTCCCCCTTGTTGCGGCTGCCATTTTCCTCTTTA    718
 L  L  V  F  F  F  F  L  I  V  P  L  V  A  A  A  I  F  L  F  I 2230       2240       2250       2260       2270       2280
TCAAGAGAGATGAACTACGGAAAACCTTCAGGAAGAAGAGATCACAAATGTCAGATGGCA    738
 S  R  E  M  N  Y  G  K  P  S  G  R  R  R  S  Q  M  S  D  G  R
         K  R  D  E  L  R  K  T  F  R  K  K  R  S  Q  M  S  D  G  R 2290       2300       2310       2320       2330       2340
GAAATCAAGCAAACGTCTCTAGACAGCCAGGAGATCCTAGTATCTCCAGACCACCAGGGG    758
 N  Q  A  N  V  S  R  Q  P  G  D  P  S  I  S  R  P  P  G  G 2350       2360       2370       2380       2390       2400
GCCCAAATGTCTCCAGACCACCAGGGGCCCAGGTGTCTCCAGACCACCAGGGGCCCAG      778
 P  N  V  S  R  P  P  G  G  G  P  G  V  S  R  P  P  G  G  P  G 2410       2420       2430       2440       2450       2460
GTGTCTCCAGACCACCAGGGGCCCAGGTGTCTCCAGACCGCCACCTGGGCATGGAAACA    798
 V  S  R  P  P  G  G  G  P  G  V  S  R  P  P  P  G  H  G  N  R
```

Fig. 4i

```
      2470      2480      2490      2500      2510      2520
GATTCCCAGTACCAACCTACGCGGCCAAGCAGCCTGCGCAGTTCCCGTCAAGGCCACCTC
  F   P   V   P   T   Y   A   A   K   Q   P   A   Q   F   P   P   S   R   P   P   P   818

2530      2540      2550      2560      2570      2580
CACCACAACCGAAAATATCTTCTCAGGGAAACTTGATTCCGGCCCGCTCGGCCCCTGCAC
  P   Q   P   K   I   S   S   Q   G   N   L   I   P   A   R   P   A   P   A   P   838

2590      2600      2610      2620      2630      2640
CTCCTTTATATAGCTCCCTCACCTGATAGTAGAATATTAGAATCTTATTTTTAAATGTC
  P   L   Y   S   S   L   T    845
```

Fig. 5a

| | | | |
|---|---|---|---|
| GCCAGAGTAG | CGCGGCGGCG | CACGCACACA | CACGGGGGAGG | GGAGAAAGTT | 50
| TTTTTTGAA | AAAATGAAAG | GCTAGACTCG | CTGCTCAGCG | ACCCGGGGCGC | 100
| TGCGCGAGGG | GGTCGCGGCA | GACTCAGGGC | AGTAGGACTT | CCCCCAGCTC | 150
| GGCGCCCGCG | TGGGATGCTG | CAGCGCTGGC | CGCGGGGCCC | CCGAAGCAGC | 200

READING FRAME

| TGCACGCCAG | GCCGGGCGACA | ATGGCAGAGC | GCCCGGGCGCG | GCGGCGGCCC | 250
| CCGCCCCGCG | CCCTCCTGCT | GGCCCCTGGCT | GGGCCCCTGC | TGGCGCCCCG | 300
| TGCAGCCCGA | GGGATGAGTT | TGTGGGACCA | GAGAGGAGCT | TACGAAGTGG | 350
| CCAGAGCCTC | CCTTCTGAGC | AAGGACCCTG | GGATCCCCAGG | ACAGAGCATC | 400
| CCAGCCAAGG | ATCATCCAGA | CGTGCTGACT | GTGCAACTGC | AGCTGGAGAG | 450
| CCGAGACCTG | ATCCTCAGCC | TGGAAAGGAA | TGAGGGACTC | ATTGCCAATG | 500
| GCTTCACGGA | GACCCATTAT | CTGCAAGATG | GTACTGATGT | CTCTCTCACT | 550
| CGAAATCACA | CGGATCATTG | TTACTACCAT | GGACATGTGC | AAGGAGATGC | 600
| TGCATCAGTG | GTCAGCCTCA | GTACTTGCTC | TGATCTCCGG | GGACTTATCA | 650

Fig. 5b

| | | | | |
|---|---|---|---|---|
| TGTTTGAAAA | TAAAACGTAC | AGCTTAGAGC | CAATGAAAAA | CACCACTGAC | 700
| AGCTACAAAC | TCGTCCCAGC | TGAGAGCATG | ACGAACATCC | AAGGGCTGTG | 750
| TGGGTCACAG | CATAACAAGT | CCAACCTCAC | CATGGAAGAT | GTCTCCCCTG | 800
| GAACCTCTCA | AATGCGGGCA | AGAAAGGCATA | AGAGAGAGAC | CCTTAAGATG | 850
| ACCAAGTACG | TAGAGCTGGT | TATTGTGGCA | GACAACAGAG | AGTTTCAGAG | 900
| GCAAGGAAAA | GACCTGGAGA | AAGTTAAGCA | GCGATTAATA | GAGATCGGAG | 950
| ATCACGTTGA | CAAGTTTTAC | AGACCACTGA | ACATCCGGAT | CGTGCTGGTA | 1000
| GGAGTGGAAG | TGTGGAATGA | CATCGACAAA | TGCTCTATAA | GCCAGGACCC | 1050
| ATTCACCAGG | CTCCATGAGT | TTCTAGACTG | GAGAAAGATA | AAGCTTCTAC | 1100
| CTCGAAAATC | CCACGACAAT | GCTCAGCTTA | TCAGTGGGGT | TTATTTCCAA | 1150
| GGAACCACCA | TCGGCATGGC | ACCCATCATG | AGCATGTGCA | CTGCCAGAACA | 1200
| GTCTGGAGGA | GTTGTCATGG | ACCATTCAGA | CAGCCCCCTT | GGTGCCGCAG | 1250
| TGACCTTGGC | ACATGAGCTG | GGCCACAACT | TCGGGATGAA | CCATGACACA | 1300
| CTGGAGAGGG | GCTGCAGCTG | CAGAATGGCC | GCAGAGAAAG | GAGGCTGCAT | 1350
| CATGAACCCG | TCCACGGGGT | TCCCATTCCC | CATGGTGTTC | AGCAGCTGCA | 1400

Fig. 5c

| | | | | |
|---|---|---|---|---|
| GCAGGAAGGA | CCTGGAGGCT | AGCCTGGAGA | AGGGCATGGG | GATGTGCCTC | 1450
| TTCAACCTAC | CAGAGGTCAA | GCAGGCCTTT | GGGGCCCGGA | AGTGTGGAAA | 1500
| TGGCTATGTG | GAAGAGGGAG | AAGAGTGTGA | CTGCGGAGAA | CCGGAGGAAT | 1550
| GCACGAATCG | CTGCTGTAAC | GCTACCACCT | GTACTCTGAA | GCCAGATGCT | 1600
| GTGTGCGCGC | ACGGGCAGTG | CTGTGAAGAC | TGTCAGCTGA | AGCCCTCCAGG | 1650
| AACTGCATGC | AGGGGCTCCA | GCAACTCCTG | TGACCCTCCCA | GAATTCTGCA | 1700
| CAGGGACTGC | CCCTCACTGT | CCAGCCAATG | TGTACCTACA | TGATGGCCAC | 1750
| CCGTGTCAGG | GCGTGGATGG | TTACTGCTAC | AACGGCATCT | GCCAGACCCA | 1800
| TGAGCAGCAG | TGTGTCACGC | TCTGGGGACC | AGGTGCTAAA | CCGGCTCCTG | 1850
| GCATCTGCTT | TGAGCGAGTC | AACTCTGCAG | AGGTGCTAAA | TGGTAACTGT | 1900
| GGCAAAGACT | CCAAGAGCGC | CTTCGCCAAA | GAGATCCTTA | GAGATGCCAA | 1950
| GTGTGGGAAA | ATCCAGTGTC | AAGGTGGTGC | AAGCCGACCT | GTCATTGGTA | 2000
| CCAATGCTGT | TTCCATAGAA | ACAAATATCC | CACAGCAGGA | AGGAGGTCGG | 2050
| ATTCTGTGCC | GGGGACCCA | TGTGTACTTG | GGTGATGACA | TGCCAGACCC | 2100
| AGGGCTTGTG | CTTGCAGGAA | CAAAGTGTGC | AGAAGGAAAA | ATCTGCCTCA | 2150

Fig. 5d

```
ATCGTCGATG TCAGAATATC AGTGTCTTCG GCGTTCACAA GTGTGCCATG  2200
CAGTGCCACG GCCGAGGGGT ATGTAACAAC AGGAAGAATT GCCACTGTGA  2250
AGCCCACTGG GCTCCACCCT TCTGTGACAA GTTTGGCTTT GGAGGAAGCA  2300
CAGACAGTGG TCCCATCAGG CAAGCAGATA ACCAGGGCTT GACTGTAGGA  2350
ATCCTGGTGA GCATCCTGTG TCTGCTTGCT GCTGGATTTG TGGTGTATCT  2400
CAAAAGGAAG ACGTTGATGC GGCTGCTGTT CACACATAAA AAAACCACCA  2450
TGGAAAAGCT AAGGTGTGTG CACCCTTCCC GGACACCCAG TGGCCCTCAC  2500
CTTGGCCAGG CTCACCACAC CCCCGGGAAA GGCCTGCTGA TGAACCGGGC  2550
ACCACATTTC AATACCCCCA AGGACAGGCA CTCGCTCGAG TGCCAGAACA  2600
TGGACATCAG CAGGCCCCTC GACGCTCCTC CCGTCCCACA GCTTCAGTCA  2650
CCTCAGCGAG TGCTCCTGCC TCTCCACCAG ACCCCACGTG CACCCAGTGG  2700
CCCTGCCAGG CCCTGCCCG CAGTCCTGC AGTCAGGCAG GCCCAGGGCA  2750
TTCGAAAACC CAGTCCTCCT CAGAAGCCTC TGCCTGCTGA TCCACTGAGC  2800
AGGACTTCTC GGCTCACTAG TGCCTTGGTG AGGACCCCAG GGCAGCAGGA  2850
```

Fig. 5e  READING FRAME

| | | | | |
|---|---|---|---|---|
| ACCTGGGCAC | CGCCCCAGCCC | CCATCAGACC | TGCCCCTAAG | CATCAAGTAC | 2900
| CCAGACCTTC | CCACAATGCC | TATATCAAGT | GAGAAGCCAG | CCCAGACCGG | 2950
| TCCTCAACAG | TGAAGACAGA | AGTTTGCCACT | ATCTTCAGCT | CCATTGGAGT | 3000
| TGTTGTTGTA | CCAACTTTCC | GAGTTTCTAA | AGTGTTTAAA | ACACCATTCT | 3050
| CTCCAGACCC | TGGAGCCACT | GCCATCGGTG | CTGTGCTGTG | GTGCTTTGTG | 3100
| TACTTGCTCA | GGAACTTGTA | AGTTATTAAT | TTATGCAGAG | TGTCTATTAC | 3150
| TGCGCAGGGC | TCCTCGTGCT | GCATTTGTAC | CATCACAGGG | CTTTTCTACA | 3200
| GAAGGAAGGC | ACCTAAGATG | AGATGTTTAC | TGGAGGACTT | GAAATACCCT | 3250
| GCTTGATGGG | TCCCCACCTT | CCCAAGGCTG | TTTCTATTCA | AGGCCTTATC | 3300
| GGAAAATAGC | CCCAGGGAGA | ACCTGGCATG | TTATGGTACC | AGACACACAG | 3350
| CTCAGGACAC | CCCAGGGGAGA | GTATCCCTAT | GGTTTTCTTT | GTTTGCTTTC | 3400
| ATTTTATCTT | TTATATTTG | CTTGGGTTGT | CTTGGGTTGT | AGCCAGGGCC | 3450
| TTCAGGAAGG | TCTTGGGCCA | CTGCATGCTA | ATGGCCCTTCA | GGTCCTGCAC | 3500

Fig. 5f

| | | | | |
|---|---|---|---|---|
| CCTGAAGCTC | TCAGACAACA | AGTAGGATCT | GCTTTCTAGC | CAGCAGCTTT | 3550
| GGAGAGAACC | TGGGGTACTG | AAAAGAAGGT | TTGGGGTGTG | GTTATACCAG | 3600
| GATGGAGACT | GGAATCCTAA | TCTGGGCAAA | CATCTGACCT | TGAGCTGAGC | 3650
| AGCCATGAGC | ACCCTCTAGGA | AGCAAGGACG | GCTGAGGTGC | TGCACAAGGC | 3700
| TCTGCTTTGA | GAGCTGGCAG | GGGCTTCTCT | CTGGCTGCCC | TTTGCAGAGT | 3750
| GCTAGCTGGC | ATGGCATGTT | GTTACATCG | CTGCAGACCT | TGTTTCTACA | 3800
| AGAAAGCCAC | TGCCTGGGCA | TTACCACATT | GGAACAGTGG | CCCATTTAGA | 3850
| GCTAAGCAAA | TTACCACATT | GTCTTCTGGA | CCGTCTCCTG | ATGACCCTGT | 3900
| GTTCTGACAG | ATAGAGGAGG | CTTTCTATGG | CTGTAATACA | ATTTTCANAT | 3950
| GTGAACTAGT | AACCAGATCT | AGTCGATCAA | AACCATAACT | AGAAATCTCC | 4000
| TTTTTACTGC | AAGGCTCGAC | TTATTAAAAA | CTCTGGAGAT | TCCATATGCT | 4050
| TGCAAAAGCT | ATAACCACGT | GGAATGCTCT | TTAGGCAGAA | CAGCCTGAGT | 4100
| CTGGTATCCT | TATTAGTAGC | CATTGGACAA | TCTCATGGCA | GTTACCTGTG | 4150
| TGTTCTCTTC | AAGGCATCCT | AATTTCTTCA | AGCACCCAAA | ACTCGGTCTT | 4200
| CCTCACATTC | TGAACATACC | TATCAATGAC | GCATAGAGAG | AGGCAATCCG | 4250

Fig. 5g

| | | | | |
|---|---|---|---|---|
| TTTCCGAATA | CTGAGTTGCT | CACGGNAAGG | CAACCTCAGC | CCAGGNAAAC | 4300 |
| TTTTTCCTC | TGNTCTTTCA | GTATGTGACT | GGGGAGCTAC | CTTCAGAAGC | 4350 |
| AAATTTTCAA | GGTGGNCTCA | ACCCCATNGG | ATGAAAGNTA | TTTTTTAAA | 4400 |
| AAATAATTAA | TGGTAAATGCC | AGAGGGCTTT | CCTGGCNTCC | AGATNGGGGC | 4450 |
| GTAGGNTTGA | CTAGCTTTCA | CGACAGAAGG | TAAATGACAG | CAGTCCTCTA | 4500 |
| CCTCGTCTGA | GCCTGTGCCT | ATCAAGGCTT | CTTTGGAAGG | GTAACTAACA | 4550 |
| TTAATGGCTG | TTTCTAGAAT | TGAAGCAGAA | GGGAAAATAC | AGATAAGGAA | 4600 |
| TTTGGTTTGC | CTGGGTAAAT | CCAAAACTGT | ATCCAGCATT | GGGAAGCATG | 4650 |
| GTCTTCATGA | CTGCCCTCTT | AAATCCACGT | CACAGATGCA | TAAAAGAATA | 4700 |
| ACTCTTATGA | CATGCCCTCT | TTTGTGGCAC | AGAGACAATA | TTGCTGCCAC | 4750 |
| TGAGATGCAT | ACAAAATTTC | TGTAACTGAT | ATGTCATTCA | GTAGTTGTAT | 4800 |
| TAAGGCCAAA | CATCCCACAAC | TGTAAAGACT | TATAGAGTTG | TGTGGGCGTT | 4850 |
| GTCTTGTGAG | ACACACAAAG | CCTCAGCTGA | AGCCGTATGAG | CTCCTCCTCC | 4900 |
| AGGTGGGAGT | GATGGGGAGG | CTAGAAAACAC | ACAAAGACAA | CAGAAGAGCT | 4950 |
| TTGGTTTGGG | GGGGTGCAG | AGAGAGTGTG | GTTAGAGGA | AGTTGGAGCC | 5000 |

Fig. 5h

| | | | | |
|---|---|---|---|---|
| ATGATCTTCT | GCCATCTCCC | CAGTGTCCAC | TAAGGATGCC | GATGGTGCCT | 5050
| TACCAGCTGT | GCAGTGCTGG | CTGCTTGCTT | TTACAGAGCC | ATGCATTCAT | 5100
| TTCTGAATAA | GAACATATTT | AATCCTGAAA | TTCCCTTACA | GGACAGACAG | 5150
| TGTTACTAAA | GGAATTCCTC | TAAGATACAG | TAGTTGTCAA | TTAAAGCATA | 5200
| TTTAGCAGTA | ACTTCAATTT | TAACAAAATT | GGGACCCAAT | AGCCAGCATG | 5250
| AGGGTTCTTT | GACAGAGGGT | AGTTTCTCTC | TCCCTTTCTC | CATCCTTCAA | 5300
| ATGACAAAGAC | GTCAAAAACTA | ATACAGTTCA | TTTGCAGTCC | ATCTCATGCT | 5350
| TATACATACT | AGAGGTATGA | CTAAAGTTGG | TTGAGTCATG | GGAGACCATC | 5400
| CCTGAGAAAG | TCCAGTCGGT | CAAGAGCCCT | GCCAGGTGGC | GTGGCTGGAC | 5450
| GTCCCTCCTTT | TGTTCCTGCA | CTGAGGAATA | GTTATAGGTT | ATGTGACCCC | 5500
| ACTTCACAGG | CAAGTGGGAG | GCGAACCCTG | CAGGCATGCC | CCTTAAAAGC | 5550
| TGGTCTCAGA | CCTACAATAG | TCCTGAGTCT | GTTTTCCCAG | CACACAGAGA | 5600
| GCAACAATGC | AGTTTTCCAT | TTCAAAATAT | GCATGCCGAG | TTTGCGCTCT | 5650
| GTGTGAGTGT | TTCCAGGTTA | CACATATGGG | ATGACATCAC | AGAAACCACA | 5700
| CAAGCAACAA | ATTAAATTCT | ACGGGAAGAA | ATCCTCCTGA | CTGGTCTCTG | 5750

Fig. 5i

| | | | | |
|---|---|---|---|---|
| AGGAGACATT | TTTATGCCTT | CTTAACTTTA | TTAGGAACTC | TCAGGCTGAA | 5800
| GCTAGGGGTC | ATTGTCCCCC | AACAAATCAA | TACAAAGCCA | TCAATGNACT | 5850
| CTCGAAGAAC | TGCCAAACCC | TGATCTGTGT | GAATGTTCTC | AGGAGCCTGT | 5900
| GATCCCCATG | GTGCTANAAA | GAGGCTGGAG | CTGGGCCAAC | AAGAAGGCCT | 5950
| AAGAGTCCTC | CTGCCTCTCA | GCAGATGTTT | ACTGAGCACT | CTGAGCCAGA | 6000
| AGCACCCCGA | CAACCAGGAG | GACGATNGCT | GGGCAGTAGG | GCGCCCAGCC | 6050
| ACTTGCAGCT | CTTTCCTCTG | AGGCCCGCTT | TGTGTTTTAA | TTCCCTTCTG | 6100
| TCAGGCCCCA | ANCAGNGGAC | ACTGTCCTAT | AGACCTCCCT | CTNAGTTTTC | 6150
| AGACGGCCTA | AGCCATACAC | AAATGCCCCA | GACTAAGAAA | CACCAATACN | 6200
| TCCCAGCAGT | CCCCAAGAAC | TGGTTTTAA | TTTTCTTTT | AAGTAGAAGA | 6250
| GGGTGTCACA | GAGGCCATTT | TTTTCTTTT | CTTCCACTC | ATACTGGAAC | 6300
| CTAGGTCCTC | TCTCTACACT | CCTAGTTCCT | TTACACAACT | CGGCAGTGGC | 6350
| TCCATTACAC | CAAGGACACA | GAAAAACACA | GGTACCGATT | TGCCTTCCTC | 6400
| TCCTGCCAAT | CACAAGTGCC | TTACTCTGAC | CAGACCCATG | ACAAAACCTC | 6450
| TGTCATCCAA | GAGAGCCAAC | TCTCTACCTT | TGTTACTACT | TCAAGCCAAT | 6500

Fig. 5j
```
GTGGTAACTG CTAACCTTCA AGGGTCACCT AAACAGTATA GTCCAACCTT 6550
CACCAGGACC ATAGCACAGA GCAACCTCCA GNACACACAC ACACACACAC 6600
CTTGAATCTA TCCCACAGCA TATCAACCCA CAGTGACCTC CCTCCCACCG 6650
CCTTGTTCTA ATTACAAGGT GAAGATGGCC ATAGAAAATC AAGTTAGCAC 6700
TAATTACAAA ATGCTTTTGA TGCAACCTGA ATTTCCCAAT GGCACCTATT 6750
GCTTTGAAAC TCTGATGAGT TAAGTCATGC TCTGGGAGCT GTGAGCCCCA 6800
TGCTCAGATC CACTGGGCAG GGGGACTCC TTGCAGGAGA CATGGGCACA 6850
CATATGAATG TACCATTTCC ATGCCTTTTG TGGAGTACAG ACATATAAAC 6900
ATAAATACTT CCATT                                       6915
```

Fig. 6a

| | | | | |
|---|---|---|---|---|
| GGCCGGGGGGC | AGGCAATGGC | AGGGGATGTG | TGATTGCGGA | CAGTGAGAGG | GCCGTTGCTA | 60 |

└─ READING FRAME

| | | | | | | |
|---|---|---|---|---|---|---|
| TCATGCCCGG | GCGGCGGGC | GTCGCCCGGT | TCTGCTTGCT | GGCTCTCGCT | CTGCAGCTAC | 120 |
| ATTGGCCGCT | GGCGGCGTGC | GAGCCGGGAT | GGACCACAAG | AGGAAGCCAA | GAAGGTAGCC | 180 |
| CTCCGCTACA | GCATGAACTC | ATAATACCTC | AGTGGCGGAC | TTCAGAAAGC | CCTGGGAGAG | 240 |
| GAAAGCATCC | ACTCAGAGCA | GAGCTCAGGG | TCATGGCTGA | AGGGCGAGAG | CTGATCCTAG | 300 |
| ACCTGGAGAA | GAACGAGCAC | CTTTTTGCTC | CAGCCTACAC | AGAAACCTGC | TACACTGCAA | 360 |
| GTGGCAATCC | TCAAACCAGC | ACGCTGAAGT | CTGAGGATCA | CTGCTTTTAC | CACGGGACTG | 420 |
| TGAGGGACGT | GGATGAGTCC | AGTGTCACGC | TCAGCACCTG | CCGGGGAATT | AGAGGACTGA | 480 |
| TTATAGTGAG | AAGTAACCTC | AGCTACATCA | TCGAGCCCGT | CCCTAACAGC | GACAGCCAAC | 540 |
| ACCGTATTTA | CAGATCCGAA | CATCTCACGC | TGCCCCCGGG | GAACTGTGGG | TTCGAGCACT | 600 |
| CCGGGCCCAC | CTCGAAGGAC | TGGGCCCTTC | AGTTACACA | TCAGACCAAA | AAGCAACCTC | 660 |
| GCAGAATGAA | ACGGGAAGAT | CTACACTCTA | TGAAGTACGT | GGAGCTTTAC | CTGGTGGCTG | 720 |
| ATTATGCAGA | GTTTCAGAAG | AATCGACATG | ACCAGGATGC | CACCAAACGC | AAGCTCATGG | 780 |

Fig. 6b

| | | | | |
|---|---|---|---|---|
| AGATTGCCAA | CTATGTTGAT | AAGTTTTACC | GCTCCCTGAA | CATCCGAATT | GCACTTGTCG | 840 |
| GCTTGGAGGT | GTGGACGCAT | GGGGATAAGT | GTGAAGTTTC | AGAGAATCCC | TACTCTACCC | 900 |
| TCTGGTCCTT | TCTTAGTTGG | AGGGCGCAAGC | TGCTTGCTCA | GAAAGAGCCAT | GACAATGCTC | 960 |
| AGCTAATCAC | GGGCAGGTCC | TTCCAAGGCA | CCACCATTGG | CCTGGCCCCC | CTCATGGCCA | 1020 |
| TGTGCTCCGT | GTACCAGTCT | GGAGGAGTTA | GCATGGACCA | CTCCGAGAAT | GCCATTGGTG | 1080 |
| TAGCCTCCAC | TGTGGCCCAT | GAGATTGGCC | ACAACTTTGG | CATGAGCCAT | GATTCTGCAC | 1140 |
| ACTGCTGTTC | TGCCAGTGCA | GCCGATGGCG | GCTGCATCAT | GGCCGCCGCC | ACCGGGCACC | 1200 |
| CTTTCCCCAA | AGTGTTCAGT | TGGTGTAACA | GGAAGGAGCT | GGACAGGTAT | CTGCAGACAG | 1260 |
| GAGGAGGGAT | GTGTCTCTCC | AACATGCCGG | ACACTAGGAC | GCTGTATGGA | GGCCGGAGGT | 1320 |
| GTGGCAACGG | GTACCTGGAA | AATGTGACTG | TGGAGAAGAG | GAGGAATGTA | 1380 |
| AGAACCCTTG | CTGCAATGCC | TCCAACTGCA | CTCTGAAGGA | AGGGGCAGAG | TGTGCCCATG | 1440 |
| GTTCCTGCTG | CCACCAGTGC | AAGCTGGTGG | CTCCCTGGAAC | CCAGTGTCGG | GAGCAGGTTC | 1500 |
| GGCAATGTGA | CCTCCCCGAG | TTCTGCACCG | GCAAGTCTCC | CCACTGCCCC | ACCAACTATT | 1560 |
| ATCAGATGGA | TGGCACCCCC | TGCGAGGGTG | GCCAGGCCTA | CTGCTACAAC | GGCATGTGCC | 1620 |
| TCACTTACCA | GGAACAGTGC | CAGCAGCTGT | GGGGACCTGG | AGCCCGGCCT | GCCCTCGATC | 1680 |

Fig. 6c

| | | | | |
|---|---|---|---|---|
| TTTGCTTTGA | GAGGGTGAAT | GCTGCTGGTG | ACACCTATGG | AAACTGTGGC | AAGGGCTTGA | 1740
| ATGGCCAATA | CAGGAAGTGC | AGTCCCAGGG | ATGCCAAGTG | TGGSAAGATT | CAGTGCCAGA | 1800
| GCACCCAGGC | CCGGCCCCTG | GAATCCAACG | CAGTATCTAT | TGACACCACC | ATCACCTTGA | 1860
| ACGGGAGGCG | GATCCACTGT | CGGGCACCC | ACGTCTACCG | GGGTCCTGAG | GAGGAGGAAG | 1920
| GGGAAGGTGA | CATGCTGGAC | CCAGGGCTGG | TGATGACTGG | AACCAAGTGT | GGCCACAACC | 1980
| ATATTTGCTT | CGAGGGGCAG | TGCAGGAACA | CCTCCTTCTT | TGAGACGGAA | GGCTGTGGGA | 2040
| AAAAGTGCAA | TGGCCACGGG | GTCTGCAACA | ACAACAAGAA | CTGTCATTGC | TTCCCTGGCT | 2100
| GGTCTCCACC | TTTCTGTAAC | ACCCCGGGAG | ATGGTGGCAG | CGTCGACAGT | GGTCCTTTGC | 2160
| CCCCTAAGAG | TGTGGGTCCC | GTGATCGCTG | GGGTGTTTC | AGCTCTCTTC | GTGTTGGCAG | 2220
| TTCTGGTGCT | ACTGTGTCAC | TGCTACAGAC | AGAGCCACAA | ACTGGGCAAA | CCCTCGGCTC | 2280
| TCCCTTTCAA | GCTGCGGCAT | CAGTTCAGT | GTCCCTTCAG | GGTATCTCAG | AGTGGTGGAA | 2340
| CTGGCCATGC | CAACCCAACT | TTCAAGTTGC | AGACCCCCCA | GGGCAAGCGA | AAGGTGACTA | 2400
| ACACCCCTGA | ATCCCTTCCGG | AAGCCGTCCC | ACCCCCCTCT | CCGGCCCCCT | CCAGACTACC | 2460
| TGCGGGTTGA | ATCGCCACCT | GCACCATTGT | CGGCACATCT | GAACAGGGCT | GCTGGGAGCT | 2520
| CCCCAGAAGC | TGGGGCTCGA | ATAGAAAGAA | AGGAGTCAGC | CAGGAGGCCT | CCCCCAAGCC | 2580

Fig. 6d

```
GACCCATGCC CCCTGCACCT AACTGCCTAC TGTCCCAGGA CTTCTCCAGG CCTCGACCAC    2640
CTCAGAAGGC ACTCCCAGCC AATCCGGTGC CAGGCCAAAG GACCGGTCCC AGGTCAGGAG    2700
GCACCTCCCT GCTTCAGCCC CCTACTTCTG GTCCTCAGCC CCCCAGGCCT CCAGCAGTGC    2760

CTGTTCCAAA GCTACCCGAG TACCGATCAC AGAGGGTTGG AGCAATAATT AGCTCCAAGA    2820

READING FRAME ⎯⎯⎯⎯⎯⎯

TCTAGAAGTG TCGAGAAGTT TCTTGTTCCG ATGGAAGACT CCGGATGCCA TGGAAGGTCC    2880
AGAAGAAAGA CGCCTTCTCA CCCATCCTGA AGCTTTGGCA GCCTTCTGGA ACGTCCCTCA    2940
TCCCCAGAAT CTCCCTTCTT ACCCGAGTGC CTCCTGCTTC CTCCGAGGCC CAGGGGGACT    3000
CATATCCAAT GGCTCCTAAG TGTTTGTCCT GTGCAATATA CAGCCCAGGG AGGGAAGGGA    3060
AGCACGGGCGA GGAGGGTGGG AAAGGTTCTC CCTCAGCCCA CTAGCCAAGA GCTACCAGCG    3120
 ⎿
```

Fig. 6e

| | | | | | |
|---|---|---|---|---|---|
| ATGCTCAGGG | AAGGCTTGAG | CTGGGGTCCT | CCTCTGCGGA | GCTTGGAGAA | GGTACCCATC | 3180
| CTGGTCCTAT | GCTGGCAGGA | ACACACGCGA | GTGTCACTGA | TTGGCCTCCT | TCTGGGATCC | 3240
| CAGGCTGCTG | AGGAAGCTAC | TGCTACATCC | CTACCCCAAG | GGGCTTGGTC | AAGGTGCCTG | 3300
| TYCCTGGCTC | TCTGGCTGCA | TGTAATAAGC | CATGCTCCCC | TCCCCTGCCT | TTCTTCACAT | 3360
| TCCCACTCCC | ATATTTACAC | GGGTCACTCT | GACTCAGACA | GGTACTATTT | GTAAGTAGCA | 3420
| TAGACAGCAG | GGGGTGGGG | TGGTCAACCT | GTGTCCCCTC | TGAGCCGTTA | TGCCAAAGGT | 3480
| CACTAAGGAC | ATTTAGAATC | CCCATCCATC | CATCCATCCA | TCCATCCATC | CATCCATTCA | 3540
| TCCATCCCCA | GTGTTCCATG | TGTCACCTTC | TCCTTTCCA | GCATCCCTAT | CCTATGGTGC | 3600
| TTTGGTGGTG | AACTATGGCA | GTCCTGACTT | GCTGATGACC | ATATGCTGGT | GACCTACAAA | 3660
| TCGGGATCCT | GCCATATGGG | GTCGCCACTG | GACTTTCTGC | ACTGGTTCTC | AAGAGCGTTG | 3720
| AGCCGAGTGG | GCGTGTATGT | TTGTGTGTGT | GTGTGTGTGT | GTGTGTGTGT | GTGTGTGTGT | 3780
| GTGTGTGTGT | GTGTGTGTGT | GTGAAAGAGA | CAGAGGCAAT | GAGAGAGACA | GACATGCAGG | 3840
| CAGGCCGACA | GCTCTGCATG | TACTTGTGTT | TTACGGCCTC | AAGCAGTATA | AGGGACCTCC | 3900
| TCCTTATTTC | TGACTCATAT | CTAAGTAAGG | TTCCCCAGGA | CMAGCCACAG | CTGTACTGAG | 3960
| GGGGGCTGAC | ATGTTTGGCA | TCCTGGCTAT | AGTATTGTAT | ACACAGGGCC | ACCAGCCCCG | 4020

Fig. 6f

```
CCCTAGTGGT CAGCTCTGAG GGGGACTGG  TGACTCTGAA CAGATCGATG TCAACAGCCA   4080
TGGTGAACCA GATCTGGGCA GGGTTCCCCA AACTCTATTC AACCAGAGTT TTATCACGCA   4140
NCTCATCGGG TCTCTCCTGG TTGCTGCCCC GAGGTGATCG TCATGGAAAA TGCTGAGAAG   4200
GTGGGAATGG GATGGGGTGG ACCTTCTCTT GCTTGGTGCT CCGCTATTTG GAACAGTTCT   4260
TACACATTTG CTGGGCCTGG CCTCTGAGAG GCCATCTTCC ACCCCCAGAA AGGTGCTAAT   4320
GGCACTGCAG AGGGCTCTCT AGGGGCCCTC CCGCCCCAAC AGCAAGCAGT TGTTAGCTCT   4380
TGGAACCCTC CAGAGGAAGA GGCAAGCGTT TGACTTCCCC TTTACCACCT GAGGCCTCCT   4440
TATATCTCTT CCCAGAGTAA GCTTTGGGAT TGTAGACATG TGGGAGCTAT GACAGACGTG   4500
GCCTGGGGTA GAAAGATCTC AGGAAAGCAC CTTTCTCCTT ATATCAGTTT CCGTGCTCTT   4560
CACACTCTCT GAGGCCTCAG TCCATGTCCT CTCACCACAA AGTTAGAAAC TGCTTTACCA   4620
AGTGGCCGGT GACTACAGGC CACCCCGATT CATTCCCTTG CTCTTTGGTA CCTCCACTTT   4680
CTGTCCCTTG AACCATATCA GAAAAAGACC TCCATCCCAT GACATTATTC ATCACTTCTG   4740
TTTTCTTC    TTCATTACTG TGCTACCACC TGCTACCACC TCCATCCCAT GACATTATTC TGTGANGTGT   4800
AAGAGGACGG TGTTTNTTA  NTCTTGGGAG ANATGTCGGC AGCTGCTCTA CACACAACTT   4860
CACTCAAGGC TTTGTCTCCA GAGGCCAGCT AGGCTGTCAC AGGCAGGAAT CCCTTCCCAT   4920
```

Fig. 6g

| | | | | | |
|---|---|---|---|---|---|
| CTGCTTTGTG | AAGGGTCCCA | TACAGGTGTA | TCTAGACTTC | AAGGACAGGG | TTTGTCTCAC | 4980
| AGGATTGTCA | CTTAGGAGAT | GAAAGAATAT | TACCACATGA | GGAGGAGGGG | CAGTTGCAAC | 5040
| AGAACACTTT | GGTCTTCCTA | CACCAAGTCT | GTGAGGGCAT | CCAAGACTGA | ATGAAAGCGC | 5100
| TTTCTTATG | CATACAATGT | GAGCAAGAAC | AAGAACTGTT | TAAGGCACCT | CTGTTCCCAG | 5160
| CCACTGAAGA | GAGACGTCAG | AAGATGTTAG | AATAGGTCAA | AACCAAGGCT | CTGGTGGACT | 5220
| GAGGGAAGGT | TTGTAGCTGC | GTTTAGTGGT | ATACATCTTT | AGTCCCAGCA | TAGGCAGGTG | 5280
| AATCTCGAGT | TTGAAGCTAG | CCTGGTCTAA | AAAGGAAGTT | CCAAGACTGC | CAGGGCCACA | 5340
| CAGAGGAAAA | AAAAAAAACCC | TCTAGAAAAA | CAAAAATGAA | GACAGGTTCT | CATGTATCGT | 5400
| AGATTGGCCT | TTAAGTCACT | TTACCAAGGA | TGATCTTTGA | ACTCCTGAGT | ACAGACTGCG | 5460
| GGTGTGTGCT | ACCATGCTTT | ATGTGGCCCT | GGGTTCAAAC | ACAGCCCTTC | ATATGTATAT | 5520
| AGCCAAACAC | TCTACAACTG | AGCTACATCC | TCCAGCCTAG | GCTGTAAATG | TTTTTTGGAG | 5580
| CTAGATTAGC | TGCCTGCCAA | CCTTAGAACT | GCAAAGCCAT | TCCTGACCTG | TAAACCTCAG | 5640
| CTCTCCATCT | CTATAAGAGG | TATAGCCTGG | GCTAATACCG | TCCAAGTTAC | AACTCCTTGC | 5700
| TTGCTTTCTG | TTCCTTCTAG | CCTTGGTGAC | TTCCACCAGG | AAGAGAATAC | CCCCTCTCTA | 5760
| CCCCTGCTCC | AAGACACTGT | AGATGCTAGT | GTCGGAGTGT | TCTCTGTAAC | GCGACAGTTC | 5820

Fig. 6h

| | | | | | |
|---|---|---|---|---|---|
| CTCTGTTGC | AATAGCCCCC | CTGCAACACT | GCAATAATCC | TTCAGTGTCT | CCCCTGGGCT | 5880 |
| CAATTCACTT | CCTTATTTGA | CAAAGTGGAG | GTGAGACTTG | TATTCTTAAA | ATTGGAGGCT | 5940 |
| AGTTATTTTG | TCAAATGCAT | GTAATGAACA | GACCCGAAGG | AATCCTCCAC | ACACAAGCCA | 6000 |
| GGGAACACCA | ACTGGAAAGG | TACCCCGTCC | CAGGGAAGCC | TGCTAGGGAG | AGGTTCTGTA | 6060 |
| GAATCCGAGC | CTAGCACCCC | AAAGTCATGC | ACCCAGTATC | CTCTTGTATG | ACTGTATATG | 6120 |
| TCTATGTCTG | GGATCCAGGG | CAAATGTGAA | TTTCCTTTTG | ATTGGGAGA | TTGTTCACAG | 6180 |
| GAAGTAGTCC | TCCCCTCTCA | TGTCCTCCTA | TTGATTGTTT | ACAATATTTG | TACATCTATG | 6240 |
| CAAAATACTT | GAATGGGCCA | TGGTGCCTTG | TTTTTTGTTG | TTGTTGTTAT | TTTTTTCTCC | 6300 |
| TTGTTTGTAT | TTAATTAAAA | CAAATTGTCA | TGAGGAAAAA | AAAAAAAAAA | AA | 6352 |

Fig. 7a

| | | | | |
|---|---|---|---|---|
| | GTTGCAAGGA | TGACCGAAGN | NCGGAGGCGG | CGGCCGGGCG | TTGAGCGGAA | CCTGCCGAAG | 60 |

└─ READING FRAME

| | | | | | | |
|---|---|---|---|---|---|---|
| CCCTCGCTAT | GGGGCCGCGC | GCGCTCTCGC | CCCTTGCCTC | TCTGCGACTA | AGGTGGCTGC | 120 |
| TGGGTGTGG | CTTGCTGGGC | CCAGTCCTCG | AGGCCGGGCG | ACCAGACTTG | GAACAGACTG | 180 |
| TCCATCTTTC | TTCTTATGAA | ATTATTACTC | CTTGGAGATT | AACTAGAGAA | AGAAGGAAAG | 240 |
| CTCTGGGGCC | CAGTTCACAG | CAGATCTCTT | ACGTCATCCA | GGCCCAAGGA | AAACAGCATA | 300 |
| TTATTCACTT | GGAAAGAAAC | ACAGACCTTT | TACCTAATGA | TTTTGTAGTT | TACACCTACG | 360 |
| ACAAGGAAGG | CTCCCTACTC | TCTGACCATC | CCAACGTACA | GAGCCATTGT | CACTATCGAG | 420 |
| GCTATGTGGA | GGGAGTGCAG | AATTCCGCGG | TTGCTGTGAG | CGCCCTGCTT | GGACTCAGAG | 480 |
| GCTTGCTGCA | TTTGGAGAAT | GCCAGTTTTG | GAATTGAACC | TCTGCACAAC | AGCTCACACT | 540 |
| TTGAGCACAT | ATTTACCCC | ATGGATGGCA | TCCACCAGGA | GCCTCTGAGA | TGTGGAGTCT | 600 |
| CTAACAGGGA | CACAGAGAAG | GAAGGCACAC | AGGGGGATGA | GGAGGAGCAT | CCGAGTGTCA | 660 |
| CTCAGCTGCT | GGCCAGAAGA | AGAGCTGTTC | TACCACAGAC | CGGCTATGTG | GAGCTGTTCA | 720 |
| TTGTTGTAGA | CAAGGAAAGG | TACGACATGA | TGGGACGGAA | CCAGACTGCT | GTGAGAGAAG | 780 |

Fig. 7b

| | | | | |
|---|---|---|---|---|
| AGATGATTCG | CTTAGCAAAC | TACCTGGATA | GCATGTACAT | CATGTTAAAC | ATTCGAATTG | 840 |
| TGCTGGTTGG | ACTAGAAATT | TGGACAGACA | GAAATCCTAT | CAATATAATT | GGAGGAGCTG | 900 |
| GAGATGTGCT | GGGCAACTTT | GTTCAGTGGC | GGGAAAAGTT | CCTTATAACT | CGTCGGAGAC | 960 |
| ACGACAGTGC | ACAGTTGGTT | TTGAAGAAAG | GCTTTGGTGG | AACTGCAGGA | ATGGGGTTTG | 1020 |
| TAGGAACAGT | ATGTTCAAGG | AGCCACGCAG | GTGGGATCAA | TGTGTTTGGG | CAAATCACTG | 1080 |
| TGGAGACATT | TGCATCCATT | GTTGCTCATG | AATTGGGGCA | TAACCTTGGA | ATGAATCATG | 1140 |
| ATGATGGGAG | AGAGTGTTTC | TGTGGAGCAA | AGAGCTGTAT | CATGAATTCA | GGAGCATCCG | 1200 |
| GGTCCAGAAA | CTTTAGCAGT | TGCAGTGCGG | AGGACTTTGA | GAAGTTAACG | TTGAATAAGG | 1260 |
| GAGGAAGCTG | CCTGCTTAAC | ATCCCGAAGC | CTGACGAAGC | CTACAGCGCG | CCCTCCTGTG | 1320 |
| GTAATAAGCT | GGTGGACCCT | GGAGAGGAGT | GTGACTGCGG | CACAGCGAAG | GAGTGTGAGG | 1380 |
| TGGACCCATG | CTGTGAAGGA | AGCACTTGTA | AGCTCAAGTC | ATTTGCTAGC | TGTGCATATG | 1440 |
| GCGACTGTTG | TAAAGATTGC | CAGTTCCTTC | CAGGAGGCTC | CATGTGCAGA | GGGAAGACCA | 1500 |
| GTGAGTGTGA | TGTTCCTGAG | TACTGCAACG | GTTCCTCTCA | GTTCTGCCCG | CCAGATGTCT | 1560 |
| TCATTCAGAA | TGGATATCCT | TGCCAGAACA | GCAAAGCCTA | CTGCTACAAT | GGCATGTGCC | 1620 |
| AATATTATGA | CGGGCAGTGT | CAGGTCATCT | TTGGTTCAAA | GGCTAAGGCT | GCCCCAAGAG | 1680 |

Fig. 7c

| | | | | | |
|---|---|---|---|---|---|
| ATTGCTTCAT | TGAAGTCAAT | TCTAAAGGTG | ACAGATTTGG | CAACTGTGGT | TTCTCCGGCA | 1740
| GTGAGTACAA | GAAGTGTGCC | ACTGGGAACG | CGCTGTGTGG | AAAGCTTCAA | TGCGAGAATG | 1800
| TACAGGACAT | GCCGGTGTTT | GGAATAGTAC | CAGCTATCAT | TCAGACACCC | AGTCGGAGGCA | 1860
| CCAAATGCTG | GGGTGTGGAT | TTCCAGCTTG | GTTCCGACGT | TCCAGACCCA | GGGATGGTGA | 1920
| ATGAAGGCAC | CAAATGTGAT | GCTGGCAAGA | TTTGCAGGAA | TTTTCAGTGT | GTAAATGCTT | 1980
| CTGTCCTGAA | TTATGACTGT | GACATTCAGG | GAAAATGTCA | TGGCCATGGG | GTATGTAACA | 2040
| GCAATAAGAA | TTGTCACTGT | GAAGATGGCT | GGGCTCCCCC | ACACTGTGAC | ACCAAAGGAT | 2100
| ATGGAGGAAG | CGTGGACAGC | GGGCCGACGT | ATAATGCAAA | GAGCACAGCA | CTGAGGGACG | 2160
| GGCTTCTGGT | CTCTTCTTC | CCCTTGTTGC | GGCTGCCATT | TCCTCTTTA | 2220
| TCAAGAGAGA | TGAACTACGG | AAAACCTTCA | GGAAGAAGAG | ATCACAAATG | TCAGATGGCA | 2280
| GAAATCAAGC | AAACGTCTCT | AGACAGCCAG | GAGATCCTAG | TATCTCCAGA | CCACCAGGGG | 2340
| GCCCAAATGT | CTCCAGACCA | CCAGGGGGCC | CAGGTGTCTC | CAGACCACCA | GGGGCCCAG | 2400
| GTGTCTCCAG | ACCACCAGGG | GGCCCAGGTG | TCTCCAGACC | GCCACCTGGG | CATGGAAACA | 2460
| GATTCCCAGT | ACCAACCTAC | GCCGCCAAGC | AGCCTGCGCA | GTTCCCGTCA | AGGCCACCTC | 2520
| CACCACAACC | GAAATATCT | TCTCAGGGAA | ACTTGATTCC | GGCTCGGCCC | GCTCCTGCAC | 2580

Fig. 7d
READING FRAME

| | | | | |
|---|---|---|---|---|
| CTCCTTTATA | TAGCTCCCTC | ACCTGATAGT | AGAATATTAG | AATCTTATTT | TTTAAATGTC | 2640 |
| TTCAGGGAAC | TGAGCAAATG | TTTGTGTTT | TTTTTTCCT | GATGTTTCT | TGAAAAGCCT | 2700 |
| TTCTCTTCCA | ACCATGAATG | AACACAAAAC | ACCACAAAAC | AAGCTTTATT | AACACAGGAG | 2760 |
| CCTAGTGGGG | ATTGCGAAAC | ACAGGAATGT | GCAGGCGCTC | CGGGGGGTGT | AAAGTGAACG | 2820 |
| TTTCCATCGT | TAGAATGTTT | TCTCTGGCCA | TTTGTGGATT | TAATGCACTT | GACGTGGATT | 2880 |
| AAGTTATTCT | GAGCATGTTA | CTGTAATGAT | TCTCAAATTA | ACTGTATTAG | TGTAAGCTTT | 2940 |
| GTCACTATGC | GCTAAACGTA | ATCCTGACTT | TTTGACCCCA | GTTACCATTA | ATAGTTTCTG | 3000 |
| GTTGACCATT | TGAACATGTA | TTAACTTAGG | AAGACTAATT | GCCAATAACG | TCTGCATTT | 3060 |
| CATCTTGCAT | GGATTAACAG | CCATTTATAT | GGACTTATGT | CTCTTAATGC | ACAAAGAAGC | 3120 |
| AGATATCTCG | AAGGAGCTTA | CACAAGAACC | ACAATTACTA | GATCATGATA | TACTTGGAAA | 3180 |
| GTGTGAAATA | TGGTGTGTAC | TCAGTTATTG | GCTTCCATTT | TTWATGATCT | TTCAACTATA | 3240 |
| ACAATTATGA | TAGAAATCGA | TTTAACACAA | TCAGTTATGG | GCTTCCATT | TCAAATATCT | 3300 |
| TTTCAACTGT | AATGACTATG | ACAGGAACTG | ATTCAACTCT | CAATTTTCTT | TATGCATCAT | 3360 |

Fig. 7e

```
GGTAAAGCAT TGCAGCAGTG TTGTTTTGTT TGAAGTGCAC ACTCTATGGT ACGAGGTGTT    3420
TAGTATACCC AAGCAGATAG GTGTCGATCG AACAGGAGCA GGGAGAATAC TTCCAACAGT    3480
TGAGGTGTTA CCAAACCACT TGAGAATTCA TGAGCACTTT AACTCTAAAC TCTGAATTTC    3540
AAAGCTTGAT GTGAAGTCCT CTAGAATGTT TACATTTACT AAGGTGTGCT GGGTCCTGTC    3600
TCTTTTGACT AATATTTTCG TAAACATTAG GCTGGAGAAA GGAAGGAAGC AGTGGTTCC     3660
TTAGATAACT ACAGAATTAT ACTGGTCTCT GGGATTACTC TCTCAGCTGT ATTAAAATGA    3720
ATTTGTACTT TGAAAGGAAT GATATTGACA CTAAAATTTT AAACATTTAA ATTTTTTCAT    3780
AATCTTTCAT AAAGAAGTTT AATAATAGGT ATATTAACTG AATTCATTA GTTTTTAAA      3840
ATAATATTGT TTGTGTATAT ATACATATTA AAATAAAAAC ATTTACAACA AATAAAATAC    3900
TTGAAATTCT AAAAAAAAAA AAAAAAAAAA A                                   3931
```

Days in the differentiation medium

Fig. 12a

```
         10         20         30         40         50         60
AAGCCTGCAGGAACAGCGTGCAGGGACTGCAGCAACTCCTGTGACCTCCCAGAGTTCTGC
 K  P  A  G  T  A  C  R  D  S  S  N  S  C  D  L  P  E  F  C                20

70         80         90        100        110        120
ACAGGGGCCAGCCCTCACTGCCCAGCCAACGTGTACCTGCACGATGGGCACTCATGTCAG
 T  G  A  S  P  H  C  P  A  N  V  Y  L  H  D  G  H  S  C  Q                40

130        140        150        160        170        180
GATGTGGACGGCTACTGCTANAATGGCATCTGCCAGACTCACGAGCAGCAGTGTCACG
 D  V  D  G  Y  C  X  N  G  I  C  Q  T  H  E  Q  Q  C  V  T                60

190        200        210        220        230        240
CTCTGGGGACCAGGTGCTAAACCTGCCCCCTGGGATCTGCTTTGAGAGAGTCAATTCTGCA
 L  W  G  P  G  A  K  P  A  P  G  I  C  F  E  R  V  N  S  A                80

250        260        270        280        290        300
GGTGAACCTTATGGCAACTGTGGCAAAGTCTCGAAGAGTTCCTTTGCCAAATGCGAGATG
 G  E  P  Y  G  N  C  G  K  V  S  K  S  S  F  A  K  C  E  M               100
```

Fig. 12b

```
              310                  320
AGAGATGCTAAAATGCGGGCAAG
  R   D   A   K   C   G   K
                            107
```

Fig. 13a

```
       10          20         30         40         50         60
GCAAAGAGCTGCATCATGAATTCAGGAGCATCGGGTTCCAGAAACTTTAGCAGTTGCAGT
 A  K  S  C  I  M  N  S  G  A  S  G  S  R  N  F  S  S  C  S 70         80         90        100        110        120
GCAGAGGACTTTGAGAAGTTAACTTTAAATAAAGGAGGAAACTGCCTTCTTAATATTCCA
 A  E  D  F  E  K  L  T  L  N  K  G  G  N  C  L  L  N  I  P 130        140        150        160        170        180
AAGCCTGATGAAGCCTATAGTGCTCCCTCCTGTGGTAATAAGTTGGTGGACGCTGGGGAA
 K  P  D  E  A  Y  S  A  P  S  C  G  N  K  L  V  D  A  G  E 190        200        210        220        230        240
GAGTGTGACTGTGGTACTCCAAAGGAATGTGAATTGGACCCCTTGCTGCGAAGGAAGTACC
 E  C  D  C  G  T  P  K  E  C  E  L  D  P  C  C  E  G  S  T 250        260        270        280        290        300
TGTAAGCTTAAATCATTGCTGCAGTGTGCATATGGTGACTGTTGTAAAGACTGTCGGTTC
 C  K  L  K  S  F  A  E  C  A  Y  G  D  C  C  K  D  C  R  F
```

```
     310       320       330       340       350       360
CTTCCAGGAGGTACTTTATGCCGAGGAAAAACCAGTGAGTGTGATGTTCCAGAGTACTGC          120
 L  P  G  G  T  L  C  R  G  K  T  S  E  C  D  V  P  E  Y  C 370       380       390       400       410       420
AATGGTTCTCTCAGTTCTGTCAGCCAGATGTTTTATTCAGAATGGATATCCTTGCCAG          140
 N  G  S  S  Q  F  C  Q  P  D  V  F  I  Q  N  G  Y  P  C  Q 430       440       450       460       470       480
AATAACAAAGCCTATTGCTACAACGGCATGTGCCAGTATTATGATGCTCAATGTCAAGTC          160
 N  N  K  A  Y  C  Y  N  G  M  C  Q  Y  Y  D  A  Q  C  Q  V 490       500       510       520       530       540
ATCTTTGGCTCAAAAGCCAAGGCTGCCCCCAAAGATTGTTTCATTGAAGTGAATTCTAAA          180
 I  F  G  S  K  A  K  A  A  P  K  D  C  F  I  E  V  N  S  K 550       560       570       580       590       600
GGTGACAGATTTGGCAATTGTGGTTTCTCTGGCAATGAATACAAGAAGTGTGCCACTGGG          200
 G  D  R  F  G  N  C  G  F  S  G  N  E  Y  K  K  C  A  T  G
```

Fig. 13c

```
       610        620        630        640        650        660
AATGCTTTGTGTGGAAAAGCTTCAGTGTGAGAATGTACAAGAGATACCTGTATTTGGAATT        220
 N  A  L  C  G  K  L  Q  C  E  N  V  Q  E  I  P  V  F  G  I 670        680        690        700        710        720
GTGCCTGCTATTATTCAAACGCCTAGTCGAGGCACCAAATGTTGGGGTGTGGATTTCCAG        240
 V  P  A  I  I  Q  T  P  S  R  G  T  K  C  W  G  V  D  F  Q 730        740        750        760        770        780
CTAGGATCAGATGTTCCAGATCCTGGGATGGTTAACGAAGGCACAAAATGTGGTGCTGGA        260
 L  G  S  D  V  P  D  P  G  M  V  N  E  G  T  K  C  G  A  G 790        800        810        820        830        840
AAGATCTGTAGAAACTTCCAGTGTGTAGATGCTTCTGTTCTGAATTATGACTGTGATGTT        280
 K  I  C  R  N  F  Q  C  V  D  A  S  V  L  N  Y  D  C  D  V 850        860        870        880        890        900
CAGAAAAAGTGTCATGGACATGGGGTATGTAATAGCAATAAGAATTGTCACTGTGAAAAT        300
 Q  K  K  C  H  G  H  G  V  C  N  S  N  K  N  C  H  C  E  N
```

Fig. 13d

```
         910        920        930        940        950        960
GGCTGGCTCCCCCAAATTGTGAGACTAAAGGATACGAGATCAAGCTTATCGATACCGTCG
 G  W  L  P  Q  I  V  R  L  K  D  T  R  S  S  L  S  I  P  S
                                                              320

ACCTCGA
 T  S
  322
```

Fig. 15a

```
GGGGACCCTCTGGATCCCAGTGAAGAGCTTCGACTCCAAGAATCATCCAGAAGTGCTGAAT    60
 G  D  L  W  I  P  V  K  S  F  D  S  K  N  H  P  E  V  L  N     20

ATTCGACTACAACGGGAAAGCAAAGAACTGATCATAAATCTGGAAAGAAATGAAGGTCTC   120
 I  R  L  Q  R  E  S  K  E  L  I  I  N  L  E  R  N  E  G  L     40

ATTGCCAGCAGTTTCACGGAAACCCACTATCTGCAAGACGGTACTGATGTCTCCCTCGCT   180
 I  A  S  S  F  T  E  T  H  Y  L  Q  D  G  T  D  V  S  L  A     60

CGAAATTACACGGGTCACTGTTACTACCATGGACATGTACGGGGATATTCTGATTCAGCA   240
 R  N  Y  T  G  H  C  Y  Y  H  G  H  V  R  G  Y  S  D  S  A     80

GTCAGTCTCAGCACTGTTCTCAGGGACTTATTGGGTTTGAAAATGAAAGCTAT   300
 V  S  L  S  T  C  S  G  L  R  G  L  I  G  F  E  N  E  S  Y    100

GTCTTAGAACCAATGAAAAGTGCAACAAACAGATACAAACTCTTCCCAGCAAGAAGCTG   360
 V  L  E  P  M  K  S  A  T  N  R  Y  K  L  F  P  A  K  K  L    120

AAAAGCGTCCGGGGATCATGTGGATCACATCACAACCAAACCTCGCTGCAAAGAAT   420
 K  S  V  R  G  S  C  G  S  H  H  N  T  P  N  L  A  A  K  N    140
```

Fig. 15b

```
GTGTTCCACCACCCTCTCAGACATGGGCAAGAAGGCATAAAAGAGAGACCCTCAAGGCA      480
 V  F  P  P  P  S  Q  T  W  A  R  R  H  K  R  E  T  L  K  A      160

ACTAAGTATGTGGAGCTGGTGATCGTGGCAGACAACCGAGAGTTTCAGAGGCAAGGAAAA      540
 T  K  Y  V  E  L  V  I  V  A  D  N  R  E  F  Q  R  Q  G  K      180

GATCTGGAAAAAGTTAAGCAGCGATTAATAGAGATTGCTAATCACGTTGACAAGTTTTAC      600
 D  L  E  K  V  K  Q  R  L  I  E  I  A  N  H  V  D  K  F  Y      200

AGACCACTGAACATTCGGATCGTGTTGGTAGGCGTGGAAGTGTGGAATGACATGGACAAA      660
 R  P  L  N  I  R  I  V  L  V  G  V  E  V  W  N  D  M  D  K      220

TGCTCTGTAAGTCAGGACCCATTCACCAGCCTCCATGAATTTCTGGACTGGAGGAAGATG      720
 C  S  V  S  Q  D  P  F  T  S  L  H  E  F  L  D  W  R  K  M      240

AAGCTTCTACCTCGCAAATCCCATGACAATGCGCAGCTTGTCAGTGGGGTTTATTCCAA      780
 K  L  L  P  R  K  S  H  D  N  A  Q  L  V  S  G  V  Y  F  Q      260

GGGACCACTCGGCATGGCCCCAATCATGAGCATGTGCACGGCAGACCAGTCTGGGGGA      840
 G  T  T  I  G  M  A  P  I  M  S  M  C  T  A  D  Q  S  G  G      280
```

Fig. 15c

```
ATTGTCATGGACCATTCAGACAATCCCCTTGGTGCAGCCGTGACCCTGGCACATGAGCTG      900
 I  V  M  D  H  S  D  N  P  L  G  A  A  V  T  L  A  H  E  L       300

GGCCACAATTCGGGATGAATCATGACACACTGGACAGGGGCTGTAGCTGTCAAATGGCG       960
 G  H  N  F  G  M  N  H  D  T  L  D  R  G  C  S  C  Q  M  A       320

GTTGAGAAAGGAGGCTGCATCATGAACGCTTCCACCGGGTACCCATTCCCATGGTGTTC      1020
 V  E  K  G  G  C  I  M  N  A  S  T  G  Y  P  F  P  M  V  F       340

AGCAGTTGCCAGCAGGAAGGACTTGGAGAGACCAGCCTGGAGAAAGGAATGGGGGTGTGCCTG  1080
 S  S  C  S  R  K  D  L  E  T  S  L  E  K  G  M  G  V  C  L       360

TTTAACCTGCCGGAAGTCAGGGAGTCTTTCGGGGGCCAGAAGTGTGGGAACAGATTTGTG    1140
 F  N  L  P  E  V  R  E  S  F  G  G  Q  K  C  G  N  R  F  V       380

GAAGAAGGAGAGGAGTGTGACTGTGGGGAGCCAGAGGAATGTATGAATCGCTGCTGCAAT    1200
 E  E  G  E  E  C  D  C  G  E  P  E  E  C  M  N  R  C  C  N       400

GCCACCACCTGTACCCTGAAGCCCGACGCGCTGTGTGCCGCACATGGGCTGTGCTGTGAAGAC 1260
 A  T  T  C  T  L  K  P  D  A  V  C  A  H  G  L  C  C  E  D       420
```

Fig. 15d

```
TGCCAGCTGAAGCCTGCAGGAACAGCGTGCAGGGACTCCAGCAACTCCTGTGACCTCCCA    1320
 C  Q  L  K  P  A  G  T  A  C  R  D  S  S  N  S  C  D  L  P      440

GAGTTCTGCACAGGGGCCAGCCCTCACTGCCCAGCCAACGTGTACCTGCACGATGGGCAC    1380
 E  F  C  T  G  A  S  P  H  C  P  A  N  V  Y  L  H  D  G  H      460

TCATGTCAGGATGTGGACGGCTACTGCTACAATGGCATCTGCCAGACTCACGAGCAGCAG    1440
 S  C  Q  D  V  D  G  Y  C  Y  N  G  I  C  Q  T  H  E  Q  Q      480

TGTGTCACGCTCTGGGGACCAGGTGCTAAACCTGCCCCTGGGATCTGCTTTGAGAGAGTC    1500
 C  V  T  L  W  G  P  G  A  K  P  A  P  G  I  C  F  E  R  V      500

AATTCTGCAGGTGATCCTTATGGCAACTGTGGCAAAGTCTCGAAGAGTTCCTTTGCCAAA    1560
 N  S  A  G  D  P  Y  G  N  C  G  K  V  S  K  S  S  F  A  K      520

TGCGAGATGAGAGATGCTAAATGTGGAAAAATCCAGTGTCAAGGAGGTGCCAGCCGGCCA    1620
 C  E  M  R  D  A  K  C  G  K  I  Q  C  Q  G  G  A  S  R  P      540

GTCATTGGTACCAATGCCCGTTTCCATAGAAACAAACATCCCCCTGCAGCAAGGAGGCCGG    1680
 V  I  G  T  N  A  V  S  I  E  T  N  I  P  L  Q  Q  G  G  R      560
```

Fig. 15e

```
ATTCTGTGCCGGGGGACCCACGTGTACTTGGGGCGATGACATGCCGGACCCAGGGCTTGTG    1740
 I  L  C  R  G  T  H  V  Y  L  G  D  D  M  P  D  P  G  L  V       580

CTTGCAGGCACAAAGTGTGCAGATGGGAAAAATCTGCCTGAATCGTCAAAATATT          1800
 L  A  G  T  K  C  A  D  G  K  I  C  L  N  R  Q  C  Q  N  I       600

AGTGTCTTTGGGGTTCACGAGTGTGCAATGCAGTGCCACGGCAGAGGGGTGTGCAACAAC    1860
 S  V  F  G  V  H  E  C  A  M  Q  C  H  G  R  G  V  C  N  N       620

AGGAAGAACTGCCACTGCGAGGCCCACTGGGCCCCTTCTGTGACAAGTTTGGCTTT        1920
 R  K  N  C  H  C  E  A  H  W  A  P  P  F  C  D  K  F  G  F       640

GGAGGAAGCACAGACAGCGGCCCCATCCGGCAAGCAGAAGCAGGAAGCTGCAGAG          1980
 G  G  S  T  D  S  G  P  I  R  Q  A  E  A  R  Q  E  A  A  E       660

TCCAACAGGGAGCGCGGCCAGGGCGGCCAGGAGCCCGTGGGATCGCAGGAGCATGCCTCTACT 2040
 S  N  R  E  R  G  Q  G  Q  E  P  V  G  S  Q  E  H  A  S  T       680

GCCTCACTGACACTCATCTGAGCCCTCCCATGACATGGAGACCGTGACCAGTGCTGCTGC    2100
 A  S  L  T  L  I  *                                              686
```

Fig. 15f

```
AGAGGAGGTCACGCGTCCCCAAGGCCCTCCTGTGACTGGCAGCATTGACTCTGTGGCTTTG    2160
CCATCGTTTCCATGACAACAGACACAACAGTTCTCGGGCTCAGGAGGGAAGTCCAG         2220
CCTACCAGGCACGTCTGCAGAAACAGTGCAAGGAGGGCAGCGACTTCCTGGTTGAGCTT      2280
CTGCTAAAACATGGACATGCTTCAGTGCTGTCCTGAGAGTAGCAGGTTACCACTCTG        2340
GCAGGCCCCAGCCCTGCAGCAAGGAGGAAGAGGACTCAAAAGTCTGGCCTTTCACTGAGC     2400
CCCCACAGCAGTGGGGGAGAAGCAAGGGTTGGGCTCTCTGGCTGTCCCCTTCCCCAGTGACAC  2460
CTCAGCCTTGGCAGCCCTGATGACTGGTCTCTGGCTGCAACTTAATGCTCTGATATGGCT     2520
TTTAGCATTATTATATGAAAATAGCAGGGTTTTAGTTTTTAATTTATCAGAGACCCTGC      2580
CACCCATTCCATCTCCATCCAAGCAAACTGAAAACAAACTGGAGAAGAAGG              2640
TAGGAGAAAGGGCGGGTGAACTCTGGCTCTTGCTGTGGACATGCGTGACCAGCAGTACTC     2700
AGGTTTGAGGGTTTGCAGAAAGTCAGGAACCCACAGAGTCACCAACCCTTCATTTAACA      2760
AGTAAGAATGTTAAAAAGTGAAAACAATGTAAGAGCCTAACTCCATCCCCCGTGGCCATT     2820
ACTGCATAAAATAGAGTGCATCCCGCCC    2848
```

Fig. 16

```
GGG GAA GAG TGT GAT TGT GGA GAA GAG GAA TGT AAC AAC CCC TGC AAT GCC TCT    60
 G   E   E   C   D   C   G   E   E   E   C   N   N   P   C   C   N   A   S  20

AAT TGT ACC CTG AGG CCG GGG GCG GAG TGT GCT CAC GGC TCC TGC CAC CAG TGT AAG  120
 N   C   T   L   R   P   G   A   E   C   A   H   G   S   C   H   Q   C   K  40

CTG TTG GCT CCT GGG ACC CTG TGC CGC GAG CAG GCC AGG CAG TGT GAC CTC CCG GAG TTC  180
 L   L   A   P   G   T   L   C   R   E   Q   A   R   Q   C   D   L   P   E   F  60

TGT ACC GGC AAG TCT CCC CAC TGC CCT ACC AAC TTC TAC CAG ATG GAT GGT ACC CCC TGT  240
 C   T   G   K   S   P   H   C   P   T   N   F   Y   Q   M   D   G   T   P   C  80

GAG GGC GGC CAG GCC TAC TGC TAC AAC GGC ATG TGC CTC ACC TAC CAG GAG CAG TGC CAG  300
 E   G   G   Q   A   Y   C   Y   N   G   M   C   L   T   Y   Q   E   Q   C   Q 100

CAG CTG TGG GGA CCC GGA GCC AGA CCC GCC CCT GAC CTC TGC TTC GAG AAg GTG AAT GTG  360
 Q   L   W   G   P   G   A   R   P   A   P   D   L   C   F   E   K   V   N   V 120

GCA GGA GAC ACC TTT GGA AAC TGT GGA AAG GAC A                              394
 A   G   D   T   F   G   N   C   G   K   D                                 131
```

Fig. 17a

```
CGGAGCTGCCACTGGGCACCCCTTTCCAAAGTGTTCAATGGATGCAACAGGAGGGAGCT    60
 G  A  T  G  H  P  F  P  K  V  F  N  G  C  N  R  R  E  L      20
GGACAGGTATCTGCAGTCAGGTGGTGGAATGTGTCTCCAACATGCCAGACACCAGGAT   120
 D  R  Y  L  Q  S  G  G  G  M  C  L  S  N  M  P  D  T  R  M   40
GTTGTATGGAGGCCGGAGGTGTGGGAACGGGTATCTGGAAGATGGGGAAGAGTGTGACTG  180
 L  Y  G  G  R  R  C  G  N  G  Y  L  E  D  G  E  E  C  D  C   60
TGGAGAAGAAGAGGAATGTAACAACCCCTGCTGCAATGCCTCTAATTGTACCCTGAGGCC  240
 G  E  E  E  E  C  N  N  P  C  C  N  A  S  N  C  T  L  R  P   80
GGGGGGCGGAGTGTGCTCACGGGCAGTGTGACCTCCCGGAGTTCTGTACGGGCAAGTCTCC 300
 G  A  E  C  A  H  G  S  C  C  H  Q  C  K  L  L  A  P  G  T  100
CCTGTGCCGCGAGCAGGCCAGGCAGTGTGACCTCCCGGAGTTCTGTACGGGCAAGTCTCC  360
 L  C  R  E  Q  A  R  Q  C  D  L  P  E  F  C  T  G  K  S  P  120
CCACTGCCCTACCAACTTCTACCAGATGGATGGTACCCCCTGTGAGGGCGGCCAGGCCTA  420
 H  C  P  T  N  F  Y  Q  M  D  G  T  P  C  E  G  G  Q  A  Y  140
```

Fig. 17b

```
CTGCTACAACGGCATGTGCCTCACTTACCAGGAGCAGTGCCAGCAGCTGTGGGGACCCGG    480
 C  Y  N  G  M  C  L  T  Y  Q  E  Q  C  Q  Q  L  W  G  P  G     160

AGCCCGACCTGCCCCTGACCTCTGCTTCGAGAAGGTGAATGTGGCAGGAGACACCTTTGG    540
 A  R  P  A  P  D  L  C  F  E  K  V  N  V  A  G  D  T  F  G     180

AAACTGTGGAAAGGACATGAATGGTGAACACAGGAAGTGCAACATGAGAGATGCGAAGTG    600
 N  C  G  K  D  M  N  G  E  H  R  K  C  N  M  R  D  A  K  C     200

TGGGAAGATCCAGTGTCAGAGCTCTGAGGCCCCTGGAGTCCAACGCGGTGCCCAT        660
 G  K  I  Q  C  Q  S  S  E  A  R  P  L  E  S  N  A  V  P  I     220

TGACACCACTATCATCATGAATGGGAGGCAGATCCAGTGCCGGGGCACCCACGTCTACCG    720
 D  T  T  I  I  M  N  G  R  Q  I  Q  C  R  G  T  H  V  Y  R     240

AGGTCCTGAGGAGGGGTGACATGCTGGACCCAGGGCTGGTGATGACTGGAACCAAGTG    780
 G  P  E  E  G  D  M  L  D  P  G  L  V  M  T  G  T  K  C     260

TGGCTACAACCATATTTGCCTTGAGGGGCAGTGCAGGAACACCTCCTTCTTTGAAACTGA    840
 G  Y  N  H  I  C  L  E  G  Q  C  R  N  T  S  F  F  E  T  E     280
```

Fig. 17c

```
AGGCTGTGGGAAGAAGTGCAATGGCCATGGGGTCTGTAACAACAACCAGAACTGCCACTG    900
 G  C  G  K  K  C  N  G  H  G  V  C  N  N  N  Q  N  C  H  C     300

CCTGCCGGGCTGGGCCCCGCCCTTCTGCAACACACCCGGGCCACGGGGCAGTATCGACAG    960
 L  P  G  W  A  P  P  F  C  N  T  P  G  H  G  G  S  I  D  S     320

TGGGCCTATGCCCCCCTGAGAGTGTGGGTCCTGTGGTAGCTGTGGAGTGTTGGTGGCCATCTT 1020
 G  P  M  P  P  E  S  V  G  P  V  V  A  G  V  L  V  A  I  L     340

GGTGCTGGGGGTCCTCATGCTGTACTACTGCTGCAGACAGAACAACAAACTAGGCCA      1080
 V  L  A  V  L  M  L  Y  Y  C  C  R  Q  N  N  K  L  G  Q       360

ACTCAAGCCCTCAGCTCCCCTTCCAAGCTGAGGCAACAGTTCAGTTGTCCCTTCAGGGT    1140
 L  K  P  S  A  L  P  S  K  L  R  Q  Q  F  S  C  P  F  R  V     380

TTCTCAGAACAGCGGGACTGGTCATGCCAACCCAACTTTCAAG                    1183
 S  Q  N  S  G  T  G  H  A  N  P  T  F  K                      394
```

Fig. 18a    Peptides used for the preparation of monoclonal antibody
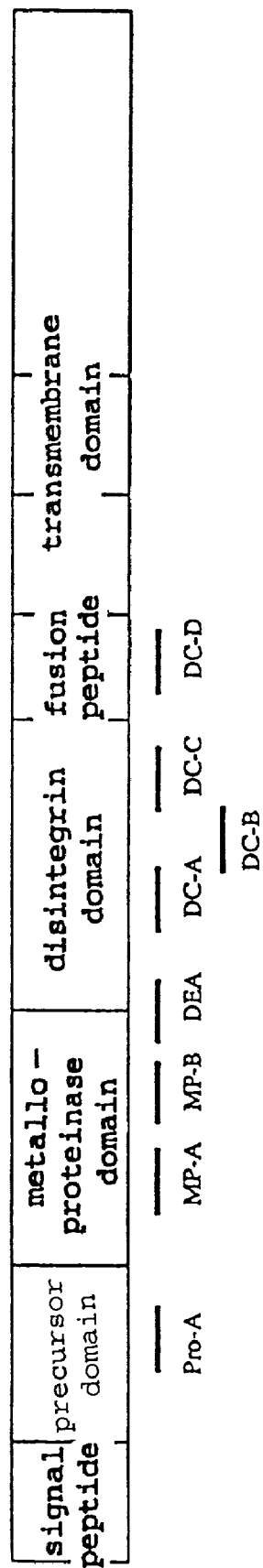

Fig. 18b  Peptide sequences used for the preparation of monoclonal antibody

| No. | Name | Sequence (N-terminal, C-terminal) |
|-----|------|-----------------------------------|
| 1 | Pro-A | TTDSYKLVPAESMTNIC |
| 2 | MP-A | ADNREFQRQGKDLEKVKC |
| 3 | MP-B | FTRLHEFLDWRKIKC |
| 4 | DC-A | QLKPPGTACRGSSNSC |
| 5 | DC-B | GTACRGSSNSCDLPEFC |
| 6 | DC-C | GKDSKSAFAKCELRDAKC |
| 7 | DC-D | QGGASRPVIGTNAVSIETNIC |
| 8 | DE-A | LFNLPEVKQAFGGRKC |

Western blotting with anti-Meltrin monoclonal antibodies

Effects of anti-mouse Meltrin antibodies on the formation of pit (bone-resorption area) in mouse unfractionated bone cells

Fig. 23a

```
GCACAAAGTGTGCAGATGGAAAATCTGCCTGAATGTCAAAATATTAGTGTCT    60
 A  K  V  C  R  W  K  I  C  L  N  V  K  I  L  V  S        
 T  K  C  A  D  G  K  I  C  L  N  R  Q  C  Q  N  I  S  V  F   20

TTGGGGTTCACGAGTGTGCAATGCAGTGCCACGGCAGAGGGGTGTGCAACAACAGGAAGA   120
 G  V  H  E  C  A  M  Q  C  H  G  R  G  V  C  N  N  R  K  N   40

ACTGCCACTGCGAGGCCCACTGGGCACCCCTCTGTGACAAGTTTGGCTTTGGAGGAA   180
 C  H  C  E  A  H  W  A  P  P  F  C  D  K  F  G  F  G  G  S   60

GCACAGACAGCGGCCCCATCCGGCAAGCAGATAACCAAGGTTAACCATAGGAATTCTGG   240
 T  D  S  G  P  I  R  Q  A  D  N  Q  G  L  T  I  G  I  L  V   80

TGACCATCCTGTGTCTTCTTGCTGCCGGATTTGTGGTTGTTATCTCAAAAGGAAGACCTTGA   300
 T  I  L  C  L  L  A  A  G  F  V  V  V  Y  L  K  R  K  T  L  I  100

TACGACTGCTGTTACAAATAAGAAGACCACCATTGAAAAACTAAGGTGTGTGCGCCCTT   360
 R  L  L  F  T  N  K  K  T  T  I  E  K  L  R  C  V  R  P  S   120

CCCGGCCACCCGTGCCTTCCAACCCTGTCAGCTCACCTCGGCCACCCTTGGAAAAGGCC   420
 R  P  P  R  G  F  Q  P  C  Q  A  H  L  G  H  L  G  K  G  L   140
```

Fig. 23b

```
TGATGAGGAAGCCCCAGATTCCTACCCACCGAAGGACAATCCCAGGAGATTGCTGCAGT      480
 M  E  E  A  P  D  S  Y  P  P  K  D  N  P  R  R  L  L  Q  C      160
GTCAGAATGTTGACATCAGCCAGAGACCCCTCAAGGGCCTGAATGTCCCTCAGCCCAGTCAA   540
 Q  N  V  D  I  S  R  P  L  N  G  L  N  V  P  Q  P  Q  S  T      180
CTCAGGGAGTGCTTCCCTCCCACGGGCTCCACGTGCCACCTAGCGTCCCTGCCAGAC        600
 Q  R  V  L  P  P  L  H  R  A  P  R  A  P  S  V  P  A  R  P      200
CCCTGCCAGCCAAGCCCTGCACTTA                                        624
 L  P  A  K  P  A  L                                             207
```

Fig. 24a

```
CGGAGCTGCCACTGGGCACCCCTTTCCCAAAGTGTTCAATGGATGCAACAGGAGGAGCT    60
 G  A  A  T  G  H  P  F  F  P  K  V  F  N  G  C  N  R  R  E  L   20

GGACAGGGTATCTGCAGTCAGGGTGGAATGTGTCTCTCCAACATGCCAGACACCAGGAT   120
 D  R  Y  L  Q  S  G  G  M  C  L  S  N  M  P  D  T  R  M       40

GTTGTATGGAGGCCGGAGGTGTGGGAACGGGTATCTGGAAGATGGGGAAGAGTGTGACTG   180
 L  Y  G  G  R  R  C  G  N  G  Y  L  E  D  G  E  E  C  D  C    60

TGGAGAAGAAGAGGAATGTAACAACCCCTGCTGCAATGCCTCTAATTGTACCCTGAGGCC   240
 G  E  E  E  C  N  N  P  C  C  N  A  S  N  C  T  L  R  P       80

GGGGGCGGAGTGTGCTCACGGCTCCTGCCACCAGTGTAAGCTGTTGGCTCCTGGGAC     300
 G  A  E  C  A  H  G  S  C  C  H  Q  C  K  L  L  A  P  G  T   100

CCTGTGCCCGAGCAGGCCAGCTGTGACCTCCCGGAGTTCTGTACGGGCAAGTCTCC      360
 L  C  R  E  Q  A  R  Q  C  D  L  P  E  F  C  T  G  K  S  P   120

CCACTGCCCTACCAACTTCTACCAGATGGATGGTACCCCTGTGAGGGCGGCCAGGCCTA   420
 H  C  P  T  N  F  Y  Q  M  D  G  T  P  C  E  G  G  Q  A  Y   140
```

Fig. 24b

```
CTGCTACAACGGCATGTGCCTCACCTACCAGGAGCAGTGCCAGCAGCTGTGGGGACCCGG    480
 C  Y  N  G  M  C  L  T  Y  Q  E  Q  C  Q  Q  L  W  G  P  G     160

AGCCCGACCTGCCCCTGACCCTCTGCTTCGAGAAGGTGAATGTGGCAGGAGACACCTTTGG    540
 A  R  P  A  P  D  L  C  F  E  K  V  N  V  A  G  D  T  F  G     180

AAACTGTGGAAAGGACATGAATGGTGAACACAGAAGTGCAACATGAGAGATGCGAAGTG     600
 N  C  G  K  D  M  N  G  E  H  R  K  C  N  M  R  D  A  K  C     200

TGGGAAGATCCAGTGTCAGAGCTCTGAGGCCCGGCCCCTGGAGTCCAACGCGGTGCCCAT    660
 G  K  I  Q  C  Q  S  S  E  A  R  P  L  E  S  N  A  V  P  I     220

TGACACCACTATCATCATGAATGGGAGGCAGATCCAGTGCCGGGGCACCCACGTCTACCG    720
 D  T  T  I  I  M  N  G  R  Q  I  Q  C  R  G  T  H  V  Y  R     240

AGGTCCTGAGGAGGGGGTGACATGCTGGACCCAGGGCTGGTGATGACTGGAACCAAGTG    780
 G  P  E  E  E  G  D  M  L  D  P  G  L  V  M  T  G  T  K  C     260

TGGCTACAACCATATTTGCCTTGAGGGGCAGTGCAGGAACACCTCCTTCTTTGAAACTGA    840
 G  Y  N  H  I  C  L  E  G  Q  C  R  N  T  S  F  F  E  T  E     280
```

Fig. 24c

```
AGGCTGTGGGAAGAAGTGCAATGGCCATGGGGTCTGTAACAACAACCAGAACTGCCACTG   900
 G  C  G  K  K  C  N  G  H  G  V  C  N  N  N  Q  N  C  H  C    300
CCTGCCCGGGCTGGGCCCCCGCCCTTCTGCAACACACCGGCCACGGGGCAGTATCGACAG   960
 L  P  G  W  A  P  P  F  C  N  T  P  G  H  G  G  S  I  D  S    320
TGGGCCTATGCCCCCTGAGAGTGTGGGTCCTGTGGTAGCTGGAGTGTTGGTGGCCATCTT  1020
 G  P  M  P  P  E  S  V  G  P  V  V  A  G  V  L  V  A  I  L    340
GGTGCTGGGGTCCTCATGCTGATGTACTACTGCTGCAGACAGAACAACAAACTAGGCCA  1080
 V  L  A  V  L  M  L  M  Y  Y  C  C  R  Q  N  N  K  L  G  Q    360
ACTCAAGCCCTCAGTCTCCCTTCCAAGCTGAGGCAACAGTTCAGTTGTCCCTTCAGGGT  1140
 L  K  P  S  A  L  P  S  K  L  R  Q  Q  F  S  C  P  F  R  V    380
TTCTCAGAACAGGGGACTGGTCATGCCAACCCAACTTTCAAGCCGGAATTCCGGGCCCC  1200
 S  Q  N  S  G  T  G  H  A  N  P  T  F  K  P  E  F  R  A  P    400
CCACAGCCCACACCACCATGACAAGGGCCACCAATTCCACGGCCACCCTCCTCCACTC  1260
 H  S  P  H  H  H  D  K  G  H  Q  F  H  G  H  T  L  L  H  S    420
```

Fig. 24d

| | |
|---|---|
| TGGGGACGACCCGGATCCTCACTGAGCTGACCACAACAGCCACTACAACTGCAGCCACTG | 1320 |
| G  D  D  P  D  P  H  * | 427 |
| GATCCACGGCCACCCTGTCCTCCACCCAGGGACCACCTGGATCCTCACAGAGCCGAGCA | 1380 |
| CTATAGCCACCGTGATGGTGCCCACGGTTCCACGGGCCACCCTCCTCCACTCTGGGAA | 1440 |
| CAGCTCACACCCCAAAGTGGTGACCACCATGGCCACCACTATGCCCACAGCCACTGCCTCCA | 1500 |
| CGGTTCCCAGTCGTCCACCGTGGGGACCACCCGCAGTGCTCCCCAGCAGCC | 1560 |
| TGCCAACCTTCAGCGTGTCCACTGTCCTCCTCAGTCCTCACCACCCTGAGACCCACTG | 1620 |
| GCTTCCCCAGCTCCCACTTCTCTACTCCCCTGCTTCTGCAGGGCATTTGGACAGTTTTCT | 1680 |
| CGCCCCGGGAAGTCATCTACAATAAGACCGAGCCGGCTGCCATTTCTACGCAGTGT | 1740 |
| GCAATCAGCACTGTGACATTGACCGCTTCCAGGGCGCCCTGTCCCACCTCCCACCGCCAG | 1800 |
| TGTCCTCCGCCGTCCCGGCCCTGCCCCCTGGCTGTGACAATGCCATCCCTC | 1860 |
| TCCGGCAGGTGAATGAGACCCTGCTGGACCCTGGAGAACCTGTGCCAGGTGGCTGGGTG | 1920 |
| ACAACCGTGTCGTCCTGCTGGACCCCAAAGCCCTCACCTGCCTGAACAAGC | 1980 |
| ACCTGCCACCATCAAGTGTCGGACCCGAGCCAGCCCTGTGACTTCCACTATGAGTGCGAGT | 2040 |
| GCATCTGCAGCATGTGGGGCGGCCCACCTATCCCACCTTTGACGGCACCCTTACACCT | 2100 |
| TCCGGGCAACTGCACCTGTCCTCATGAGAGATCCATGCACGGCTTGGGAATCTCA | 2160 |
| GCCTCTACCTGGACAACCACTGCCACTACACAAGTCCATGGATATCGTCCTACTGTGGTGC | 2220 |
| CCCGCCCCTCAGCATCCACTACAAGTCCATGGATATCGTCCTCACTGTCACTGGTGC | 2220 |
| ATGGGAAGGAGGAGGGCCTGATCCTGTTTGACCAAATTCCGGTGAGCAGCGGTTTCAGCA | 2340 |

Fig. 24e

```
AGAACGGGCTGCTTGTGTCTGTGCTGGGGACCACCACCATGCGTGTGGACATTCCTGCCC  2400
TGGGCGTGAGCGTCACCTTCAATGGCCAAGTCTTCCAGCCCGCTGCCCTACAGCCTCT    2460
TCCACAACAACACCGAGGGCCAGTGCGGCCACCTGCACCAACAACCAGAGGGACGACTGTC 2520
TCCAGCGGGACGGAACCACTGCCGCCAGTTGCAAGGACATGGCCAAGACGTGGCTGGTCC  2580
CCGACAGAAAGGATGGCTGCTGGGCCCGACTGGCACACCCCACTGCCAGCCCCG        2640
CAGCCCCGGTGTCTAGCACACCCACCCCG  2669
```

MELTRINS

This application is a continuation of U.S. patent application Ser. No. 09/138,675, filed Aug. 24, 1998, now abandoned, which in turn is a continuation of PCT Application No. PCT/JP96/03017, filed Oct. 17, 1996, which claims priority of Japanese Patent Application No. Hei 8/61756, filed Feb. 23, 1996. The entire disclosure of all of the above applications is hereby incorporated by reference herein.

TECHNICAL FIELD

This invention relates to Meltrins and polypeptides of the respective domains thereof; DNAs encoding the same; antisense oligonucleotides for these DNAs; various antibodies against these Meltrins and the polypeptides of the respective domains thereof; expression vectors comprising the DNAs; transformants constructed by using these expression vectors; a process for producing the above-mentioned meltirins and the polypeptides of the respective domains thereof by means of the transformants; and medical compositions comprising the Meltrins or Meltrin antagonists as an effective ingredient.

BACKGROUND ART

In the course of myotube formation, myoblasts, which have divided from myogenic cells originating in undifferentiated mesodermal cells and grown to differentiate, will start synthesizing muscle-specific substances such as myosin and actin after its final division, and will lose cell boundaries at the fusion surface to be tansformed into multinucleate syncytium named myotube through adhesion and fusion of cytoplasmic membranes with neighbouring cells of the same kind.

There have been already reported several kinds of membrane proteins involved in the myotube formation, such as N-Cadherin (Knudsen, K. A. et al., Expl. Cell Res., 188, 175–184 (1990), Merge, R. M. et al., J. Cell Sci., 103, 897–906 (1992)), M-Cadherin (Donalies, M. et al., Proc. Natl. Acad. Sci., U.S.A. 88, 8024–8028 (1991)), N-CAMs (Merge, R. M. et al., J. Cell Sci., 103, 897–906 (1992) and others), V-CAMs and Integrins (Rosen, G. D. et al., Cell 69, 1107–1119 (1992) and others).

However, the molecular mechanism has not yet been sufficiently understood concerning the course of formation of the multinucleate syncytium named myotube through adhesion and fusion of the cytoplasmic membranes of the myoblasts with each other.

On the other hand, the substances named "fusion peptides" have been known as an adhesion factor involved in the course of infection of cells with viruses (Morrison, T. G. Virus Res., 10, 113–136 (1998) and others). Fertilin, which was recently isolated as a factor involved in sperm-egg adhesion, has been found to contain a sequence similar to the fusion peptide of rubella virus (Blobel, C. P. et al., Nature 356, 248–252 (1992) and the others).

Many substances having adhesion activity are known as mentioned above, and substances which may inhibit the activity of Integrins and the like have been developed and studied as potential medical agents.

The present inventors have now isolated novel substances involved in adhesion. Particularly, on the assumption that some fusion peptide-like adhesion factor like in sperm-egg adhesion may be involved in adhesion and fusion of the myoblasts with each other in the course of myotube formation, the novel substances involved in cell adhesion have been cloned and named "Meltrins", by using highly conserved sequences in Fertilin α and β as a probe.

DISCLOSURE OF INVENTION

The present invention relates to novel substances "Meltrins." "Meltrins" are characterized as proteins which are expressed in the course of differentiation-induction of muscle cells and to contain the highly conserved sequences in Fertilin α and β. Meltrins are also characterized as proteins which are involved in fusion, adhesion, or aggregation of cells. Thus, some kinds of cells such as muscle ones may fuse, aggregate or adhere via Meltrins.

Cell fusion means that more than two cells fuse with each other to form one multinucleate syncytium. Adhesion of cells means that more than two cells adhere to each other. Aggregation of cells means that more than two cells (particularly the cells present in liquid) flock together to form a mass of cells. It may be considered that cells adhere to each other, followed by cell fusion and aggregation.

The origin of the present Meltrins is not specifically limited. Accordingly, Meltrins in the present specification comprise polypeptides originating in any animals as long as they have the above features, unless otherwise particularly noted. As will be demonstrated in the following examples, at least three kinds of molecules (α, β and γ) have been isolated from one animal species. Meltrins in the present specification therefore comprise any one of the above three molecules.

The specific examples of Meltrins of the present invention are mouse Meltrins α, β and γ, which are characterized by amino acid sequences shown in FIG. 2a~FIG. 2j, FIG. 3a~FIG. 3j and FIG. 4a~FIG. 4i, respectively, or partial sequences thereof.

Other examples may contain human Meltrins α, β and γ, which are characterized by amino acid sequences shown in any one of FIG. 12a~FIG. 12b, FIG. 15a~FIG. 15f or FIG. 23a~FIG. 23b; any one of FIG. 16 or FIG. 17a~FIG. 17c; or FIG. 13a~FIG. 13d, respectively, or partial sequences thereof.

The above amino acid sequences should be considered only examples of Meltrins of the present invention. Any variant of the above amino acid sequences wherein a part of the sequences has changed due to deletion, substitution, addition, insertion and the like of amino acids is therefore contained in Meltrins of the present invention, as long as it is expressed in muscle cells, and have the highly conserved sequences in Fertilin α and β or is involved in fusion, adhesion or aggregation of cells. As cleared now by the present inventors, a high homology is seen in the part from disintegrin domain to cysteine-rich region of mouse amino acid sequences shown in FIG. 2a~FIG. 2j and human amino acid sequences shown in FIG. 12a~FIG. 12b. It is considered that such substances as showing homology of about 80% or more, preferably about 90% or more to the above amino acid sequences may keep the function as Meltrin. Particularly, it is believed that the substances having the sequences with homology of about 80% or more, preferably about 90% or more to the region from metalloproteinase domain to disintegrin domain of mouse or human Meltrins α, β and γ will have substantially the same activity, even if all of the other sequences are different from them. Accordingly, Meltrins of the present invention may include substances having a high homology to the above amino acid sequences or to a part thereof and showing substantially the same activity as mouse or human Meltrins.

In other words, Meltrins of the present invention may be characterized by having amino acid sequences encoded by base sequences that may hybridize the sequences complementary to the base sequences encoding any one of the amino acids shown in FIG. 2a~FIG. 2j, FIG. 3a~FIG. 3j, FIG. 4a~FIG. 4i, FIG. 12a~FIG. 12b, FIG. 13a~FIG. 13d, FIG. 15a~FIG. 15f, FIG. 16, FIG. 17a~FIG. 17c or FIG. 23a~FIG. 23b.

Meltrins exist in bodies as a membrane protein consisting of intracellular domain, transmembrane domain, and extracellular domain; and as a soluble protein having no transmembrane domain. The extracellular domain contains precursor domain, metalloproteinase domain, disintegrin domain, and cysteine-rich region. Meltrin α has a fusion peptide-like sequence in its cysteine-rich region (Refer to FIG. 8).

The disintegrin domain is indispensable for the function of Meltrins such as adhesion, fusion and aggregation of cells. On the other hand, the precursor and metalloproteinase domains are thought to be regulating sequences for Meltrins to show the activity in a specific organ or tissue, or under specific conditions. It is known that the disintegrin found in snake venom will adhere to platelet IIb/IIIa. It is therefore presumed that the disintegrin domain by itself may have the function to adhere to cells. The metalloproteinase domain may act by itself as a protease as such.

The present invention relates to polypeptides comprising any part of Meltrins. The present polypeptides include the respective domain per se of Meltrins, polypeptides comprising at least the respective domain of Meltrins, any part of the sequences of Meltrins, polypeptides comprising at least any part of the sequences of Meltrins, and polypeptides comprising at least the sequence having the combination of any of the respective domains of Meltrins and any part of Meltrins in any order. The present invention may further include the above polypeptides which are chemically modified or formed into salts thereof.

The preferable examples of the present polypeptides include polypeptides consisting of a part of the disintegrin domain, polypeptides consisting of the disintegrin domain per se, polypeptides comprising at least the disintegrin domain, polypeptides comprising at least the disintegrin and cysteine-rich regions, polypeptides comprising at least the metalloproteinase, disintegrin and cysteine-rich regions, polypeptides consisting of a part of the metalloproteinase domain, and polypeptides consisting of the metalloproteinase domain per se.

There may be mentioned as other preferable examples of the present polypeptides those comprising at least the disintegrin and cysteine-rich regions, but not comprising the transmembrane domain, or comprising neither the transmembrane domain nor intracellular domain; and those comprising at least the metalloproteinase, disintegrin and cysteine-rich regions, but not comprising the transmembrane domain, or comprising neither the transmembrane domain nor intracellular domain. Such polypeptides comprising no transmembrane domain are a soluble one which will be secreted through a cell membrane into an extracellular area. The soluble polypeptides may be collected from a supernatant of the culture medium of cells. When optionally combined downstream of a suitable signal sequence and expressed by cells in a genetic engineering process, it will be secreted into the culture supernatant and advantageously collected therefrom with a high efficiency.

The amino acid sequences in FIG. 2a~FIG. 2j, FIG. 3a~FIG. 3j, FIG. 4a~FIG. 4i, FIG. 12a~FIG. 12b, FIG. 13a~FIG. 13d, FIG. 15a~FIG. 15f, FIG. 16, FIG. 17a~FIG. 17c and FIG. 23a~FIG. 23b, which correspond to the precursor domain, metalloproteinase domain, disintegrin domain, cysteine-rich region, intracellular domain, and transmembrane domain of mouse and human Meltrins α, β and γ, are discussed in the Examples. It should be noted, however, that the polypeptides having the above corresponding amino acid sequences constitute only examples of the polypepetides of the present invention. The polypeptides essentially comprising the same amino acid sequences also belong to the scope of the present invention. Thus, the boundaries of each domain are not limited to those defined in the Examples. And the polypeptides comprising the domains wherein the boundaries are shifted to N-, C-terminals or both by 1 to about 20 amino acids from the boundaries defined in the Examples are contained in the polypeptides of the present invention, as long as they have substantially the same function as that of the above polypeptides. Similarly, the polypeptides wherein a part of the amino acid sequences has changed due to deletion, substitution, addition, insertion and the like of amino acids are therefore contained in the polypeptides of the present invention, as long as they have substantially the same function as that of each domain.

As it is considered that the polypeptides comprising such amino acid sequences as showing homology of about 80% or more, preferably about 90% or more to the amino acid sequences in each domain of the above figures may have the same function as that of the polypeptides of the present invention, they are also considered to be contained in the present invention.

Meltrins of the present invention may be used to bond cells to each other or to apparatuses such as a plate. They may be also fused with any other substances to efficiently deliver the substances to muscle cells upon its application into culture systems of the muscle cells, tissues or bodies.

On the other hand, the polypeptides comprising at least a part of Meltrins may be added to the culture systems to competitively inhibit the adhesion, fusion or aggregation of cells. Particularly, the disintegrin domain per se, a part thereof, or a soluble polypeptide comprising the disintegrin domain may be used as an effective ingredient in a medical composition for inhibiting the adhesion of cells. For example, such medical composition may be used as an anticoagulant to inhibit thrombus formation or blood coagulation, and be used to treat thrombosis, DIC and multi-organ failure. Furthermore, since it is considered that adhesion factors such as integrin family are involved in metastasis of cancer cells, the polypeptides comprising the disintegrin domain may be used as a drug for inhibiting the growth of cancers, or the adhesion of cancer cells to other cells so as to prevent their metastasis. In addition to the above, it is known that the adhesion of cells plays an important role in the formation of osteoclasts. The examples will demonstrate that Meltrins are involved in the adhesion in the formation of osteoclasts, and anti-Meltrin antibodies may inhibit the formation of osteoclasts and the increase of bone resorption Accordingly, the polypeptides of the present invention comprising disintegrin domain of Meltrins, particularly of Meltrins α or β, may be used as an effective ingredient in a medical composition for inhibiting the increase of bone resorption, like as anti-Meltrin antibodies.

Among the polypeptides comprising at least a part of Meltrins of the present invention, those comprising the metalloproteinase domain may act as a protease by itself, or be used to competitively inhibit the activity of other proteases so that they may be utilized as a drug for treating inflammatory diseases.

The polypeptides and Meltrins of the present invention may also be used as antigens for producing antibodies.

The present invention also relates to DNAs comprising the base sequences encoding the amino acid sequences of Meltrins of the present invention or the polypeptides comprising any parts thereof.

The above DNAs include any type of DNAs such as genomic DNAs and cDNAs.

The origin of the present DNAs is not specifically limited. The examples of the present DNAs are those encoding mouse Meltrins α, β, and γ, or the polypeptides comprising any parts thereof, which are characterized by the coding regions shown as the base sequences in FIG. 5a~FIG. 5j, FIG. 6a~FIG. 6h, and FIG. 7a~FIG. 7e, respectively, or partial sequences thereof. Other examples are those encoding human Meltrins α, β, and γ, or the polypeptides comprising any parts thereof, which are characterized by the coding regions of the sequences shown as the base sequences in any one of FIG. 12a~FIG. 12b, FIG. 15a~FIG. 15f or FIG. 23a~FIG. 23b; any one of FIG. 16 or FIG. 17a~FIG. 17c; or FIG. 13a~FIG. 13d, respectively, or partial sequences thereof.

The base sequences in the above figures, which correspond to the precursor domain, metalloproteinase domain, disintegrin domain, cystein-rich domain, intracellular domain, and transmembrane domain of mouse and human Meltrins α, β and γ, are discussed in the Examples. It should be noted, however, that they constitute only examples of the DNAs of the present invention. The DNAs essentially comprising the same base sequences also belong to the scope of the present invention. Thus, the boundaries of each domain are not limited to those defined in the Examples. And the DNAs comprising sequences encoding the domains wherein the boundaries are shifted to 5'-, and/or 3'-ends by 1 to about 60 base pairs from the boundaries defined in the Examples are contained in the DNAs of the present invention, as long as they encode the polypeptides having substantially the same function as that of each domain.

In addition of the above base sequences, the present DNAs include those comprising the base sequences or partial sequences thereof, which encode the same amino acid sequences as above prepared by means of chemical synthesis or genetic engineering in consideration of degeneracy of codons.

As cleared now by the present inventors, a high homology is seen in mouse and human Meltrins. It is therefore considered that the substances showing homology of about 80% or more, preferably about 90% or more to the above amino acid sequences may keep the function as Meltrin, and that DNAs encoding such homologous polypeptides will hybridize with each other. Accordingly, the present DNAs also include DNA fragments which may be obtained by hybridization under stringent conditions using the DNAs having the base sequences complementary to those in the above figures as a probe.

The DNAs of mouse or human Meltrins α,β and γ, or partial sequences thereof may be inserted into plasmid vectors. Strains of *E. coli* transformed by the same plasmid vectors have been deposited with the National Institute of Bioscience and Human-Technology, Agency of Industrial Science and Technology.

The present DNAs may be prepared by known methods. The cDNAs, for example, may be prepared by using cDNA library and known PCR (e.g., Michael A. I. et al., PCR Protocols, a guide to method and application, Academic Press, 1990) with degenerative primers for a part of the amino acid sequences (for example, the degenerative primer encoding the amino acid sequences of the disintegrin domain) shown in FIG. 2a~FIG. 2j, FIG. 3a~FIG. 3j, FIG. 4a~FIG. 4i, FIG. 12a~FIG. 12b, FIG. 13a~FIG. 13d, FIG. 15a~FIG. 15f, FIG. 16, FIG. 17a~FIG. 17c and FIG. 23a~FIG. 23b. The present DNAs may also be prepared by hybridization method using a probe prepared on the basis of the base sequences of the above amplified DNA fragments.

As demonstrated in the Examples, the preferable source of cDNA library include cells obtained by inducing myoblast to differentiate, bone marrow and fetal pulmonary cells. Known cDNA libraries prepared from placenta, chorionic cells and fetal cells may also serve as the source of cDNA library in the present invention.

Among the present DNA, one encoding the polypeptide in which any parts of Meltrins are combined in any order may be prepared by the following steps. That is, each DNA fragment encoding any part of Meltrins is amplified by PCR, in which the primers may be optionally modified in order to provide an appropriate restriction enzyme site. The amplified DNA fragments are ligated with each other by DNA ligase, so that a reading frame should not be shifted.

The present DNAs may be used for producing the Meltrins or polypeptides of the present invention by means of genetic engineering. Such prodution may be carried out with reference to known methods (for example, Sambrook J. et al., Molecular Cloning a Laboratory Manual 2nd ed., Cold Spring Harbor Laboratory, New York, 1989).

The present DNAs inserted into suitable vectors may also be used in gene therapy. The base sequence encoding any physiologically active substances is fused downstream of the present DNAs followed by insertion of the resulting fused DNA into a vector originated in an appropriate virus, and cells in a living body are transformed with the resulting vector, so that the physiologically active substances may be expressed as a fused protein with Meltrins of the present invention. The thus expressed physiologically active substances will be delievered near to the cells to which Meltrins adhere.

The present invention further relates to antisense oligonucleotides and derivatives thereof for the DNAs encoding Meltrins of the present invention or for the polypeptides comprising any part thereof.

The present antisense oligonucleotides and derivatives thereof are characterized by their base sequences complementary to those encoding Meltrins or a part thereof, or by their function to inhibit the expression of Meltrins or the polypeptides comprising any part thereof. The antisense oligonucleotides and derivatives thereof characterized by the latter feature include those complementarily bonding to the non-coding regions existing upstream or downstream of the coding regions of Meltrins as well as those complementarily bonding to the coding regions of Meltrins or any part thereof.

The examples of the present antisense oligonucleotides and derivatives thereof include the base sequences complementary to the DNAs of the present invention or any part thereof, particularly to those shown in FIG. 5a~FIG. 5j, FIG. 6a~FIG. 6h, FIG. 7a~FIG. 7e, FIG. 12a~FIG. 12b, FIG. 13a~FIG. 13d, FIG. 15a~FIG. 15f, FIG. 16, FIG. 17a~FIG. 17c and FIG. 23a~FIG. 23b. Uracil (U) may be used instead of thymine (T) as a complementary base to adenine (A).

The derivatives of the present antisense oligonucleotides include any one that is similar to the antisense oligonucleotides in steric structure and function, such as those wherein other substances are bound to 3'- or 5'-end of the oligonucleotides; those wherein at least one of bases, sugars or phosphoric acids in the oligonucleotides has substitution or modification; those having non-naturally occurring bases, sugars or phosphoric acids; and those having back bone other than that of sugars-phosphoric acids.

The present antisense oligonucleotides and derivatives thereof may be prepared by known methods (for example, ed., Stanley T. Crooke and Bernald Lebleu, in Antisense Research and Applications, CRC Publishing, Florida, 1993).

The present antisense oligonucleotides of a naturally occurring type may be prepared by chemically synthesizing sense-primers and antisense-primsers having the base sequences complementary to 3'- or 5'-end of the antisense oligonucleotide sequences, followed by PCR using the Meltrin genes or RNAs encoding Meltrins as a template. Otherwise, the derivatives of the antisense oligonucleotides such as a methylphosphonate and phosphorothionate types may be prepared by means of a chemical synthesizer (e.g., Perkin Elmer Japan Co., Type 394) accoding to the manual attached to the chemical synthesizer, followed by, if necessary, purification of the synthesized products in HPLC method using reversed phase chromatography and the like.

The present antisense oligonucleotides and derivatives thereof may be labelled with radioisotopes, fluorescent substances, enzymes or luminescent substances and used as a probe for detecting the existence of Meltrins or any part thereof in a sample. The present antisense oligonucleotides may also be used as a medical composition for inhibiting the expression of Meltrins in a living body.

For the purpose of inhibiting the expression of Meltrins by using the present antisense oligonucleotides and derivatives, they may be solubilized or suspended in a suitable solvent, enclosed in a liposome, or inserted into a suitable vector.

It is preferred that the present antisense oligonucleotides and derivatives thereof used in the medical composition should have a pharmaceutically acceptable purity and be used in a pharmaceutically acceptable way.

As already mentioned in the above, it is considered that Meltrins are involved in formation of osteoclasts, growth and metastasis of cancers as well as skeletal myogenesis. Accordingly, the present antisense oligonucleotides and their derivatives which are capable of inhibiting the expression of Meltrins may be used in treatment and prevention of cancers, treatment of osteoporosis and hypercalcemia by inhibiting bone resorption.

The present invention also relates to antibodies recognizing Meltrins of the present invention or the polypeptides comprising at least any part thereof. In other words, they include those recognizing only Meltrins of the present invention, those recognizing only the polypeptides of the present invention and those recognizing both of them.

The present antibodies include those cross reacting with other polypeptides in addition to those specifically recognizing Meltrins and the polypeptides of the present invention. They also include those specifically recognizing any one of Meltrins α, β and γ, and those specifically recognizing more than two of Meltrins α, β and γ, as well as those recognizing only Meltrins originated in a particular animal such as human and mouse or only the polypeptides comprising at least any part thereof, and those recognizing Meltrins originated in more than two kinds of animals or the polypeptides comprising at least any part thereof.

The preferable present antidodies are those recognizing the amino acid sequences in FIG. 2a~FIG. 2j, FIG. 3a~FIG. 3j, FIG. 4a~FIG. 4i, FIG. 12a~FIG. 12b, FIG. 13a~FIG. 13d, FIG. 15a~FIG. 15f, FIG. 16, FIG. 17a~FIG. 17c or FIG. 23a~FIG. 23b, or any part thereof.

More preferably, the present antidodies are those obtained by immunization of animals with the polypeptides comprising said amino acid sequences or any part thereof as an antigen, which may be optionally conjugated with a suitable carrier.

Such preferred antibodies may be prepared by inserting DNA comprising the base sequences shown in FIG. 5a~FIG. 5j, FIG. 6a~FIG. 6h, FIG. 7a~FIG. 7e, FIG. 12a~FIG. 12b, FIG. 13a~FIG. 13d, FIG. 15a~FIG. 15f, FIG. 16, FIG. 17a~FIG. 17c or FIG. 23a~FIG. 23b or any part thereof into a suitable expression vector, tranforming a suitable host cell by the vector to produce Meltrins, which are purified from cell bodies of the transformant or culture medium and administered as an antigen. The cell bodies per se of the transformant or any cells expressing Meltrins per se may be administered as an antigen. Such transformant or cells may express any one of Meltrins α, β and γ, or more than two kinds of them. The present antibodies may be also prepared by chemically synthesizing the polypeptides having a part of the amino acid sequences of Meltrins, conjugating them with a carrier such as KLH (Keyhole Limpet Hemocyanin) and administering them as an antigen.

It is possible to prepare the present antibody that may recognize the whole of Meltrins even when the part of Meltrins is used as an antigen to be administered. It is also possible to prepare the present antibody that may recognize human Meltrins or any part thereof even when mouse Meltrins or any part thereof are used as an antigen to administered.

The antibodies of the present invention include monoclonal and polyclonal ones, and may belong to any class or subclass.

The antibodies of the present invention may be prepared according to known methods (e.g., "Meneki jikkenho (Laboratory manual of Immunology)" published by Japan Immunological Society). An example of the known methods will be described below.

A suitable cell is transformed by an expression vector comprising the coding regions of the base sequences shown in FIG. 5a~FIG. 5j, FIG. 6a~FIG. 6h, FIG. 7a~FIG. 7e, FIG. 12a~FIG. 12b, FIG. 13a~FIG. 13d, FIG. 15a~FIG. 15f, FIG. 16, FIG. 17a~FIG. 17c or FIG. 23a~FIG. 23b or any part thereof, and used as an antigen as such. Alternatively, Meltrins produced by the transformant are purified from cell bodies of the transformant or culture medium to be used as an antigen, or polypeptides consisting of amino acid sequences shown in the above figures are chemically synthesized, cojugated with a carrier such as KLH (Keyhole Limpet Hemocyanin) and purified to be used as an antigen.

Animals are inoculated with the antigen thus prepared, alone or together with a suitable adjuvant such as Freund's complete adjuvant (FCA) or Freund's incomplete adjuvant (FIA), subjected to boosting at two to four-week intervals. After boosting, the blood is drawn from the animals and antiserum is obtained therefrom. Animals to be immunized may be selected from rat, mouse, rabbit, sheep, horse, fowl, goat, pig, cattle and the like, depending on the kind of the antibody to be desired. Polyclonal antibodies may be obtained by purification of the antiserum by known methods such as salting-out, ion-exchange chromatography, affinity chromatography and any combination thereof.

Monoclonal antibodies may be prepared as follows. Antibody-producing cells such as spleen cells and lymphocytes are collected from the immunized animals, fused with myeloma and the like by known methods using polyethyleneglycol, Sendai virus, electrical pulse to give hybridomas. Clones which produce the antibodies bonding to Meltrins of the present invention are then selected and cultured. Monoclonal antibodies of the present invention are purified from the culture supernatant of the selected clones by known methods such as salting-out, ion-exchange chromatography, affinity chromatography and any combination thereof.

The present antibodies may be neutralizing antibodies, which inhibit the fusion, adhesion or aggregation of cells by Meltrins. The neutralizing antibodies of the present invention include those that can completely inhibit the activity of Meltrins, and those partially inhibit the same.

The neutralizing antibodies may be screened by adding antiserum or culture supernatant of the hybridomas to the culture system of Meltrin-expressing cells to evaluate the degree of inhibition of fusion or aggregation of cells. After the screening, the desired antibodies may be purified from the thus selected antiserum or culture supernatant of the hybridomas by the known methods.

The antibodies of the present invention include Fab, F(ab'), F(ab')$_2$ and Fv, as long as they recognize and bond to the present polypeptides or any part thereof. A single chain Fv may be also included in the present antibodies, which is obtained by constructing a gene encoding the single chain Fv wherein H and L chains are linked into a single chain and being expressed by a suitable host cell. Chimera antibodies, human antibodies and humanized antibodies are also included in the present invention, as long as they recognize and bond to the present polypeptides or any part thereof.

For example, the chimera anitbodies may be prepared by substituting a gene encoding the constant region of human antibodies for a gene encoding the constant region of the mouse antibodies recognizing Meltrins or the polypeptides of the present invention, expressing the thus reconstituted gene in animal cells. The human antibodies may be prepared by, for example, in vitro sensitization method (Borrebaeck, C. A. K. J. Immunol., Meth., 123, 157, 1989) or the method using SCID mouse (Toshio KUDO, Tissue Culture, 19, 61–65, 1993). The humanized antibodies may be prepared by reconstituting a gene so that complementary determining regions (CDR) of the human antibodies are replaced with those of the mouse antibodies, and expressing the gene in animal cells (Carter et al., Pro. Nat. Acad. Sci, 89, 4285, 1992).

If necessary, amino acids in a framework of the variable region of the humanized antibodies thus reconstituted may be replaced, so that the framework should have a high homology to that of the mouse antibodies and CDR of said humanized antibodies may form an appropriate antigen-binding site. The preferred examples of the humanized antibodies are those having the same CDR as the neutralizing antibodies F932-15-2 and F937-9-2. For the preparation of these preferred humanized antibodies, the DNA encoding the antibodies is prepared from the hyridoma F932-15-2 or F937-9-2, and linked with the DNAs encoding human antibodies so that the sequences other than CDRs should originate in the human antibodies. Any variation may be optionally introduced into the DNA encoding the framework portion. The thus obtained DNA is then inserted into a suitable expression vector to transform a suitable cell, and the humanized antibodies are purified from the culture supernatant of the transformant.

The present antibodies may be labelled with fluorescent substances, enzymes, luminescent substances or radioisotopes to detect Meltrins or their decomposed products present in body fluid or tissues. Since it is considered that Meltrins are involved in formation of myotubes, resorption of bone and metastasis of cancers as already mentioned in the above, the detection of the existence of Meltrins in body fluid or tissues would make it possible to estimate the progress of diseases and prognosis and to confirm the effects of treatments. The present antibodies may be also used to provide an antibody affinity column, or to detect Meltrins in a fraction during the course of purification of Meltrins.

The neutralizing antibodies of the present invention may serve as an effective ingredient of a medical composition for inhibiting bone resorption, inflammatory diseases, blood coagulation and metastasis of cancers, owing to their ability to inhibit fusion or adhesion of cells. They may serve as an agent used in culture to inhibit the aggregation of cultured cells. When used as the effective ingredient of the medical composition, the human or humanized antibodies are preferred from the viewpoint of their antigenicity.

Also, the present invention relates to a vector comprising the DNA of the present invention. The present vector may further contain, if necessary, an enhancer sequence, promoter sequence, ribosome-binding sequence, base sequence for amplification of the number of copies, sequence encoding signal peptides, sequences encoding other polypeptides, poly(A)-additional sequence, splicing sequence, origin of replication, base sequence of the gene for selective markers and so on.

The present vector may be prepared by inserting the DNAs of the present invention into any vectors according to known methods (e.g., Molecular Cloning, a Laboratory Manual 2nd ed., Cold Spring Harbor Laboratory, New York, 1989). The preferable examples of the DNAs encoding Meltrins or any part thereof have been already disclosed in the present specification. The present vectors include a plasmid vector, phage vector and virus vector; pUC118, pBR322, pSV2-dhfr, pBluescriptII, PHIL-S1, λZap II, λgt10, pAc700, YRP17, pEF-BOS and pEFN-II being preferred.

The preferred vectors of the present invention may optionally comprise the origin of replication, selective markers, and promoter in addition to the DNAs encoding Meltrins or the polypeptides comprising at least any part thereof so as to be used to express Meltrins or the same polypeptides. As the origin of replication, ColEl, R factor, F factor and so on may be used in the vectors for *E.coli*; SV40- or adenovirus-derived ones in the vectors for animal cells; and ARS1-derived one in the vectors for yeast. As the promoter, trp, lac and tac promoters may be used in the vectors for *E.coli*; SV40-, cytomegalovirus-, and adenovirus-derived ones, and those intrinsically existing in the genes of human or animals such as the promoter region of an elongation factor 1α in the vectors for animal cells; and α promoter in the vectors for yeast, especially AOX1 promoter in the case of Pichia yeast. In the addition to the above sequences, the present vectors may further comprise, if necessary, RNA splicing site, signal for poly-adenylation and the like for the transforamtion of eucaryotic cells. The present vectors may be used for the production of Meltrins or any part thereof by means of genetic engineering, and used in gene therapy for Meltrins-related diseases.

The present invention therefore relates to transformants transformed by the above vectors.

The present transformants may be prepared by transforming suitable host cells by the above vectors according to known methods (e.g., Idenshi Kogaku Handbook (Handbook of gene technology), extra edition of Jikkenigaku, Yodo, 1991)). The host cells may be selected from procaryotic ones such as *E.coli* and *Bacillus,* or eucaryotic cells such as yeast, insect cells, and animal ones. The preferred transformants of the present invention are those derived from

*E.coli*, yeast or CHO cell as a host cell to express Meltrins or the polypeptides of the present invention.

The present invention further relates to a process for producing Meltrins or the present polypeptides comprising at least any part thereof, comprising the step of culturing the above transformants.

In the present producing process, the transformants of the present invention are cultured, optionally with amplification of the gene or expression-induction, if necessary, according to known methods (e.g., Biseibutsugaku Jikkenho (Laboratory manual of microbiology), Tokyo Kagaku Dojin, 1992). The culture mixture, i.e., the cells and culture supernatant, is collected and optionally subjected to concentration, solubilization, dialysis, and various chromatography to purify Meltrins or the present polypeptides comprising any part thereof. The purification of the present polypeptides may be carried out by an optional combination of the above known methods for the purification of proteins, and an efficient purification could be performed by using an affinity column with the antibodies of the present invention.

In the present producing process, the polypeptides of the present invention may be produced by the transformants as a fused protein with other proteins such as $\beta$-galactosidase. In such case, the fused protein should be treated with chemicals such as cyanogen bromide or enzymes such as protease in a certain step in the purification process, so that the polypeptides of the present invention may be excised.

The present invention relates to medical compositions comprising a novel effective ingredient, which is Meltrins of the present invention or Meltrin-antagonist. The "Meltrin-antagonist" means a molecule which is able to inhibit fusion, adhesion or aggregation of cells through Meltrins. It includes, for example, the present antibodies recognizing Meltrins and having a neutralizing activity, the fragments of the same antibodies, the polypeptides consisting of any part of Meltrins or any combination thereof in any order, the antisense oligonucleotides for the DNAs encoding Meltrins or derivatives thereof.

The antibodies recognizing Meltrins may be prepared by the methods already mentioned in the above, and from which the antibodies which may completely or partially neutralize fusion, adhesion or aggregation of muscle cells, osteoclasts or cancer cells are selected and used as the effective ingredient of the present medical composistions. The antibodies to be used as the effective ingredient include those prepared by administering any polypeptides as the antigen into any animals, as long as they may recognize human Meltrins and inhibit fusion, adhesion or aggregation of human muscle cells, osteoclast or cancer cells. They may be polyclonal or monoclonal ones, being preferably the human or humanized antibodies, considering the fact that the medical compositions will be administered to human. The human or humanized antibodies may be prepared according to the methods already described in the above.

The above fragments to be used as the effective ingredient in the present medical compositions include Fab, F(ab'), F(ab')$_2$ and Fv.

The polypeptides having any part of Meltrins or any combination thereof in any order may be used as the effective ingredient of the medical compositions, as long as they have the activity of inhibiting fusion, adhesion or aggregation of cells.

The preferable examples of the above polypeptides include those comprising a part or the whole of the disintegrin domain of Meltrins, those comprising the metalloproteinase, disintegrin and cysteine-rich regions of Meltrins, those comprising the disintegrin domain, but not comprising the transmembrane domain of Meltrins, and those comprising at least the metalloproteinase and disintegrin domains, but not comprising the transmembrane domain of Meltrins. These polypeptides may be chemically synthesized or produced by means of genetic engineering, as already mentioned in the above.

The antisense oligonucleotides or derivatives thereof to be used as the effective ingredient of the medical compositions may have any base sequences or any structure, as long as they are suitable for administration to human, and will complementarily bond to the gene for Meltrins to completely or partially inhibit their expression.

As already mentioned, Meltrins are involved in formation of osteoclasts and metastasis of cancer cells. Accordingly, the medical comosition comprising the Meltrin-antagonist as the effective ingredient may be used for the purpose of inhibition of bone resorption or metastasis of cancers. The antagonist against human Meltrin $\alpha$ or $\beta$ is more preferably used as the effective ingredient in the medical composition for inhibition of bone resorption, while the antagonist against human Meltrin $\gamma$ is more preferably used as the effective ingredient in the medical composition for inhibition of cancer metastasis.

The Meltrins or Meltrin antagonist used as the effective ingredient in the present medical composition may be formed into their salts or be modified with pharmaceutically acceptable chemical agents, as long as they will never lose their essential activities. There may be exemplilfied as the salts those with inorganic acids such as hydrochloric acid, phosphoric acid, hydrobromic acid and sulfuric acid; those with organic acids such as maleic acid, succinic acid, malic acid and tartaric acid.

The medical compositions of the present invention include those administered by any route such as oral, subcutaneous, intravenous, intramuscular, intraperitoneal, intracutaneous, and intraintestinal ones.

Any administration methods and intervals may be adopted. The present medical compositions may comprise, depending on the administration route, pharmaceutically acceptable auxiliaries such as fillers, packing agents, thickeners, binding agents, humidifying agents, disintegrating agents, surfactants, solution aids, buffers, pain-easing agents, preservatives and stabilizers. In the case of injections, for example, they may comprise stabilizers such as gelatin, human serum albumin (HSA) and polyethylene glycol; alcohols and saccharides such as D-mannitol, D-sorbitol, and glucose; and surfactants such as Polysorbate 80 (TM).

The medical compositions of the present invention may be mainly used for the prevention and treatment of osteoporosis and hypercalcemia, or the prevention of infiltration and metastasis of cancers.

The present medical compositions may be administered in an amount of about 0.1~100 mg/kg/day, preferably of about 1~50 mg/kg/day, more preferably of about 1~10 mg/kg/day, depending on the conditions or ages of patients, or administration routes. It may also be continuously administered by an intravenous drip, or administered by a single dose or doses at appropriate intervals per day.

The present medical compositions may be formulated according to the conventional manners. The injection, for example, may be formulated by dissolving the Meltrins or their antagonists aseptically prepared to a pharmaceutically acceptable purity into physiological saline, buffers and the like, followed by addition of gelatin or HSA, if necessary. Such injections may also be lyophilized, which will be dissolved into distilled water for the injections, physiological saline and the like when they are used.

The screening of the substances which may bind to Meltrins, inhibit the activity of Meltrins or regulate their expression may be carried out by using the Meltrins, various polypeptides, DNAs encoding them and the like.

BRIEF DESCRIPTION OF THE DRAWINGS

FIG. 1a~FIG. 1b show the comparison between parts of mouse Meltrins α, β, γ (referred to as "Mα", "Mβ", "Mγ") and the known sequences (macrophage specific antigen (MS2), Jararhagin (JR), fertilin-α (fα).

FIG. 2a~FIG. 2j show the amino acid sequence of mouse Meltrin α and its corresponding DNA sequence.

FIG. 3a~FIG. 3j show the amino acid sequence of mouse Meltrin β and its corresponding DNA sequence, wherein "N" means unidentified base.

FIG. 4a~FIG. 4i show the amino acid sequence of mouse Meltrin γ and its corresponding DNA sequence. "N" means unidentified base.

FIG. 5a~FIG. 5j show the result of DNA sequence analysis of the DNA inserted into pBSMelα, which comprises the base sequence encoding mouse Meltrin α. "N", "M", "W" and "S" mean unidentified bases.

FIG. 6a~FIG. 6h show the result of DNA sequence analysis of the DNA inserted into pBSMelβ, which comprises the base sequence encoding mouse Meltrin β. "N", "M", "W" and "S" mean unidentified bases.

FIG. 7a~FIG. 7e show the result of DNA sequence analysis of the DNA inserted into pBSMelγ, which comprises the base sequence encoding mouse Meltrin γ. "N", "M", "W" and "S" mean unidentified bases.

FIG. 12a~FIG. 12b show the result of base sequence analysis of the DNA inserted into pBShuMα300, which encodes human Meltrin α. "N" and "X" mean unidentified bases and unidentified amino acids, respectively.

FIG. 13a~FIG. 13d show the result of base sequence analysis of the DNA inserted into pBShuMγG238, which encodes human Meltrin γ.

FIG. 15a~FIG. 15f show partial amino acid sequence and its corresponding base sequence of human Meltrin α, determined based on the result of analysis of the DNA inserted into pMelα-26N, pMelα-25C.

FIG. 16 shows amino acid sequence and its corresponding base sequence of human Meltrin β.

FIG. 17a~FIG. 17c show partial amino acid sequence and its corresponding base sequence of human Meltrin β, determined based on the result of analysis of the DNA inserted into pMelβ-24C, pMelβ-24N.

FIG. 18a shows schematically the sites of the peptides administered as the antigens in mouse Meltrin α.

FIG. 18b shows amino acid sequences of the peptides administered as the antigens.

FIG. 23a~FIG. 23b show the amino acid sequence comprising the transmembrane domain of human Meltrin α and its corresponding base sequence.

FIG. 24a~FIG. 24e show the result of base sequence analysis of the DNA inserted into pMelβ-24C, pMelβ-24N.

BEST MODE FOR CARRYING OUT THE INVENTION

Figure 8:
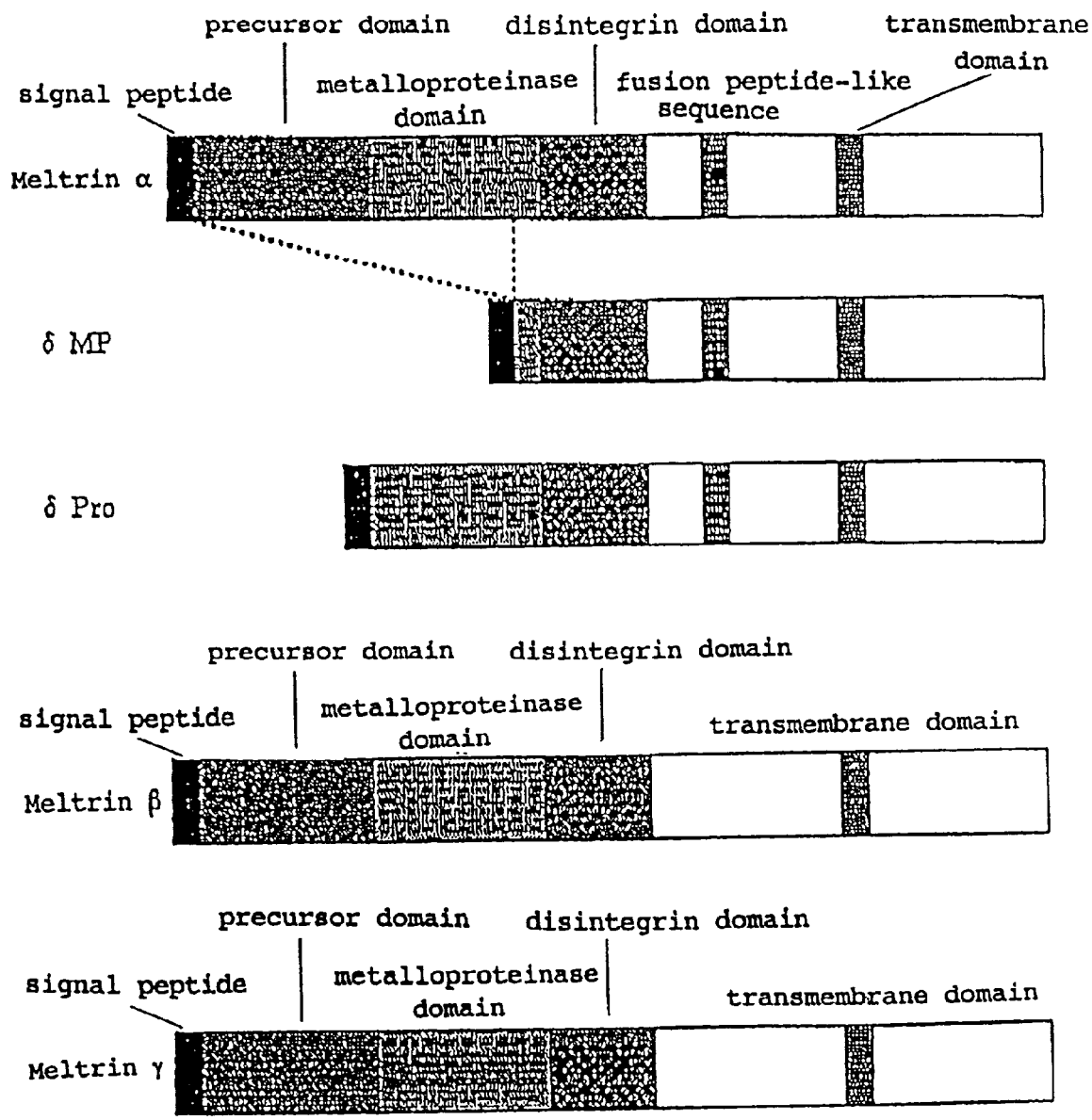
FIG. 8 shows schematically the structures of Meltrins α, β, γ, δMP, δPro.

The present invention will be further illustrated by the following Examples, which should not be construed to limit the scope of the present invention.

EXAMPLES

The abbreviations used in the following description are based on the conventional ones in the art.

The processes used in the following Examples are based on Sambrook J. et al., Molecular Cloning, a Laboratory Manual 2nd ed., Cold Spring Harbor Laboratory, New York, 1989; E. Harlow, D. Lane et al., Antibodies, A Laboratory Manual, Cold Spring Harbor Laboratory; and the like.

Example 1

Acquisition of the DNAs Encoding Mouse Meltrins by RT-PCR

1 Preparation of RNA, cDNA

A myogenic cell line derived from fetal fibroblast C3H10T1/2, (a clone transfected by the gene encoding "myogenin", a muscle differentiation-controlling factor and expressing the myogenin) was proliferated to the extent of $10^6$ cells/φ 10 cm plate in DMEM supplemented with 10% fetal bovine serum (Moregate), and cultured at 37° C. for 2 days in differentiation medium (DMEM containing 2% horse serum from GIBCO) for differentiation and induction. Total RNA was separated according to the Guanidine isothiocyanate/acid phenol method (Chomczynski P. and Sacchi N., Anal. Biochem., 162, 156–159, 1987), and poly (A) RNA was selectively separated by repeating twice oligo(dT)-cellulose column chromatography. By using the poly(A) RNA as a template and random primers (N6, Pharmacia), cDNAs were synthesized with MLV reverse transcriptase (GIBCO BRL) according to its manual for synthesis. The obtained cDNAs were then used as a template for the next PCR, and double strand DNAs were synthesized and inserted into a phage (λZapII(stratagene)) to give a cDNA library.

(2) RT-PCR

RT-PCR was carried out by using the cDNAs prepared in the above (1) as a template in the following steps:

A degenerative primer encoding the amino acid sequence EDCDCG or EECDCG was synthesized and used as a sense primer, and a degenerative primer encoding the amino acid sequence KCGKLIC was synthesized and used as an antisense primer.

The primers were mixed with the above cDNAs, Taq polymerase and the reaction agents (Boehringer Manheim), and subjected to 36 reaction cycles of 95° C. for 1 min, 55° C. for 2 min, and 72° C. for 3 min. The amplification product of around 450 bp was then collected by 1.5% agarose gel electrophoresis.

Figure 1A:
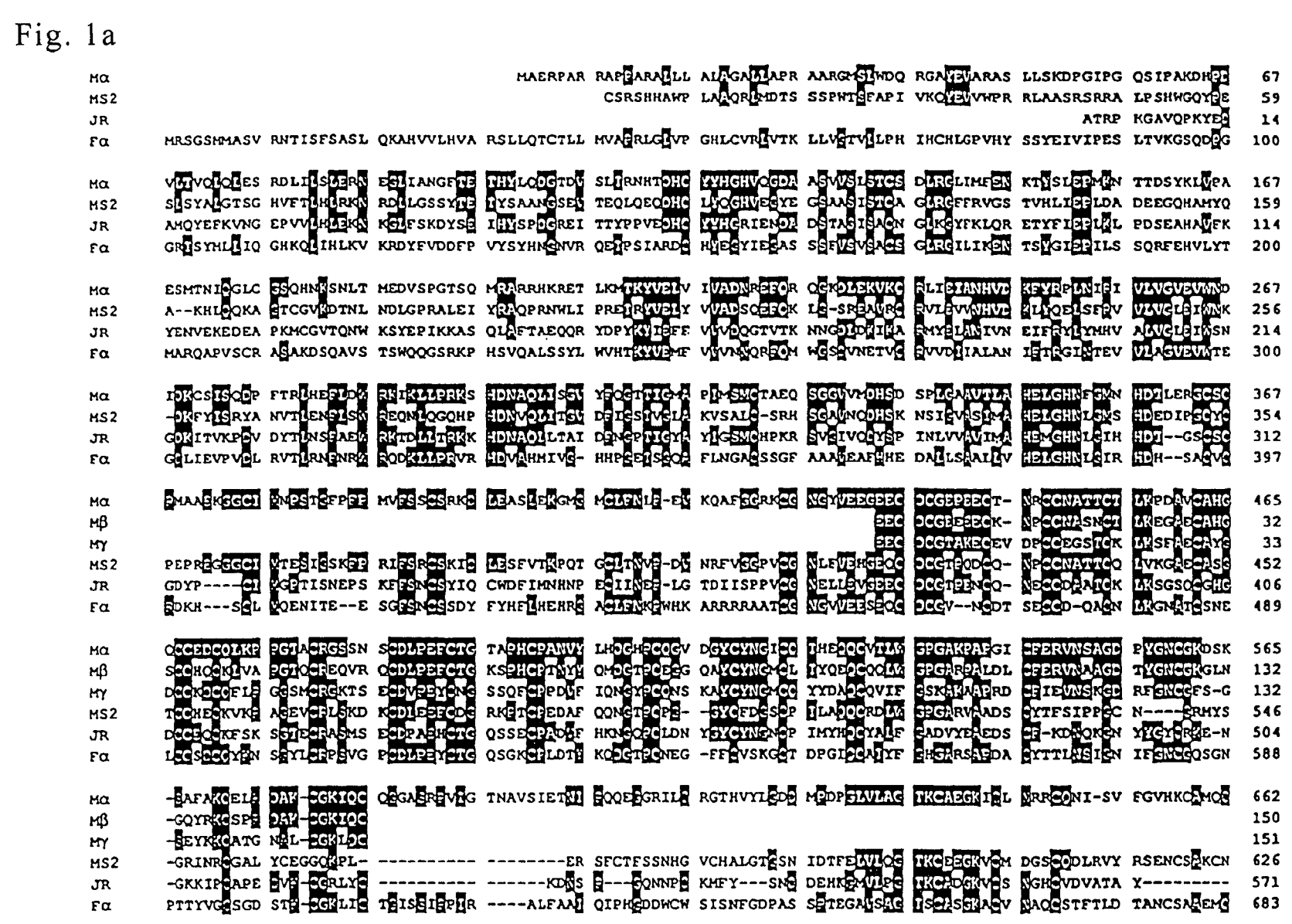

The amplified fragments thus obtained were inserted into a SmaI site in the plasmid pBS-SKII(−) (stratagene), and subjected to DNA sequence analysis by means of a DNA sequencer (370A type, Applied Biosystems). As a result, it was found that three kinds of molecules (DNA fragments) existed (FIG. 1), which were then used as a probe to screen the cDNA library so as to isolate cDNAs comprising an open reading frame with 903, 920 and 845 amino acid residues, respectively (FIG. 2a~FIG. 2j, FIG. 3a~FIG. 3j, FIG. 4a~FIG. 4i). The products of the respective genes were named Meltrins α, β, and γ (FIG. 5a~FIG. 5j, FIG. 6a~FIG. 6h, FIG. 7a~FIG. 7e). These cDNAs were inserted into pBS-SKII(−) to give the plasmids, "pBSMelα", "pBSMelβ", and "pBSMelγ", respectively.

E.coli strain JM109 was transformed according to a known method by the above plasmids "pBSMelα", "pBSMelβ", and "pBSMelγ", respectively, and the resulting transformants "JM109(pBSMelα)", "JM109(pBSMelβ)", and "JM109(pBSMelγ)" were deposited in the National Institute of Bioscience and Human-Technology, Agency of Industrial Science and Technology (1–3, Higashi 1-chome, Tsukuba-shi, Ibaraki-ken 350 Japan) on Feb. 19, 1996 under accession numbers FERM P-15451, FERM P-15452, and FERM P-15453, respectively, and then transferred on Oct. 8, 1996 to the deposit under the terms of the Budapest Treaty on the International Recognition of the Deposit of Microorganisms for the Purposes of Patent Procedure and Regulation under accession numbers FERM BP-5701, FERM BP-5702, and FERM BP-5703, respectively.

(3) Analysis of the Structure of Meltrins

From the structure analysis of Meltrins on the basis of the DNA sequences determined in the above (2), it was supposed that Meltrins α, β, and γ were a transmembrane-type protein consisting of an extracellular domain, transmembrane (TM) domain, and intracellular domain, and that the extracellular domain consists of a precursor domain (pro region) comprising a signal peptide-like sequence, metalloproteinase domain, disintegrin domain, and the following cysteine-rich region. A fusion peptide-like sequence was contained in the cysteine-rich domain of Meltrin α (FIG. 8).

Based on their homology to the snake venom, Jararhagin, it has been considered that in Meltrin α, the precursor domain corresponded to the sequence from N-terminal to Arg (No.205) and to the bases No.221–835, the metalloproteinase domain to the sequence from Glu (No.206) to Pro (No.414) and to the bases No.836–1462, the disintegrin domain to the sequence from Phe (No.420) to Gly (No.509) and to the bases No.1478–1747, the cysteine-rich region to the sequence from His (No.510) to Gly (No.706) and to the bases No.1748–2338, the fusion peptide-like sequence to the sequence from Gly (No.585) to Glu (No.607) and to the bases No.1973–2041, the transmembrane domain to the sequence from Leu (No.707) to Leu (No.727) and to the bases No.2339–2401.

Similarly, it was considered that in Meltrin β, the precursor domain corresponded to the sequence from N-terminal to Arg (No.204) and to the bases No.63–674, the metalloproteinase domain to the sequence from Glu (No.205) to Pro (No.409) and to the bases No.675–1289, the disintegrin domain to the sequence from Tyr (No. 415) to Gly (No.504) and to the bases No.1305–1574, the cysteine-rich region to the sequence from Thr (No.505) to Pro (No.706) and to the bases No.1575–2180, the transmembrane domain to the sequence from Val (No.707) to Arg (No.729) or to Leu (No.724) and to the bases No.2181–2249 or 2181–2234.

Similarly, it was considered that in Meltrin γ, the precursor domain corresponded to the sequence from N-terminal to Arg (No.205) and to the bases No.69–683, the metalloproteinase domain to the sequence from Ala (No.206) to Pro (No.406) and to the bases No.684–1292, the disintegrin domain to the sequence from Tyr (No.412) to Gly (No.502) and to the bases No.1302–1574, the cysteine-rich region to the sequence from Tyr (No.503) to Ala (No.694) and to the bases No.1575–2150, the transmembrane domain to the sequence from Leu (No.695) to Ile (No.714) and to the bases No.2151–2210.

Example 2

Establishment of Anti-Meltrin α Antibodies (1) Preparation of Immunogen

A chimera polypeptide was prepared as follows, which consisted of glutathione-S-transferase (GST) (Smith, D. B. & Johnson, K. S., Gene, Vol.67, 31–40, 1988) and the polypeptide having the amino acid sequence from Ser. (No.483) to Lys (No.635) of Meltrin α in FIG. 2a~FIG. 2j, said polypeptide being attached to the C-terminal of GST. First, the plasmid, pGEX2T (Pharmacia) comprising the cDNA encoding GST was digested at a BamHI site and used as a vector. On the other hand, the cDNA corresponding to the amino acid sequence from Ser. (No.483) to Lys (No.635) of Meltrin α in FIG. 2a~FIG. 2j was amplified from pBSMelα by PCR, and ligated with a BamHI linker by a DNA ligase. The resulting cDNA was then ligated with the above vector by a DNA ligase to give a plasmid, which was then tranformed into E.coli strain NM522.

The transformed E.coli was cultured in L-broth with 1 mM IPTG to produce a large amount of the chimera polypeptide in the inclusion bodies upon expression-induction. The strain was suspended into MTPBS (150 mM NaCl, 16 mM $Na_2HPO_4$, 4 mM $NaH_2PO_4$, 0.1 mM PMSF), subjected to ultrasonication, and solubilized with 1% Triton. The supernatant of the thus treated mixture was collected. Glutathione agarose (Sigma) was mixed with the supernatant to adsorb the chimera polypeptide which was then eluted with an elution buffer (50 mM Tris-HCl, pH 8.0, 0.5 mM glutathione) and used as an immunogen.

(2) Preparation of Antiserum

The antigen (1 mg) prepared in the above (1) in 0.5 ml PBS and RIBI in PBS 0.5 ml (MPL+TDM+CWS Emulsion, Funakoshi) were mixed with each other, and subcutaneously or intracutaneously administered into a rabbit (12 weeks old, female). After boosting three times with 500 μg dose at 4 week intervals, the blood was collected and serum was separated to give antiserum.

(3) Affinity Purification of Antiserum

The chimera polypeptide expressed in E.coli and solubilized in the above (1), or GST having no fused polypeptide was bound to the glutathione agarose beads. The resulting beads were washed with 0.2 M sodium borate (pH 9.0), and mixed with dimethyl pimelidiate (a final concentration of 20 mM) so that the antigen was irreversibly bound to the beads, so as to give chimera polypeptide-affinity beads and GST-affinity beads, respectively.

The antiserum diluted ten times with 10 mM Tris-HCl (pH 7.5) was first mixed with the GST-affinity beads for anti-GST antibodies to be absorbed and removed, and then mixed with chimera polypeptide-affinity beads for anti-Meltrin α antibodies to be adsorbed thereon. The resulting chimera polypeptide-affinity beads were washed with 10 mM Tris (pH 7.5) and 500 mM NaCl, and the anti-Meltrin α antibodies were eluted with 100 mM glycine and collected as purified anti-Meltrin α antibodies.

(4) Western Blotting

C2 cell was proliferated to the extent of $10^6$ cells/φ 10 cm plate in DMEM supplemented with 15% fetal bovine serum, then cultured at 37° C. in differentiation medium (DMEM supplemented with 2% horse serum) and collected on the second day (C2DM d2) and on the 4th day (C2DM d4).

Further, C2 cell transformed by pBOSMelα (+) prepared in the following Example 5 (3) was cultured in DMEM supplemented with 15% fetal bovine serum at 37 ° C. for three days, inoculated into a plastic dish (φ 6 cm) at a density of $2\times10^5$/dish, further cultured for one day and transferred into the above differentiation medium for differentiation induction. After two day-culture in the differentiation medium, the cells were collected.

The collected C2DM d2, C2DM d4 or transformants by pBOSMela (+) were mixed with SDS solubilizing buffer (100 mM Tris-HCl (pH 6.8), 4% SDS, 20% Glycerol), subjected to ultrasonication and centrifuged to give their supernatant as a sample. The sample were mixed with an equiamount of a gel loading buffer, supplied to SDS-PAGE, and electrophoresed. After the electrophoresis was finished, the contents were transferred to a membrane.

A membrane was washed twice with a washing solution. The antiserum prepared in the above (3) was diluted 20 times with 5% skim milk solution in TBS-T, into which the membrane was soaked and incubated at 37° C. for one hour. After the incubation, the membrane was washed twice with the washing solution. The membrane was then soaked into a biotin-labelled anti-rabbit immunoglobulin antibody (Daco) diluted 4,000 times with the above skim milk solution and incubated at 37° C. for one hour. After the incubation, the membrane was washed twice with the washing solution. The membrane was reacted with a peroxidase-labelled streptoavidin for one hour, washed twice, and detected by ECL system (Amersham).

Figure 9:
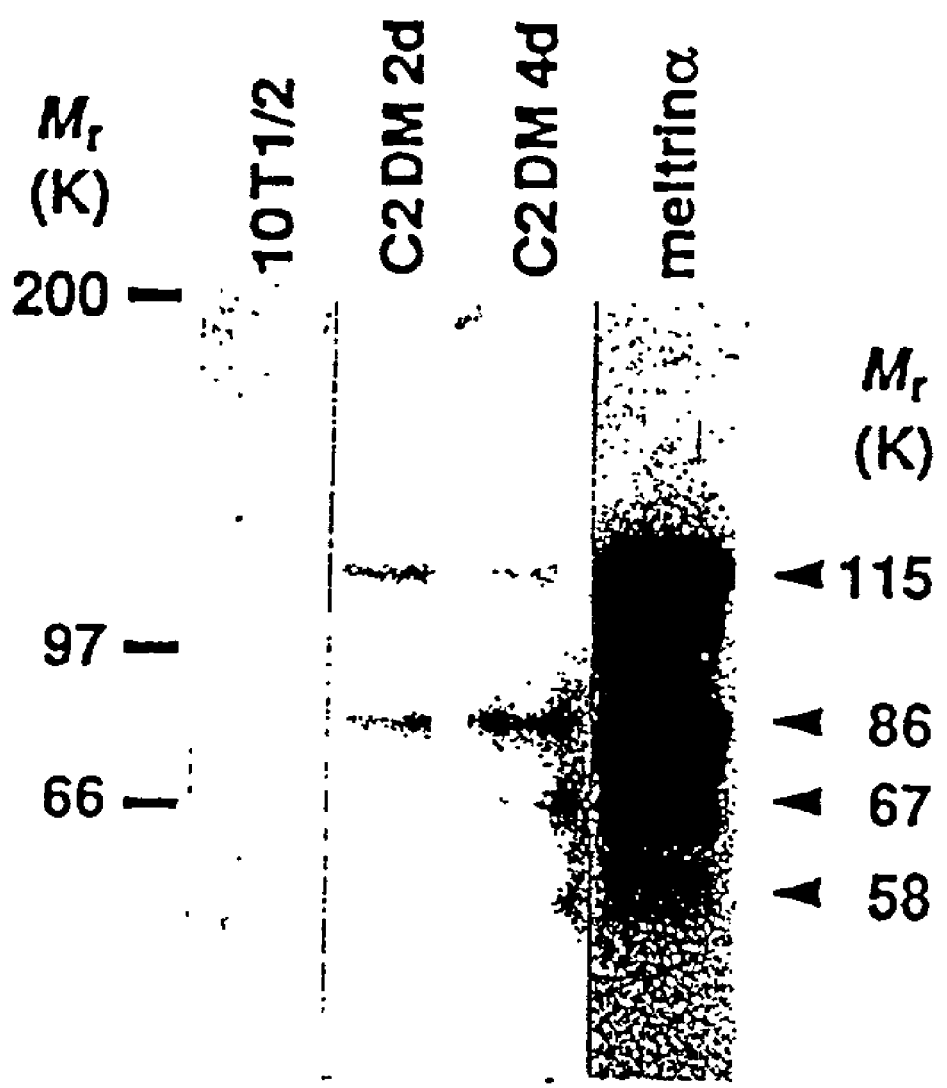
FIG. 9 is a photograph of electrophoresis showing the result of Western blotting.

The results are shown in FIG. 9.

The Western blotting revealed the bands at about 115 KD, 86 KD, 67 KD, and 58 KD, indicating that Meltrin α was expressed as a glycoprotein. It was also considered that the precursor domain was deleted in the molecule of 86 KD, and both the precursor and metalloproteinase domains were deleted in the molecule of 67 KD or 56 KD.

Example 3

Northern Blotting

Poly $(A)^+$ RNAs were prepared from various tissues of mouse (bone, brain, liver, heart and skeletal muscle of adult mouse; bone and skeletal muscle of newborn mouse; and bone and skeletal muscle of fetal mouse) by using a mRNA purification kit of Pharmacia according to the method described in Example 1. RNAs were denatured by heating at 65° C. for 5 min in 50% formamide, subjected to elecrto-phoresis on 1.5% agarose gel comprising 6.6% formalin, and transferred onto a nylon membrane (Highbond-N, Amersham).

On the other hand, cDNAs encoding a part of the disintegrin and cysteine-rich regions (Glu(No.434)-Cys(No.583) in FIG. 2a~FIG. 2j, Clu(No.429)-Cys(No.578) in FIG. 3a~FIG. 3j, Glu(No.426)-Cys(No.575) in FIG. 4a~FIG. 4i) were prepared by PCR, and labelled with $^{32}P$ using a random primer labelling kit (Megaprime, Amersham). As a control probe, cDNA encoding G3PDH (glyceraldehyde 3-phosphate dehydrogenase) was also labelled with $^{32}P$ in the same way. The above mRNAs were hybridized with the radiolabelled cDNAs under high stringency conditions according to the method of Sambrook J.et al. (Molecular Cloning: A Laboratory Manual, 2nd ed., Cold Spring Habor Laboratory, New York, 1989).

Figure 10:
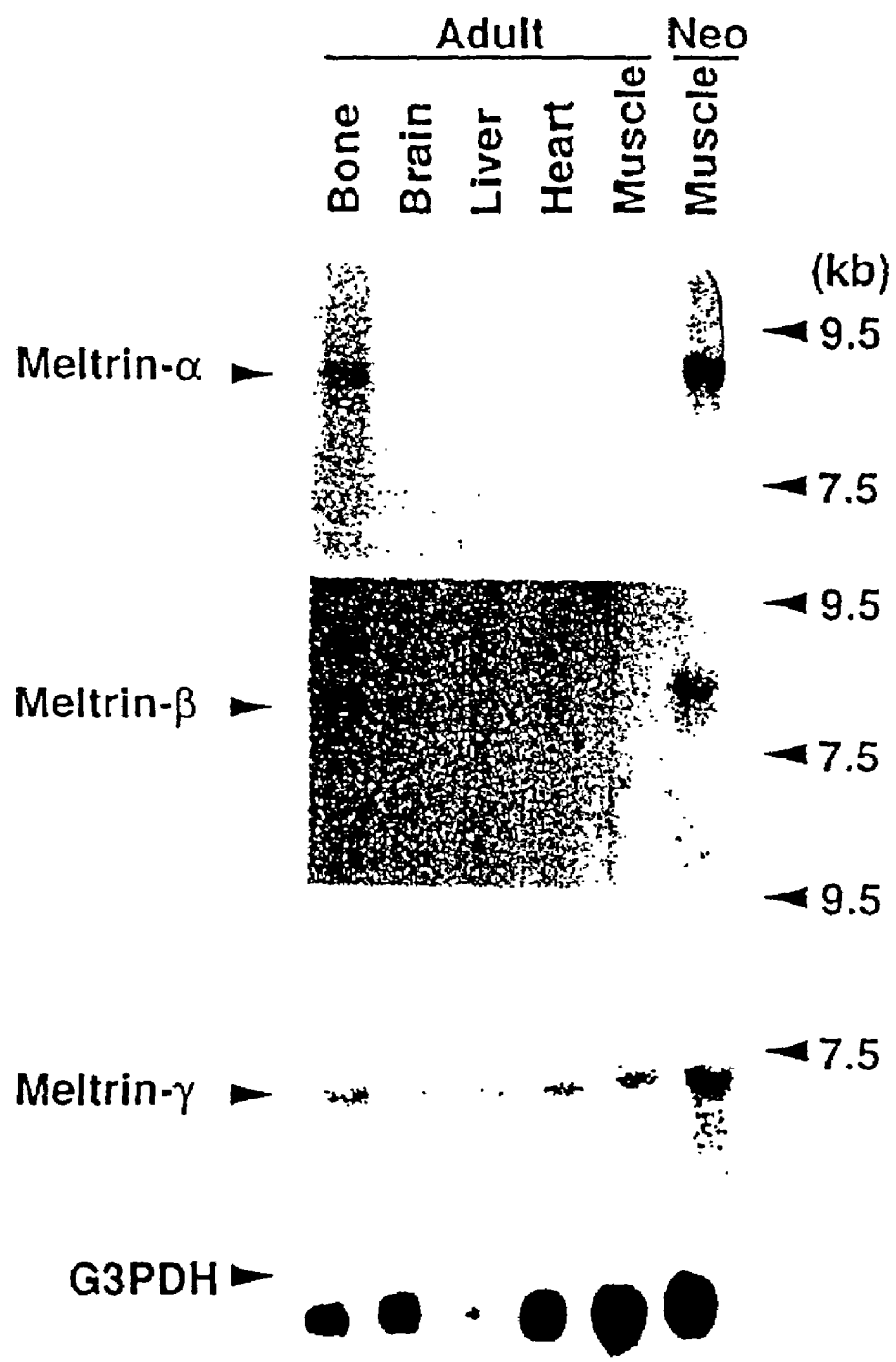
FIG. 10 is a photograph of electrophoresis showing the result of Northern blotting.

Their results are shown in FIG. 10.

FIG. 10 has revealed that Meltrin α and β were expressed only in bones of adult and newborn mice, and skeletal muscles of newborn and fetal mouses (the results from the fetal mouse are not shown in FIG. 10). There was no tissue-specificity in the expression of Meltrin δ, since it was universally expressed in all the tissues.

Example 4

Confirmation of Adhering Activity of Meltrin α

(1) Construction of Plasmids pBOSMelαδMP(+) and pBOSMelαδMP(−)

A deletion type Meltrin δMP wherein the precursor and metalloproteinase domains in the extracellualr domain of Meltrin α had been deleted was prepared in the followig method.

The plasmid, pBSMelα was partially digested at MscI and subjected to electrophresis on 1% agarose gel to give a linear plasmid DNA. The resulting DNA was partially digested at NheI, treated with a Klenow fragment to generate blunt ends, and subjected to intramolecular ligation. Vectors having the right deletion were selected and their DNA sequences were confirmed. After digestion at multicloning sites of EcoRV and NotI in the vectors, a deletion type δMP fragment of about 5.8 kb was obtained.

On the other hand, the plasmid, pEFBOS (Mizushima S. & Nagata S, Nucleic Acid Res. Vol.18, p.5322, 1990) was digested by a restriction enzyme XbaI, dephosphorylated, treated with a Klenow fragment to generate blunt ends and subjected to electrophresis on 1% agarose gel to give a linear plasmid DNA. The resulting linear DNA was then ligated with the above fragment of about 5.8 kb by a DNA ligase to give the plasmids pBOSMelαδMP(+) and pBOSMelαδMP(−). They were the constructs comprising the inserted DNA encoding the δMP fragment wherein the amino acid sequence of from Ile(55) to Glu(399) of Meltrin α was deleted, in sense direction and antisense direction, respectively.

(2) Construction of Plasmid pBOSMelα(+)

The plasmid, pBSMelα, was partially digested by EcoRV and NotI to give a fragment of about 7 kb. The above pEFBOS plasmid was digested by a restriction enzyme XbaI, dephosphorylated, treated with a Klenow fragment to generate blunt ends, and subjected to electrophresis on 1% agarose gel to give a linear plasmid DNA. The resulting linear DNA was then ligated with the above fragment of about 7 kb by a DNA ligase to give the plasmids pBOSMelα (+).

(3) Preparation of Plasmid pBOSMelαδPro(+)

There was a AflII site in the boundary region between the precursor and metalloproteinase domains of Meltrin α, and there was a NheI site in the boundary region between metalloproteinase and disintegrin domains of Meltrin α. On the other hand, there remained the NheI site in the boundary region between the signal peptide-like sequence and disintegrin domain in pBOSMelαδMP(+) prepared in the above (1). Accordingly, pBOSMelα was digested at AflII, ligated with a NheI linker immediately before its metalloproteinase domain and digested at NheI, so that the metalloproteinase would be excised. The excised domain was inserted into the NheI site between the signal peptide-like sequence and the disintegrin domain of pBOSMelαδMP(+) to give the expression plasmid, pBOSMelαδPro(+) encoding δPro wherein there a deletion was found around the precursor domain (the amino acid sequence of from Ile(No.55) to Glu(No.206) of Meltrin α).

(4) Confirmation of Myoblast Fusion-Promoting Activity

Myoblast cell line C2 was transfected by the mixture comprising the plasmid pBOSMelα(+) or pBOSMelαδMP(+), and the plasmid pSV2NEO in a molar ratio of 20:1 by using LIPOFECTAMINE (Gibco BRL) according to its protocol. The transfected cells were diluted and inoculated on a plate (φ 10 cm) coated with collagen (IWAKI) so that the transformants would be obtained at a density of 10–20 clones per plate. The inoculated cells were cultured for 12 days in DMEM containing 20% fetal bovine serum and 5 ng/ml of bFGF (Gibco BRL) followed by isolation thereof.

For the purpose of the examination of myoblast fusion-promoting activity, the resulting transformants and the parent strain C2 were cultured for 3–4 days in the absence of bFGF, inoculated onto a plastic dish (φ 6 cm) at a density of $2 \times 10^5$/dish, and further cultured for one day, followed by the 4 day culture in the above differentiation medium for differentiation induction. Upon differentiation induction, C2 began to form myotubes. After the 4 day culture followed by fixation with methnol and staining with Giemsa and Wright's reagents (Merck), the number of nuclei were determined at any four independent fields of 1 mm² on the dish and fusion index was calculated as follows:

Fusion Index =100*(The number of nuclei in multicleate syncytium having three or more nuclei)/ (The number of the total nuclei)

Further, the time course of the fusion index was observed after differentiation induction every one day for five days.

Figure 11A:
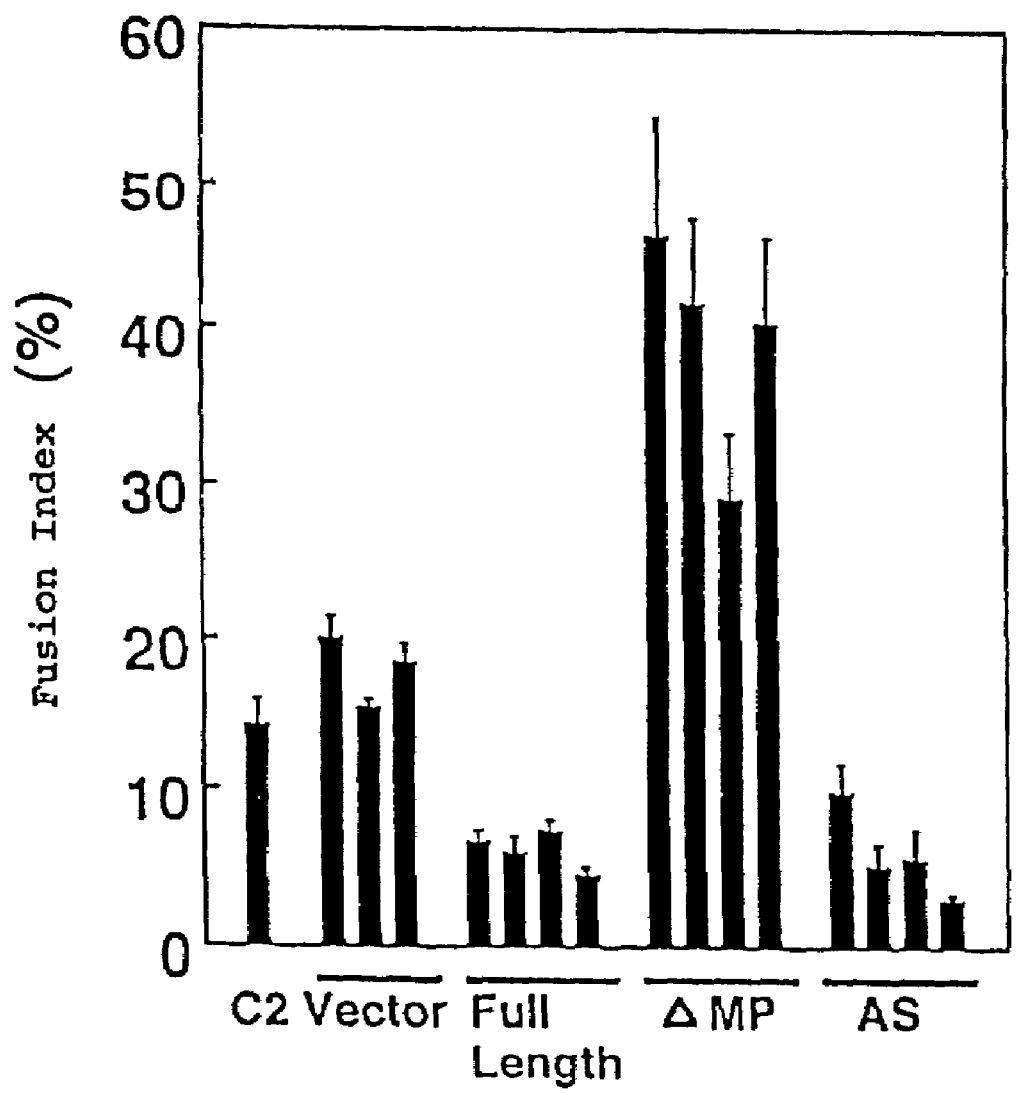
FIG. 11a~FIG. 11b show fusion-promoting activity of Meltrins for myoblast.
Figure 11B:
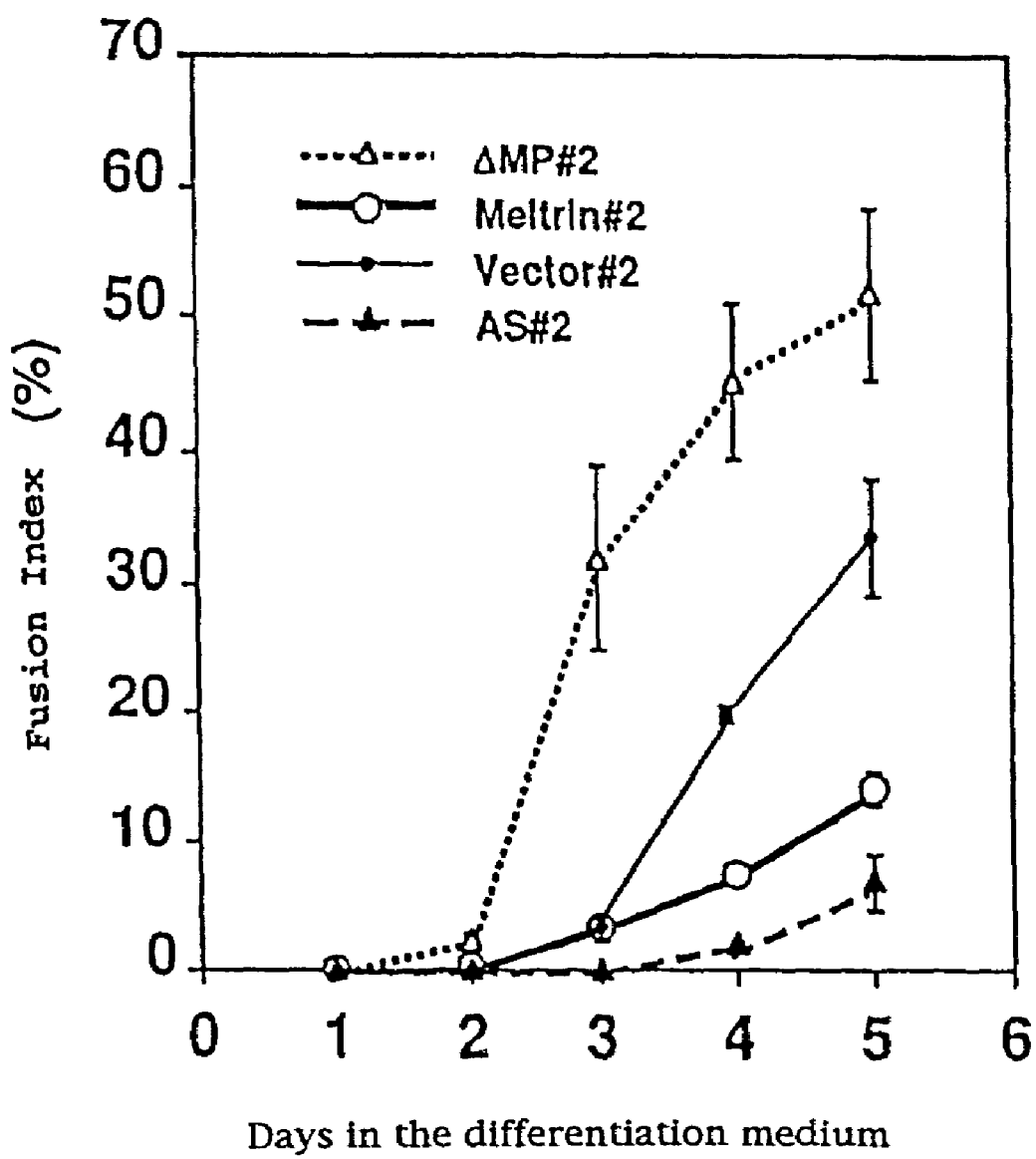

The results are shown in FIG. 11a~FIG. 11b. As seen from these figures, the fusion activity of the transformant expressing the full length of Meltrin α (pBOSMelα(+) which was referred to as "full length" in FIG. 11a) become lower than that of the parent cell, and it was therefore considered that the full length of Meltrin α would suppress the cell fusion in some way. On the other hand, the transfomant harboring pBOSMelαδMP(+), which was referred to as "ΔMP" in the figures, significantly promoted the cell fusion activity. It was also observed that the transformant harboring pBOSMelαδPro(+) promoted the cell fusion activity.

On the other hand, the C2 cell transformed by the plasmid pBOSMelβ(+) prepared by the insertion of the DNA encoding the full length of Meltrin β in the same way as in the above (2) could not cause any significant change in the fusion activity for muscle cells. However, The C2 transformant cotransfected by pBOSMelα(+) and pBOSMelβ(+) promoted the cell fusion activity compared with that of parent cell.

On the other hand, neither the C2 cell transformed by the plasmid pBOSMelγ(+) prepared by the insertion of the DNA encoding the full length of Meltrin γ in the same way as in the above (2), nor the C2 transformant cotransfected by pBOSMelα(+) and pBOSMelγ(+) could cause any significant change in the fusion activity for muscle cells.

These results demonstrate that Meltrin α is involved in the fusion of muscle cells, and will show its activity to promote the cell fusion upon its processing. It is estimated that Meltrin α or Meltrin β does not act alone, but act in the form of a heteromer between them, since the transformant expressing both Meltrin α and Meltrin β promoted the fusion of muscle cells.

(5) Examination of the Function of Meltrins in Non-muscle Cells

The mouse fibroblast L929 was transformed by pBOSMelα(+) or pBOSMelβ(+) and the transformants expressing Meltrin α or Meltrin β were isolated. These transformants did not aggregate, nor fuse with each other. This was also true for the case of the transformant expressing both Meltrin α and Meltrin β.

On the other hand, the L929 cells transformed by pBOSMelγ(+) could showed a significant aggregation activity upon the addition of calcium ion, after the cells had been torn from a plate in a medium comprising no calcium ion.

These results demonstrate that Meltrin γ has a cell aggregation activity, and by considering the similarity of these molecules it is suggested that myoblast fusion-promoting activity of Meltrin α and Meltrin β may be attributed to their myoblast aggregation-promoting activity.

Example 5

Inhibition of Adhering Activity by Antisense

The plasmid BOSMelαδMP(−) prepared in Example 4 (1) was mixed with the plasmid PSV2NEO at a molar ratio of 20:1, by which C2 cells were tranformed according to the method of Example 4 (4) followed by isolation of the transformants expressing antisense RNA. The adhering activity of the thus isolated transfomants was determined by the method of Example 4. The results are shown in FIG. 11a~FIG. 11b, which demonstrated that the fusion of C2 cells was inhibited by the expression of antisense RNA for δMP (referred to as "AS" in the figures).

The above results have revealed that Meltrin α plays an essential role in the cell fusion of muscle cells.

Example 6

Preparation of cDNA Fragments Encoding Human Meltrins α and γ

By using mRNA purified from human myelocytes (Clonetech Co.) as a template, cDNAs were prepared according to the method of Example 1 (1), and 36 cycles of PCR was then carried out by using the degenerative primer obtained in Example 1 (2) and said cDNAs as a template. The amplified product was inserted into a EcoRV site of pBS-SKII(−), and named "pBShuMα300." The results of DNA sequencing are shown in FIG. 12a and FIG. 12b.

It was found that the DNA sequence comprised the base sequence encoding the part from an intermediate position of the disintegrin domain to an intermediate position of the cysteine-rich region of human Meltrin α (the disintegrin domain is located to Gly (No.36), followed by the cysteine-rich region in FIG. 12a and FIG. 12b).

On the other hand, by using a part of a human sequence (D-14665) registered with a data base, whose function had not yet identified, a senseprimer (5'-CACGATGATGG-GAGAGATTG-3') and antisense primer (3'-CACTCT-GATTTCCTATGCCTC-5') were synthesized. PCR was carried out according to the above method to give the amplified product, which was then inserted into the EcoRV site of pBS-SKII(−), and named "pBShuMγG238." The results of DNA sequencing are shown in FIG. 13a and FIG. 13b.

It was found that the DNA sequence comprised the base sequence encoding the part from an intermediate position of the metalloproteinase domain to an intermediate position of the cysteine-rich region of human Meltrin γ (the metalloproteinase domain is located from N-termial to Pro (No.40), the disintegrin domain from Lys (No.41) to Gly (No.136) or from Tyr (No.46) to Gly (No.136), followed by the cysteine-rich region from Tyr (No.137)). The $E.\ coli$ strain JM109 was transfomed by those plasmids to give JM109(pB-ShuMα300) and JM109(pBShuMγG238), which were deposited in the National Institute of Bioscience and Human-Technology, Agency of Industrial Science and Technology (1–3, Higashi 1-chome, Tsukuba-shi, Ibaraki-ken 350 Japan) on Feb. 19, 1996 under accession numbers FERM P-15454 and 15455, respectively, and then transferred on Oct. 8, 1996 to the deposit under the terms of the Budapest Treaty on the International Recognition of the Deposit of Microorganisms for the Purposes of Patent Procedure and Regulation under accession numbers FERM BP-5704 and 5705, respectively.

Example 7

Preparation of cDNA Fragment Encoding Human Meltrin α by Usig cDNA Library Derived from Human Placenta-1

(1) First Screening

Based on the cDNA sequence of Meltrin α obtained in Example 6, sense primer MA-1 and antisense primer MA-2 were synthersized (see Table 1). The human placenta λgtll cDNA library (Clonetech Co., code No. CLHL1008b) was inoculated onto LB plate (φ 10 cm) at such a density that 10,000 plaques per plate may be obtained. After the formation of plaques, SM buffer 5 ml was added to each plate, the plates were put by incubation at a room temperature for 4 hours, and phages were collected from each plate (plate lysate method). PCR was carried out by using the collected phage solution as a template. Thus, MA-1 and MA-2 primers, Ex Taq polymerase (TaKaRa Co.,), and its reagents (TaKaRa Co.,) were mixed, followed by 35 cycles of the reactions at 94° C. for 30 sec, 55° C. for 30sec, and 72° C. for one min. A part of the amplified products was subjected to an agarose gel electrophoresis, and a phage solution of the clone comprising Meltrin α cDNA was selected.

(2) Second Screening

The phage solution of the desired clone obtained in the first screening was inoculated at such a density that 400 plaques per plate may be obtained. After the formation of plaques, phages were collected in the same manner as above and a phage solution comprising the desired clone was selected.

(3) Third Screening

The phage solution of the desired clone obtained in the second screening was inoculated at such a density that 40 plaques per plate may be obtained. After the formation of plaques, phages were collected in the same manner as above and a phage solution comprising the desired clone was selected.

(4) Forth Screening

The phage solution of the desired clone obtained in the third screening was inoculated at such a density that 10 plaques per plate may be obtained. After the formation of plaques, phages were collected in the same manner as above and a phage solution comprising the desired clone was selected.

(5) Final Screening

The phage solution of the desired clone obtained in the forth screening was inoculated at such a density that 20 plaques per plate may be obtained. After the formation of plaques, each plaque was stuck with a toothpick, and the sticking material was suspended as a template into PCR solution. The above 35 cycles of the PCR with MA-1 and MA-2 primers finally gave two psitive clones. A single positive plaque comprising the desired clone was collected in SM buffer, and the phage was lysed thereinto.

PCR was carried out by using λgtll Forward primer and λgtll Reverse primer (Table 1) to give a fragment of human Meltrin α cDNA in the phage vector.

Figure 14A:
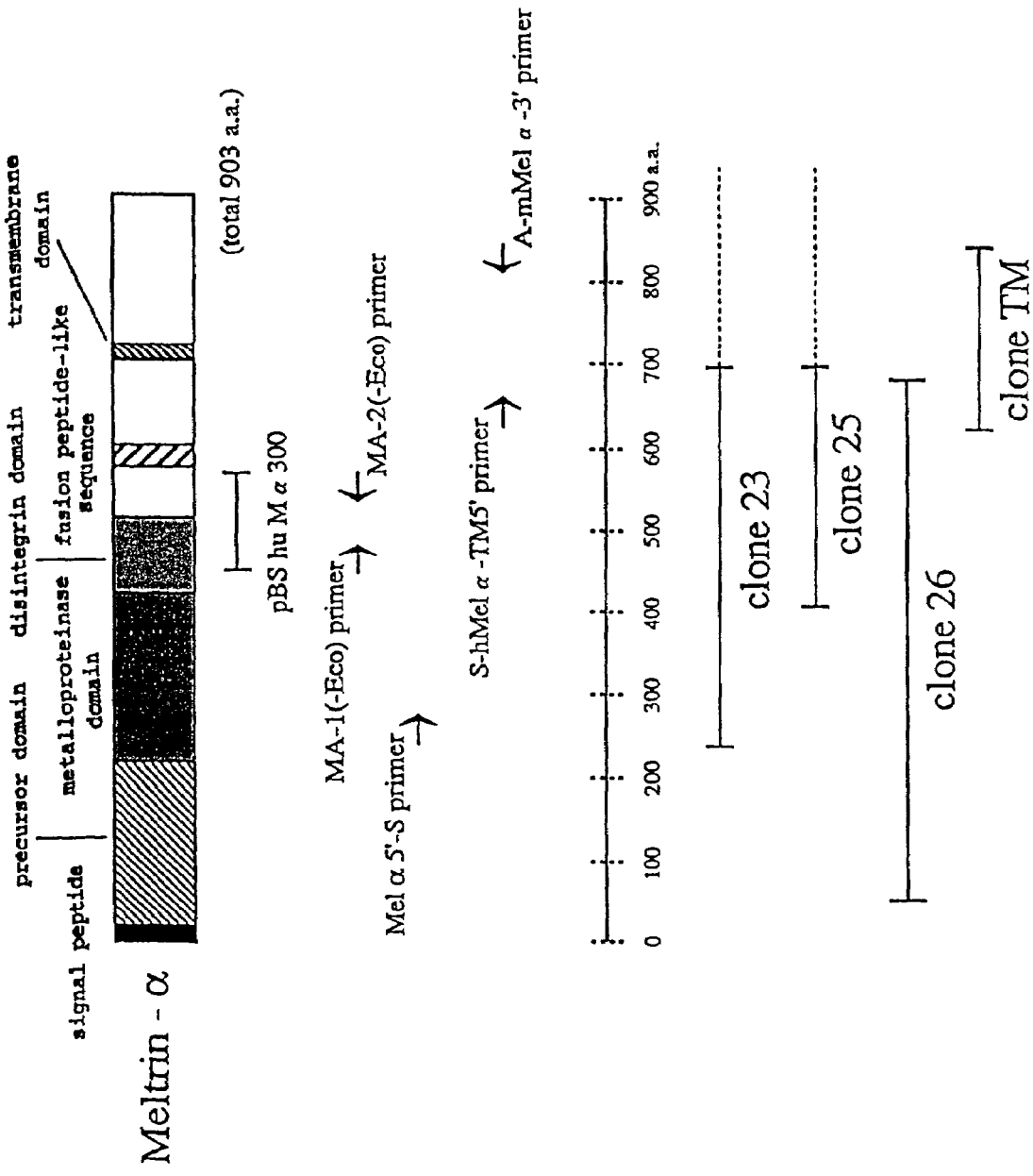
FIG. 14a shows schematically the cloning region in the cloning of human Meltrin α.
Figure 14B:
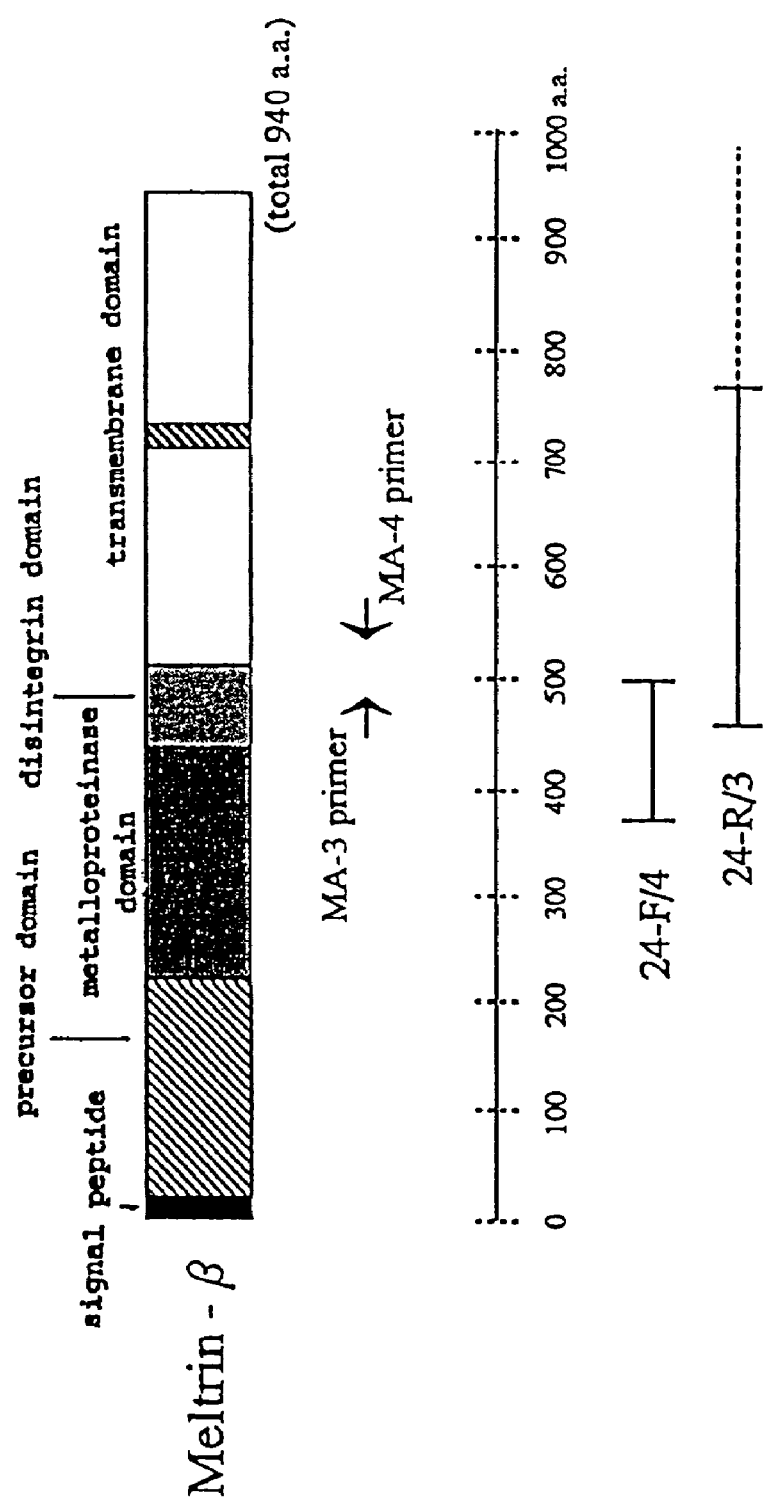
FIG. 14b shows schematically the cloning region in the cloning of human Meltrin β.

From a partial DNA sequencing of the terminal bases of the resulting fragments it was estimated that those cDNAs comprised the base sequences encoding human Meltrin α obtained in Example 6, and corresponded to about 650 amino acids (Clone 23) or about 500 amino acids (Clone 25) of mouse Meltrin (FIG. 14).

Example 8

Preparation of cDNA Fragment Encoding Human Meltrin α by Usig cDNA Library Derived from Human Placenta-2

A sense primer Mel α-5'S was designed based on the sequence encoding the N-terminal of the cDNA sequence of the clone 23 revealed in Example 7. The human placenta λgtll cDNA library (Clonetech Co.) was screened by the sense primer Mel α-5'S and antisense primer MA-2 to give cDNA encoding about 700 amino acids (Clone 26) (FIG. 14a). For the purpose of the analysis of the base sequence of Meltrin gene, the four primers, λgtll Forward-Eco, λgtll Reverse-Eco, MA-1-Eco, and MA-2-Eco were synthesized (Table 1).

TABLE 1

The base sequences of the primers for PCR

| | |
|---|---|
| MA-1 | 5' ACG ATG GGC ACT CAT GTC AG 3' |
| MA-2 | 5' CAT CTC GCA TTT GGC AAA GG 3' |
| λ gt11 Forward | 5' GGT GGC GAC GAC TCC TGG AGC CCG 3' |
| λ gt11 Reverse | 5' TTG ACA CCA GAC CAA CTG GTA ATG 3' |
| Mel α-5'S | 5' CAC TGA ACA TTC GGA TCG TG 3' |
| λ gt11 Forward-Eco | 5' CCG GAA TTC GGT GGC GAC GAC TCC TGG AGC CCG 3' |
| λ gt11 Reverse-Eco | 5' CCG GAA TTC TTG ACA CCA GAC CAA CTG GTA ATG 3' |
| MA-1-Eco | 5' CCG GAA TTC ACG ATG GGC ACT CAT GTC AG 3' |
| MA-2-Eco | 5' CCG GAA TTC CAT CTC GCA TTT GGC AAA GG 3' |
| S-hMel α-TM5' | 5' GCA CAA AGT GTG CAG ATG GA |
| A-mMel α-3' | 5' CAG AGG CTT CTG AGG AGG N |

The second half of the Meltrin gene was amplified by PCR using Clone 25 as a template, and MA-1-Eco and λgt11 Reverse-Eco primers. The first half of the Meltrin gene was amplified by PCR using Clone 26 as a template, and MA-2-Eco and λgt11 Forward-Eco primers. These cDNA fragments were digested at EcoRI and cloned into the EcoRI site of pUC 118 to give the plasmid vectors "pMelα-26N" and "pMelα-25C", respectively. The sequences of Meltrin α cDNA comprised in these plasmids were determined by a conventional method.

The *E.coli* strain JM109 was transfomed by those plasmids according to the known method of Hanahan et al. to give JM109(pMelα-26N) and JM109(pMelα-25C), and were deposited in the National Institute of Bioscience and Human-Technology, Agency of Industrial Science and Technology (1–3, Higashi 1-chome, Tsukuba-shi, Ibaraki-ken 350 Japan) on Oct. 3, 1996 under the terms of the Budapest Treaty on the International Recognition of the Deposit of Microorganisms for the Purposes of Patent Procedure and Regulation under accession numbers FERM BP-5689 and 5688, respectively.

The base sequence and its corresponding amino acid sequence of human Meltrin α which had been revealed by the base sequencing of pMelα-26N and pMelα-25C are shown in FIG. 15a~FIG. 15f.

Comparison of the DNA sequence thus obtained with that obtained in Example 6 indicated four discrepancies in base pairs, the three of which being silent mutation, and the other discrepancy causing substitution of Asp (No.505) in the above figures for Glu in the sequence of Example 6.

The analysis of the structure of the base sequence showed that the DNA encoded the sequence from an intermediate part of the precursor domain to the C-terminal of Meltrin α. Thus, it has been considered that in the amino acid sequence shown in FIG. 15a~FIG. 15f, the partial sequence (C-terminal) of the precursor domain corresponds to the the sequence from Gly N-terminal to Arg (No.155) and to the bases No.1–465, the metalloproteinase domain to the sequence from Glu (No.156) to Pro (No.364) and to the bases No.466-1092, the disintegrin domain to the sequence from Glu (No.365) or Phe (No.370) to Gly (No.459) and to the bases No.1093 or 1108–1377, the cysteine-rich region to the sequence from His (No.460) to Gln (No.656) or Ala (No.652) and to the bases No.1378–1968 or 1956, the fusion peptide-like sequence to the sequence from Gly (No.535) to Gln (No.557) and to the bases No.1603–1671. There was no transmembrane domain in this sequence, suggesting that human Meltrin α existed as a soluble protein without a transmembrane domain in a body. In other words, it is considered that Meltrin α having the amino acid sequence of FIG. 15a~FIG. 15f is extracellularly secreted and present in blood or body fluid. It is considered that such soluble Meltrin α takes a part in regulating adhesion, fusion and aggregation of cells in the body.

It is considered that Meltrin α having the amino acid sequence of FIG. 15a~FIG. 15f has generated as a result of an alternative splicing of the gene. It is also considered that the DNA encoding the region downstream of the cysteine-rich region, and the DNA encoding transmembrane domain and intracellular domain are located on different exons, and that the splicing out of either DNA would yield a soluble type Meltrin, or a membrane-binding type Meltrin.

Example 9

Preparation of cDNA Fragments Encoding Human Meltrins β

(1) Preparation of cDNA Fragment Encoding a Part of the Disintegrin Domain of Human Meltrin β

By using mRNA purified from human myelocytes (Clonetech Co.) as a template, cDNAs were prepared according to the method of Example 1 (1), and 36 cycles of PCR were then carried out by using the degenerative primers obtained in Example 1 (2) and said cDNAs as a template. The amplified product was inserted into pBS-SKII(−). The analysis of the resulting DNA sequence revealed that it was a partial sequence of Meltrin β. The determined DNA sequence is shown in FIG. 16.

(2) First Screening by Using cDNA Library Originated in Human Fetal Lung

Based on the partial cDNA sequence of Meltrin β obtained in the above (1), sense primer MA-3 and antisense primer MA-4 were synthesized (see Table 2). The human fetal lung λgt11 cDNA library (Clonetech Co., code No.

CLHL1072) was inoculated onto LB plate (φ 10 cm) at such a density that 10,000 plaques per plate may be obtained. After the formation of plaques, SM buffer 5 ml was added to each plate. And the plates were put at a room temperature for 4 hours, and phages were collected from each plate (plate lysate method). PCR was carried out by using the collected phage solution as a template. Thus, MA-3 and MA-4 primers, Ex Taq polymerase (TaKaRa Co.,), and its reagents (TaKaRa Co.,) were mixed, followed by 35 cycles of the reactions at 94° C. for 30 sec, 55° C. for 30 sec, and 72° C. for one min by means of DNA thermal cycler (Perkin Elmer Co.,). A part of the amplified products was subjected to an agarose gel electrophoresis, and a phage solution of the clone comprising Meltrin β cDNA was selected.

(3) Second Screening

The phage solution of the desired clone obtained in the first screening was inoculated at such a density that 1000 plaques per plate may be obtained. After the formation of plaques, phages were collected in the same manner as above and a phage solution comprising the desired clone was selected.

(4) Third Screening

The phage solution of the desired clone obtained in the second screening was inoculated at such a density that 100 plaques per plate may be obtained. After the formation of plaques, phages were collected in the same manner as above and a phage solution comprising the desired clone was selected.

(5) Forth Screening

The phage solution of the desired clone obtained in the third screening was inoculated at such a density that 10 plaques per plate may be obtained. After the formation of plaques, phages were collected in the same manner as above and a phage solution comprising the desired clone was selected.

(6) Collection and Confirmation of DNA Fragment Comprising Partial cDNA Sequence The PCR was carried out using the phage solution of the desired clone obtained in the forth screening (#24) as a template, and a combination of λgtll Forward primer (Table 1) and MA-4 primer or a combination of λgtll Reverse primer (Table 1) and MA-3 primer to give amplified products with about 500 bp (24-F/4) and about 5 kbp (24-R/3), respectively. From a partial DNA sequencing of the terminal bases of the resulting two DNA fragments, it was estimated that those cDNA comprised the base sequences determined in the above (1).

(7) Analysis of Base Sequences

For the purpose of subcloning of the cDNA fragments comprising the cDNA partial sequence of human Meltrin β, two primers MA-3-Eco and MA-4-Eco were newly synthersized (see Table 2).

The PCR was carried out using the phage solution (#24) as a template, and a combination of λgtll Forward-Eco primer (Table 1) and MA-4-Eco primer or a combination of λgtll Reverse-Eco primer (Table 1) and MA-3-Eco primer. The resulting amplified products were digested with EcoRI and inserted into the EcoRI site of pUC118 to give the plasmids, "pMelβ-24C" and "pMelβ-24N", respectively. The sequence of Meltrin β cDNA comprised in these plasmids was determined by a conventional method.

The E. coli strain JM109 was transfomed by those plasmids according to the known method of Hanahan et al. to give JM109(pMelβ-24C) and JM109(pMelβ-24N), and were deposited in the National Institute of Bioscience and Human-Technology, Agency of Industrial Science and Technology (1–3, Higashi 1-chome, Tsukuba-shi, Ibaraki-ken 350 Japan) on Oct. 3, 1996 under the terms of the Budapest Treaty on the International Recognition of the Deposit of Microorganisms for the Purposes of Patent Procedure and Regulation under accession numbers FERM BP-5690 and 5691, respectively.

The base sequence and its corresponding amino acid sequence which had been revealed by the base sequencing of pMelβ-24C and pMelβ-24N are shown in FIG. 24a~FIG. 24e.

Comparison of the DNA sequence thus obtained with that obtained in the above (1) showed one discrepancy in base pairs, which was a silent mutation, causing no change of amino acid.

The analysis of the structure of the base sequence showed that the DNA encoded the sequence from an intermediate part of the metalloproteinase domain to the C-terminal of human Meltrin-β. Thus, it has been considered that in the sequence shown in FIG. 24a~FIG. 24e, the partial sequence at C-terminal of the metalloproteinase domain corresponds to the the sequence from Gly (N-terminal) to Pro (No.36) and to the bases No.2–109, the disintegrin domain to the sequence from Asp (No.37) or Tyr (No.42) to Gly (No.131) and to the bases No.110 or 125–394, the cysteine-rich region to the sequence from Thr (No.132) to Pro (No.330) and to the bases No.395–991, the transmembrane domain to the sequence from Val (No.331) to Met (No.348) or Arg (No.353) and to the bases No.992–1045 or 1060. It is considered that the sequence from Tyr (No.349) or Gln (No.354) corresponds to the intracellular domain. However, as homology analysis to mouse Meltrin β shows a very low homology in the sequence from Pro (No.395), it is estimated that the sequence up to His (No.394) is involved in the function of extracellular domain of human Meltrin β. The sequence up to Pro (No.395) in FIG. 24a~FIG. 24e is shown in FIG. 17a~FIG. 17c.

TABLE 2

The base sequences of the primers for PCR

MA-3
5' TGC TGC CAC CAG TGT AAG 3'

MA-4
5' TCC TGG TAG GTG AGG CAC ATG 3'

MA-3-Eco
5' CCG GAA TTC TGC TGC CAC CAG TGT AAG 3'

MA-4-Eco
5' CCG GAA TTC TCC TGG TAG GTG AGG CAC ATG 3'

Example 10

Preparation of Anti-Meltrin α Monoclonal Antibodies (1) Selection of Peptides

Based on the amino acid sequence of mouse Meltrin α determined in Example 1, their epitopes were analysed.

Eight kinds of peptide sequences were selected as a potential epitope, based on the secondary structure estimated from the regions wherein discrepancy in amino acids is seen between Meltrins α and β, the estimated non-RGD region, and the region wherein metalloproteinase had been cleaved (FIGS. 18a and b). These eight kinds of peptides were synthesized by Peptide Synthesizer (ABI 432A) so that they would have Cys at their C-terminal, cleaved, and purified by HPLC of a reverse phase column (YMC-ODS).

(2) Preparation of Antiserum

After lyophilization of the peptides obtained in the above (1), each peptide 0.55 mg was dissolved in 0.1 M phosphate buffer (pH 7.0) 55 µl. Maleimidated KLH (Boehringer Manheim) 0.77 mg was dissolved in distilled water 77 µl. The two resulting solutions were combined, and reacted at a room temperature for two hours, followed by the purification by Nick column (Pharmacia) equilibrated with physiological saline to give antigens to be used in the following experiments.

Each antigen 50 µg was diluted with physiological saline to 0.1 ml, mixed with the same amount of Freund's complete adjuvant (DIFCO) and administered intraperitoneally into Wistar rat (5 weeks old, female). The antigen was mixed with the same amount of Freund's incomplete adjuvant (DIFCO) and administered two weeks later in the same way as above.

(3) Evaluation of Antiserum (Plate Assay)

After one week from the administration, the blood was drawn from the eyeground of the rat, and an increase of the antibody titer for the administered peptides was confirmed by the reaction between immobilized peptides and the antiserum according to a plate assay as follows.

First, 50 mM phosphate buffered saline (0.9% NaCl, pH 7.2) comprising 0.5 mg/ml of Sulfo-SMCC (Pierce) was poured into each well of an amino plate (Sumitomo Bakelite). After incubation at 37° C. for 2 hours, the wells were washed five times with ion-exchanged water, and the above buffer comprising 0.5 µg/ml of each peptide was added. After incubation at 37° C. for one hour, the well were blocked by 0.076 M phosphate buffered saline (0.45% NaCl, pH 6.4), which will be referred to hereinafter as "PBS", comprising 0.1% of BSA and 4 mg/ml of cysteamine. The blocking agent was removed, each antiserum diluted 1,000 to 100,000 times with PBS was added followed by incubation at 37° C. for one hour. After two repeats of washing of the wells with 0.9% NaCl comprising 0.005% Tween20, an anti-rat immunoglobulin abtibody labelled with peroxidase (Dako) and diluted with PBS comprising 10% rabbit serum was added to each well followed by incubation at 37° C. for one hour. Upon the completion of the reaction, the wells were washed five times with a washing liquid and two times with ion-exchanged water. And 0.1 M McIlvaine buffer (pH 5.0) comprising 3 mg/ml of o-phenylene diamine and 0.027% hydro peroxide was added and reacted for 5 min. The reaction was terminated by the addition of 1N HCl, and absorbance at 490 nm was measured. The results are shown in Table 3, in which (++) means a reactivity, and (+) means a week reactivity.

TABLE 3

Reaction of antiserum with the peptide antigens

| peptide antigens | Reaction of Antiserum |
| --- | --- |
| 1 ProA | ++ |
| 2 MP-A | ++ |
| 3 MP-B | ++ |
| 4 DC-A | + |
| 5 DC-B | + |
| 6 DC-C | ++ |
| 7 DC-D | N.D. |
| 8 DEA | ++ |

N.D. (not determined)

(4) Evaluation of Antiserum (Western Blotting)

For the confirmation of the binding of the antiserum prepared in the above (2) to Meltrins, Western blotting was carried out.

Mouse myoblast C2 was transformed by pBOSMelαβPro (+) and pBOSMelβ(+), which will be referred to hereinafter as "#9-3", and mouse myoblast C2 was transformed by pBOSMelαβMP(+), which will be referred to hereinafter as "#3-5."

Transformed C2 cells of 1×10⁷ cells were washed with PBS-(GIBCO BRL) and collected by centrifugation. The density of the collected cells was adjusted to 5×10⁶ cells/ml, mixed with a proteolysis inhibitor, Cφmplete (Boehringer Manheim) in amount of one 25th of the volume of the cell mixture, and mixed with SDS to a final concentration of 0.2%. After incubation at a room temperature for 30 min, the cells were subjected to sonication at 4° C. for 10 sec (1 sec×10), and centrifuged. The resulting supernatant was collected and used as a cell lysate. Another cell lysate was prepared from fibroblast L929 (ATCC No.CCL-1) in the same way, and used as a negative control.

The resulting cell lysate (10 µl) was mixed with an equiamount of a gel loading buffer (0.25 M Tris-HCl, 2% SDS, 30% Glycerol, 0.01% BPB(pH 6.8)), the resulting solution (6 µl) was applied to SDS-PAGE of 4~20T % (Tefco), and electrophoresed under 25 mA at a room temperature for about one hour. After the completion of the electrophoresis, the contents were transferred to PVDF membrane (Millipore) under the conditions of 150 mA, 4° C. and 45min. The membrane was blocked by shaking in 4% skim milk (Meiji Milk Co.) at a room temperature for one hour, and each lane was cut. Each excised lane was soaked and shaken in antiserum (1 ml) diluted 500 times with 50 mM Tris-HCl (pH 7.2) comprising 0.05% Tween20 (referred to hereinafter as "T-TBS") and 4% skim milk at a room temperature for one hour. After the completion of the reaction, each lane was washed two times with T-PBS, soaked in 1ml of an anti-rat immunoglobulins antibody labelled with HRPO (Dako) diluted 500 times with T-PBS comprising 4% skim milk, and reacted at a room temperature for one hour. After washing five times with T-PBS, it was detected by ECL system (Amersham). The results are shown in Table 4. Bands were detected in the three kinds of the antiserums by the Western blotting.

TABLE 4

Reaction of antiserum with the cell lysate in Western blotting

| Peptide antigens | Western blotting |
| --- | --- |
| 1 ProA | + |
| 2 MP-A | − |
| 3 MP-B | − |
| 4 DC-A | N.D. |
| 5 DC-B | N.D. |
| 6 DC-C | + |
| 7 DC-D | N.D. |
| 8 DEA | + |

N.D. (not determined)

(5) Preparation of Monoclonal Antibody

The antigens (ProA, MP-B, DC-C, DEA) (50 µg each) were diluted with 400 µl of physiological saline, and injected into the tail vein of the rats whose antibody titer had increased. Three days later, cell fusion was carried out by using myeloma P3X63Ag8U.1 according to the known method (Monoclonal antibody Jikken Sosa Nyumon (Guide of monoclonal antibody preparation), Tamie Ando and Jo Chiba, Koudan-sha Scientific). Six days later, the culture supernatant was collected and subjected to the plate assay according to the method of the above (3). The wells that showed reactivity with the peptide antigens were subjected to cloning by limiting dilution(Monoclonal antibody Jikken Sosa Nyumon (Guide of monoclonal antibody preparation), Tamie Ando and Jo Chiba, Koudan-sha Scientific). After cloning, the screening by the plate assay was performed again to give 27 clones of the hybridomas producing an anti-mouse Meltrin α monoclonal antibody which reacted with the peptide antigens. The results are shown in Table 5.

TABLE 5

Hybridomas producing anti-Meltrin peptides monoclonal antibody

| Peptide antigens | Hybridoma No. | The number of Hb |
| --- | --- | --- |
| ProA | F936 | 10 |
| MP-B | F939 | 4 |
| DC-C | F933 | 4 |
| DEA | F934 | 8 |

Purified antibodies were obtained from the thus established anti-Meltrin monoclonal antibody-producing hybridoma cell lines by the following method.

The hybridomas were cultured in RPMI1640 supplemented with 10% fetal bovine serum and 1 ng/ml of human IL6 till a final density of $2 \times 10^5$ cells/ml. The medium was then exchanged with a serum-free medium (Hybridoma-SFM, GIBCO BRL), and the culture was continued until the cells died. The resulting culture supernatant was filtered through filter paper for the removal of the cells, and subjected to purification by Protein G column (Prosep-G, Bioprocessing INC) as follows. The culture supernatant (1 L) was applied to Prosep-G column (20 ml) at a flow rate of 10 ml/min, followed by washing with 0.1 M phosphate buffer (pH 7.5) comprising 0.15 M NaCl. After the absorbance at 280 nm had decreased, the bound monoclonal antibody was eluted by 0.1 M citric acid buffer (pH 3.0). After neutralization of the pH, the eluate was concentrated with DIAFLO (Grace Japan), and dialysed against 0.076 M phosphate buffered saline (pH 6.4) comprising 0.45% NaCl. The concentration of the purified antibody was calculated on the basis of the absorbance at 280 nm.

(6) Evaluation of Monoconal Antibody

Figure 19:
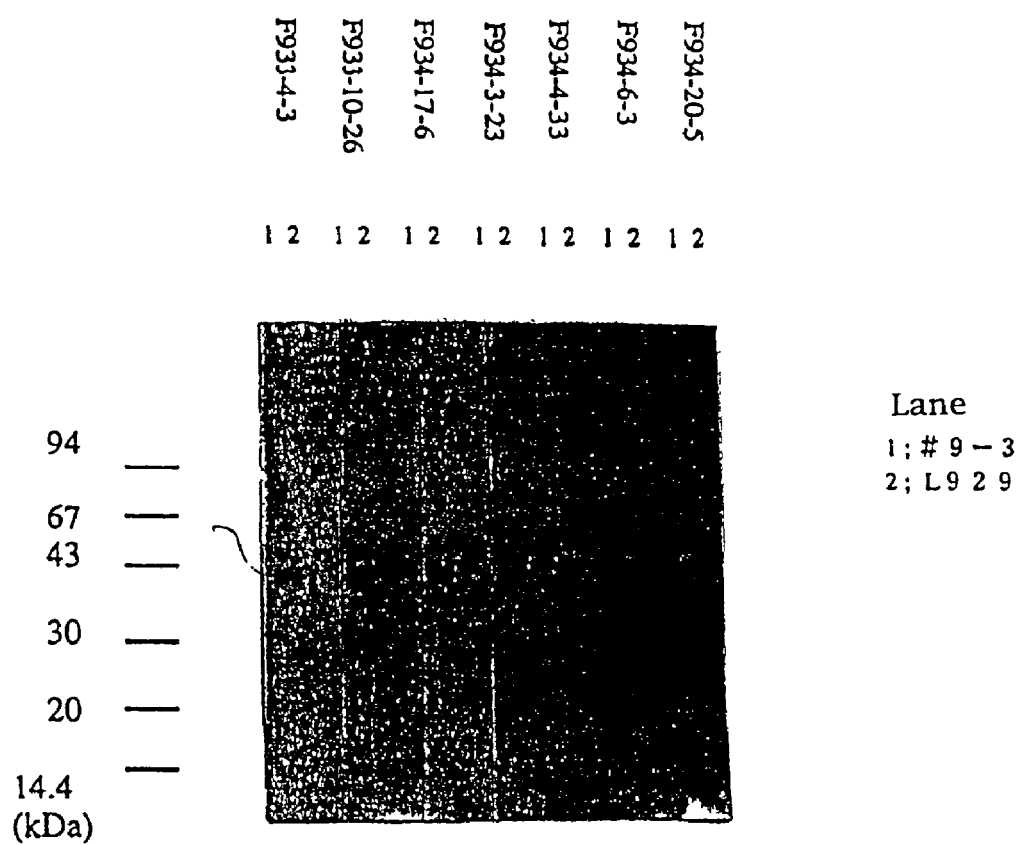
FIG. 19 is a photograph of electrophoresis showing the result of Western blotting with anti-mouse Meltrin α antibodies.

The binding activity of 7 lots of the purified antibodies (10 μg/ml each) obtained in the above (5) to Meltrin was confirmed by Western blotting according to the method of the above (4) using the cell lysate of #9-3 cell. The results are shown in FIG. 19. The band of about 67 kDa specific to the cell lysate of #9-3 cell was detected by the reaction with F933-4-3 (subclass IgG2a), F933-10-26 (subclass IgG2a), F934-17-6 (subclass IgG2a), F934-3-23 (subclass IgG2a), F934-4-33 (subclass IgG2a), F934-6-3 (subclass IgG2a), and F934-20-5 (subclass IgG2c). As these bands were not detected in the case of the cell lysate of L929 cell, it was confirmed that the monoclonal antibodies obtained in the above (5) were bound to Meltrin.

Example 11

Preparation of Anti-mouse Meltrin Monoclonal Antibody (1) Preparation of the Antigen to be Adminitered and Immunization of Rat Rats were immunized with #9-3 and #3-5 cells as the antigen to be administered as follows. The cells used as the antigen to be administered were cultured in the absence of bFGF. First, the cells cultured in four dishes to a density of about $5 \times 10^5$ cells/φ 10 cm dish were subcultured in 20 dishes to until the same density as the above, then again subcultured in 40 dishes (φ 15 cm) up to a density of about $5-6 \times 10^6$ cells / dish, and futher cultured in a differentiation medium (DMEM supplemented with 2% horse serum) for two days to finally form myotube. These cells were then scraped with a silicon rubber Policeman, washed two times with PBS, and suspended into the medium comprising 10% DMSO for storage at −80° C.

The #9-3 and #3-5 cells were suspended in physiological saline (200 μl), mixed with an equiamount of Freund's complete adjuvant (DIFCO) and intraperitoneally administered into Wistar rat (5 weeks old, female) in an amount of $1 \times 10^7$ cells/rat. The antigen was mixed with the same amount of Freund's incomplete adjuvant (DIFCO) and administered two weeks later in the same way as above.

(2) Evaluation of Antiserum

After one week from the boosting, the blood was drawn from the eyeground of the rat, and a binding of antiserum to Meltrin was determined by using the cell extract according to the plate assay of Example 10 (3). The cell extracts of #9-3, #3-5 and L929 cells were prepared according to the method of Example 10 (4), except that NP-40 (Nacarai Tesque Co.) was used at a final concentration of 0.5% as a surfactant.

First, each cell extract was diluted with PBS to a concentration of 40 μg/ml, each 50 μl of which was separately poured into each well of an immuno plate (Maxisorp Nunc). After incubation at 56° C. for 30 min for binding of the antigen, the wells were washed five times with ion-exchanged water, blocked by 20% Block Ace (Yukijirushi Milk Co.)/PBS 100 μl, followed by incubation at a room temperature for 30 min. After removal of the blocking agent, each antiserum (50 μl) was added and incubated at 37° C. for one hour. After two repeats of washing of the wells with the washing liquid, 50 μl of an anti-rat immunoglobulins antibody labelled with peroxidase (Dako) and diluted 1,000 times with 10% Block Ace/PBS was added to each well followed by incubation at 37° C. for one hour. Upon the completion of the reaction, the wells were washed five times with the washing liquid and two times with ion-exchanged water, and 50 μl of 0.1 M McIlvaine buffer (pH 5.0) comprising 3 mg/ml of o-phenylene diamine and 0.027% hydro peroxide was added and reacted for 10 min. The reaction was terminated by the addition of 1N HCl (50 μl), and the absorbance at 490 nm was measured.

Western blotting was also carried out by using the cell extract of L4-3 described in the following (4) to confirm its binding to Meltrin. The results are shown in Table 6.

It was confirmed that the antiserum obtained from the rats immunized with #9-3 and #3-5 cells reacted with the corresponding cell extract, and were bound to Meltrin in the Western blotting.

TABLE 6

Reaction of antiserum of the rats immunized with #9-3 and #3-5 cells to Meltrin

| Antiserum | Plate Assay | | | Western blotting |
|---|---|---|---|---|
| | #9-3 | #3-5 | L929 | L4-3 |
| rat immunized with #9-3 cell | + | N.D. | − | + |
| rat immunized with #3-5 cell | N.D. | + | − | + |

N.D. (not determined)

(3) Preparation of Monoclonal Antibody

The #9-3 and #3-5 cells (1×10$^7$ cells each) were suspended in physiological saline (200 μl), and intraperitoneally administered into the rat whose antibody titer had increased. Three days later, cell fusion was carried out by using myeloma P3X63Ag8U.1 according to the known method (Monoclonal antibody Jikken Sosa Nyumon (Guide of monoclonal antibody preparation), Tamie Ando and Jo Chiba, Koudan-sha Scientific). Six days later, the culture supernatant was screened by its reactivity with the immobilized cell extracts. The wells that showed reactivity with the cell extracts were subjected to cloning by limiting dilution (Monoclonal antibody Jikken Sosa Nyumon (Guide of monoclonal antibody preparation), Tamie Ando and Jo Chiba, Koudan-sha Scientific). After cloning, the above screening was repeated to give 13 clones, 5 clone from the rat immunized with #9-3 (δPro; hybridoma No. F932) and 8 clones from the rat immunized with #3-5 (δMP; hybridoma No. F937).

(4) Evaluation of Monoconal Antibody

The monoclonal antibodies F932-15-2 (subclass IgG1) and F937-9-2 (subclass IgG1) that showed a high reactivity with the cell extracts were evaluated.

First, the staining of myotube formed by C2 cells was examined by a cell immunofluorescence staining method. C2 cells were suspended in 10% FCS/DMEM at a density of 3×10$^4$ cells/ml, each 100 μl of which was then separately poured into the wells of chamber slide (Lab-TEK, Nunc Co.). After the culture at 37° C. and 5% CO$_2$ for two days, the medium was exchanged with 2% horse serum/DMEM. The cell staining was carried out by using myotube formed two days later. The cells were washed two times with PBS$^−$, and 4% formaldehyde was added followed by the reaction at a room temperature for 30 min to fix the cells. The cells were washed three times with PBS$^−$ and blocked with 20% Block Ace T-PBS. After removal of the blocking agent, antibodies diluted to 10 μg/ml with 20% Block Ace/T-PBS was added and reacted at a room temperature for one hour. After three repeats of washing of the wells with PBS$^−$, an anti-rat immunoglobulins antibody FITC (Dako) diluted 20 times with 10% rabbit serum/T-PBS was added to each well followed by incubation a room temperature for one hour. After the completion of the incubation, the cells were washed three times with PBS$^−$, and subjected to fluorescence microscopy. It was observed that myotube was stained by both the antibodies, but not stained by rat IgG (ZYMED) used as a negative control.

Next, L929 cells experssing mouse Meltrin α or β were prepared and subjected to cell staining for the purpose of confirmation of the specificity of the above antibodies. Thus, fibroblast L929 was transfected with the mixture comprising the plasmids pBOSMelα(+) and pBOSMelβ(+) prepared in Example 4, and the plasmid pSV2NEO in a molar ratio of 12:12:1 by using LIPOFECTAMINE (Gibco BRL) according to its protocol to give L4-3 cells expressing mouse Meltrins α and β. Similarly, L929 was transfected with the mixture comprising the plasmids pBOSMelβ(+) and the plasmid pSV2NEO in a molar ratio of 20:1 to give L2-10 cells expressing mouse Meltrin β. Similarly, L929 was transfected with the plasmids pBOSMelαδPro(+) to give L8-5 cells expressing mouse Meltrin α δPro. The transfected cells were cultured in 10% FCS/DMEM and subcultured onto a chamber slide. The specificity of the antibodies was confirmed by cell staining using L929, L4-3, L2-10 and L8-5 cells. The results shown in Table 7 indicated that F932-15-2 was bound to Meltrins α and β, and F937-9-2 was bound to Meltrin α.

The hybridoma expressing the monoclonal antibody F932-15-2 was deposited with the National Institute of Bioscience and Human-Technology, Agency of Industrial Science and Technology (1–3, Higashi 1-chome, Tsukuba-shi, Ibaraki-ken 350 Japan) on Oct. 3, 1996 under the terms of the Budapest Treaty on the International Recognition of the Deposit of Microorganisms for the Purposes of Patent Procedure and Regulation under accession numbers FERM BP-5687.

TABLE 7

| Cell | Expression | F932-15-2 | F937-9-2 |
|---|---|---|---|
| L929 | − | − | − |
| L4-3 | α and β | + | + |
| L2-10 | β | + | − |
| L8-5 | α (δPro) | + | + |

(5) Determination of Neutralizing Activity

Figure 20:
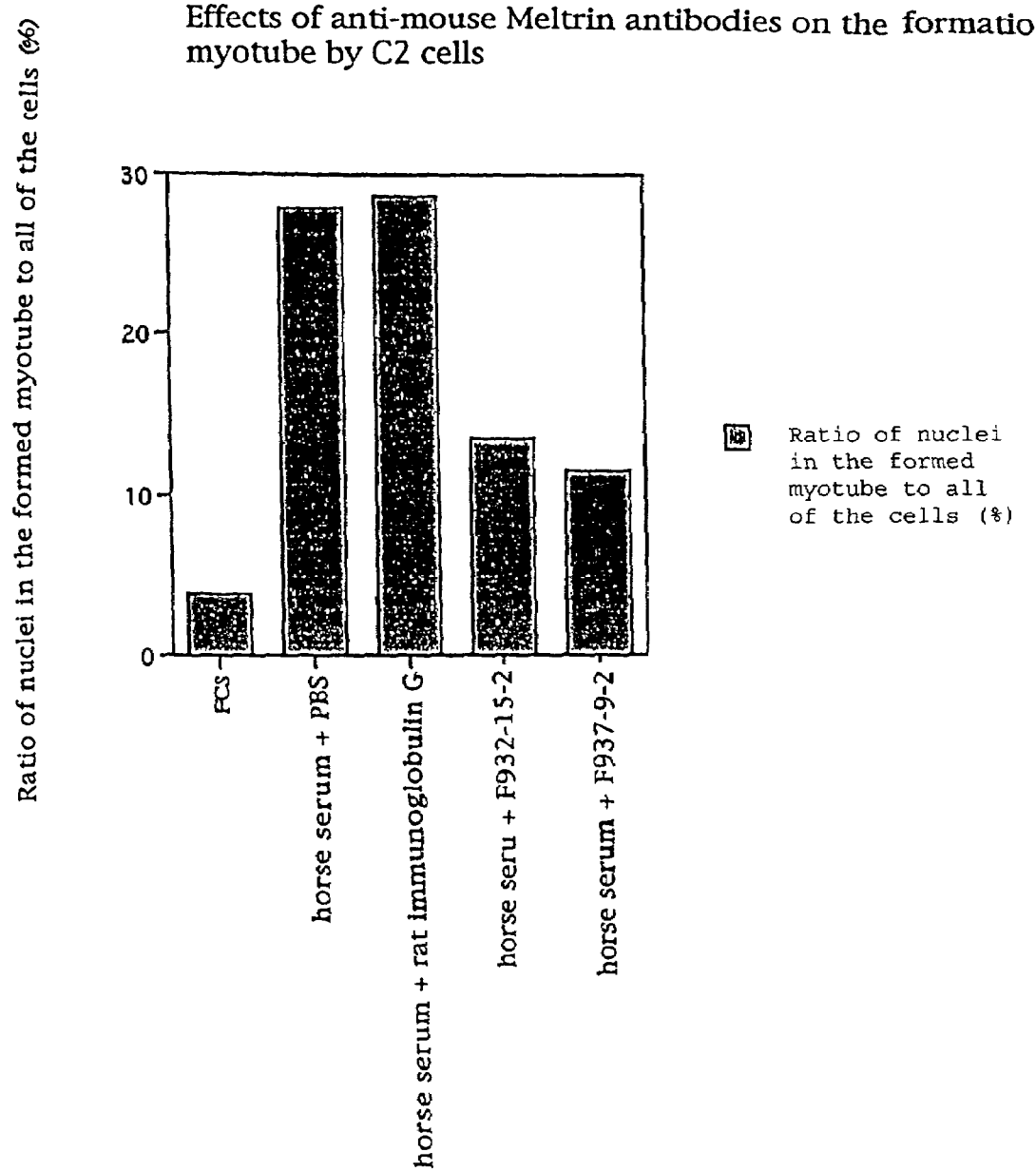
FIG. 20 is a graph showing the inhibition of myotube formation by anti-mouse Meltrin antibodies.

The neutralizing activity of the monoclonal antibodies obtained in the above (3) was confirmed by their inhibition of the formation of myotube by C2 cells. C2 cells were cultured in a collagen-coated dish contianing 10% FCS/DMEM till 80% of confluence, followed by exchange of the medium with 2% horse serum/DMEM supplemented with 0 or 40 μg/ml of the antibodies to be tested. The formation of byotube was then observed and the ratio of nuclei in the formed myotube was calculated. As seen from FIG. 20, the formation of myotube on the day 2 was inhibited, showing that both F932-15-2 and F937-9-2 have the neutralizing activity.

Example 12

The Activity of Meltrin Neutralizing Antibodies to Inhibit the Formation of Bone Resorption Area (Pit) in Mouse Unfractionated Bone Cells Femur and tibia extracted from 13-day-old ICR mouse were crushed in MEM α medium (GIBCO) supplemented with 5% FBS. After being allowed to stand still for 2 min, the precipitaed bone residues were removed. The supernatant of the suspending cells was adjusted to 1×10$^7$ cells/ml, 100 μl of which was then added to each well of a 96 well microplate provided with ivory fragments. The ivory fragments had been thinly sliced, punched into 6 mm in diameter, washed with 70% ethanol and sterilized. The mouse Meltrin-neutralizing antibody (F932-15-2) obtained in Example 11, and rat IgG were diluted with MEM a medium (GIBCO) supplemented with 5% FBS to final concentrations of 5, 50, and 500 μg/ml, 100 μl of which was then added to each well. After incubation at 37° C. and 5% $CO_2$ for three days, the cells were removed with a scraper, and resorption area was stained with an acid hematoxylin solution (SIGMA) for about 7 min and the number of the stained resorption area was caluculated using an ocular micrometer under a microscope by counting the number of squares wherein resorption fossa was contained.

Figure 21:
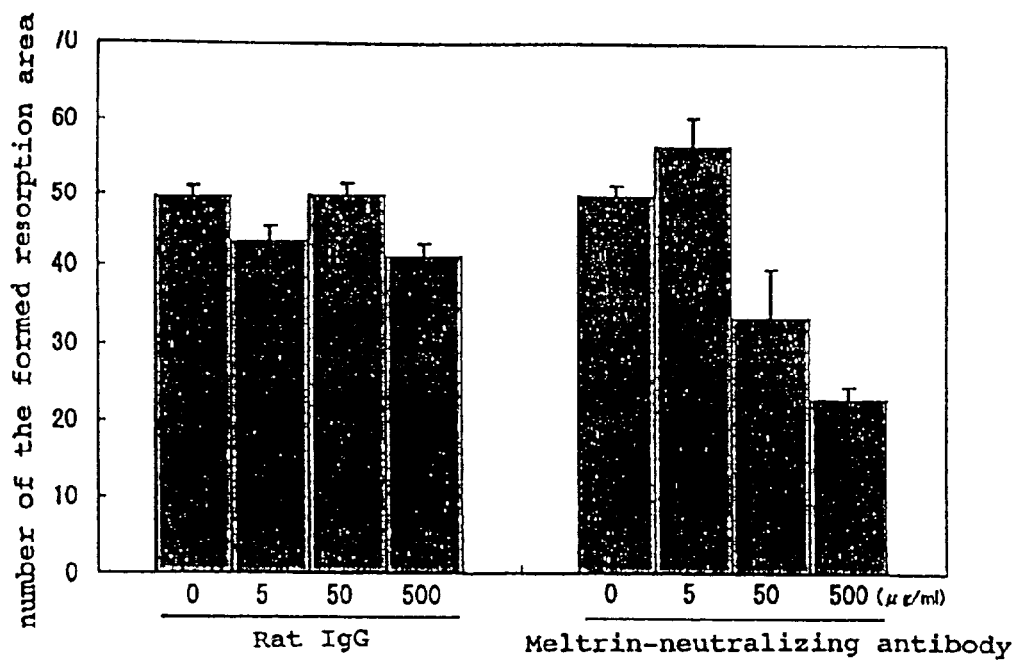
FIG. 21 is a graph showing the effects by anti-mouse Meltrin antibodies on the formation of pit (bone-resorption area) by mouse all bone cells.

The results are shown in FIG. 21, which demonstrates that the number of the formed resorption area was inhibited in a dose-depending manner by the mouse Meltrin-neutralizing antibody. Accordingly, it was suggested that the Meltrin-neutralizing antibody would affect directly or indirectly osteoclast and inhibit bone resorption.

Example 13

Serum Ca-decreasing Activity of Meltrin-Neutralizing Antibody in Mouse Having Enhanced Bone Resorption Seven-week-old ICR mice (male) were fed for five days with low Ca feed with Ca content of 0.02% or less. The mouse Meltrin-neutralizing antibody (F932-15-2) obtained in Example 11 was injected into the tail vein of the mice (one group consisting of five mice) at doses of 0.1 mg and 1 mg per mouse). Rat IgG (1 mg per mouse) and phosphate buffer physiological saline were also injected as a control in the same way. Before injection and one day later, the blood was collected from the vein under eyes, and serum was separated. The value of Ca in the serum was then determined by an autoanalyzer (COBAS FARAII, ROCHE) using Ca determination kit (CalciumHR-II, WAKO Pure Pharmaceuticals). The results are shown in FIG. 22.

Figure 22:
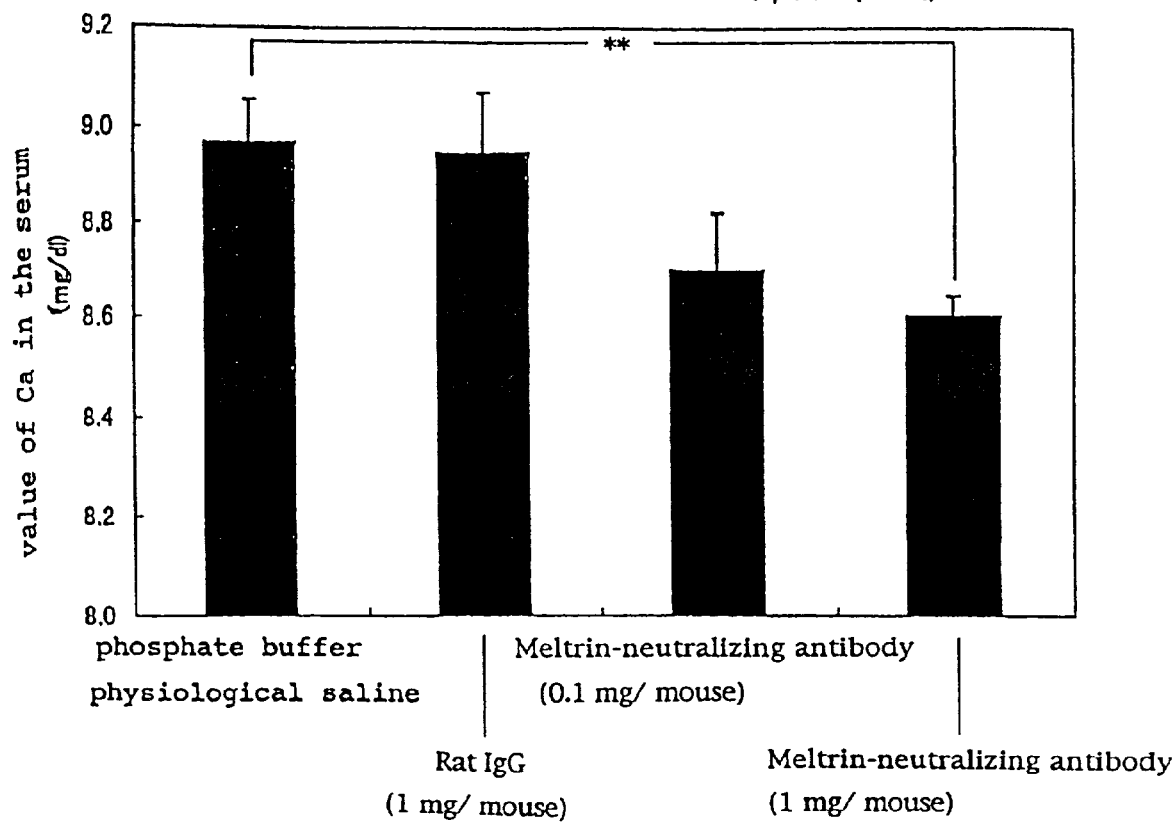
FIG. 22 is a graph showing the effects on the serum Ca values of the mouse fed with low Ca-content feed by anti-mouse Meltrin antibodies.

As seen from FIG. 22, the serum Ca value after one day from the injection in the groups treated with the mouse Meltrin-neutralizing antibody was lower than that of the groups treated with rat IgG or physiological saline. These results suggested that the Meltrin-neutralizing antibody would inhibit an unhealthly enhanced bone resorption due to hyperparathyroidism or malignant hypercalcemia.

Example 14

Preparation of cDNA Fragment Encoding Human Meltrin α Comprising Transmembrane Domain A sense primer S-hMelα-TM5' was synthesized based on the partial cDNA sequence of human Meltrin α obtained in Example 8, and an antisense primer A-mMelα-3' was synthersized based on the cDNA sequence of mouse Meltrin α (see Table 1).

PCR was carried out by mixing the human placenta λgt11 cDNA library (Clonetech Co., code No. CLHL1008b) as a template, with S-hMelα-TM5'and A-mMelα-3' primers, Ex Taq polymerase (TaKaRa Co.,), and its reagents (TaKaRa Co.,), followed by 35 cycles of the reactions at 94° C. for 30 sec, 55° C. for 30 sec, and 72° C. for one min. The base sequencing of the resulting amplified fragment (clone TM) suggested that the fragment was a human cDNA fragment corresponding to about 220 amino acids comprising the transmembrane domain of mouse Meltrin.

The obtained base sequence and its corresponding amino acid sequence are shown in FIG. 23a~FIG. 23b.

Example 15

Acute Toxicity Test

The mouse Meltrin-neutralizing antibody (F932-15-2) obtained in Example 11 was injected into seven-week-old ICR male mice (one group consisting of five mice) at doses of 1 mg and 3 mg per mouse). Phosphate buffer physiological saline was also injected into a control group in the same way. Neither significant decrease of body weight nor side effect was observed in any group after the injection. No dead mouse was observed, either.

Reference Example 1

Preparation of Monoclonal Antibody Recognizing Human Meltrin (1) Preparation of Antibody Using a Peptide Having the Amino Acid Sequence Derived from Human Meltrin as an Antigen In consideration of the results obtained in Example 10, the sequence "GKVSKSSFAKCEMRDAKC" corresponding to DC-C in the amino acid sequence of human Meltrin α obtained in Example 8 was synthesized in the same way as in Example 10 (1), purified and conjugated with maleimidated KLH to give an antigen to be administered. 20 μg of the antigen was dissolved in 0.1 ml of physiological saline and mixed with an equiamount of FCA followed by injection to ddy mouse (5 weeks old, female). The same amount of the antigen was mixed with FIA and injected two weeks later. The blood was collected from the eyeground one week later and antiserum was prepared. Evaluation of the reactivity of the resulting antiserum with the administered peptide according to the method of Example 10 (3) revealed its specific reactivity with the administered peptide. Accordingly, mouse, rat, hamster and the like are immunized with the peptide antigen, and monoclonal antibody may be prepared in the same manner as in Example 10 (5). Such antibody may also be used in Western blotting.

As it is estimated that the amino acid sequence in FIG. 15a~FIG. 15f is Meltrin α of a soluble type, an antibody, which may be effectively used in the determination of soluble Meltrin in the body, may be prepared by immunization of a peptide having the amino acid sequence adjacent to C-termial of the above sequence.

Similarly, antibodies recognizing human Meltrin β and Meltrin γ may be prepared by chemically synthesizing peptides having the amino acid sequences of suitable parts in the amino acid sequences in FIG. 17a~FIG. 17c or FIG. 13a~FIG. 13d and injecting the thus synthesized peptides into animals. In any case, the amino acid sequence will be selected from the extracellular domain.

For the preparation of an antibody specific to each one of Meltrins α, β and γ, the amino acid sequence should be selected from the parts with a low homology among them, and a peptide having the thus selected amino acid sequence is synthesized and injected to animals such as mouse, rat and hamster in the same way as in Example 10 (2).

In any case, monoclonal antibodies are prepared in the same way as in Example 10 (5).

(2) Preparation of Anti-Meltrin Monoclonal Antibody Using Cells Expressing Human Meltrin as an Antigen DNA encoding the amino acid sequence wherein the amino acid sequence located downstream of the transmembrane domain shown in FIG. 23a~FIG. 23b is fused downstream of the sequence from the metalloproteinase or the disintegrin domain to the cysteine-rich region shown in FIG. 15a~FIG. 15f is prepared, and inserted into an expression vector pEFBOS, followed by transformation of C2 cells by the resulting vector. The transformant is treated as in Example 11 (1), and used as an antigen for immunization of animals such as mouse, rat and hamster. Antibodies recognizing human Meltrin α is screened as in Example 11 (2), and monoclonal antibodies are prepared as in Example 11 (3).

Similarly, DNA encoding the amino acid sequence shown in FIG. 17a~FIG. 17c or the sequence located downstream of the disintegrin domain of the above sequence is prepared, and inserted into an expression vector pEFBOS, followed by transformation of C2 cells by the resulting vector. The transformant is treated as in Example 11 (1), and used as an antigen for immunization of animals such as mouse, rat and hamster. Antibodies recognizing human Meltrin β is screened as in Example 11 (2), and monoclonal antibodies are prepared as in Example 11 (3).

Similarly, DNA encoding the amino acid sequence shown in FIG. 13a~FIG. 13d or the sequence located downstream of the disintegrin domain of the above sequence is prepared, and inserted into an expression vector pEFBOS, followed by transformation of C2 cells by the resulting vector. The transformant is treated as in Example 11 (1), and used as an antigen for immunization of animals such as mouse, rat and hamster. Antibodies recognizing human Meltrin γ is screened as in Example 11 (2), and monoclonal antibodies are prepared as in Example 11 (3).

---

The invention claimed is:

1. An isolated polypeptide consisting of an amino acid sequence selected from the group consisting of:
   (1) an amino acid sequence of Gly (No. 1) to Arg (No. 155) in Seq. ID No. 12;
   (2) an amino acid sequence of Glu (No. 156) to Pro (No. 364) in Seq. ID No. 12;
   (3) an amino acid sequence of Phe (No. 370) to Gly (No. 459) in Seq. ID No. 12; and
   (4) an amino acid sequence of Gly (No. 535) to Gln (No. 557) in Seq. ID No. 12.

2. An isolated polypeptide consisting of an amino acid sequence selected from the group consisting of:
   (1) an amino acid sequence of Glu (No. 156) to Pro (No. 364) in Seq. ID No. 12; and
   (2) an amino acid sequence of Phe (No. 370) to Gly (No. 459) in Seq. ID No. 12.

* * * * *

SEQUENCE LISTING

```
<160> NUMBER OF SEQ ID NOS: 44

<210> SEQ ID NO 1
<211> LENGTH: 6915
<212> TYPE: DNA
<213> ORGANISM: Unknown Organism
<220> FEATURE:
<223> OTHER INFORMATION: Description of Unknown Organism:
      JM109(pBSMel-alpha), mouse meltrin alpha
<221> NAME/KEY: CDS
<222> LOCATION: (221)..(2929)
<221> NAME/KEY: unsure
<222> LOCATION: (2930)..(6915)
<223> OTHER INFORMATION: Nucleotide "n" is unknown

<400> SEQUENCE: 1
gccagagtag cgcgcgcgcg cacgcacaca cacggggagg ggagaaagtt ttttttgaa         60 aaaatgaaag gctagactcg ctgctcagcg acccgggcgc tgcgcgaggg ggtcgcggca       120
gactcagggc agtaggactt cccccagctc ggcgcccgcg tgggatgctg cagcgctggc       180
cgcggggccc ccgaagcagc tgcacgccag gccggcgaca atg gca gag cgc ccg        235
                                              Met Ala Glu Arg Pro
                                                1               5 gcg cgg cgc gcg ccc ccc gcc cgc gcc ctc ctg ctg gcc ctg gct ggg        283
Ala Arg Arg Ala Pro Pro Ala Arg Ala Leu Leu Leu Ala Leu Ala Gly
            10                  15                  20 gcc ctg ctg gcg ccc cgt gca gcc cga ggg atg agt ttg tgg gac cag        331
Ala Leu Leu Ala Pro Arg Ala Ala Arg Gly Met Ser Leu Trp Asp Gln
        25                  30                  35 aga gga gct tac gaa gtg gcc aga gcc tcc ctt ctg agc aag gac cct        379
Arg Gly Ala Tyr Glu Val Ala Arg Ala Ser Leu Leu Ser Lys Asp Pro
    40                  45                  50 ggg atc cca gga cag agc atc cca gcc aag gat cat cca gac gtg ctg        427
Gly Ile Pro Gly Gln Ser Ile Pro Ala Lys Asp His Pro Asp Val Leu
55                  60                  65 act gtg caa ctg cag ctg gag agc cga gac ctg atc ctc agc ctg gaa        475
Thr Val Gln Leu Gln Leu Glu Ser Arg Asp Leu Ile Leu Ser Leu Glu
70                  75                  80                  85 agg aat gag gga ctc att gcc aat ggc ttc acg gag acc cat tat ctg        523
Arg Asn Glu Gly Leu Ile Ala Asn Gly Phe Thr Glu Thr His Tyr Leu
                90                  95                 100 caa gat ggt act gat gtc tct ctc act cga aat cac acg gat cat tgt        571
Gln Asp Gly Thr Asp Val Ser Leu Thr Arg Asn His Thr Asp His Cys
            105                 110                 115 tac tac cat gga cat gtg caa gga gat gct gca tca gtg gtc agc ctc        619
```

```
                                                            -continued

Tyr Tyr His Gly His Val Gln Gly Asp Ala Ala Ser Val Val Ser Leu
        120             125             130 agt act tgc tct gat ctc cgg gga ctt atc atg ttt gaa aat aaa acg           667
Ser Thr Cys Ser Asp Leu Arg Gly Leu Ile Met Phe Glu Asn Lys Thr
135             140             145 tac agc tta gag cca atg aaa aac acc act gac agc tac aaa ctc gtc           715
Tyr Ser Leu Glu Pro Met Lys Asn Thr Thr Asp Ser Tyr Lys Leu Val
150             155             160             165 cca gct gag agc atg acg aac atc caa ggg ctg tgt ggg tca cag cat           763
Pro Ala Glu Ser Met Thr Asn Ile Gln Gly Leu Cys Gly Ser Gln His
                170             175             180 aac aag tcc aac ctc acc atg gaa gat gtc tcc cct gga acc tct caa           811
Asn Lys Ser Asn Leu Thr Met Glu Asp Val Ser Pro Gly Thr Ser Gln
            185             190             195 atg cgg gca aga agg cat aag aga gag acc ctt aag atg acc aag tac           859
Met Arg Ala Arg Arg His Lys Arg Glu Thr Leu Lys Met Thr Lys Tyr
        200             205             210 gta gag ctg gtt att gtg gca gac aac aga gag ttt cag agg caa gga           907
Val Glu Leu Val Ile Val Ala Asp Asn Arg Glu Phe Gln Arg Gln Gly
    215             220             225 aaa gac ctg gag aaa gtt aag cag cga tta ata gag atc gcc aat cac           955
Lys Asp Leu Glu Lys Val Lys Gln Arg Leu Ile Glu Ile Ala Asn His
230             235             240             245 gtt gac aag ttt tac aga cca ctg aac atc cgg atc gtg ctg gta gga          1003
Val Asp Lys Phe Tyr Arg Pro Leu Asn Ile Arg Ile Val Leu Val Gly
                250             255             260 gtg gaa gtg tgg aat gac atc gac aaa tgc tct ata agc cag gac cca          1051
Val Glu Val Trp Asn Asp Ile Asp Lys Cys Ser Ile Ser Gln Asp Pro
            265             270             275 ttc acc agg ctc cat gag ttt cta gac tgg aga aag ata aag ctt cta          1099
Phe Thr Arg Leu His Glu Phe Leu Asp Trp Arg Lys Ile Lys Leu Leu
        280             285             290 cct cga aaa tcc cac gac aat gct cag ctt atc agt ggg gtt tat ttc          1147
Pro Arg Lys Ser His Asp Asn Ala Gln Leu Ile Ser Gly Val Tyr Phe
    295             300             305 caa gga acc acc atc ggc atg gca ccc atc atg agc atg tgc act gca          1195
Gln Gly Thr Thr Ile Gly Met Ala Pro Ile Met Ser Met Cys Thr Ala
310             315             320             325 gaa cag tct gga gga gtt gtc atg gac cat tca gac agc ccc ctt ggt          1243
Glu Gln Ser Gly Gly Val Val Met Asp His Ser Asp Ser Pro Leu Gly
                330             335             340 gcc gca gtg acc ttg gca cat gag ctg ggc cac aac ttc ggg atg aac          1291
Ala Ala Val Thr Leu Ala His Glu Leu Gly His Asn Phe Gly Met Asn
            345             350             355 cat gac aca ctg gag agg ggc tgc agc tgc aga atg gcc gca gag aaa          1339
His Asp Thr Leu Glu Arg Gly Cys Ser Cys Arg Met Ala Ala Glu Lys
        360             365             370 gga ggc tgc atc atg aac ccg tcc acg ggg ttc cca ttc ccc atg gtg          1387
Gly Gly Cys Ile Met Asn Pro Ser Thr Gly Phe Pro Phe Pro Met Val
    375             380             385 ttc agc agc tgc agc agg aag gac ctg gag gct agc ctg gag aag ggc          1435
Phe Ser Ser Cys Ser Arg Lys Asp Leu Glu Ala Ser Leu Glu Lys Gly
390             395             400             405 atg ggg atg tgc ctc ttc aac cta cca gag gtc aag cag gcc ttt ggg          1483
Met Gly Met Cys Leu Phe Asn Leu Pro Glu Val Lys Gln Ala Phe Gly
                410             415             420 ggc cgg aag tgt gga aat ggc tat gtg gaa gag gga gaa gag tgt gac          1531
Gly Arg Lys Cys Gly Asn Gly Tyr Val Glu Glu Gly Glu Glu Cys Asp
            425             430             435
```

```
tgc gga gaa ccg gag gaa tgc acg aat cgc tgc tgt aac gct acc acc    1579
Cys Gly Glu Pro Glu Glu Cys Thr Asn Arg Cys Cys Asn Ala Thr Thr
            440                 445                 450 tgt act ctg aag cca gat gct gtg tgc gcg cac ggg cag tgc tgt gaa    1627
Cys Thr Leu Lys Pro Asp Ala Val Cys Ala His Gly Gln Cys Cys Glu
455                 460                 465 gac tgt cag ctg aag cct cca gga act gca tgc agg ggc tcc agc aac    1675
Asp Cys Gln Leu Lys Pro Pro Gly Thr Ala Cys Arg Gly Ser Ser Asn
470                 475                 480                 485 tcc tgt gac ctc cca gaa ttc tgc aca ggg act gcc cct cac tgt cca    1723
Ser Cys Asp Leu Pro Glu Phe Cys Thr Gly Thr Ala Pro His Cys Pro
                490                 495                 500 gcc aat gtg tac cta cat gat ggc cac ccg tgt cag ggc gtg gat ggt    1771
Ala Asn Val Tyr Leu His Asp Gly His Pro Cys Gln Gly Val Asp Gly
            505                 510                 515 tac tgc tac aac ggc atc tgc cag acc cat gag cag cag tgt gtc acg    1819
Tyr Cys Tyr Asn Gly Ile Cys Gln Thr His Glu Gln Gln Cys Val Thr
        520                 525                 530 ctc tgg gga cca ggt gct aaa ccg gct cct ggc atc tgc ttt gag cga    1867
Leu Trp Gly Pro Gly Ala Lys Pro Ala Pro Gly Ile Cys Phe Glu Arg
535                 540                 545 gtc aac tct gca gga gat cct tat ggt aac tgt ggc aaa gac tcc aag    1915
Val Asn Ser Ala Gly Asp Pro Tyr Gly Asn Cys Gly Lys Asp Ser Lys
550                 555                 560                 565 agc gcc ttc gcc aaa tgt gag ctg aga gat gcc aag tgt ggg aaa atc    1963
Ser Ala Phe Ala Lys Cys Glu Leu Arg Asp Ala Lys Cys Gly Lys Ile
                570                 575                 580 cag tgt caa ggt ggt gca agc cga cct gtc att ggt acc aat gct gtt    2011
Gln Cys Gln Gly Gly Ala Ser Arg Pro Val Ile Gly Thr Asn Ala Val
            585                 590                 595 tcc ata gaa aca aat atc cca cag cag gaa gga ggt cgg att ctg tgc    2059
Ser Ile Glu Thr Asn Ile Pro Gln Gln Glu Gly Gly Arg Ile Leu Cys
        600                 605                 610 cgg ggg acc cat gtg tac ttg ggt gat gac atg cca gac cca ggg ctt    2107
Arg Gly Thr His Val Tyr Leu Gly Asp Asp Met Pro Asp Pro Gly Leu
615                 620                 625 gtg ctt gca gga aca aag tgt gca gaa gga aaa atc tgc ctc aat cgt    2155
Val Leu Ala Gly Thr Lys Cys Ala Glu Gly Lys Ile Cys Leu Asn Arg
630                 635                 640                 645 cga tgt cag aat atc agt gtc ttc ggc gtt cac aag tgt gcc atg cag    2203
Arg Cys Gln Asn Ile Ser Val Phe Gly Val His Lys Cys Ala Met Gln
                650                 655                 660 tgc cac ggc cga ggg gta tgt aac aac agg aag aat tgc cac tgt gaa    2251
Cys His Gly Arg Gly Val Cys Asn Asn Arg Lys Asn Cys His Cys Glu
            665                 670                 675 gcc cac tgg gct cca ccc ttc tgt gac aag ttt ggc ttt gga gga agc    2299
Ala His Trp Ala Pro Pro Phe Cys Asp Lys Phe Gly Phe Gly Gly Ser
        680                 685                 690 aca gac agt ggt ccc atc agg caa gca gat aac cag ggc ttg act gta    2347
Thr Asp Ser Gly Pro Ile Arg Gln Ala Asp Asn Gln Gly Leu Thr Val
695                 700                 705 gga atc ctg gtg agc atc ctg tgt ctt ctt gct gct gga ttt gtg gtg    2395
Gly Ile Leu Val Ser Ile Leu Cys Leu Leu Ala Ala Gly Phe Val Val
710                 715                 720                 725 tat ctc aaa agg aag acg ttg atg cgg ctg ctg ttc aca cat aaa aaa    2443
Tyr Leu Lys Arg Lys Thr Leu Met Arg Leu Leu Phe Thr His Lys Lys
                730                 735                 740 acc acc atg gaa aag cta agg tgt gtg cac cct tcc cgg aca ccc agt    2491
Thr Thr Met Glu Lys Leu Arg Cys Val His Pro Ser Arg Thr Pro Ser
            745                 750                 755
```

```
ggc cct cac ctt ggc cag gct cac cac acc ccc ggg aaa ggc ctg ctg      2539
Gly Pro His Leu Gly Gln Ala His His Thr Pro Gly Lys Gly Leu Leu
        760                 765                 770 atg aac cgg gca cca cat ttc aat acc ccc aag gac agg cac tcg ctg      2587
Met Asn Arg Ala Pro His Phe Asn Thr Pro Lys Asp Arg His Ser Leu
    775                 780                 785 aaa tgc cag aac atg gac atc agc agg ccc ctc gac gct cga gcc gtc      2635
Lys Cys Gln Asn Met Asp Ile Ser Arg Pro Leu Asp Ala Arg Ala Val
790                 795                 800                 805 cca cag ctt cag tca cct cag cga gtg ctc ctg cct ctc cac cag acc      2683
Pro Gln Leu Gln Ser Pro Gln Arg Val Leu Leu Pro Leu His Gln Thr
                810                 815                 820 cca cgt gca ccc agt ggc cct gcc agg ccc ctg ccc gcc agt cct gca      2731
Pro Arg Ala Pro Ser Gly Pro Ala Arg Pro Leu Pro Ala Ser Pro Ala
            825                 830                 835 gtc agg cag gcc cag ggc att cga aaa ccc agt cct cct cag aag cct      2779
Val Arg Gln Ala Gln Gly Ile Arg Lys Pro Ser Pro Pro Gln Lys Pro
        840                 845                 850 ctg cct gct gat cca ctg agc agg act tct cgg ctc act agt gcc ttg      2827
Leu Pro Ala Asp Pro Leu Ser Arg Thr Ser Arg Leu Thr Ser Ala Leu
    855                 860                 865 gtg agg acc cca ggg cag cag gaa cct ggg cac cgc cca gcc ccc atc      2875
Val Arg Thr Pro Gly Gln Gln Glu Pro Gly His Arg Pro Ala Pro Ile
870                 875                 880                 885 aga cct gcc cct aag cat caa gta ccc aga cct tcc cac aat gcc tat      2923
Arg Pro Ala Pro Lys His Gln Val Pro Arg Pro Ser His Asn Ala Tyr
                890                 895                 900 atc aag tgagaagcca gcccagaccg gtcctcaaca gtgaagacag aagtttgcac       2979
Ile Lys tatcttcagc tccattggag ttgttgttgt accaactttc cgagtttcta aagtgtttaa    3039
aacaccattc tctccagacc ctggagccac tgccatcggt gctgtgctgt ggtgctttgt    3099
gtacttgctc aggaacttgt aagttattaa tttatgcaga gtgtctatta ctgcgcaggg    3159
cgccgtagca ggcatttgta ccatcacagg gcttttctac agaaggaagg ctcctcgtgc    3219
ttttgttttt ctggaggact tgaaataccc tgcttgatgg gacctaagat gagatgttta    3279
ctttctattc aaggccttat cggaaaatag ctccccacct tcccaaggct gttatggtac    3339
cagacacaca gctcaggaca ccccagggag aacctggcat gggttttctt tgtttgcttt    3399
cattttatct tttatatttt ggtatcccta tcttgggttg tagccagggc cttcaggaag    3459
gtcttgggcc actgcatgct aatggccttc aggtcctgca ccctgaagct ctcagacaac    3519
aagtaggatc tgcttttcag ccagcagctt tggagagaac ctggggtact gaaaagaagg    3579 tttgggtgt ggttataccda ggatggagac tggaatccta atctgggcaa acatctgacc    3639
ttgagctgag cagccatgag cacctctagg aagcaaggac ggctgaggtg ctgcacaagg    3699
ctctgctttg agagctggca ggggcttctc tctggctgcc ctttgcagag tgctagctgg    3759
catggcatgt tgtttacatc gggaacagtg gtgtttctac aagaaagcca ctgcctgggc    3819
actgcagacc tccgtctcct gcccatttag agctaagcaa attaccacat tgtcttctgg    3879
actgtaatac aatgaccctg tgttctgaca gatagaggag gctttctatg aaccataac     3939 tattttcana tgtgaactag taaccagatc tagtcgatca actctggaga tagaaatctc    3999 cttttactg caaggctcga cttattaaaa attaggcaga atccatatgc ttgcaaaagc     4059
tataaccacg tggaatgctc ttctcatggc acagcctgag tctggtatcc ttattagtag    4119
ccattggaca aagcacccaa agttacctgt gtgttctctt caaggcatcc taatttcttc    4179
```

-continued

```
agcatagaga gactcggtct tcctcacatt ctgaacatac ctatcaatga ctaagncagc    4239
aaggcaatcc gtttccgaat actgagttgc tcacggnaag gcaacctcag cccaggnaaa    4299
ctttttttcct ctgntctttc agtatgtgac tggggagcta ccttcagaag caaattttca   4359
aggtggnctc aaccccatng gatgaaagnt atttttttaa aaaataatta atggtaatgc    4419
cagagggctt tcctggcntc cagatngggg cgtaggnttg actagctttc acgacagaag    4479
gtaaatgaca gcagtcctct acctcgtctg actgctttaa gatcaaggct tctttggaag    4539
ggtaactaac attaatggct ggcctgtgcc ttgaagcaga agggaaaata cagataagga    4599
atttggtttg ctttctagaa tccaaaactg tatccagcat tgggaagcat ggtcttcatg    4659
actgggtaaa taaatccacg tcacagatgc ataaaagaat aactcttatg acatgcctct    4719
ttttgtggca cagagacaat attgctgcca ctgagatgca tacaaaattt ctgtaactga    4779
tatgtcattc agtagttgta ttaaggccaa acatccacaa ctgtaaagac ttatagagtt    4839
gtgtgggcgt tgtcttgtga gacacacaaa gcctcagctg aagcgtatga gctcctcctc    4899
caggtgggag tgatggggag gctagaaaca cacaaagaca acagaagagc tttggtttgg    4959
gggggtgca gagagagtgt ggtttagagg aagttggagc catgatcttc tgccatctcc     5019
ccagtgtcca ctaaggatgc cgatggtgcc ttaccagctg tgcagtgctg gctgcttgct    5079
tttacagagc catgcattca tttctgaata agaacatatt taatcctgaa attcccttac    5139
aggacagaca gtgttactaa aggaattcct ctaagataca gtagttgtca attaaagcat    5199
atttagcagt aacttcaatt ttaacaaaat tgggacccaa tagccagcat gagggttctt    5259
tgacagaggg tagtttctct ctccctttct ccatccttca aatgacaaga cgtcaaaact    5319
aatacagttc atttgcagtc catctcatgc ttatacatac tagaggtatg actaaagttg    5379
gttgagtcat gggagaccat ccctgagaaa gtccagtcgg tcaagagcct tgccaggtgg    5439
cgtggctgga cgtcctcctt tgttcctgc actgaggaat agtttataggt tatgtgaccc    5499
cacttcacag gcaagtggga ggcgaacctt gcaggcatgc cccttaaaag ctggtctcag    5559
acctacaata gtcctgagtc tgttttccca gcacacagag agcaacaatg cagttttcca    5619
tttcaaaata tgcatgccga gtttgcgctc tgtgtgagtg tttccaggtt acacatatgg    5679
gatgacatca cagaaaccac acaagcaaca aattaaattc tacgggaaga aatcctcctg    5739
actggtctct gaggagacat ttttatgcct tcttaacttt attaggaact ctcaggctga    5799
agctaggggt cattgtcccc caacaaatca atacaaagcc atcaatgnac tctcgaagaa    5859
ctgccaaacc ctgatctgtg tgaatgttct caggagcctg tgatccccat ggtgctanaa    5919
agaggctgga gctgggccaa caagaaggcc taagagtcct cctgcctctc agcagatgtt    5979
tactgagcac tctgagccag aagcaccccg acaaccagga ggacgatngc tgggcagtag    6039
ggcgcccagc cacttgcagc tctttcctct gaggcccgct ttgtgttta attcccttct     6099
gtcaggcccc aancagngga cactgtccta tagacctccc tctnagtttt cagacggcct    6159
aagccataca caaatgcccc agactaagaa acaccaatac ntcccagcag tccccaagaa    6219
ctggttttta aacactatga caagtagaag agggtgtcac agaggccatt tttttttctt    6279
tctttccact catactggaa cctaggtcct ctctctacac tcctagttcc tttacacaac    6339
tcggcagtgg ctccattaca ccaaggacac agaaaaacac aggtaccgat ttgccttcct    6399
ctcctgccaa tcacaagtgc cttactctga ccagacccat gacaaaacct ctgtcatcca    6459
agagagccaa ctctctacct ttgttactac ttcaagccaa tgtggtaact gctaaccttc    6519
```

-continued

```
aagggtcacc taaacagtat agtccaacct tcaccaggac catagcacag agcaacctcc    6579
agnacacaca cacacacaca ccttgaatct atcccacagc atatcaaccc acagtgacct    6639
ccctcccacc gccttgttct aattacaagg tgaagatggc catagaaaat caagttagca    6699
ctaattacaa aatgcttttg atgcaacctg aatttcccaa tggcacctat tgctttgaaa    6759
ctctgatgag ttaagtcatg ctctgggagc tgtgagcccc atgctcagat ccactgggca    6819
ggggggactc cttgcaggag acatgggcac acatatgaat gtaccatttc catgccttt     6879 gtggagtaca gacatataaa cataaatact tccatt                             6915
```

<210> SEQ ID NO 2
<211> LENGTH: 903
<212> TYPE: PRT
<213> ORGANISM: Unknown Organism
<220> FEATURE:
<223> OTHER INFORMATION: Description of Unknown Organism:
      JM109(pBSMel-alpha), mouse meltrin alpha

<400> SEQUENCE: 2

```
Met Ala Glu Arg Pro Ala Arg Arg Ala Pro Ala Arg Ala Leu Leu
 1               5                  10                  15

Leu Ala Leu Ala Gly Ala Leu Leu Ala Pro Arg Ala Ala Arg Gly Met
                20                  25                  30

Ser Leu Trp Asp Gln Arg Gly Ala Tyr Glu Val Ala Arg Ala Ser Leu
            35                  40                  45

Leu Ser Lys Asp Pro Gly Ile Pro Gly Gln Ser Ile Pro Ala Lys Asp
        50                  55                  60

His Pro Asp Val Leu Thr Val Gln Leu Gln Leu Glu Ser Arg Asp Leu
    65                  70                  75                  80

Ile Leu Ser Leu Glu Arg Asn Glu Gly Leu Ile Ala Asn Gly Phe Thr
                85                  90                  95

Glu Thr His Tyr Leu Gln Asp Gly Thr Asp Val Ser Leu Thr Arg Asn
            100                 105                 110

His Thr Asp His Cys Tyr Tyr His Gly His Val Gln Gly Asp Ala Ala
        115                 120                 125

Ser Val Val Ser Leu Ser Thr Cys Ser Asp Leu Arg Gly Leu Ile Met
    130                 135                 140

Phe Glu Asn Lys Thr Tyr Ser Leu Glu Pro Met Lys Asn Thr Thr Asp
145                 150                 155                 160

Ser Tyr Lys Leu Val Pro Ala Glu Ser Met Thr Asn Ile Gln Gly Leu
                165                 170                 175

Cys Gly Ser Gln His Asn Lys Ser Asn Leu Thr Met Glu Asp Val Ser
            180                 185                 190

Pro Gly Thr Ser Gln Met Arg Ala Arg Arg His Lys Arg Glu Thr Leu
        195                 200                 205

Lys Met Thr Lys Tyr Val Glu Leu Val Ile Val Ala Asp Asn Arg Glu
    210                 215                 220

Phe Gln Arg Gln Gly Lys Asp Leu Glu Lys Val Lys Gln Arg Leu Ile
225                 230                 235                 240

Glu Ile Ala Asn His Val Asp Lys Phe Tyr Arg Pro Leu Asn Ile Arg
                245                 250                 255

Ile Val Leu Val Gly Val Glu Val Trp Asn Asp Ile Asp Lys Cys Ser
            260                 265                 270

Ile Ser Gln Asp Pro Phe Thr Arg Leu His Glu Phe Leu Asp Trp Arg
        275                 280                 285
```

-continued

```
Lys Ile Lys Leu Leu Pro Arg Lys Ser His Asp Asn Ala Gln Leu Ile
    290                 295                 300

Ser Gly Val Tyr Phe Gln Gly Thr Thr Ile Gly Met Ala Pro Ile Met
305                 310                 315                 320

Ser Met Cys Thr Ala Glu Gln Ser Gly Gly Val Val Met Asp His Ser
                325                 330                 335

Asp Ser Pro Leu Gly Ala Ala Val Thr Leu Ala His Glu Leu Gly His
            340                 345                 350

Asn Phe Gly Met Asn His Asp Thr Leu Glu Arg Gly Cys Ser Cys Arg
        355                 360                 365

Met Ala Ala Glu Lys Gly Gly Cys Ile Met Asn Pro Ser Thr Gly Phe
    370                 375                 380

Pro Phe Pro Met Val Phe Ser Ser Cys Ser Arg Lys Asp Leu Glu Ala
385                 390                 395                 400

Ser Leu Glu Lys Gly Met Gly Met Cys Leu Phe Asn Leu Pro Glu Val
                405                 410                 415

Lys Gln Ala Phe Gly Gly Arg Lys Cys Gly Asn Gly Tyr Val Glu Glu
            420                 425                 430

Gly Glu Glu Cys Asp Cys Gly Glu Pro Glu Glu Cys Thr Asn Arg Cys
        435                 440                 445

Cys Asn Ala Thr Thr Cys Thr Leu Lys Pro Asp Ala Val Cys Ala His
    450                 455                 460

Gly Gln Cys Cys Glu Asp Cys Gln Leu Lys Pro Pro Gly Thr Ala Cys
465                 470                 475                 480

Arg Gly Ser Ser Asn Ser Cys Asp Leu Pro Glu Phe Cys Thr Gly Thr
                485                 490                 495

Ala Pro His Cys Pro Ala Asn Val Tyr Leu His Asp Gly His Pro Cys
            500                 505                 510

Gln Gly Val Asp Gly Tyr Cys Tyr Asn Gly Ile Cys Gln Thr His Glu
        515                 520                 525

Gln Gln Cys Val Thr Leu Trp Gly Pro Gly Ala Lys Pro Ala Pro Gly
    530                 535                 540

Ile Cys Phe Glu Arg Val Asn Ser Ala Gly Asp Pro Tyr Gly Asn Cys
545                 550                 555                 560

Gly Lys Asp Ser Lys Ser Ala Phe Ala Lys Cys Glu Leu Arg Asp Ala
                565                 570                 575

Lys Cys Gly Lys Ile Gln Cys Gln Gly Gly Ala Ser Arg Pro Val Ile
            580                 585                 590

Gly Thr Asn Ala Val Ser Ile Glu Thr Asn Ile Pro Gln Gln Glu Gly
        595                 600                 605

Gly Arg Ile Leu Cys Arg Gly Thr His Val Tyr Leu Gly Asp Asp Met
    610                 615                 620

Pro Asp Pro Gly Leu Val Leu Ala Gly Thr Lys Cys Ala Glu Gly Lys
625                 630                 635                 640

Ile Cys Leu Asn Arg Arg Cys Gln Asn Ile Ser Val Phe Gly Val His
                645                 650                 655

Lys Cys Ala Met Gln Cys His Gly Arg Gly Val Cys Asn Asn Arg Lys
            660                 665                 670

Asn Cys His Cys Glu Ala His Trp Ala Pro Pro Phe Cys Asp Lys Phe
        675                 680                 685

Gly Phe Gly Gly Ser Thr Asp Ser Gly Pro Ile Arg Gln Ala Asp Asn
    690                 695                 700

Gln Gly Leu Thr Val Gly Ile Leu Val Ser Ile Leu Cys Leu Leu Ala
```

```
                            705                 710                 715                 720
                       Ala Gly Phe Val Val Tyr Leu Lys Arg Lys Thr Leu Met Arg Leu Leu
                                           725                 730                 735
                       Phe Thr His Lys Lys Thr Thr Met Glu Lys Leu Arg Cys Val His Pro
                                       740                 745                 750
                       Ser Arg Thr Pro Ser Gly Pro His Leu Gly Gln Ala His His Thr Pro
                                   755                 760                 765
                       Gly Lys Gly Leu Leu Met Asn Arg Ala Pro His Phe Asn Thr Pro Lys
                               770                 775                 780
                       Asp Arg His Ser Leu Lys Cys Gln Asn Met Asp Ile Ser Arg Pro Leu
                       785                 790                 795                 800
                       Asp Ala Arg Ala Val Pro Gln Leu Gln Ser Pro Gln Arg Val Leu Leu
                                           805                 810                 815
                       Pro Leu His Gln Thr Pro Arg Ala Pro Ser Gly Pro Ala Arg Pro Leu
                                       820                 825                 830
                       Pro Ala Ser Pro Ala Val Arg Gln Ala Gln Gly Ile Arg Lys Pro Ser
                                   835                 840                 845
                       Pro Pro Gln Lys Pro Leu Pro Ala Asp Pro Leu Ser Arg Thr Ser Arg
                               850                 855                 860
                       Leu Thr Ser Ala Leu Val Arg Thr Pro Gly Gln Gln Glu Pro Gly His
                       865                 870                 875                 880
                       Arg Pro Ala Pro Ile Arg Pro Ala Pro Lys His Gln Val Pro Arg Pro
                                           885                 890                 895
                       Ser His Asn Ala Tyr Ile Lys
                                           900

<210> SEQ ID NO 3
<211> LENGTH: 6352
<212> TYPE: DNA
<213> ORGANISM: Unknown Organism
<220> FEATURE:
<223> OTHER INFORMATION: Description of Unknown Organism: Clone:
      JM109(pBSMel-beta), mouse beta meltrin
<221> NAME/KEY: CDS
<222> LOCATION: (63)..(2822)
<221> NAME/KEY: unsure
<222> LOCATION: (1782)..(2822)
<223> OTHER INFORMATION: Amino Acid "Xaa" unknown

<400> SEQUENCE: 3
ggccgggggc aggcaatggc agggatgtg tgattgcgga cagtgagagg gccgttgcta            60 tc atg ccc ggg cgc gcg ggc gtc gcc cgg ttc tgc ttg ctg gct ctc            107
   Met Pro Gly Arg Ala Gly Val Ala Arg Phe Cys Leu Leu Ala Leu
   1               5                   10                  15 gct ctg cag cta cat tgg ccg ctg gcg gcg tgc gag ccg gga tgg acc           155
Ala Leu Gln Leu His Trp Pro Leu Ala Ala Cys Glu Pro Gly Trp Thr
                20                  25                  30 aca aga gga agc caa gaa ggt agc cct ccg cta cag cat gaa ctc ata           203
Thr Arg Gly Ser Gln Glu Gly Ser Pro Pro Leu Gln His Glu Leu Ile
            35                  40                  45 ata cct cag tgg cgg act tca gaa agc cct ggg aga gga aag cat cca           251
Ile Pro Gln Trp Arg Thr Ser Glu Ser Pro Gly Arg Gly Lys His Pro
        50                  55                  60 ctc aga gca gag ctc agg gtc atg gct gaa ggg cga gag ctg atc cta           299
Leu Arg Ala Glu Leu Arg Val Met Ala Glu Gly Arg Glu Leu Ile Leu
    65                  70                  75 gac ctg gag aag aac gag cac ctt ttt gct cca gcc tac aca gaa acc           347
Asp Leu Glu Lys Asn Glu His Leu Phe Ala Pro Ala Tyr Thr Glu Thr
80                  85                  90                  95
```

-continued

| | |
|---|---|
| tgc tac act gca agt ggc aat cct caa acc agc acg ctg aag tct gag<br>Cys Tyr Thr Ala Ser Gly Asn Pro Gln Thr Ser Thr Leu Lys Ser Glu<br>                            100                        105                        110 | 395 |
| gat cac tgc ttt tac cac ggg act gtg agg gac gtg gat gag tcc agt<br>Asp His Cys Phe Tyr His Gly Thr Val Arg Asp Val Asp Glu Ser Ser<br>             115                        120                      125 | 443 |
| gtc acg ctc agc acc tgc cgg gga att aga gga ctg att ata gtg aga<br>Val Thr Leu Ser Thr Cys Arg Gly Ile Arg Gly Leu Ile Ile Val Arg<br>130                        135                      140 | 491 |
| agt aac ctc agc tac atc atc gag ccc gtc cct aac agc gac agc caa<br>Ser Asn Leu Ser Tyr Ile Ile Glu Pro Val Pro Asn Ser Asp Ser Gln<br>     145                      150                      155 | 539 |
| cac cgt att tac aga tcc gaa cat ctc acg ctg ccc ccg ggg aac tgt<br>His Arg Ile Tyr Arg Ser Glu His Leu Thr Leu Pro Pro Gly Asn Cys<br>160                        165                      170                      175 | 587 |
| ggg ttc gag cac tcc ggg ccc acc tcg aag gac tgg gcc ctt cag ttt<br>Gly Phe Glu His Ser Gly Pro Thr Ser Lys Asp Trp Ala Leu Gln Phe<br>             180                        185                      190 | 635 |
| aca cat cag acc aaa aag caa cct cgc aga atg aaa cgg gaa gat cta<br>Thr His Gln Thr Lys Lys Gln Pro Arg Arg Met Lys Arg Glu Asp Leu<br>               195                      200                      205 | 683 |
| cac tct atg aag tac gtg gag ctt tac ctg gtg gct gat tat gca gag<br>His Ser Met Lys Tyr Val Glu Leu Tyr Leu Val Ala Asp Tyr Ala Glu<br>210                        215                      220 | 731 |
| ttt cag aag aat cga cat gac cag gat gcc acc aaa cgc aag ctc atg<br>Phe Gln Lys Asn Arg His Asp Gln Asp Ala Thr Lys Arg Lys Leu Met<br>     225                      230                      235 | 779 |
| gag att gcc aac tat gtt gat aag ttt tac cgc tcc ctg aac atc cga<br>Glu Ile Ala Asn Tyr Val Asp Lys Phe Tyr Arg Ser Leu Asn Ile Arg<br>240                        245                      250                      255 | 827 |
| att gca ctt gtc ggc ttg gag gtg tgg acg cat ggg gat aag tgt gaa<br>Ile Ala Leu Val Gly Leu Glu Val Trp Thr His Gly Asp Lys Cys Glu<br>             260                        265                      270 | 875 |
| gtt tca gag aat ccc tac tct acc ctc tgg tcc ttt ctt agt tgg agg<br>Val Ser Glu Asn Pro Tyr Ser Thr Leu Trp Ser Phe Leu Ser Trp Arg<br>               275                      280                      285 | 923 |
| cgc aag ctg ctt gct cag aag agc cat gac aat gct cag cta atc acg<br>Arg Lys Leu Leu Ala Gln Lys Ser His Asp Asn Ala Gln Leu Ile Thr<br>                   290                      295                      300 | 971 |
| ggc agg tcc ttc caa ggc acc acc att ggc ctg gcc ccc ctc atg gcc<br>Gly Arg Ser Phe Gln Gly Thr Thr Ile Gly Leu Ala Pro Leu Met Ala<br>305                        310                      315 | 1019 |
| atg tgc tcc gtg tac cag tct gga gga gtt agc atg gac cac tcc gag<br>Met Cys Ser Val Tyr Gln Ser Gly Gly Val Ser Met Asp His Ser Glu<br>320                        325                      330                      335 | 1067 |
| aat gcc att ggt gta gcc tcc act gtg gcc cat gag att ggc cac aac<br>Asn Ala Ile Gly Val Ala Ser Thr Val Ala His Glu Ile Gly His Asn<br>             340                        345                      350 | 1115 |
| ttt ggc atg agc cat gat tct gca cac tgc tgt tct gcc agt gca gcc<br>Phe Gly Met Ser His Asp Ser Ala His Cys Cys Ser Ala Ser Ala Ala<br>               355                      360                      365 | 1163 |
| gat ggc ggc tgc atc atg gcc gcc gcc acc ggg cac cct ttc ccc aaa<br>Asp Gly Gly Cys Ile Met Ala Ala Ala Thr Gly His Pro Phe Pro Lys<br>370                        375                      380 | 1211 |
| gtg ttc agt tgg tgt aac agg aag gag ctg gac agg tat ctg cag aca<br>Val Phe Ser Trp Cys Asn Arg Lys Glu Leu Asp Arg Tyr Leu Gln Thr<br>385                        390                      395 | 1259 |
| gga gga ggg atg tgt ctc tcc aac atg ccg gac act agg acg ctg tat<br>Gly Gly Gly Met Cys Leu Ser Asn Met Pro Asp Thr Arg Thr Leu Tyr | 1307 |

```
                                        -continued
       400                 405                 410                 415
gga ggc cgg agg tgt ggc aac ggg tac ctg gaa gac ggt gaa gaa tgt        1355
Gly Gly Arg Arg Cys Gly Asn Gly Tyr Leu Glu Asp Gly Glu Glu Cys
                420                 425                 430 gac tgt gga gaa gag gag gaa tgt aag aac cct tgc tgc aat gcc tcc        1403
Asp Cys Gly Glu Glu Glu Glu Cys Lys Asn Pro Cys Cys Asn Ala Ser
                435                 440                 445 aac tgc act ctg aag gaa ggg gca gag tgt gcc cat ggt tcc tgc tgc        1451
Asn Cys Thr Leu Lys Glu Gly Ala Glu Cys Ala His Gly Ser Cys Cys
                450                 455                 460 cac cag tgc aag ctg gtg gct cct gga acc cag tgt cgg gag cag gtt        1499
His Gln Cys Lys Leu Val Ala Pro Gly Thr Gln Cys Arg Glu Gln Val
465                 470                 475 cgg caa tgt gac ctc ccc gag ttc tgc acc ggc aag tct ccc cac tgc        1547
Arg Gln Cys Asp Leu Pro Glu Phe Cys Thr Gly Lys Ser Pro His Cys
480                 485                 490                 495 ccc acc aac tat tat cag atg gat ggc acc ccc tgc gag ggt ggc cag        1595
Pro Thr Asn Tyr Tyr Gln Met Asp Gly Thr Pro Cys Glu Gly Gly Gln
                500                 505                 510 gcc tac tgc tac aac ggc atg tgc ctc act tac cag gaa cag tgc cag        1643
Ala Tyr Cys Tyr Asn Gly Met Cys Leu Thr Tyr Gln Glu Gln Cys Gln
                515                 520                 525 cag ctg tgg gga cct gga gcc cgg cct gcc ctc gat ctt tgc ttt gag        1691
Gln Leu Trp Gly Pro Gly Ala Arg Pro Ala Leu Asp Leu Cys Phe Glu
                530                 535                 540 agg gtg aat gct gct ggt gac acc tat gga aac tgt ggc aag ggc ttg        1739
Arg Val Asn Ala Ala Gly Asp Thr Tyr Gly Asn Cys Gly Lys Gly Leu
545                 550                 555 aat ggc caa tac agg aag tgc agt ccc agg gat gcc aag tgt ggs aag        1787
Asn Gly Gln Tyr Arg Lys Cys Ser Pro Arg Asp Ala Lys Cys Xaa Lys
560                 565                 570                 575 att cag tgc cag agc acc cag gcc cgg ccc ctg gaa tcc aac gca gta        1835
Ile Gln Cys Gln Ser Thr Gln Ala Arg Pro Leu Glu Ser Asn Ala Val
                580                 585                 590 tct att gac acc acc atc acc ttg aac ggg agg cgg atc cac tgt cgg        1883
Ser Ile Asp Thr Thr Ile Thr Leu Asn Gly Arg Arg Ile His Cys Arg
                595                 600                 605 ggc acc cac gtc tac cgg ggt cct gag gag gag gaa ggg gaa ggt gac        1931
Gly Thr His Val Tyr Arg Gly Pro Glu Glu Glu Glu Gly Glu Gly Asp
                610                 615                 620 atg ctg gac cca ggg ctg gtg atg act gga acc aag tgt ggc cac aac        1979
Met Leu Asp Pro Gly Leu Val Met Thr Gly Thr Lys Cys Gly His Asn
625                 630                 635 cat att tgc ttc gag ggg cag tgc agg aac acc tcc ttc ttt gag acg        2027
His Ile Cys Phe Glu Gly Gln Cys Arg Asn Thr Ser Phe Phe Glu Thr
640                 645                 650                 655 gaa ggc tgt ggg aaa aag tgc aat ggc cac ggg gtc tgc aac aac aac        2075
Glu Gly Cys Gly Lys Lys Cys Asn Gly His Gly Val Cys Asn Asn Asn
                660                 665                 670 aag aac tgt cat tgc ttc cct ggc tgg tct cca cct ttc tgt aac acc        2123
Lys Asn Cys His Cys Phe Pro Gly Trp Ser Pro Pro Phe Cys Asn Thr
                675                 680                 685 ccg gga gat ggt ggc agc gtc gac agt ggt cct ttg ccc cct aag agt        2171
Pro Gly Asp Gly Gly Ser Val Asp Ser Gly Pro Leu Pro Pro Lys Ser
                690                 695                 700 gtg ggt ccc gtg atc gct ggg gtg ttt tca gct ctc ttc gtg ttg gca        2219
Val Gly Pro Val Ile Ala Gly Val Phe Ser Ala Leu Phe Val Leu Ala
705                 710                 715 gtt ctg gtg cta ctg tgt cac tgc tac aga cag agc cac aaa ctg ggc        2267
```

```
Val Leu Val Leu Leu Cys His Cys Tyr Arg Gln Ser His Lys Leu Gly
720                 725                 730                 735 aaa ccc tcg gct ctc cct ttc aag ctg cgg cat cag ttc agt tgt ccc      2315
Lys Pro Ser Ala Leu Pro Phe Lys Leu Arg His Gln Phe Ser Cys Pro
                740                 745                 750 ttc agg gta tct cag agt ggt gga act ggc cat gcc aac cca act ttc      2363
Phe Arg Val Ser Gln Ser Gly Gly Thr Gly His Ala Asn Pro Thr Phe
                755                 760                 765 aag ttg cag acc ccc cag ggc aag cga aag gtg act aac acc cct gaa      2411
Lys Leu Gln Thr Pro Gln Gly Lys Arg Lys Val Thr Asn Thr Pro Glu
                770                 775                 780 tcc ctc cgg aag ccg tcc cac ccc cct ctc cgg ccc cct cca gac tac      2459
Ser Leu Arg Lys Pro Ser His Pro Pro Leu Arg Pro Pro Pro Asp Tyr
785                 790                 795 ctg cgc gtt gaa tcg cca cct gca cca ttg tcg gca cat ctg aac agg      2507
Leu Arg Val Glu Ser Pro Pro Ala Pro Leu Ser Ala His Leu Asn Arg
800                 805                 810                 815 gct gct ggg agc tcc cca gaa gct ggg gct cga ata gaa aga aag gag      2555
Ala Ala Gly Ser Ser Pro Glu Ala Gly Ala Arg Ile Glu Arg Lys Glu
                820                 825                 830 tca gcc agg agg cct ccc cca agc cga ccc atg ccc cct gca cct aac      2603
Ser Ala Arg Arg Pro Pro Pro Ser Arg Pro Met Pro Pro Ala Pro Asn
                835                 840                 845 tgc cta ctg tcc cag gac ttc tcc agg cct cga cca cct cag aag gca      2651
Cys Leu Leu Ser Gln Asp Phe Ser Arg Pro Arg Pro Pro Gln Lys Ala
                850                 855                 860 ctc cca gcc aat ccg gtg cca ggc caa agg acc ggt ccc agg tca gga      2699
Leu Pro Ala Asn Pro Val Pro Gly Gln Arg Thr Gly Pro Arg Ser Gly
865                 870                 875 ggc acc tcc ctg ctt cag ccc cct act tct ggt cct cag ccc ccc agg      2747
Gly Thr Ser Leu Leu Gln Pro Pro Thr Ser Gly Pro Gln Pro Pro Arg
880                 885                 890                 895 cct cca gca gtg cct gtt cca aag cta ccc gag tac cga tca cag agg      2795
Pro Pro Ala Val Pro Val Pro Lys Leu Pro Glu Tyr Arg Ser Gln Arg
                900                 905                 910 gtt gga gca ata att agc tcc aag atc tagaagtgtc gagaagtttc            2842
Val Gly Ala Ile Ile Ser Ser Lys Ile
                915                 920 ttgttccgat ggaagactcc ggatgccatg gaaggtccag aagaaagacg ccttctcacc    2902
catcctgaag ctttggcagc cttctggaac gtccctcatc cccagaatct cccttcttac    2962
ccgagtgcct cctgcttcct ccgaggccca gggggactca tatccaatgg ctcctaagtg    3022
tttgtcctgt gcaatataca gcccagggag ggaagggaag cacggcgagg agggtgggaa    3082
aggttctccc tcagcccact agccaagagc taccagcgat gctcagggaa ggcttgagct    3142
ggggtcctcc tctgcggagc ttggagaagg tacccatcct ggtcctatgc tggcaggaac    3202
acacgcgagt gtcactgatt ggcctccttc tgggatccca ggctgctgag gaagctactg    3262
ctacatccct accccaaggg gcttggtcaa ggtgcctgty cctggctctc tggctgcatg    3322
taataagcca tgctcccctc ccctgccttt cttcacattc ccactcccat atttacacgg    3382
gtcactctga ctcagacagg tactatttgt aagtagcata gacagcaggg gggtgggtg     3442 gtcaacctgt gtccctctg agccgttatg ccaaaggtca ctaaggacat ttagaatccc     3502
catccatcca tccatccatc catccatcca tccattcatc catccccagt gttccatgtg    3562
tcaccttctc cttttccagc atccctatcc tatggtgctt tggtggtgaa ctatggcagt    3622
cctgacttgc tgatgaccat atgctggtga cctacaaatc gggatcctgc catatgggt     3682
```

```
cgccactgga ctttctgcac tggttctcaa gagcgttgag ccgagtgggc gtgtatgttt    3742
gtgtgtgtgt gtgtgtgtgt gtgtgtgtgt gtgtgtgtgt gtgtgtgtgt gtgtgtgtgt    3802
gaaagagaca gaggcaatga gagagacaga catgcaggca ggccgacagc tctgcatgta    3862
cttgtgtttt acggcctcaa gcagtataag ggacctcctc cttatttctg actcatatct    3922
aagtaaggtt ccccaggacm agccacagct gtactgaggg gggctgacat gtttggcatc    3982
ctggctatag tattgtatac acagggccac cagccccgcc ctagtggtca gctctgaggg    4042
gggactggtg actctgaaca gatcgatgtc aacagccatg gtgaaccaga tctgggcagg    4102 gttcccaaa ctctattcaa ccagagtttt atcacgcanc tcatcgggtc tctcctggtt    4162
gctgccccga ggtgatcgtc atggaaaatg ctgagaaggt gggaatggga tggggtggac    4222
cttctcttgc ttggtgctcc gctatttgga acagttctta cacatttgct gggcctggcc    4282
tctgagaggc catcttccac ccccagaaag gtgctaatgg cactgcagag ggctctctag    4342
gggcctcccc gccccaacag caagcagttg ttagctcttg gaaccctcca gaggaagagg    4402
caagcgtttg acttccccctt taccacctga ggcctcctta tatctcttcc cagagtaagc    4462
tttgggattg tagacatgtg ggagctatga cagacgtggc ctggggtaga aagatctcag    4522
gaaagcacct ttctcctttt cagggtgacc gtgctcttca cactctctga ggcctcagtc    4582
catgtcctat atcagtttct cttttgtgtg ctttaccaag tggccggtga ctacaggcca    4642
ccccgattct caccacaaag ttagaaaccc tccactttct gtcccttgaa ccatatcaga    4702
aaaagaccca tttccttgct cttttggtaat cacttctgtt ttttcttctt cattactgtg    4762
ctaccacctc catcccatga cattattctg tgangtgtaa gaggacggtg ttttnttant    4822
cttgggagan atgtcggcag ctgctctaca cacaacttca ctcaaggctt tgtctccaga    4882
ggccagctag gctgtcacag gcaggaatcc cttcccatct gctttgtgaa gggtcccata    4942
caggtgtatc tagacttcaa ggacagggtt tgtctcacag gattgtcact taggagatga    5002
aagaatatta ccacatgagg aggaggggca gttgcaacag aacactttgg tcttcctaca    5062
ccaagtctgt gagggcatcc aagactgaat gaaagcgctt ttcttatgca tacaatgtga    5122
gcaagaacaa gaactgttta aggcacctct gttcccagcc actgaagaga gacgtcagaa    5182
gatgttagaa taggtcaaaa ccaaggctct ggtggactga gggaaggttt gtagctgcgt    5242
ttagtggtat acatctttag tcccagcata ggcaggtgaa tctcgagttt gaagctagcc    5302
tggtctaaaa aggaagttcc aagactgcca gggccacaca gaggaaaaaa aaaaaccctc    5362
tagaaaaaca aaaatgaaga caggttctca tgtatcgtag attggccttt aagtcacttt    5422
accaaggatg atctttgaac tcctgagtac agactgcggg tgtgtgctac catgctttat    5482
gtggccctgg gttcaaacac agcccttcat atgtatatag ccaaacactc tacaactgag    5542
ctacatcctc cagcctaggc tgtaaatgtt ttttggagct agattagctg cctgccaacc    5602
ttagaactgc aaagccattc ctgacctgta aacctcagct ctccatctct ataagaggta    5662
tagcctgggc taataccgtc caagttacaa ctccttgctt gctttctgtt ccttctagcc    5722
ttggtgactt ccaccaggaa gagaataccc cctctctacc cctgctccaa gacactgtag    5782
atgctagtgt cggagtgttc tctgtaacgc gacagttcct tctgttgcaa tagcccccct    5842
gcaacactgc aataatcctt cagtgtctcc cctgggctca attcacttcc ttatttgaca    5902
aagtggaggt gagacttgta ttcttaaaat tggaggctag ttattttgtc aaatgcatgt    5962
aatgaacaga cccgaaggaa tcctccacac acaagccagg gaacaccaac tggaaaggta    6022
ccccgtccca gggaagcctg ctagggagag gttctgtaga atccgagcct agcaccccaa    6082
```

-continued

```
agtcatgcac ccagtatcct cttgtatgac tgtatatgtc tatgtctggg atccagggca    6142
aatgtgaatt tccttttgat ttgggagatt gttcacagga agtagtcctc ccctctcatg    6202
tcctcctatt gattgtttac aatatttgta catctatgca aaatacttga atgggccatg    6262
gtgccttgtt ttttgttgtt gttgttattt ttttctcctt gtttgtattt aattaaaaca    6322
aattgtcatg aggaaaaaaa aaaaaaaaaa                                      6352
```

<210> SEQ ID NO 4
<211> LENGTH: 920
<212> TYPE: PRT
<213> ORGANISM: Unknown Organism
<220> FEATURE:
<223> OTHER INFORMATION: Description of Unknown Organism: Clone:
      JM109(pBSMel-beta), mouse beta meltrin
<221> NAME/KEY: Unsure
<222> LOCATION: 574
<223> OTHER INFORMATION: Amino acid "Xaa" is unknown

<400> SEQUENCE: 4

```
Met Pro Gly Arg Ala Gly Val Ala Arg Phe Cys Leu Leu Ala Leu Ala
1               5                   10                  15

Leu Gln Leu His Trp Pro Leu Ala Ala Cys Glu Pro Gly Trp Thr Thr
            20                  25                  30

Arg Gly Ser Gln Glu Gly Ser Pro Pro Leu Gln His Glu Leu Ile Ile
        35                  40                  45

Pro Gln Trp Arg Thr Ser Glu Ser Pro Gly Arg Gly Lys His Pro Leu
    50                  55                  60

Arg Ala Glu Leu Arg Val Met Ala Glu Gly Arg Glu Leu Ile Leu Asp
65                  70                  75                  80

Leu Glu Lys Asn Glu His Leu Phe Ala Pro Ala Tyr Thr Glu Thr Cys
                85                  90                  95

Tyr Thr Ala Ser Gly Asn Pro Gln Thr Ser Thr Leu Lys Ser Glu Asp
            100                 105                 110

His Cys Phe Tyr His Gly Thr Val Arg Asp Val Asp Glu Ser Ser Val
        115                 120                 125

Thr Leu Ser Thr Cys Arg Gly Ile Arg Gly Leu Ile Ile Val Arg Ser
    130                 135                 140

Asn Leu Ser Tyr Ile Ile Glu Pro Val Pro Asn Ser Asp Ser Gln His
145                 150                 155                 160

Arg Ile Tyr Arg Ser Glu His Leu Thr Leu Pro Pro Gly Asn Cys Gly
                165                 170                 175

Phe Glu His Ser Gly Pro Thr Ser Lys Asp Trp Ala Leu Gln Phe Thr
            180                 185                 190

His Gln Thr Lys Lys Gln Pro Arg Arg Met Lys Arg Glu Asp Leu His
        195                 200                 205

Ser Met Lys Tyr Val Glu Leu Tyr Leu Val Ala Asp Tyr Ala Glu Phe
    210                 215                 220

Gln Lys Asn Arg His Asp Gln Asp Ala Thr Lys Arg Lys Leu Met Glu
225                 230                 235                 240

Ile Ala Asn Tyr Val Asp Lys Phe Tyr Arg Ser Leu Asn Ile Arg Ile
                245                 250                 255

Ala Leu Val Gly Leu Glu Val Trp Thr His Gly Asp Lys Cys Glu Val
            260                 265                 270

Ser Glu Asn Pro Tyr Ser Thr Leu Trp Ser Phe Leu Ser Trp Arg Arg
        275                 280                 285
```

-continued

```
Lys Leu Leu Ala Gln Lys Ser His Asp Asn Ala Gln Leu Ile Thr Gly
    290                 295                 300
Arg Ser Phe Gln Gly Thr Thr Ile Gly Leu Ala Pro Leu Met Ala Met
305                 310                 315                 320
Cys Ser Val Tyr Gln Ser Gly Val Ser Met Asp His Ser Glu Asn
                    325                 330                 335
Ala Ile Gly Val Ala Ser Thr Val Ala His Glu Ile Gly His Asn Phe
                340                 345                 350
Gly Met Ser His Asp Ser Ala His Cys Cys Ser Ala Ser Ala Ala Asp
            355                 360                 365
Gly Gly Cys Ile Met Ala Ala Ala Thr Gly His Pro Phe Pro Lys Val
    370                 375                 380
Phe Ser Trp Cys Asn Arg Lys Glu Leu Asp Arg Tyr Leu Gln Thr Gly
385                 390                 395                 400
Gly Gly Met Cys Leu Ser Asn Met Pro Asp Thr Arg Thr Leu Tyr Gly
                    405                 410                 415
Gly Arg Arg Cys Gly Asn Gly Tyr Leu Glu Asp Gly Glu Glu Cys Asp
                420                 425                 430
Cys Gly Glu Glu Glu Cys Lys Asn Pro Cys Cys Asn Ala Ser Asn
            435                 440                 445
Cys Thr Leu Lys Glu Gly Ala Glu Cys Ala His Gly Ser Cys Cys His
    450                 455                 460
Gln Cys Lys Leu Val Ala Pro Gly Thr Gln Cys Arg Glu Gln Val Arg
465                 470                 475                 480
Gln Cys Asp Leu Pro Glu Phe Cys Thr Gly Lys Ser Pro His Cys Pro
                    485                 490                 495
Thr Asn Tyr Tyr Gln Met Asp Gly Thr Pro Cys Glu Gly Gly Gln Ala
                500                 505                 510
Tyr Cys Tyr Asn Gly Met Cys Leu Thr Tyr Gln Glu Gln Cys Gln Gln
            515                 520                 525
Leu Trp Gly Pro Gly Ala Arg Pro Ala Leu Asp Leu Cys Phe Glu Arg
    530                 535                 540
Val Asn Ala Ala Gly Asp Thr Tyr Gly Asn Cys Gly Lys Gly Leu Asn
545                 550                 555                 560
Gly Gln Tyr Arg Lys Cys Ser Pro Arg Asp Ala Lys Cys Xaa Lys Ile
                    565                 570                 575
Gln Cys Gln Ser Thr Gln Ala Arg Pro Leu Glu Ser Asn Ala Val Ser
                580                 585                 590
Ile Asp Thr Thr Ile Thr Leu Asn Gly Arg Arg Ile His Cys Arg Gly
            595                 600                 605
Thr His Val Tyr Arg Gly Pro Glu Glu Glu Gly Glu Gly Asp Met
    610                 615                 620
Leu Asp Pro Gly Leu Val Met Thr Gly Thr Lys Cys Gly His Asn His
625                 630                 635                 640
Ile Cys Phe Glu Gly Gln Cys Arg Asn Thr Ser Phe Glu Thr Glu
                    645                 650                 655
Gly Cys Gly Lys Lys Cys Asn Gly His Gly Val Cys Asn Asn Asn Lys
                660                 665                 670
Asn Cys His Cys Phe Pro Gly Trp Ser Pro Pro Phe Cys Asn Thr Pro
            675                 680                 685
Gly Asp Gly Gly Ser Val Asp Ser Gly Pro Leu Pro Pro Lys Ser Val
    690                 695                 700
Gly Pro Val Ile Ala Gly Val Phe Ser Ala Leu Phe Val Leu Ala Val
```

```
                  705                 710                 715                 720
    Leu Val Leu Leu Cys His Cys Tyr Arg Gln Ser His Lys Leu Gly Lys
                    725                 730                 735

Pro Ser Ala Leu Pro Phe Lys Leu Arg His Gln Phe Ser Cys Pro Phe
                    740                 745                 750

Arg Val Ser Gln Ser Gly Gly Thr Gly His Ala Asn Pro Thr Phe Lys
                    755                 760                 765

Leu Gln Thr Pro Gln Gly Lys Arg Lys Val Thr Asn Thr Pro Glu Ser
                    770                 775                 780

Leu Arg Lys Pro Ser His Pro Pro Leu Arg Pro Pro Asp Tyr Leu
    785                 790                 795                 800

Arg Val Glu Ser Pro Ala Pro Leu Ser Ala His Leu Asn Arg Ala
                    805                 810                 815

Ala Gly Ser Ser Pro Glu Ala Gly Arg Ile Glu Arg Lys Glu Ser
                    820                 825                 830

Ala Arg Arg Pro Pro Pro Ser Arg Pro Met Pro Ala Pro Asn Cys
                    835                 840                 845

Leu Leu Ser Gln Asp Phe Ser Arg Pro Arg Pro Gln Lys Ala Leu
        850                 855                 860

Pro Ala Asn Pro Val Pro Gly Gln Arg Thr Gly Pro Arg Ser Gly
    865                 870                 875                 880

Thr Ser Leu Leu Gln Pro Pro Thr Ser Gly Pro Gln Pro Arg Pro
                    885                 890                 895

Pro Ala Val Pro Val Pro Lys Leu Pro Glu Tyr Arg Ser Gln Arg Val
                    900                 905                 910

Gly Ala Ile Ile Ser Ser Lys Ile
                    915                 920

<210> SEQ ID NO 5
<211> LENGTH: 3931
<212> TYPE: DNA
<213> ORGANISM: Unknown Organism
<220> FEATURE:
<223> OTHER INFORMATION: Description of Unknown Organism: Clone,
      JM109(pBSMel-gamma), mouse meltrin gamma
<221> NAME/KEY: CDS
<222> LOCATION: (69)..(2603)

<400> SEQUENCE: 5
gttgcaagga tgaccgaagn ncggaggcgg cggccgcgcg ttgagcggaa cctgccgaag        60 ccctcgct atg ggg ccg cgc gcg ctc tcg ccc ctt gcc tct ctg cga cta       110
         Met Gly Pro Arg Ala Leu Ser Pro Leu Ala Ser Leu Arg Leu
           1               5                  10 agg tgg ctg ctg gcg tgt ggc ttg ctg ggc cca gtc ctc gag gcc ggg       158
Arg Trp Leu Leu Ala Cys Gly Leu Leu Gly Pro Val Leu Glu Ala Gly
 15                  20                  25                  30 cga cca gac ttg gaa cag act gtc cat ctt tct tct tat gaa att att       206
Arg Pro Asp Leu Glu Gln Thr Val His Leu Ser Ser Tyr Glu Ile Ile
                 35                  40                  45 act cct tgg aga tta act aga gaa aga agg gaa gct ctg ggg ccc agt       254
Thr Pro Trp Arg Leu Thr Arg Glu Arg Arg Glu Ala Leu Gly Pro Ser
             50                  55                  60 tca cag cag atc tct tac gtc atc cag gcc caa gga aaa cag cat att       302
Ser Gln Gln Ile Ser Tyr Val Ile Gln Ala Gln Gly Lys Gln His Ile
         65                  70                  75 att cac ttg gaa aga aac aca gac ctt tta cct aat gat ttt gta gtt       350
Ile His Leu Glu Arg Asn Thr Asp Leu Leu Pro Asn Asp Phe Val Val
     80                  85                  90
```

```
tac acc tac gac aag gaa ggc tcc cta ctc tct gac cat ccc aac gta    398
Tyr Thr Tyr Asp Lys Glu Gly Ser Leu Leu Ser Asp His Pro Asn Val
 95                 100                 105                 110 cag agc cat tgt cac tat cga ggc tat gtg gag gga gtg cag aat tcc    446
Gln Ser His Cys His Tyr Arg Gly Tyr Val Glu Gly Val Gln Asn Ser
                115                 120                 125 gcg gtt gct gtg agc gcc tgc ttt gga ctc aga ggc ttg ctc cat ttg    494
Ala Val Ala Val Ser Ala Cys Phe Gly Leu Arg Gly Leu Leu His Leu
        130                 135                 140 gag aat gcc agt ttt gga att gaa cct ctg cac aac agc tca cac ttt    542
Glu Asn Ala Ser Phe Gly Ile Glu Pro Leu His Asn Ser Ser His Phe
145                 150                 155 gag cac ata ttt tac ccc atg gat ggc atc cac cag gag cct ctg aga    590
Glu His Ile Phe Tyr Pro Met Asp Gly Ile His Gln Glu Pro Leu Arg
    160                 165                 170 tgt gga gtc tct aac agg gac aca gag aag gaa ggc aca cag ggg gat    638
Cys Gly Val Ser Asn Arg Asp Thr Glu Lys Glu Gly Thr Gln Gly Asp
175                 180                 185                 190 gag gag gag cat ccg agt gtc act cag ctg ctg cgc aga aga aga gct    686
Glu Glu Glu His Pro Ser Val Thr Gln Leu Leu Arg Arg Arg Arg Ala
                195                 200                 205 gtt cta cca cag acc cgc tat gtg gag ctg ttc att gtt gta gac aag    734
Val Leu Pro Gln Thr Arg Tyr Val Glu Leu Phe Ile Val Val Asp Lys
        210                 215                 220 gaa agg tac gac atg atg gga cgg aac cag act gct gtg aga gaa gag    782
Glu Arg Tyr Asp Met Met Gly Arg Asn Gln Thr Ala Val Arg Glu Glu
                225                 230                 235 atg att cgc tta gca aac tac ctg gat agc atg tac atc atg tta aac    830
Met Ile Arg Leu Ala Asn Tyr Leu Asp Ser Met Tyr Ile Met Leu Asn
240                 245                 250 att cga att gtg ctg gtt gga cta gaa att tgg aca gac aga aat cct    878
Ile Arg Ile Val Leu Val Gly Leu Glu Ile Trp Thr Asp Arg Asn Pro
255                 260                 265                 270 atc aat ata att gga gga gct gga gat gtg ctg ggc aac ttt gtt cag    926
Ile Asn Ile Ile Gly Gly Ala Gly Asp Val Leu Gly Asn Phe Val Gln
                275                 280                 285 tgg cgg gaa aag ttc ctt ata act cgt cgg aga cac gac agt gca cag    974
Trp Arg Glu Lys Phe Leu Ile Thr Arg Arg Arg His Asp Ser Ala Gln
        290                 295                 300 ttg gtt ttg aag aaa ggc ttt ggt gga act gca gga atg gcg ttt gta   1022
Leu Val Leu Lys Lys Gly Phe Gly Gly Thr Ala Gly Met Ala Phe Val
                305                 310                 315 gga aca gta tgt tca agg agc cac gca ggt ggg atc aat gtg ttt ggg   1070
Gly Thr Val Cys Ser Arg Ser His Ala Gly Gly Ile Asn Val Phe Gly
320                 325                 330 caa atc act gtg gag aca ttt gca tcc att gtt gct cat gaa ttg ggg   1118
Gln Ile Thr Val Glu Thr Phe Ala Ser Ile Val Ala His Glu Leu Gly
335                 340                 345                 350 cat aac ctt gga atg aat cat gat gat ggg aga gag tgt ttc tgt gga   1166
His Asn Leu Gly Met Asn His Asp Asp Gly Arg Glu Cys Phe Cys Gly
                355                 360                 365 gca aag agc tgt atc atg aat tca gga gca tcc ggg tcc aga aac ttt   1214
Ala Lys Ser Cys Ile Met Asn Ser Gly Ala Ser Gly Ser Arg Asn Phe
        370                 375                 380 agc agt tgc agt gcg gag gac ttt gag aag tta acg ttg aat aag gga   1262
Ser Ser Cys Ser Ala Glu Asp Phe Glu Lys Leu Thr Leu Asn Lys Gly
                385                 390                 395 gga agc tgc ctg ctt aac atc ccg aag cct gac gaa gcc tac agc gcg   1310
Gly Ser Cys Leu Leu Asn Ile Pro Lys Pro Asp Glu Ala Tyr Ser Ala
```

-continued

| | | | | | | | | | | | | | | | | |
|---|---|---|---|---|---|---|---|---|---|---|---|---|---|---|---|---|
| | | 400 | | | | | 405 | | | | | 410 | | | | |
| ccc | tcc | tgt | ggt | aat | aag | ctg | gtg | gac | cct | gga | gag | gag | tgt | gac | tgc | 1358 |
| Pro | Ser | Cys | Gly | Asn | Lys | Leu | Val | Asp | Pro | Gly | Glu | Glu | Cys | Asp | Cys | |
| 415 | | | | | 420 | | | | | 425 | | | | | 430 | |
| ggc | aca | gcg | aag | gag | tgt | gag | gtg | gac | cca | tgc | tgt | gaa | gga | agc | act | 1406 |
| Gly | Thr | Ala | Lys | Glu | Cys | Glu | Val | Asp | Pro | Cys | Cys | Glu | Gly | Ser | Thr | |
| | | | | 435 | | | | | 440 | | | | | 445 | | |
| tgt | aag | ctc | aag | tca | ttt | gct | gag | tgt | gca | tat | ggc | gac | tgt | tgt | aaa | 1454 |
| Cys | Lys | Leu | Lys | Ser | Phe | Ala | Glu | Cys | Ala | Tyr | Gly | Asp | Cys | Cys | Lys | |
| | | | 450 | | | | | 455 | | | | | 460 | | | |
| gat | tgc | cag | ttc | ctt | cca | gga | ggc | tcc | atg | tgc | aga | ggg | aag | acc | agt | 1502 |
| Asp | Cys | Gln | Phe | Leu | Pro | Gly | Gly | Ser | Met | Cys | Arg | Gly | Lys | Thr | Ser | |
| | | 465 | | | | | 470 | | | | | 475 | | | | |
| gag | tgt | gat | gtt | cct | gag | tac | tgc | aac | ggt | tcc | tct | cag | ttc | tgc | ccg | 1550 |
| Glu | Cys | Asp | Val | Pro | Glu | Tyr | Cys | Asn | Gly | Ser | Ser | Gln | Phe | Cys | Pro | |
| | 480 | | | | | 485 | | | | | 490 | | | | | |
| cca | gat | gtc | ttc | att | cag | aat | gga | tat | cct | tgc | cag | aac | agc | aaa | gcc | 1598 |
| Pro | Asp | Val | Phe | Ile | Gln | Asn | Gly | Tyr | Pro | Cys | Gln | Asn | Ser | Lys | Ala | |
| 495 | | | | | 500 | | | | | 505 | | | | | 510 | |
| tac | tgc | tac | aat | ggc | atg | tgc | caa | tat | tat | gac | gcg | cag | tgt | cag | gtc | 1646 |
| Tyr | Cys | Tyr | Asn | Gly | Met | Cys | Gln | Tyr | Tyr | Asp | Ala | Gln | Cys | Gln | Val | |
| | | | | 515 | | | | | 520 | | | | | 525 | | |
| atc | ttt | ggt | tca | aag | gct | aag | gct | gcc | cca | aga | gat | tgc | ttc | att | gaa | 1694 |
| Ile | Phe | Gly | Ser | Lys | Ala | Lys | Ala | Ala | Pro | Arg | Asp | Cys | Phe | Ile | Glu | |
| | | | 530 | | | | | 535 | | | | | 540 | | | |
| gtc | aat | tct | aaa | ggt | gac | aga | ttt | ggc | aac | tgt | ggt | ttc | tcc | ggc | agt | 1742 |
| Val | Asn | Ser | Lys | Gly | Asp | Arg | Phe | Gly | Asn | Cys | Gly | Phe | Ser | Gly | Ser | |
| | | 545 | | | | | 550 | | | | | 555 | | | | |
| gag | tac | aag | aag | tgt | gcc | act | ggg | aac | gcg | ctg | tgt | gga | aag | ctt | caa | 1790 |
| Glu | Tyr | Lys | Lys | Cys | Ala | Thr | Gly | Asn | Ala | Leu | Cys | Gly | Lys | Leu | Gln | |
| | 560 | | | | | 565 | | | | | 570 | | | | | |
| tgc | gag | aat | gta | cag | gac | atg | ccg | gtg | ttt | gga | ata | gta | cca | gct | atc | 1838 |
| Cys | Glu | Asn | Val | Gln | Asp | Met | Pro | Val | Phe | Gly | Ile | Val | Pro | Ala | Ile | |
| 575 | | | | | 580 | | | | | 585 | | | | | 590 | |
| att | cag | aca | ccc | agt | cga | ggc | acc | aaa | tgc | tgg | ggt | gtg | gat | ttc | cag | 1886 |
| Ile | Gln | Thr | Pro | Ser | Arg | Gly | Thr | Lys | Cys | Trp | Gly | Val | Asp | Phe | Gln | |
| | | | | 595 | | | | | 600 | | | | | 605 | | |
| ctt | ggt | tcc | gac | gtt | cca | gac | cca | ggg | atg | gtg | aat | gaa | ggc | acc | aaa | 1934 |
| Leu | Gly | Ser | Asp | Val | Pro | Asp | Pro | Gly | Met | Val | Asn | Glu | Gly | Thr | Lys | |
| | | | 610 | | | | | 615 | | | | | 620 | | | |
| tgt | gat | gct | ggc | aag | att | tgc | agg | aat | ttt | cag | tgt | gta | aat | gct | tct | 1982 |
| Cys | Asp | Ala | Gly | Lys | Ile | Cys | Arg | Asn | Phe | Gln | Cys | Val | Asn | Ala | Ser | |
| | | 625 | | | | | 630 | | | | | 635 | | | | |
| gtc | ctg | aat | tat | gac | tgt | gac | att | cag | gga | aaa | tgt | cat | ggc | cat | ggg | 2030 |
| Val | Leu | Asn | Tyr | Asp | Cys | Asp | Ile | Gln | Gly | Lys | Cys | His | Gly | His | Gly | |
| | 640 | | | | | 645 | | | | | 650 | | | | | |
| gta | tgt | aac | agc | aat | aag | aat | tgt | cac | tgt | gaa | gat | ggc | tgg | gct | ccc | 2078 |
| Val | Cys | Asn | Ser | Asn | Lys | Asn | Cys | His | Cys | Glu | Asp | Gly | Trp | Ala | Pro | |
| 655 | | | | | 660 | | | | | 665 | | | | | 670 | |
| cca | cac | tgt | gac | acc | aaa | gga | tat | gga | gga | agc | gtg | gac | agc | ggg | ccg | 2126 |
| Pro | His | Cys | Asp | Thr | Lys | Gly | Tyr | Gly | Gly | Ser | Val | Asp | Ser | Gly | Pro | |
| | | | | 675 | | | | | 680 | | | | | 685 | | |
| acg | tat | aat | gca | aag | agc | aca | gca | ctg | agg | gac | ggg | ctt | ctg | gtc | ttc | 2174 |
| Thr | Tyr | Asn | Ala | Lys | Ser | Thr | Ala | Leu | Arg | Asp | Gly | Leu | Leu | Val | Phe | |
| | | | 690 | | | | | 695 | | | | | 700 | | | |
| ttc | ttc | cta | atc | gtc | ccc | ctt | gtt | gcg | gct | gcc | att | ttc | ctc | ttt | atc | 2222 |
| Phe | Phe | Leu | Ile | Val | Pro | Leu | Val | Ala | Ala | Ala | Ile | Phe | Leu | Phe | Ile | |
| | | 705 | | | | | 710 | | | | | 715 | | | | |
| aag | aga | gat | gaa | cta | cgg | aaa | acc | ttc | agg | aag | aag | aga | tca | caa | atg | 2270 |

```
                                  -continued

Lys Arg Asp Glu Leu Arg Lys Thr Phe Arg Lys Lys Arg Ser Gln Met
    720                 725                 730 tca gat ggc aga aat caa gca aac gtc tct aga cag cca gga gat cct      2318
Ser Asp Gly Arg Asn Gln Ala Asn Val Ser Arg Gln Pro Gly Asp Pro
735                 740                 745                 750 agt atc tcc aga cca cca ggg ggc cca aat gtc tcc aga cca cca ggg      2366
Ser Ile Ser Arg Pro Pro Gly Gly Pro Asn Val Ser Arg Pro Pro Gly
                755                 760                 765 ggc cca ggt gtc tcc aga cca cca ggg ggc cca ggt gtc tcc aga cca      2414
Gly Pro Gly Val Ser Arg Pro Pro Gly Gly Pro Gly Val Ser Arg Pro
            770                 775                 780 cca ggg ggc cca ggt gtc tcc aga ccg cca cct ggg cat gga aac aga      2462
Pro Gly Gly Pro Gly Val Ser Arg Pro Pro Gly His Gly Asn Arg
        785                 790                 795 ttc cca gta cca acc tac gcc gcc aag cag cct gcg cag ttc ccg tca      2510
Phe Pro Val Pro Thr Tyr Ala Ala Lys Gln Pro Ala Gln Phe Pro Ser
    800                 805                 810 agg cca cct cca cca caa ccg aaa ata tct tct cag gga aac ttg att      2558
Arg Pro Pro Pro Pro Gln Pro Lys Ile Ser Ser Gln Gly Asn Leu Ile
815                 820                 825                 830 ccg gct cgg ccc gct cct gca cct cct tta tat agc tcc ctc acc          2603
Pro Ala Arg Pro Ala Pro Ala Pro Pro Leu Tyr Ser Ser Leu Thr
                835                 840                 845 tgatagtaga atattagaat cttatttttt aaatgtcttc agggaactga gcaaatgttt    2663 gttgttttt ttttcctgat gttttcttga aaagcctttc tcttccaacc atgaatgaac     2723
acaaaccacc acaaaacaag ctttattaac acaggagcct agtggggatt gcgaaacaca    2783
ggaatgtgca ggcgctccgg ggggtgtaaa gtgaacgttt ccatcgttag aatgttttct    2843
ctggccattt gtggatttaa tgcacttgac gtggattaag ttattctgag catgttactg    2903
taatgattct caaattaact gtattagtgt aagctttgtc actatgcgct aaacgtaatc    2963 ctgactttt gaccccagtt accattaata gtttctggtt gaccatttga acatgtatta     3023
acttaggaag actaattgcc aataacgtct gcattttcat cttgcatgga ttaacagcca    3083
tttatatgga cttatgtctc ttaatgcaca agaagcaga tatctcgaag gagcttacac     3143
aagaaccaca attactagat catgatatac ttggaaagtg tgaaatatgg tgtgtactca    3203
gttattggct tccattttw atgatctttc aactataaca attatgatag aaatcgattt     3263
aacacaatca gttatgggct tccattttca aatatctttt caactgtaat gactatgaca    3323
ggaactgatt caactctcaa ttttctttat gcatcatggt aaagcattgc agcagtgttg    3383
ttttgtttga agtgcacact ctatggtacg aggtgtttag tatacccaag cagataggtg    3443
tcgatcgaac aggagcaggg agaatacttc caacagttga ggtgttacca aaccacttga    3503
gaattcatga gcactttaac tctaaactct gaatttcaaa gcttgatgtg aagtcctcta    3563
gaatgtttac atttactaag gtgtgctggg tcctgtctct tttgactaat attttcgtaa    3623
acattaggct ggagaaagga aggaagcagt ggtttcctta gataactaca gaattatact    3683
ggtctctggg attactctct cagctgtatt aaaatgaatt tgtactttga aaggaatgat    3743
attgacacta aaatttaaa catttaaatt ttttcataat ctttcataaa gaagtttaat     3803
aataggtata ttaactgaat ttcattagtt ttttaaaata atattgtttg tgtatatata    3863
catattaaaa taaaaacatt tacaacaaat aaaatacttg aaattctaaa aaaaaaaaa     3923 aaaaaaaa                                                             3931

<210> SEQ ID NO 6
```

```
<211> LENGTH: 845
<212> TYPE: PRT
<213> ORGANISM: Unknown Organism
<220> FEATURE:
<223> OTHER INFORMATION: Description of Unknown Organism: Clone,
      JM109(pBSMel-gamma), mouse meltrin gamma

<400> SEQUENCE: 6
```

Met Gly Pro Arg Ala Leu Ser Pro Leu Ala Ser Leu Arg Leu Arg Trp
 1               5                  10                  15

Leu Leu Ala Cys Gly Leu Leu Gly Pro Val Leu Glu Ala Gly Arg Pro
            20                  25                  30

Asp Leu Glu Gln Thr Val His Leu Ser Ser Tyr Glu Ile Thr Pro
         35                  40                  45

Trp Arg Leu Thr Arg Glu Arg Glu Ala Leu Gly Pro Ser Ser Gln
 50                  55                  60

Gln Ile Ser Tyr Val Ile Gln Ala Gln Gly Lys Gln His Ile Ile His
 65                  70                  75                  80

Leu Glu Arg Asn Thr Asp Leu Leu Pro Asn Asp Phe Val Val Tyr Thr
                 85                  90                  95

Tyr Asp Lys Glu Gly Ser Leu Leu Ser Asp His Pro Asn Val Gln Ser
                100                 105                 110

His Cys His Tyr Arg Gly Tyr Val Glu Gly Val Gln Asn Ser Ala Val
            115                 120                 125

Ala Val Ser Ala Cys Phe Gly Leu Arg Gly Leu Leu His Leu Glu Asn
130                 135                 140

Ala Ser Phe Gly Ile Glu Pro Leu His Asn Ser Ser His Phe Glu His
145                 150                 155                 160

Ile Phe Tyr Pro Met Asp Gly Ile His Gln Glu Pro Leu Arg Cys Gly
                165                 170                 175

Val Ser Asn Arg Asp Thr Glu Lys Glu Gly Thr Gln Gly Asp Glu Glu
            180                 185                 190

Glu His Pro Ser Val Thr Gln Leu Leu Arg Arg Arg Ala Val Leu
        195                 200                 205

Pro Gln Thr Arg Tyr Val Glu Leu Phe Ile Val Asp Lys Glu Arg
210                 215                 220

Tyr Asp Met Met Gly Arg Asn Gln Thr Ala Val Arg Glu Glu Met Ile
225                 230                 235                 240

Arg Leu Ala Asn Tyr Leu Asp Ser Met Tyr Ile Met Leu Asn Ile Arg
                245                 250                 255

Ile Val Leu Val Gly Leu Glu Ile Trp Thr Asp Arg Asn Pro Ile Asn
            260                 265                 270

Ile Ile Gly Gly Ala Gly Asp Val Leu Gly Asn Phe Val Gln Trp Arg
        275                 280                 285

Glu Lys Phe Leu Ile Thr Arg Arg His Asp Ser Ala Gln Leu Val
290                 295                 300

Leu Lys Lys Gly Phe Gly Gly Thr Ala Gly Met Ala Phe Val Gly Thr
305                 310                 315                 320

Val Cys Ser Arg Ser His Ala Gly Gly Ile Asn Val Phe Gly Gln Ile
                325                 330                 335

Thr Val Glu Thr Phe Ala Ser Ile Val Ala His Glu Leu Gly His Asn
            340                 345                 350

Leu Gly Met Asn His Asp Asp Gly Arg Glu Cys Phe Cys Gly Ala Lys
        355                 360                 365

Ser Cys Ile Met Asn Ser Gly Ala Ser Gly Ser Arg Asn Phe Ser Ser

-continued

```
            370                 375                 380
Cys Ser Ala Glu Asp Phe Glu Lys Leu Thr Leu Asn Lys Gly Gly Ser
385                 390                 395                 400

Cys Leu Leu Asn Ile Pro Lys Pro Asp Glu Ala Tyr Ser Ala Pro Ser
                405                 410                 415

Cys Gly Asn Lys Leu Val Asp Pro Gly Glu Glu Cys Asp Cys Gly Thr
                420                 425                 430

Ala Lys Glu Cys Glu Val Asp Pro Cys Cys Glu Gly Ser Thr Cys Lys
                435                 440                 445

Leu Lys Ser Phe Ala Glu Cys Ala Tyr Gly Asp Cys Cys Lys Asp Cys
450                 455                 460

Gln Phe Leu Pro Gly Gly Ser Met Cys Arg Gly Lys Thr Ser Glu Cys
465                 470                 475                 480

Asp Val Pro Glu Tyr Cys Asn Gly Ser Ser Gln Phe Cys Pro Pro Asp
                485                 490                 495

Val Phe Ile Gln Asn Gly Tyr Pro Cys Gln Asn Ser Lys Ala Tyr Cys
                500                 505                 510

Tyr Asn Gly Met Cys Gln Tyr Tyr Asp Ala Gln Cys Gln Val Ile Phe
                515                 520                 525

Gly Ser Lys Ala Lys Ala Ala Pro Arg Asp Cys Phe Ile Glu Val Asn
530                 535                 540

Ser Lys Gly Asp Arg Phe Gly Asn Cys Gly Phe Ser Gly Ser Glu Tyr
545                 550                 555                 560

Lys Lys Cys Ala Thr Gly Asn Ala Leu Cys Gly Lys Leu Gln Cys Glu
                565                 570                 575

Asn Val Gln Asp Met Pro Val Phe Gly Ile Val Pro Ala Ile Ile Gln
                580                 585                 590

Thr Pro Ser Arg Gly Thr Lys Cys Trp Gly Val Asp Phe Gln Leu Gly
                595                 600                 605

Ser Asp Val Pro Asp Pro Gly Met Val Asn Glu Gly Thr Lys Cys Asp
610                 615                 620

Ala Gly Lys Ile Cys Arg Asn Phe Gln Cys Val Asn Ala Ser Val Leu
625                 630                 635                 640

Asn Tyr Asp Cys Asp Ile Gln Gly Lys Cys His Gly His Gly Val Cys
                645                 650                 655

Asn Ser Asn Lys Asn Cys His Cys Glu Asp Gly Trp Ala Pro Pro His
                660                 665                 670

Cys Asp Thr Lys Gly Tyr Gly Gly Ser Val Asp Ser Gly Pro Thr Tyr
                675                 680                 685

Asn Ala Lys Ser Thr Ala Leu Arg Asp Gly Leu Leu Val Phe Phe Phe
690                 695                 700

Leu Ile Val Pro Leu Val Ala Ala Ile Phe Leu Phe Ile Lys Arg
705                 710                 715                 720

Asp Glu Leu Arg Lys Thr Phe Arg Lys Lys Arg Ser Gln Met Ser Asp
                725                 730                 735

Gly Arg Asn Gln Ala Asn Val Ser Arg Gln Pro Gly Asp Pro Ser Ile
                740                 745                 750

Ser Arg Pro Pro Gly Gly Pro Asn Val Ser Arg Pro Gly Gly Pro
                755                 760                 765

Gly Val Ser Arg Pro Pro Gly Pro Gly Val Ser Arg Pro Gly
                770                 775                 780

Gly Pro Gly Val Ser Arg Pro Pro Gly His Gly Asn Arg Phe Pro
785                 790                 795                 800
```

```
Val Pro Thr Tyr Ala Ala Lys Gln Pro Ala Gln Phe Pro Ser Arg Pro
            805                 810                 815
Pro Pro Pro Gln Pro Lys Ile Ser Ser Gln Gly Asn Leu Ile Pro Ala
            820                 825                 830
Arg Pro Ala Pro Ala Pro Leu Tyr Ser Ser Leu Thr
            835                 840             845

<210> SEQ ID NO 7
<211> LENGTH: 321
<212> TYPE: DNA
<213> ORGANISM: Unknown Organism
<220> FEATURE:
<223> OTHER INFORMATION: Description of Unknown Organism: Clone:
      JM109(pBShuM-alpha 300), human meltrin alpha
<221> NAME/KEY: CDS
<222> LOCATION: (1)..(321)
<221> NAME/KEY: unsure
<222> LOCATION: (139)..(321)
<223> OTHER INFORMATION: Amino Acid "Xaa" is unknown

<400> SEQUENCE: 7 aag cct gca gga aca gcg tgc agg gac tcc agc aac tcc tgt gac ctc      48
Lys Pro Ala Gly Thr Ala Cys Arg Asp Ser Ser Asn Ser Cys Asp Leu
  1               5                  10                  15 cca gag ttc tgc aca ggg gcc agc cct cac tgc cca gcc aac gtg tac      96
Pro Glu Phe Cys Thr Gly Ala Ser Pro His Cys Pro Ala Asn Val Tyr
             20                  25                  30 ctg cac gat ggg cac tca tgt cag gat gtg gac ggc tac tgc tan aat     144
Leu His Asp Gly His Ser Cys Gln Asp Val Asp Gly Tyr Cys Xaa Asn
         35                  40                  45 ggc atc tgc cag act cac gag cag cag tgt gtc acg ctc tgg gga cca     192
Gly Ile Cys Gln Thr His Glu Gln Gln Cys Val Thr Leu Trp Gly Pro
     50                  55                  60 ggt gct aaa cct gcc cct ggg atc tgc ttt gag aga gtc aat tct gca     240
Gly Ala Lys Pro Ala Pro Gly Ile Cys Phe Glu Arg Val Asn Ser Ala
 65                  70                  75                  80 ggt gaa cct tat ggc aac tgt ggc aaa gtc tcg aag agt tcc ttt gcc     288
Gly Glu Pro Tyr Gly Asn Cys Gly Lys Val Ser Lys Ser Ser Phe Ala
                 85                  90                  95 aaa tgc gag atg aga gat gct aaa tgc ggc aag                         321
Lys Cys Glu Met Arg Asp Ala Lys Cys Gly Lys
                100                 105

<210> SEQ ID NO 8
<211> LENGTH: 107
<212> TYPE: PRT
<213> ORGANISM: Unknown Organism
<220> FEATURE:
<223> OTHER INFORMATION: Description of Unknown Organism: Clone:
      JM109(pBShuM-alpha 300), human meltrin alpha
<221> NAME/KEY: Unsure
<222> LOCATION: 47
<223> OTHER INFORMATION: Amino acid "Xaa" is unknown

<400> SEQUENCE: 8

Lys Pro Ala Gly Thr Ala Cys Arg Asp Ser Ser Asn Ser Cys Asp Leu
  1               5                  10                  15

Pro Glu Phe Cys Thr Gly Ala Ser Pro His Cys Pro Ala Asn Val Tyr
             20                  25                  30

Leu His Asp Gly His Ser Cys Gln Asp Val Asp Gly Tyr Cys Xaa Asn
         35                  40                  45

Gly Ile Cys Gln Thr His Glu Gln Gln Cys Val Thr Leu Trp Gly Pro
     50                  55                  60
```

```
Gly Ala Lys Pro Ala Pro Gly Ile Cys Phe Glu Arg Val Asn Ser Ala
 65                  70                  75                  80

Gly Glu Pro Tyr Gly Asn Cys Gly Lys Val Ser Lys Ser Ser Phe Ala
                 85                  90                  95

Lys Cys Glu Met Arg Asp Ala Lys Cys Gly Lys
            100                 105

<210> SEQ ID NO 9
<211> LENGTH: 967
<212> TYPE: DNA
<213> ORGANISM: Unknown Organism
<220> FEATURE:
<223> OTHER INFORMATION: Description of Unknown Organism:  Clone:
      JM109(pBShuM-gamma-G238), human meltrin gamma
<221> NAME/KEY: CDS
<222> LOCATION: (1)..(966)

<400> SEQUENCE: 9 gca aag agc tgc atc atg aat tca gga gca tcg ggt tcc aga aac ttt      48
Ala Lys Ser Cys Ile Met Asn Ser Gly Ala Ser Gly Ser Arg Asn Phe
  1               5                  10                  15 agc agt tgc agt gca gag gac ttt gag aag tta act tta aat aaa gga     96
Ser Ser Cys Ser Ala Glu Asp Phe Glu Lys Leu Thr Leu Asn Lys Gly
             20                  25                  30 gga aac tgc ctt ctt aat att cca aag cct gat gaa gcc tat agt gct    144
Gly Asn Cys Leu Leu Asn Ile Pro Lys Pro Asp Glu Ala Tyr Ser Ala
         35                  40                  45 ccc tcc tgt ggt aat aag ttg gtg gac gct ggg gaa gag tgt gac tgt    192
Pro Ser Cys Gly Asn Lys Leu Val Asp Ala Gly Glu Glu Cys Asp Cys
     50                  55                  60 ggt act cca aag gaa tgt gaa ttg gac cct tgc tgc gaa gga agt acc    240
Gly Thr Pro Lys Glu Cys Glu Leu Asp Pro Cys Cys Glu Gly Ser Thr
 65                  70                  75                  80 tgt aag ctt aaa tca ttt gct gag tgt gca tat ggt gac tgt tgt aaa    288
Cys Lys Leu Lys Ser Phe Ala Glu Cys Ala Tyr Gly Asp Cys Cys Lys
                 85                  90                  95 gac tgt cgg ttc ctt cca gga ggt act tta tgc cga gga aaa acc agt    336
Asp Cys Arg Phe Leu Pro Gly Gly Thr Leu Cys Arg Gly Lys Thr Ser
            100                 105                 110 gag tgt gat gtt cca gag tac tgc aat ggt tct tct cag ttc tgt cag    384
Glu Cys Asp Val Pro Glu Tyr Cys Asn Gly Ser Ser Gln Phe Cys Gln
        115                 120                 125 cca gat gtt ttt att cag aat gga tat cct tgc cag aat aac aaa gcc    432
Pro Asp Val Phe Ile Gln Asn Gly Tyr Pro Cys Gln Asn Asn Lys Ala
    130                 135                 140 tat tgc tac aac ggc atg tgc cag tat tat gat gct caa tgt caa gtc    480
Tyr Cys Tyr Asn Gly Met Cys Gln Tyr Tyr Asp Ala Gln Cys Gln Val
145                 150                 155                 160 atc ttt ggc tca aaa gcc aag gct gcc ccc aaa gat tgt ttc att gaa    528
Ile Phe Gly Ser Lys Ala Lys Ala Ala Pro Lys Asp Cys Phe Ile Glu
                165                 170                 175 gtg aat tct aaa ggt gac aga ttt ggc aat tgt ggt ttc tct ggc aat    576
Val Asn Ser Lys Gly Asp Arg Phe Gly Asn Cys Gly Phe Ser Gly Asn
            180                 185                 190 gaa tac aag aag tgt gcc act ggg aat gct ttg tgt gga aag ctt cag    624
Glu Tyr Lys Lys Cys Ala Thr Gly Asn Ala Leu Cys Gly Lys Leu Gln
        195                 200                 205 tgt gag aat gta caa gag ata cct gta ttt gga att gtg cct gct att    672
Cys Glu Asn Val Gln Glu Ile Pro Val Phe Gly Ile Val Pro Ala Ile
    210                 215                 220
```

```
att caa acg cct agt cga ggc acc aaa tgt tgg ggt gtg gat ttc cag        720
Ile Gln Thr Pro Ser Arg Gly Thr Lys Cys Trp Gly Val Asp Phe Gln
225                 230                 235                 240 cta gga tca gat gtt cca gat cct ggg atg gtt aac gaa ggc aca aaa        768
Leu Gly Ser Asp Val Pro Asp Pro Gly Met Val Asn Glu Gly Thr Lys
                245                 250                 255 tgt ggt gct gga aag atc tgt aga aac ttc cag tgt gta gat gct tct        816
Cys Gly Ala Gly Lys Ile Cys Arg Asn Phe Gln Cys Val Asp Ala Ser
            260                 265                 270 gtt ctg aat tat gac tgt gat gtt cag aaa aag tgt cat gga cat ggg        864
Val Leu Asn Tyr Asp Cys Asp Val Gln Lys Lys Cys His Gly His Gly
        275                 280                 285 gta tgt aat agc aat aag aat tgt cac tgt gaa aat ggc tgg ctc ccc        912
Val Cys Asn Ser Asn Lys Asn Cys His Cys Glu Asn Gly Trp Leu Pro
    290                 295                 300 caa att gtg aga cta aag gat acg aga tca agc tta tcg ata ccg tcg        960
Gln Ile Val Arg Leu Lys Asp Thr Arg Ser Ser Leu Ser Ile Pro Ser
305                 310                 315                 320 acc tcg a                                                              967
Thr Ser <210> SEQ ID NO 10
<211> LENGTH: 322
<212> TYPE: PRT
<213> ORGANISM: Unknown Organism
<220> FEATURE:
<223> OTHER INFORMATION: Description of Unknown Organism:  Clone:
      JM109(pBShuM-gamma-G238), human meltrin gamma

<400> SEQUENCE: 10

Ala Lys Ser Cys Ile Met Asn Ser Gly Ala Ser Gly Ser Arg Asn Phe
1               5                   10                  15

Ser Ser Cys Ser Ala Glu Asp Phe Glu Lys Leu Thr Leu Asn Lys Gly
                20                  25                  30

Gly Asn Cys Leu Leu Asn Ile Pro Lys Pro Asp Glu Ala Tyr Ser Ala
            35                  40                  45

Pro Ser Cys Gly Asn Lys Leu Val Asp Ala Gly Glu Glu Cys Asp Cys
        50                  55                  60

Gly Thr Pro Lys Glu Cys Glu Leu Asp Pro Cys Cys Glu Gly Ser Thr
65                  70                  75                  80

Cys Lys Leu Lys Ser Phe Ala Glu Cys Ala Tyr Gly Asp Cys Cys Lys
                85                  90                  95

Asp Cys Arg Phe Leu Pro Gly Gly Thr Leu Cys Arg Gly Lys Thr Ser
            100                 105                 110

Glu Cys Asp Val Pro Glu Tyr Cys Asn Gly Ser Ser Gln Phe Cys Gln
        115                 120                 125

Pro Asp Val Phe Ile Gln Asn Gly Tyr Pro Cys Gln Asn Asn Lys Ala
    130                 135                 140

Tyr Cys Tyr Asn Gly Met Cys Gln Tyr Tyr Asp Ala Gln Cys Gln Val
145                 150                 155                 160

Ile Phe Gly Ser Lys Ala Lys Ala Ala Pro Lys Asp Cys Phe Ile Glu
                165                 170                 175

Val Asn Ser Lys Gly Asp Arg Phe Gly Asn Cys Gly Phe Ser Gly Asn
            180                 185                 190

Glu Tyr Lys Lys Cys Ala Thr Gly Asn Ala Leu Cys Gly Lys Leu Gln
        195                 200                 205

Cys Glu Asn Val Gln Glu Ile Pro Val Phe Gly Ile Val Pro Ala Ile
    210                 215                 220
```

```
Ile Gln Thr Pro Ser Arg Gly Thr Lys Cys Trp Gly Val Asp Phe Gln
225                 230                 235                 240

Leu Gly Ser Asp Val Pro Asp Pro Gly Met Val Asn Glu Gly Thr Lys
                245                 250                 255

Cys Gly Ala Gly Lys Ile Cys Arg Asn Phe Gln Cys Val Asp Ala Ser
                260                 265                 270

Val Leu Asn Tyr Asp Cys Asp Val Gln Lys Lys Cys His Gly His Gly
                275                 280                 285

Val Cys Asn Ser Asn Lys Asn Cys His Cys Glu Asn Gly Trp Leu Pro
                290                 295                 300

Gln Ile Val Arg Leu Lys Asp Thr Arg Ser Ser Leu Ser Ile Pro Ser
305                 310                 315                 320

Thr Ser

<210> SEQ ID NO 11
<211> LENGTH: 2848
<212> TYPE: DNA
<213> ORGANISM: Unknown Organism
<220> FEATURE:
<223> OTHER INFORMATION: Description of Unknown Organism: Clones:
      JM109(pMel-alpha-25C), human meltrin alpha, and
      JM109(pMel-alpha-26N), human meltrin alpha
<223> OTHER INFORMATION: CDC at (1) ... (2058)

<400> SEQUENCE: 11
ggggacctct ggatcccagt gaagagcttc gactccaaga atcatccaga agtgctgaat      60
attcgactac aacgggaaag caaagaactg atcataaatc tggaaagaaa tgaaggtctc     120
attgccagca gtttcacgga aacccactat ctgcaagacg gtactgatgt ctccctcgct     180
cgaaattaca cgggtcactg ttactaccat ggacatgtac ggggatattc tgattcagca     240
gtcagtctca gcacgtgttc tggtctcagg gacttattg ggtttgaaaa tgaaagctat      300
gtcttagaac caatgaaaag tgcaaccaac agatacaaac tcttcccagc gaagaagctg     360
aaaagcgtcc ggggatcatg tggatcacat cacaacacac aaacctcgc tgcaaagaat      420 gtgtttccac caccctctca gacatgggca agaaggcata aagagagac cctcaaggca      480 actaagtatg tggagctggt gatcgtggca gacaaccgag agtttcagag gcaaggaaaa     540
gatctggaaa aagttaagca gcgattaata gagattgcta atcacgttga caagttttac     600
agaccactga acattcggat cgtgttggta ggcgtggaag tgtggaatga catggacaaa     660
tgctctgtaa gtcaggaccc attcaccagc ctccatgaat ttctggactg gaggaagatg     720
aagcttctac ctcgcaaatc ccatgacaat gcgcagcttg tcagtggggt ttatttccaa     780
gggaccacca tcggcatggc cccaatcatg agcatgtgca cggcagacca gtctggggga     840
attgtcatgg accattcaga caatccccctt ggtgcagccg tgaccctggc acatgagctg     900
ggccacaatt tcgggatgaa tcatgacaca ctggacaggg gctgtagctg tcaaatggcg     960
gttgagaaag gaggctgcat catgaacgct tccaccgggt acccatttcc catggtgttc    1020
agcagttgca gcaggaagga cttggagacc agcctggaga aggaatggg ggtgtgcctg     1080 tttaacctgc cggaagtcag ggagtctttc ggggccaga agtgtgggaa cagatttgtg     1140
gaagaaggag aggagtgtga ctgtggggag ccagaggaat gtatgaatcg ctgctgcaat    1200
gccaccacct gtaccctgaa gccggacgct gtgtgcgcac atgggctgtg ctgtgaagac    1260
tgccagctga gcctgcagg aacagcgtga agggactcca gcaactcctg tgacctccca    1320
gagttctgca caggggccag ccctcactgc ccagccaacg tgtacctgca cgatgggcac    1380
```

```
tcatgtcagg atgtggacgg ctactgctac aatggcatct gccagactca cgagcagcag    1440
tgtgtcacgc tctggggacc aggtgctaaa cctgccctg ggatctgctt tgagagagtc     1500
aattctgcag gtgatcctta tggcaactgt ggcaaagtct cgaagagttc ctttgccaaa    1560
tgcgagatga gagatgctaa atgtggaaaa atccagtgtc aaggaggtgc cagccggcca    1620
gtcattggta ccaatgccgt tccatagaa caaacatcc ccctgcagca aggaggccgg      1680
attctgtgcc gggggaccca cgtgtacttg ggcgatgaca tgccggaccc agggcttgtg    1740
cttgcaggca caaagtgtgc agatggaaaa atctgcctga atcgtcaatg tcaaaatatt    1800
agtgtctttg gggttcacga gtgtgcaatg cagtgccacg gcagagggt gtgcaacaac     1860 aggaagaact gccactgcga ggcccactgg gcacctccct tctgtgacaa gtttggcttt    1920
ggaggaagca cagacagcgg ccccatccgg caagcagaag caaggcagga agctgcagag    1980
tccaacaggg agcgcggcca gggccaggag cccgtgggat cgcaggagca tgcgtctact    2040
gcctcactga cactcatctg agccctccca tgacatggag accgtgacca gtgctgctgc    2100
agaggaggtc acgcgtcccc aaggcctcct gtgactggca gcattgactc tgtggctttg    2160
ccatcgtttc catgacaaca gacacaacac agttctcggg gctcaggagg ggaagtccag    2220
cctaccaggc acgtctgcag aaacagtgca aggaagggca gcgacttcct ggttgagctt    2280
ctgctaaaac atggacatgc ttcagtgctg ctcctgagag agtagcaggt taccactctg    2340
gcaggcccca gccctgcagc aaggaggaag aggactcaaa agtctggcct ttcactgagc    2400
ccccacagca gtgggggaga agcaagggtt gggcccagtg tccccttcc ccagtgacac     2460 ctcagccttg gcagccctga tgactggtct ctggctgcaa cttaatgctc tgatatggct    2520
tttagcattt attatatgaa aatagcaggg ttttagtttt taatttatca gagaccctgc    2580
cacccattcc atctccatcc aagcaaactg aatggcattg aaacaaactg gagaagaagg    2640
taggagaaag ggcggtgaac tctggctctt tgctgtggac atgcgtgacc agcagtactc    2700
aggtttgagg gtttgcagaa agccagggaa cccacagagt caccaaccct tcatttaaca    2760
agtaagaatg ttaaaaagtg aaaacaatgt aagagcctaa ctccatcccc cgtggccatt    2820
actgcataaa atagagtgca tcccgccc                                       2848
```

<210> SEQ ID NO 12
<211> LENGTH: 686
<212> TYPE: PRT
<213> ORGANISM: Unknown Organism
<220> FEATURE:
<223> OTHER INFORMATION: Description of Unknown Organism: Clones:
    JM109(pMel-alpha-25C), human meltrin alpha, and
    JM109 (pMel-alpha-26N), human meltrin alpha

<400> SEQUENCE: 12

```
Gly Asp Leu Trp Ile Pro Val Lys Ser Phe Asp Ser Lys Asn His Pro
  1               5                  10                  15

Glu Val Leu Asn Ile Arg Leu Gln Arg Glu Ser Lys Glu Leu Ile Ile
              20                  25                  30

Asn Leu Glu Arg Asn Glu Gly Leu Ile Ala Ser Ser Phe Thr Glu Thr
          35                  40                  45

His Tyr Leu Gln Asp Gly Thr Asp Val Ser Leu Ala Arg Asn Tyr Thr
      50                  55                  60

Gly His Cys Tyr Tyr His Gly His Val Arg Gly Tyr Ser Asp Ser Ala
 65                  70                  75                  80

Val Ser Leu Ser Thr Cys Ser Gly Leu Arg Gly Leu Ile Gly Phe Glu
```

```
                    85               90                  95
Asn Glu Ser Tyr Val Leu Glu Pro Met Lys Ser Ala Thr Asn Arg Tyr
                100             105             110
Lys Leu Phe Pro Ala Lys Lys Leu Lys Ser Val Arg Gly Ser Cys Gly
            115             120             125
Ser His His Asn Thr Pro Asn Leu Ala Ala Lys Asn Val Phe Pro Pro
        130             135             140
Pro Ser Gln Thr Trp Ala Arg Arg His Lys Arg Glu Thr Leu Lys Ala
145             150             155             160
Thr Lys Tyr Val Glu Leu Val Ile Val Ala Asp Asn Arg Glu Phe Gln
                165             170             175
Arg Gln Gly Lys Asp Leu Glu Lys Val Lys Gln Arg Leu Ile Glu Ile
            180             185             190
Ala Asn His Val Asp Lys Phe Tyr Arg Pro Leu Asn Ile Arg Ile Val
        195             200             205
Leu Val Gly Val Glu Val Trp Asn Asp Met Asp Lys Cys Ser Val Ser
    210             215             220
Gln Asp Pro Phe Thr Ser Leu His Glu Phe Leu Asp Trp Arg Lys Met
225             230             235             240
Lys Leu Leu Pro Arg Lys Ser His Asp Asn Ala Gln Leu Val Ser Gly
                245             250             255
Val Tyr Phe Gln Gly Thr Thr Ile Gly Met Ala Pro Ile Met Ser Met
            260             265             270
Cys Thr Ala Asp Gln Ser Gly Gly Ile Val Met Asp His Ser Asp Asn
        275             280             285
Pro Leu Gly Ala Ala Val Thr Leu Ala His Glu Leu Gly His Asn Phe
    290             295             300
Gly Met Asn His Asp Thr Leu Asp Arg Gly Cys Ser Cys Gln Met Ala
305             310             315             320
Val Glu Lys Gly Gly Cys Ile Met Asn Ala Ser Thr Gly Tyr Pro Phe
                325             330             335
Pro Met Val Phe Ser Ser Cys Ser Arg Lys Asp Leu Glu Thr Ser Leu
            340             345             350
Glu Lys Gly Met Gly Val Cys Leu Phe Asn Leu Pro Glu Val Arg Glu
        355             360             365
Ser Phe Gly Gly Gln Lys Cys Gly Asn Arg Phe Val Glu Glu Gly Glu
    370             375             380
Glu Cys Asp Cys Gly Glu Pro Glu Glu Cys Met Asn Arg Cys Cys Asn
385             390             395             400
Ala Thr Thr Cys Thr Leu Lys Pro Asp Ala Val Cys Ala His Gly Leu
                405             410             415
Cys Cys Glu Asp Cys Gln Leu Lys Pro Ala Gly Thr Ala Cys Arg Asp
            420             425             430
Ser Ser Asn Ser Cys Asp Leu Pro Glu Phe Cys Thr Gly Ala Ser Pro
        435             440             445
His Cys Pro Ala Asn Val Tyr Leu His Asp Gly His Ser Cys Gln Asp
    450             455             460
Val Asp Gly Tyr Cys Tyr Asn Gly Ile Cys Gln Thr His Glu Gln Gln
465             470             475             480
Cys Val Thr Leu Trp Gly Pro Gly Ala Lys Pro Ala Pro Gly Ile Cys
                485             490             495
Phe Glu Arg Val Asn Ser Ala Gly Asp Pro Tyr Gly Asn Cys Gly Lys
            500             505             510
```

```
Val Ser Lys Ser Ser Phe Ala Lys Cys Glu Met Arg Asp Ala Lys Cys
        515                 520                 525

Gly Lys Ile Gln Cys Gln Gly Gly Ala Ser Arg Pro Val Ile Gly Thr
    530                 535                 540

Asn Ala Val Ser Ile Glu Thr Asn Ile Pro Leu Gln Gln Gly Gly Arg
545                 550                 555                 560

Ile Leu Cys Arg Gly Thr His Val Tyr Leu Gly Asp Asp Met Pro Asp
                565                 570                 575

Pro Gly Leu Val Leu Ala Gly Thr Lys Cys Ala Asp Gly Lys Ile Cys
            580                 585                 590

Leu Asn Arg Gln Cys Gln Asn Ile Ser Val Phe Gly Val His Glu Cys
        595                 600                 605

Ala Met Gln Cys His Gly Arg Gly Val Cys Asn Asn Arg Lys Asn Cys
    610                 615                 620

His Cys Glu Ala His Trp Ala Pro Pro Phe Cys Asp Lys Phe Gly Phe
625                 630                 635                 640

Gly Gly Ser Thr Asp Ser Gly Pro Ile Arg Gln Ala Glu Ala Arg Gln
                645                 650                 655

Glu Ala Ala Glu Ser Asn Arg Glu Arg Gly Gln Gly Gln Glu Pro Val
            660                 665                 670

Gly Ser Gln Glu His Ala Ser Thr Ala Ser Leu Thr Leu Ile
        675                 680                 685

<210> SEQ ID NO 13
<211> LENGTH: 394
<212> TYPE: DNA
<213> ORGANISM: Unknown Organism
<220> FEATURE:
<223> OTHER INFORMATION: Description of Unknown Organism: Partial
      sequence of human meltrin beta derived from cDNA
<221> NAME/KEY: CDS
<222> LOCATION: (1)..(393)

<400> SEQUENCE: 13 ggg gaa gag tgt gat tgt gga gaa gaa gag gaa tgt aac aac ccc tgc      48
Gly Glu Glu Cys Asp Cys Gly Glu Glu Glu Cys Asn Asn Pro Cys
 1               5                  10                  15 tgc aat gcc tct aat tgt acc ctg agg ccg ggg gcg gag tgt gct cac      96
Cys Asn Ala Ser Asn Cys Thr Leu Arg Pro Gly Ala Glu Cys Ala His
             20                  25                  30 ggc tcc tgc tgc cac cag tgt aag ctg ttg gct cct ggg acc ctg tgc     144
Gly Ser Cys Cys His Gln Cys Lys Leu Leu Ala Pro Gly Thr Leu Cys
         35                  40                  45 cgc gag cag gcc agg cag tgt gac ctc ccg gag ttc tgt acg ggc aag     192
Arg Glu Gln Ala Arg Gln Cys Asp Leu Pro Glu Phe Cys Thr Gly Lys
     50                  55                  60 tct ccc cac tgc cct acc aac ttc tac cag atg gat ggt acc ccc tgt     240
Ser Pro His Cys Pro Thr Asn Phe Tyr Gln Met Asp Gly Thr Pro Cys
 65                  70                  75                  80 gag ggc ggc cag gcc tac tgc tac aac ggc atg tgc ctc acc tac cag     288
Glu Gly Gly Gln Ala Tyr Cys Tyr Asn Gly Met Cys Leu Thr Tyr Gln
                 85                  90                  95 gag cag tgc cag cag ctg tgg gga ccc gga gcc cga cct gcc cct gac     336
Glu Gln Cys Gln Gln Leu Trp Gly Pro Gly Ala Arg Pro Ala Pro Asp
            100                 105                 110 ctc tgc ttc gag aag gtg aat gtg gca gga gac acc ttt gga aac tgt     384
Leu Cys Phe Glu Lys Val Asn Val Ala Gly Asp Thr Phe Gly Asn Cys
        115                 120                 125
```

```
gga aag gac a                                                     394
Gly Lys Asp
    130

<210> SEQ ID NO 14
<211> LENGTH: 131
<212> TYPE: PRT
<213> ORGANISM: Unknown Organism
<220> FEATURE:
<223> OTHER INFORMATION: Description of Unknown Organism: Partial
      sequence of human meltrin beta derived from cDNA

<400> SEQUENCE: 14

Gly Glu Glu Cys Asp Cys Gly Glu Glu Glu Cys Asn Asn Pro Cys
1               5                   10                  15

Cys Asn Ala Ser Asn Cys Thr Leu Arg Pro Gly Ala Glu Cys Ala His
                20                  25                  30

Gly Ser Cys Cys His Gln Cys Lys Leu Leu Ala Pro Gly Thr Leu Cys
            35                  40                  45

Arg Glu Gln Ala Arg Gln Cys Asp Leu Pro Glu Phe Cys Thr Gly Lys
        50                  55                  60

Ser Pro His Cys Pro Thr Asn Phe Tyr Gln Met Asp Gly Thr Pro Cys
65                  70                  75                  80

Glu Gly Gly Gln Ala Tyr Cys Tyr Asn Gly Met Cys Leu Thr Tyr Gln
                85                  90                  95

Glu Gln Cys Gln Gln Leu Trp Gly Pro Gly Ala Arg Pro Ala Pro Asp
            100                 105                 110

Leu Cys Phe Glu Lys Val Asn Val Ala Gly Asp Thr Phe Gly Asn Cys
        115                 120                 125

Gly Lys Asp
    130

<210> SEQ ID NO 15
<211> LENGTH: 1183
<212> TYPE: DNA
<213> ORGANISM: Unknown Organism
<220> FEATURE:
<223> OTHER INFORMATION: Description of Unknown Organism:  Human meltrin
      beta derived from cDNA
<221> NAME/KEY: CDS
<222> LOCATION: (2)..(1183)

<400> SEQUENCE: 15 c gga gct gcc act ggg cac ccc ttt ccc aaa gtg ttc aat gga tgc aac    49
  Gly Ala Ala Thr Gly His Pro Phe Pro Lys Val Phe Asn Gly Cys Asn
  1               5                   10                  15 agg agg gag ctg gac agg tat ctg cag tca ggt ggt gga atg tgt ctc     97
Arg Arg Glu Leu Asp Arg Tyr Leu Gln Ser Gly Gly Gly Met Cys Leu
                20                  25                  30 tcc aac atg cca gac acc agg atg ttg tat gga ggc cgg agg tgt ggg    145
Ser Asn Met Pro Asp Thr Arg Met Leu Tyr Gly Gly Arg Arg Cys Gly
            35                  40                  45 aac ggg tat ctg gaa gat ggg gaa gag tgt gac tgt gga gaa gaa gag    193
Asn Gly Tyr Leu Glu Asp Gly Glu Glu Cys Asp Cys Gly Glu Glu Glu
        50                  55                  60 gaa tgt aac aac ccc tgc tgc aat gcc tct aat tgt acc ctg agg ccg    241
Glu Cys Asn Asn Pro Cys Cys Asn Ala Ser Asn Cys Thr Leu Arg Pro
65                  70                  75                  80 ggg gcg gag tgt gct cac ggc tcc tgc tgc cac cag tgt aag ctg ttg    289
Gly Ala Glu Cys Ala His Gly Ser Cys Cys His Gln Cys Lys Leu Leu
                85                  90                  95
```

```
gct cct ggg acc ctg tgc cgc gag cag gcc agg cag tgt gac ctc ccg      337
Ala Pro Gly Thr Leu Cys Arg Glu Gln Ala Arg Gln Cys Asp Leu Pro
            100                 105                 110 gag ttc tgt acg ggc aag tct ccc cac tgc cct acc aac ttc tac cag      385
Glu Phe Cys Thr Gly Lys Ser Pro His Cys Pro Thr Asn Phe Tyr Gln
        115                 120                 125 atg gat ggt acc ccc tgt gag ggc ggc cag gcc tac tgc tac aac ggc      433
Met Asp Gly Thr Pro Cys Glu Gly Gly Gln Ala Tyr Cys Tyr Asn Gly
130                 135                 140 atg tgc ctc acc tac cag gag cag tgc cag cag ctg tgg gga ccc gga      481
Met Cys Leu Thr Tyr Gln Glu Gln Cys Gln Gln Leu Trp Gly Pro Gly
145                 150                 155                 160 gcc cga cct gcc cct gac ctc tgc ttc gag aag gtg aat gtg gca gga      529
Ala Arg Pro Ala Pro Asp Leu Cys Phe Glu Lys Val Asn Val Ala Gly
            165                 170                 175 gac acc ttt gga aac tgt gga aag gac atg aat ggt gaa cac agg aag      577
Asp Thr Phe Gly Asn Cys Gly Lys Asp Met Asn Gly Glu His Arg Lys
        180                 185                 190 tgc aac atg aga gat gcg aag tgt ggg aag atc cag tgt cag agc tct      625
Cys Asn Met Arg Asp Ala Lys Cys Gly Lys Ile Gln Cys Gln Ser Ser
    195                 200                 205 gag gcc cgg ccc ctg gag tcc aac gcg gtg ccc att gac acc act atc      673
Glu Ala Arg Pro Leu Glu Ser Asn Ala Val Pro Ile Asp Thr Thr Ile
210                 215                 220 atc atg aat ggg agg cag atc cag tgc cgg ggc acc cac gtc tac cga      721
Ile Met Asn Gly Arg Gln Ile Gln Cys Arg Gly Thr His Val Tyr Arg
225                 230                 235                 240 ggt cct gag gag gag ggt gac atg ctg gac cca ggg ctg gtg atg act      769
Gly Pro Glu Glu Glu Gly Asp Met Leu Asp Pro Gly Leu Val Met Thr
            245                 250                 255 gga acc aag tgt ggc tac aac cat att tgc ctt gag ggg cag tgc agg      817
Gly Thr Lys Cys Gly Tyr Asn His Ile Cys Leu Glu Gly Gln Cys Arg
        260                 265                 270 aac acc tcc ttc ttt gaa act gaa ggc tgt ggg aag aag tgc aat ggc      865
Asn Thr Ser Phe Phe Glu Thr Glu Gly Cys Gly Lys Lys Cys Asn Gly
    275                 280                 285 cat ggg gtc tgt aac aac aac cag aac tgc cac tgc ctg ccg ggc tgg      913
His Gly Val Cys Asn Asn Asn Gln Asn Cys His Cys Leu Pro Gly Trp
290                 295                 300 gcc ccg ccc ttc tgc aac aca ccg ggc cac ggg ggc agt atc gac agt      961
Ala Pro Pro Phe Cys Asn Thr Pro Gly His Gly Gly Ser Ile Asp Ser
305                 310                 315                 320 ggg cct atg ccc cct gag agt gtg ggt cct gtg gta gct gga gtg ttg     1009
Gly Pro Met Pro Pro Glu Ser Val Gly Pro Val Val Ala Gly Val Leu
            325                 330                 335 gtg gcc atc ttg gtg ctg gcg gtc ctc atg ctg atg tac tac tgc tgc     1057
Val Ala Ile Leu Val Leu Ala Val Leu Met Leu Met Tyr Tyr Cys Cys
        340                 345                 350 aga cag aac aac aaa cta ggc caa ctc aag ccc tca gct ctc cct tcc     1105
Arg Gln Asn Asn Lys Leu Gly Gln Leu Lys Pro Ser Ala Leu Pro Ser
    355                 360                 365 aag ctg agg caa cag ttc agt tgt ccc ttc agg gtt tct cag aac agc     1153
Lys Leu Arg Gln Gln Phe Ser Cys Pro Phe Arg Val Ser Gln Asn Ser
370                 375                 380 ggg act ggt cat gcc aac cca act ttc aag                              1183
Gly Thr Gly His Ala Asn Pro Thr Phe Lys
385                 390

<210> SEQ ID NO 16
<211> LENGTH: 394
```

```
<212> TYPE: PRT
<213> ORGANISM: Unknown Organism
<220> FEATURE:
<223> OTHER INFORMATION: Description of Unknown Organism: Human meltrin
      beta derived from cDNA

<400> SEQUENCE: 16
```

| | | | | | | | | | | | | | | |
|---|---|---|---|---|---|---|---|---|---|---|---|---|---|---|
| Gly | Ala | Ala | Thr | Gly | His | Pro | Phe | Pro | Lys | Val | Phe | Asn | Gly | Cys | Asn |
| 1 | | | | 5 | | | | | 10 | | | | | 15 |
| Arg | Arg | Glu | Leu | Asp | Arg | Tyr | Leu | Gln | Ser | Gly | Gly | Met | Cys | Leu |
| | | | 20 | | | | | 25 | | | | 30 | | |
| Ser | Asn | Met | Pro | Asp | Thr | Arg | Met | Leu | Tyr | Gly | Gly | Arg | Arg | Cys | Gly |
| | 35 | | | | | 40 | | | | | 45 | | | |
| Asn | Gly | Tyr | Leu | Glu | Asp | Gly | Glu | Glu | Cys | Asp | Cys | Gly | Glu | Glu | Glu |
| | 50 | | | | | 55 | | | | | 60 | | | |
| Glu | Cys | Asn | Asn | Pro | Cys | Cys | Asn | Ala | Ser | Asn | Cys | Thr | Leu | Arg | Pro |
| 65 | | | | | 70 | | | | | 75 | | | | | 80 |
| Gly | Ala | Glu | Cys | Ala | His | Gly | Ser | Cys | Cys | His | Gln | Cys | Lys | Leu | Leu |
| | | | | 85 | | | | | 90 | | | | | 95 | |
| Ala | Pro | Gly | Thr | Leu | Cys | Arg | Glu | Gln | Ala | Arg | Gln | Cys | Asp | Leu | Pro |
| | | | 100 | | | | | 105 | | | | | 110 | | |
| Glu | Phe | Cys | Thr | Gly | Lys | Ser | Pro | His | Cys | Pro | Thr | Asn | Phe | Tyr | Gln |
| | | 115 | | | | | 120 | | | | | 125 | | | |
| Met | Asp | Gly | Thr | Pro | Cys | Glu | Gly | Gly | Gln | Ala | Tyr | Cys | Tyr | Asn | Gly |
| | 130 | | | | | 135 | | | | | 140 | | | | |
| Met | Cys | Leu | Thr | Tyr | Gln | Glu | Gln | Cys | Gln | Gln | Leu | Trp | Gly | Pro | Gly |
| 145 | | | | | 150 | | | | | 155 | | | | | 160 |
| Ala | Arg | Pro | Ala | Pro | Asp | Leu | Cys | Phe | Glu | Lys | Val | Asn | Val | Ala | Gly |
| | | | | 165 | | | | | 170 | | | | | 175 | |
| Asp | Thr | Phe | Gly | Asn | Cys | Gly | Lys | Asp | Met | Asn | Gly | Glu | His | Arg | Lys |
| | | | 180 | | | | | 185 | | | | | 190 | | |
| Cys | Asn | Met | Arg | Asp | Ala | Lys | Cys | Gly | Lys | Ile | Gln | Cys | Gln | Ser | Ser |
| | | 195 | | | | | 200 | | | | | 205 | | | |
| Glu | Ala | Arg | Pro | Leu | Glu | Ser | Asn | Ala | Val | Pro | Ile | Asp | Thr | Thr | Ile |
| | 210 | | | | | 215 | | | | | 220 | | | | |
| Ile | Met | Asn | Gly | Arg | Gln | Ile | Gln | Cys | Arg | Gly | Thr | His | Val | Tyr | Arg |
| 225 | | | | | 230 | | | | | 235 | | | | | 240 |
| Gly | Pro | Glu | Glu | Glu | Gly | Asp | Met | Leu | Asp | Pro | Gly | Leu | Val | Met | Thr |
| | | | | 245 | | | | | 250 | | | | | 255 | |
| Gly | Thr | Lys | Cys | Gly | Tyr | Asn | His | Ile | Cys | Leu | Glu | Gly | Gln | Cys | Arg |
| | | | 260 | | | | | 265 | | | | | 270 | | |
| Asn | Thr | Ser | Phe | Phe | Glu | Thr | Glu | Gly | Cys | Gly | Lys | Lys | Cys | Asn | Gly |
| | | 275 | | | | | 280 | | | | | 285 | | | |
| His | Gly | Val | Cys | Asn | Asn | Gln | Asn | Cys | His | Cys | Leu | Pro | Gly | Trp |
| | 290 | | | | | 295 | | | | | 300 | | | | |
| Ala | Pro | Pro | Phe | Cys | Asn | Thr | Pro | Gly | His | Gly | Gly | Ser | Ile | Asp | Ser |
| 305 | | | | | 310 | | | | | 315 | | | | | 320 |
| Gly | Pro | Met | Pro | Pro | Glu | Ser | Val | Gly | Pro | Val | Val | Ala | Gly | Val | Leu |
| | | | | 325 | | | | | 330 | | | | | 335 | |
| Val | Ala | Ile | Leu | Val | Leu | Ala | Val | Leu | Met | Leu | Met | Tyr | Tyr | Cys | Cys |
| | | | 340 | | | | | 345 | | | | | 350 | | |
| Arg | Gln | Asn | Asn | Lys | Leu | Gly | Gln | Leu | Lys | Pro | Ser | Ala | Leu | Pro | Ser |
| | | 355 | | | | | 360 | | | | | 365 | | | |
| Lys | Leu | Arg | Gln | Gln | Phe | Ser | Cys | Pro | Phe | Arg | Val | Ser | Gln | Asn | Ser |
| | 370 | | | | | 375 | | | | | 380 | | | | |

```
Gly Thr Gly His Ala Asn Pro Thr Phe Lys
385                 390

<210> SEQ ID NO 17
<211> LENGTH: 624
<212> TYPE: DNA
<213> ORGANISM: Unknown Organism
<220> FEATURE:
<223> OTHER INFORMATION: Description of Unknown Organism: Clone TM:
      Human meltrin alpha derived from cDNA
<221> NAME/KEY: CDS
<222> LOCATION: (3)..(623)

<400> SEQUENCE: 17 gc aca aag tgt gca gat gga aaa atc tgc ctg aat cgt caa tgt caa          47
   Thr Lys Cys Ala Asp Gly Lys Ile Cys Leu Asn Arg Gln Cys Gln
     1               5                  10                  15 aat att agt gtc ttt ggg gtt cac gag tgt gca atg cag tgc cac ggc         95
Asn Ile Ser Val Phe Gly Val His Glu Cys Ala Met Gln Cys His Gly
             20                  25                  30 aga ggg gtg tgc aac aac agg aag aac tgc cac tgc gag gcc cac tgg        143
Arg Gly Val Cys Asn Asn Arg Lys Asn Cys His Cys Glu Ala His Trp
 35                  40                  45 gca cct ccc ttc tgt gac aag ttt ggc ttt gga gga agc aca gac agc        191
Ala Pro Pro Phe Cys Asp Lys Phe Gly Phe Gly Gly Ser Thr Asp Ser
     50                  55                  60 ggc ccc atc cgg caa gca gat aac caa ggt tta acc ata gga att ctg        239
Gly Pro Ile Arg Gln Ala Asp Asn Gln Gly Leu Thr Ile Gly Ile Leu
 65                  70                  75 gtg acc atc ctg tgt ctt ctt gct gcc gga ttt gtg gtt tat ctc aaa        287
Val Thr Ile Leu Cys Leu Leu Ala Ala Gly Phe Val Val Tyr Leu Lys
 80                  85                  90                  95 agg aag acc ttg ata cga ctg ctg ttt aca aat aag aag acc acc att        335
Arg Lys Thr Leu Ile Arg Leu Leu Phe Thr Asn Lys Lys Thr Thr Ile
                100                 105                 110 gaa aaa cta agg tgt gtg cgc cct tcc cgg cca ccc cgt ggc ttc caa        383
Glu Lys Leu Arg Cys Val Arg Pro Ser Arg Pro Pro Arg Gly Phe Gln
            115                 120                 125 ccc tgt cag gct cac ctc ggc cac ctt gga aaa ggc ctg atg agg aag        431
Pro Cys Gln Ala His Leu Gly His Leu Gly Lys Gly Leu Met Arg Lys
        130                 135                 140 ccg cca gat tcc tac cca ccg aag gac aat ccc agg aga ttg ctg cag        479
Pro Pro Asp Ser Tyr Pro Pro Lys Asp Asn Pro Arg Arg Leu Leu Gln
145                 150                 155 tgt cag aat gtt gac atc agc aga ccc ctc aac ggc ctg aat gtc cct        527
Cys Gln Asn Val Asp Ile Ser Arg Pro Leu Asn Gly Leu Asn Val Pro
160                 165                 170                 175 cag ccc cag tca act cag cga gtg ctt cct ccc ctc cac cgg gct cca        575
Gln Pro Gln Ser Thr Gln Arg Val Leu Pro Pro Leu His Arg Ala Pro
                180                 185                 190 cgt gca cct agc gtc cct gcc aga ccc ctg cca gcc aag cct gca ctt a     624
Arg Ala Pro Ser Val Pro Ala Arg Pro Leu Pro Ala Lys Pro Ala Leu
            195                 200                 205

<210> SEQ ID NO 18
<211> LENGTH: 207
<212> TYPE: PRT
<213> ORGANISM: Unknown Organism
<220> FEATURE:
<223> OTHER INFORMATION: Description of Unknown Organism: Clone TM:
      Human meltrin alpha derived from cDNA

<400> SEQUENCE: 18
```

```
Thr Lys Cys Ala Asp Gly Lys Ile Cys Leu Asn Arg Gln Cys Gln Asn
  1               5                  10                  15

Ile Ser Val Phe Gly Val His Glu Cys Ala Met Gln Cys His Gly Arg
             20                  25                  30

Gly Val Cys Asn Asn Arg Lys Asn Cys His Cys Glu Ala His Trp Ala
         35                  40                  45

Pro Pro Phe Cys Asp Lys Phe Gly Phe Gly Ser Thr Asp Ser Gly
     50                  55                  60

Pro Ile Arg Gln Ala Asp Asn Gln Gly Leu Thr Ile Gly Ile Leu Val
 65                  70                  75                  80

Thr Ile Leu Cys Leu Leu Ala Ala Gly Phe Val Val Tyr Leu Lys Arg
                 85                  90                  95

Lys Thr Leu Ile Arg Leu Leu Phe Thr Asn Lys Lys Thr Thr Ile Glu
                100                 105                 110

Lys Leu Arg Cys Val Arg Pro Ser Arg Pro Pro Arg Gly Phe Gln Pro
            115                 120                 125

Cys Gln Ala His Leu Gly His Leu Gly Lys Gly Leu Met Arg Lys Pro
130                 135                 140

Pro Asp Ser Tyr Pro Pro Lys Asp Asn Pro Arg Arg Leu Leu Gln Cys
145                 150                 155                 160

Gln Asn Val Asp Ile Ser Arg Pro Leu Asn Gly Leu Asn Val Pro Gln
                165                 170                 175

Pro Gln Ser Thr Gln Arg Val Leu Pro Pro Leu His Arg Ala Pro Arg
                180                 185                 190

Ala Pro Ser Val Pro Ala Arg Pro Leu Pro Ala Lys Pro Ala Leu
            195                 200                 205

<210> SEQ ID NO 19
<211> LENGTH: 2669
<212> TYPE: DNA
<213> ORGANISM: Unknown Organism
<220> FEATURE:
<223> OTHER INFORMATION: Description of Unknown Organism:  Clones:
      JM109(pMel-beta-24C) and JM109(pMel-beta-24N),
      both human meltrin beta
<221> NAME/KEY: CDS
<222> LOCATION: (2)..(1282)

<400> SEQUENCE: 19 c gga gct gcc act ggg cac ccc ttt ccc aaa gtg ttc aat gga tgc aac     49
  Gly Ala Ala Thr Gly His Pro Phe Pro Lys Val Phe Asn Gly Cys Asn
   1               5                  10                  15 agg agg gag ctg gac agg tat ctg cag tca ggt ggt gga atg tgt ctc       97
Arg Arg Glu Leu Asp Arg Tyr Leu Gln Ser Gly Gly Gly Met Cys Leu
             20                  25                  30 tcc aac atg cca gac acc agg atg ttg tat gga ggc cgg agg tgt ggg      145
Ser Asn Met Pro Asp Thr Arg Met Leu Tyr Gly Gly Arg Arg Cys Gly
         35                  40                  45 aac ggg tat ctg gaa gat ggg gaa gag tgt gac tgt gga gaa gaa gag      193
Asn Gly Tyr Leu Glu Asp Gly Glu Glu Cys Asp Cys Gly Glu Glu Glu
     50                  55                  60 gaa tgt aac aac ccc tgc tgc aat gcc tct aat tgt acc ctg agg ccg      241
Glu Cys Asn Asn Pro Cys Cys Asn Ala Ser Asn Cys Thr Leu Arg Pro
 65                  70                  75                  80 ggg gcg gag tgt gct cac ggc tcc tgc tgc cac cag tgt aag ctg ttg      289
Gly Ala Glu Cys Ala His Gly Ser Cys Cys His Gln Cys Lys Leu Leu
                 85                  90                  95 gct cct ggg acc ctg tgc cgc gag cag gcc agg cag tgt gac ctc ccg      337
```

```
Ala Pro Gly Thr Leu Cys Arg Glu Gln Ala Arg Gln Cys Asp Leu Pro
            100                 105                 110 gag ttc tgt acg ggc aag tct ccc cac tgc cct acc aac ttc tac cag      385
Glu Phe Cys Thr Gly Lys Ser Pro His Cys Pro Thr Asn Phe Tyr Gln
        115                 120                 125 atg gat ggt acc ccc tgt gag ggc ggc cag gcc tac tgc tac aac ggc      433
Met Asp Gly Thr Pro Cys Glu Gly Gly Gln Ala Tyr Cys Tyr Asn Gly
    130                 135                 140 atg tgc ctc acc tac cag gag cag tgc cag cag ctg tgg gga ccc gga      481
Met Cys Leu Thr Tyr Gln Glu Gln Cys Gln Gln Leu Trp Gly Pro Gly
145                 150                 155                 160 gcc cga cct gcc cct gac ctc tgc ttc gag aag gtg aat gtg gca gga      529
Ala Arg Pro Ala Pro Asp Leu Cys Phe Glu Lys Val Asn Val Ala Gly
                165                 170                 175 gac acc ttt gga aac tgt gga aag gac atg aat ggt gaa cac agg aag      577
Asp Thr Phe Gly Asn Cys Gly Lys Asp Met Asn Gly Glu His Arg Lys
            180                 185                 190 tgc aac atg aga gat gcg aag tgt ggg aag atc cag tgt cag agc tct      625
Cys Asn Met Arg Asp Ala Lys Cys Gly Lys Ile Gln Cys Gln Ser Ser
        195                 200                 205 gag gcc cgg ccc ctg gag tcc aac gcg gtg ccc att gac acc act atc      673
Glu Ala Arg Pro Leu Glu Ser Asn Ala Val Pro Ile Asp Thr Thr Ile
    210                 215                 220 atc atg aat ggg agg cag atc cag tgc cgg ggc acc cac gtc tac cga      721
Ile Met Asn Gly Arg Gln Ile Gln Cys Arg Gly Thr His Val Tyr Arg
225                 230                 235                 240 ggt cct gag gag gag ggt gac atg ctg gac cca ggg ctg gtg atg act      769
Gly Pro Glu Glu Glu Gly Asp Met Leu Asp Pro Gly Leu Val Met Thr
                245                 250                 255 gga acc aag tgt ggc tac aac cat att tgc ctt gag ggg cag tgc agg      817
Gly Thr Lys Cys Gly Tyr Asn His Ile Cys Leu Glu Gly Gln Cys Arg
            260                 265                 270 aac acc tcc ttc ttt gaa act gaa ggc tgt ggg aag aag tgc aat ggc      865
Asn Thr Ser Phe Phe Glu Thr Glu Gly Cys Gly Lys Lys Cys Asn Gly
        275                 280                 285 cat ggg gtc tgt aac aac aac cag aac tgc cac tgc ctg ccg ggc tgg      913
His Gly Val Cys Asn Asn Asn Gln Asn Cys His Cys Leu Pro Gly Trp
    290                 295                 300 gcc ccg ccc ttc tgc aac aca ccg ggc cac ggg ggc agt atc gac agt      961
Ala Pro Pro Phe Cys Asn Thr Pro Gly His Gly Gly Ser Ile Asp Ser
305                 310                 315                 320 ggg cct atg ccc cct gag agt gtg ggt cct gtg gta gct gga gtg ttg     1009
Gly Pro Met Pro Pro Glu Ser Val Gly Pro Val Val Ala Gly Val Leu
                325                 330                 335 gtg gcc atc ttg gtg ctg gcg gtc ctc atg ctg atg tac tgc tgc         1057
Val Ala Ile Leu Val Leu Ala Val Leu Met Leu Met Tyr Tyr Cys Cys
            340                 345                 350 aga cag aac aac aaa cta ggc caa ctc aag ccc tca gct ctc cct tcc     1105
Arg Gln Asn Asn Lys Leu Gly Gln Leu Lys Pro Ser Ala Leu Pro Ser
        355                 360                 365 aag ctg agg caa cag ttc agt tgt ccc ttc agg gtt tct cag aac agc     1153
Lys Leu Arg Gln Gln Phe Ser Cys Pro Phe Arg Val Ser Gln Asn Ser
    370                 375                 380 ggg act ggt cat gcc aac cca act ttc aag ccg gaa ttc cgg gcc ccc     1201
Gly Thr Gly His Ala Asn Pro Thr Phe Lys Pro Glu Phe Arg Ala Pro
385                 390                 395                 400 cac agc cca cac cac cat gac aag ggc cac caa ttc cac ggc cac acc     1249
His Ser Pro His His His Asp Lys Gly His Gln Phe His Gly His Thr
                405                 410                 415
```

-continued

```
ctc ctc cac tct ggg gac gac ccg gat cct cac tgagctgacc acaacagcca    1302
Leu Leu His Ser Gly Asp Asp Pro Asp Pro His
        420                 425 ctacaactgc agccactgga tccacggcca ccctgtcctc cacccagggg accacctgga    1362
tcctcacaga gccgagcact atagccaccg tgatggtgcc caccggttcc acggccaccg    1422
cctcctccac tctgggaaca gctcacaccc ccaaagtggt gaccaccatg ccactatgc    1482 ccacagccca tgcctccacg gttcccagct cgtccaccgt ggggaccacc cgcacccctg    1542
cagtgctccc cagcagcctg ccaaccttca gcgtgtccac tgtgtcctcc tcagtcctca    1602
ccaccctgag acccactggc ttccccagct cccacttctc tactccctgc ttctgcaggg    1662
catttggaca gttttttctcg cccggggaag tcatctacaa taagaccgac cgagccggct    1722
gccatttcta cgcagtgtgc aatcagcact gtgacattga ccgcttccag ggcgcctgtc    1782
ccacctcccc accgccagtg tcctccgccc cgctgtcctc gccctcccct gccctggct    1842 gtgacaatgc catccctctc cggcaggtga atgagacctg gacctggag aactgcacgg    1902 tggccaggtg cgtgggtgac aaccgtgtcg tcctgctgga cccaaagcct gtggccaacg    1962
tcacctgcgt gaacaagcac ctgcccatca agtgtcgga cccgagccag ccctgtgact    2022
tccactatga gtgcgagtgc atctgcagca tgtggggcgg ctcccactat ccaccttg    2082 acggcacctc ttacaccttc cggggcaact gcacctatgt cctcatgaga gagatccatg    2142
cacgctttgg gaatctcagc ctctacctgg acaaccacta ctgcacggcc tctgccactg    2202
ccgctgccgc ccgctgcccc cgcgccctca gcatccacta caagtccatg gatatcgtcc    2262
tcactgtcac catggtgcat gggaaggagg agggcctgat cctgtttgac caaattccgg    2322
tgagcagcgg tttcagcaag aacggcgtgc ttgtgtctgt gctggggacc accaccatgc    2382
gtgtggacat tcctgccctg gcgtgagcg tcaccttcaa tggccaagtc ttccaggccc    2442
ggctgcccta cagcctcttc cacaacaaca ccgagggcca gtgcggcacc tgcaccaaca    2502
accagaggga cgactgtctc cagcgggacg gaaccactgc cgccagttgc aaggacatgg    2562
ccaagacgtg gctggtcccc gacagcagaa aggatggctg ctgggccccg actggcacac    2622 ccccactgc cagccccgca gccccggtgt ctagcacacc cacccg             2669
```

<210> SEQ ID NO 20
<211> LENGTH: 427
<212> TYPE: PRT
<213> ORGANISM: Unknown Organism
<220> FEATURE:
<223> OTHER INFORMATION: Description of Unknown Organism: Clones:
    JM109(pMel-beta-24C) and JM109(pMel-beta-24N),
    both human meltrin beta

<400> SEQUENCE: 20

```
Gly Ala Ala Thr Gly His Pro Phe Pro Lys Val Phe Asn Gly Cys Asn
 1               5                  10                  15

Arg Arg Glu Leu Asp Arg Tyr Leu Gln Ser Gly Gly Met Cys Leu
            20                  25                  30

Ser Asn Met Pro Asp Thr Arg Met Leu Tyr Gly Gly Arg Arg Cys Gly
        35                  40                  45

Asn Gly Tyr Leu Glu Asp Gly Glu Glu Cys Asp Cys Gly Glu Glu Glu
    50                  55                  60

Glu Cys Asn Asn Pro Cys Cys Asn Ala Ser Asn Cys Thr Leu Arg Pro
65                  70                  75                  80

Gly Ala Glu Cys Ala His Gly Ser Cys Cys His Gln Cys Lys Leu Leu
                85                  90                  95
```

```
Ala Pro Gly Thr Leu Cys Arg Glu Gln Ala Arg Gln Cys Asp Leu Pro
            100                 105                 110

Glu Phe Cys Thr Gly Lys Ser Pro His Cys Pro Thr Asn Phe Tyr Gln
        115                 120                 125

Met Asp Gly Thr Pro Cys Glu Gly Gln Ala Tyr Cys Tyr Asn Gly
    130                 135                 140

Met Cys Leu Thr Tyr Gln Glu Gln Cys Gln Gln Leu Trp Gly Pro Gly
145                 150                 155                 160

Ala Arg Pro Ala Pro Asp Leu Cys Phe Glu Lys Val Asn Val Ala Gly
                165                 170                 175

Asp Thr Phe Gly Asn Cys Gly Lys Asp Met Asn Gly Glu His Arg Lys
            180                 185                 190

Cys Asn Met Arg Asp Ala Lys Cys Gly Lys Ile Gln Cys Gln Ser Ser
        195                 200                 205

Glu Ala Arg Pro Leu Glu Ser Asn Ala Val Pro Ile Asp Thr Thr Ile
    210                 215                 220

Ile Met Asn Gly Arg Gln Ile Gln Cys Arg Gly Thr His Val Tyr Arg
225                 230                 235                 240

Gly Pro Glu Glu Glu Gly Asp Met Leu Asp Pro Gly Leu Val Met Thr
                245                 250                 255

Gly Thr Lys Cys Gly Tyr Asn His Ile Cys Leu Glu Gly Gln Cys Arg
            260                 265                 270

Asn Thr Ser Phe Phe Glu Thr Glu Gly Cys Gly Lys Lys Cys Asn Gly
        275                 280                 285

His Gly Val Cys Asn Asn Gln Asn Cys His Cys Leu Pro Gly Trp
    290                 295                 300

Ala Pro Pro Phe Cys Asn Thr Pro Gly His Gly Gly Ser Ile Asp Ser
305                 310                 315                 320

Gly Pro Met Pro Pro Glu Ser Val Gly Pro Val Val Ala Gly Val Leu
                325                 330                 335

Val Ala Ile Leu Val Leu Ala Val Leu Met Leu Met Tyr Tyr Cys Cys
            340                 345                 350

Arg Gln Asn Asn Lys Leu Gly Gln Leu Lys Pro Ser Ala Leu Pro Ser
        355                 360                 365

Lys Leu Arg Gln Gln Phe Ser Cys Pro Phe Arg Val Ser Gln Asn Ser
370                 375                 380

Gly Thr Gly His Ala Asn Pro Thr Phe Lys Pro Glu Phe Arg Ala Pro
385                 390                 395                 400

His Ser Pro His His His Asp Lys Gly His Gln Phe His Gly His Thr
                405                 410                 415

Leu Leu His Ser Gly Asp Asp Pro Asp Pro His
            420                 425
```

<210> SEQ ID NO 21
<211> LENGTH: 1483
<212> TYPE: DNA
<213> ORGANISM: Unknown Organism
<220> FEATURE:
<223> OTHER INFORMATION: Description of Unknown Organism: Clone:
    JM109(pMel-alpha-25C), human meltrin alpha
<221> NAME/KEY: CDS
<222> LOCATION: (1)..(687)

<400> SEQUENCE: 21

```
gat ggg cac tca tgt cag gat gtg gac ggc tac tgc tac aat ggc atc      48
Asp Gly His Ser Cys Gln Asp Val Asp Gly Tyr Cys Tyr Asn Gly Ile
```

|   |   |
|---|---|
| tgc cag act cac gag cag cag tgt gtc acg ctc tgg gga cca ggt gct<br>Cys Gln Thr His Glu Gln Gln Cys Val Thr Leu Trp Gly Pro Gly Ala<br>1               5                   10                  15<br>                    20                  25                  30 | 96 |
| aaa cct gcc cct ggg atc tgc ttt gag aga gtc aat tct gca ggt gat<br>Lys Pro Ala Pro Gly Ile Cys Phe Glu Arg Val Asn Ser Ala Gly Asp<br>              35                  40                  45 | 144 |
| cct tat ggc aac tgt ggc aaa gtc tcg aag agt tcc ttt gcc aaa tgc<br>Pro Tyr Gly Asn Cys Gly Lys Val Ser Lys Ser Ser Phe Ala Lys Cys<br>          50                  55                  60 | 192 |
| gag atg aga gat gct aaa tgt gga aaa atc cag tgt caa gga ggt gcc<br>Glu Met Arg Asp Ala Lys Cys Gly Lys Ile Gln Cys Gln Gly Gly Ala<br>65                  70                  75                  80 | 240 |
| agc cgg cca gtc att ggt acc aat gcc gtt tcc ata gaa aca aac atc<br>Ser Arg Pro Val Ile Gly Thr Asn Ala Val Ser Ile Glu Thr Asn Ile<br>                    85                  90                  95 | 288 |
| ccc ctg cag caa gga ggc cgg att ctg tgc cgg ggg acc cac gtg tac<br>Pro Leu Gln Gln Gly Gly Arg Ile Leu Cys Arg Gly Thr His Val Tyr<br>                100                 105                 110 | 336 |
| ttg ggc gat gac atg ccg gac cca ggg ctt gtg ctt gca ggc aca aag<br>Leu Gly Asp Asp Met Pro Asp Pro Gly Leu Val Leu Ala Gly Thr Lys<br>            115                 120                 125 | 384 |
| tgt gca gat gga aaa atc tgc ctg aat cgt caa tgt caa aat att agt<br>Cys Ala Asp Gly Lys Ile Cys Leu Asn Arg Gln Cys Gln Asn Ile Ser<br>        130                 135                 140 | 432 |
| gtc ttt ggg gtt cac gag tgt gca atg cag tgc cac ggc aga ggg gtg<br>Val Phe Gly Val His Glu Cys Ala Met Gln Cys His Gly Arg Gly Val<br>145                 150                 155                 160 | 480 |
| tgc aac aac agg aag aac tgc cac tgc gag gcc cac tgg gca cct ccc<br>Cys Asn Asn Arg Lys Asn Cys His Cys Glu Ala His Trp Ala Pro Pro<br>                165                 170                 175 | 528 |
| ttc tgt gac aag ttt ggc ttt gga gga agc aca gac agc ggc ccc atc<br>Phe Cys Asp Lys Phe Gly Phe Gly Gly Ser Thr Asp Ser Gly Pro Ile<br>            180                 185                 190 | 576 |
| cgg caa gca gaa gca agg cag gaa gct gca gag tcc aac agg gag cgc<br>Arg Gln Ala Glu Ala Arg Gln Glu Ala Ala Glu Ser Asn Arg Glu Arg<br>        195                 200                 205 | 624 |
| ggc cag ggc cag gag ccc gtg gga tcg cag gag cat gcg tct act gcc<br>Gly Gln Gly Gln Glu Pro Val Gly Ser Gln Glu His Ala Ser Thr Ala<br>    210                 215                 220 | 672 |
| tca ctg aca ctc atc tgagccctcc catgacatgg agaccgtgac cagtgctgct<br>Ser Leu Thr Leu Ile<br>225 | 727 |
| gcagaggagg tcacgcgtcc ccaaggcctc ctgtgactgg cagcattgac tctgtggctt | 787 |
| tgccatcgtt tccatgacaa cagacacaac acagttctcg gggctcagga ggggaagtcc | 847 |
| agcctaccag gcacgtctgc agaaacagtg caaggaaggg cagcgacttc ctggttgagc | 907 |
| ttctgctaaa acatggacat gcttcagtgc tgctcctgag agagtagcag gttaccactc | 967 |
| tggcaggccc cagccctgca gcaaggagga agaggactca aaagtctggc ctttcactga | 1027 |
| gcccccacag cagtggggga gaagcaaggg ttgggcccag tgtccccttt ccccagtgac | 1087 |
| acctcagcct tggcagccct gatgactggt ctctggctgc aacttaatgc tctgatatgg | 1147 |
| cttttagcat ttattatatg aaaatagcag ggttttagtt tttaatttat cagagaccct | 1207 |
| gccacccatt ccatctccat ccaagcaaac tgaatggcat tgaaacaaac tggagaagaa | 1267 |
| ggtaggagaa agggcggtga actctggctc tttgctgtgg acatgcgtga ccagcagtac | 1327 |
| tcaggtttga gggtttgcag aaagccaggg aacccacaga gtcaccaacc cttcatttaa | 1387 |

```
caagtaagaa tgttaaaaag tgaaaacaat gtaagagcct aactccatcc cccgtggcca      1447
ttactgcata aaatagagtg catcccgccc gaattc                                1483
```

<210> SEQ ID NO 22
<211> LENGTH: 229
<212> TYPE: PRT
<213> ORGANISM: Unknown Organism
<220> FEATURE:
<223> OTHER INFORMATION: Description of Unknown Organism: Clone:
     JM109(pMel-alpha-25C), human meltrin alpha

<400> SEQUENCE: 22

```
Asp Gly His Ser Cys Gln Asp Val Asp Gly Tyr Cys Tyr Asn Gly Ile
 1               5                  10                  15

Cys Gln Thr His Glu Gln Gln Cys Val Thr Leu Trp Gly Pro Gly Ala
             20                  25                  30

Lys Pro Ala Pro Gly Ile Cys Phe Glu Arg Val Asn Ser Ala Gly Asp
         35                  40                  45

Pro Tyr Gly Asn Cys Gly Lys Val Ser Lys Ser Ser Phe Ala Lys Cys
     50                  55                  60

Glu Met Arg Asp Ala Lys Cys Gly Lys Ile Gln Cys Gln Gly Gly Ala
 65                  70                  75                  80

Ser Arg Pro Val Ile Gly Thr Asn Ala Val Ser Ile Glu Thr Asn Ile
                 85                  90                  95

Pro Leu Gln Gln Gly Gly Arg Ile Leu Cys Arg Gly Thr His Val Tyr
            100                 105                 110

Leu Gly Asp Asp Met Pro Asp Pro Gly Leu Val Leu Ala Gly Thr Lys
        115                 120                 125

Cys Ala Asp Gly Lys Ile Cys Leu Asn Arg Gln Cys Gln Asn Ile Ser
    130                 135                 140

Val Phe Gly Val His Glu Cys Ala Met Gln Cys His Gly Arg Gly Val
145                 150                 155                 160

Cys Asn Asn Arg Lys Asn Cys His Cys Glu Ala His Trp Ala Pro Pro
                165                 170                 175

Phe Cys Asp Lys Phe Gly Phe Gly Gly Ser Thr Asp Ser Gly Pro Ile
            180                 185                 190

Arg Gln Ala Glu Ala Arg Gln Glu Ala Glu Ser Asn Arg Glu Arg
        195                 200                 205

Gly Gln Gly Gln Glu Pro Val Gly Ser Gln Glu His Ala Ser Thr Ala
    210                 215                 220

Ser Leu Thr Leu Ile
225
```

<210> SEQ ID NO 23
<211> LENGTH: 1569
<212> TYPE: DNA
<213> ORGANISM: Unknown Organism
<220> FEATURE:
<223> OTHER INFORMATION: Description of Unknown Organism: Clone:
     JM109(pMel-alpha-26N), human meltrin alpha
<221> NAME/KEY: CDS
<222> LOCATION: (1)..(1569)

<400> SEQUENCE: 23

```
ggg gac ctc tgg atc cca gtg aag agc ttc gac tcc aag aat cat cca      48
Gly Asp Leu Trp Ile Pro Val Lys Ser Phe Asp Ser Lys Asn His Pro
 1               5                  10                  15 gaa gtg ctg aat att cga cta caa cgg gaa agc aaa gaa ctg atc ata      96
```

-continued

```
                Glu Val Leu Asn Ile Arg Leu Gln Arg Glu Ser Lys Glu Leu Ile Ile
                             20                  25                  30 aat ctg gaa aga aat gaa ggt ctc att gcc agc agt ttc acg gaa acc          144
Asn Leu Glu Arg Asn Glu Gly Leu Ile Ala Ser Ser Phe Thr Glu Thr
             35                  40                  45 cac tat ctg caa gac ggt act gat gtc tcc ctc gct cga aat tac acg          192
His Tyr Leu Gln Asp Gly Thr Asp Val Ser Leu Ala Arg Asn Tyr Thr
 50                  55                  60 ggt cac tgt tac tac cat gga cat gta cgg gga tat tct gat tca gca          240
Gly His Cys Tyr Tyr His Gly His Val Arg Gly Tyr Ser Asp Ser Ala
 65                  70                  75                  80 gtc agt ctc agc acg tgt tct ggt ctc agg gga ctt att ggg ttt gaa          288
Val Ser Leu Ser Thr Cys Ser Gly Leu Arg Gly Leu Ile Gly Phe Glu
                 85                  90                  95 aat gaa agc tat gtc tta gaa cca atg aaa agt gca acc aac aga tac          336
Asn Glu Ser Tyr Val Leu Glu Pro Met Lys Ser Ala Thr Asn Arg Tyr
                100                 105                 110 aaa ctc ttc cca gcg aag aag ctg aaa agc gtc cgg gga tca tgt gga          384
Lys Leu Phe Pro Ala Lys Lys Leu Lys Ser Val Arg Gly Ser Cys Gly
            115                 120                 125 tca cat cac aac aca cca aac ctc gct gca aag aat gtg ttt cca cca          432
Ser His His Asn Thr Pro Asn Leu Ala Ala Lys Asn Val Phe Pro Pro
130                 135                 140 ccc tct cag aca tgg gca aga agg cat aaa aga gag acc ctc aag gca          480
Pro Ser Gln Thr Trp Ala Arg Arg His Lys Arg Glu Thr Leu Lys Ala
145                 150                 155                 160 act aag tat gtg gag ctg gtg atc gtg gca gac aac cga gag ttt cag          528
Thr Lys Tyr Val Glu Leu Val Ile Val Ala Asp Asn Arg Glu Phe Gln
                165                 170                 175 agg caa gga aaa gat ctg gaa aaa gtt aag cag cga tta ata gag att          576
Arg Gln Gly Lys Asp Leu Glu Lys Val Lys Gln Arg Leu Ile Glu Ile
            180                 185                 190 gct aat cac gtt gac aag ttt tac aga cca ctg aac att cgg atc gtg          624
Ala Asn His Val Asp Lys Phe Tyr Arg Pro Leu Asn Ile Arg Ile Val
        195                 200                 205 ttg gta ggc gtg gaa gtg tgg aat gac atg gac aaa tgc tct gta agt          672
Leu Val Gly Val Glu Val Trp Asn Asp Met Asp Lys Cys Ser Val Ser
210                 215                 220 cag gac cca ttc acc agc ctc cat gaa ttt ctg gac tgg agg aag atg          720
Gln Asp Pro Phe Thr Ser Leu His Glu Phe Leu Asp Trp Arg Lys Met
225                 230                 235                 240 aag ctt cta cct cgc aaa tcc cat gac aat gcg cag ctt gtc agt ggg          768
Lys Leu Leu Pro Arg Lys Ser His Asp Asn Ala Gln Leu Val Ser Gly
                245                 250                 255 gtt tat ttc caa ggg acc acc atc ggc atg gcc cca atc atg agc atg          816
Val Tyr Phe Gln Gly Thr Thr Ile Gly Met Ala Pro Ile Met Ser Met
            260                 265                 270 tgc acg gca gac cag tct ggg gga att gtc atg gac cat tca gac aat          864
Cys Thr Ala Asp Gln Ser Gly Gly Ile Val Met Asp His Ser Asp Asn
        275                 280                 285 ccc ctt ggt gca gcc gtg acc ctg gca cat gag ctg ggc cac aat ttc          912
Pro Leu Gly Ala Ala Val Thr Leu Ala His Glu Leu Gly His Asn Phe
290                 295                 300 ggg atg aat cat gac aca ctg gac agg ggc tgt agc tgt caa atg gcg          960
Gly Met Asn His Asp Thr Leu Asp Arg Gly Cys Ser Cys Gln Met Ala
305                 310                 315                 320 gtt gag aaa gga ggc tgc atc atg aac gct tcc acc ggg tac cca ttt         1008
Val Glu Lys Gly Gly Cys Ile Met Asn Ala Ser Thr Gly Tyr Pro Phe
                325                 330                 335
```

-continued

```
ccc atg gtg ttc agc agt tgc agc agg aag gac ttg gag acc agc ctg    1056
Pro Met Val Phe Ser Ser Cys Ser Arg Lys Asp Leu Glu Thr Ser Leu
        340                 345                 350 gag aaa gga atg ggg gtg tgc ctg ttt aac ctg ccg gaa gtc agg gag    1104
Glu Lys Gly Met Gly Val Cys Leu Phe Asn Leu Pro Glu Val Arg Glu
355                 360                 365 tct ttc ggg ggc cag aag tgt ggg aac aga ttt gtg gaa gaa gga gag    1152
Ser Phe Gly Gly Gln Lys Cys Gly Asn Arg Phe Val Glu Glu Gly Glu
    370                 375                 380 gag tgt gac tgt ggg gag cca gag gaa tgt atg aat cgc tgc tgc aat    1200
Glu Cys Asp Cys Gly Glu Pro Glu Glu Cys Met Asn Arg Cys Cys Asn
385                 390                 395                 400 gcc acc acc tgt acc ctg aag ccg gac gct gtg tgc gca cat ggg ctg    1248
Ala Thr Thr Cys Thr Leu Lys Pro Asp Ala Val Cys Ala His Gly Leu
                405                 410                 415 tgt tgt gaa gac tgc cag ctg aag cct gca gga aca gcg tgc agg gac    1296
Cys Cys Glu Asp Cys Gln Leu Lys Pro Ala Gly Thr Ala Cys Arg Asp
            420                 425                 430 tcc agc aac tcc tgt gac ctc cca gag ttc tgc aca ggg gcc agc cct    1344
Ser Ser Asn Ser Cys Asp Leu Pro Glu Phe Cys Thr Gly Ala Ser Pro
        435                 440                 445 cac tgc cca gcc aac gtg tac ctg cac gat ggg cac tca tgt cag gat    1392
His Cys Pro Ala Asn Val Tyr Leu His Asp Gly His Ser Cys Gln Asp
450                 455                 460 gtg gac ggc tac tgc tac aat ggc atc tgc cag act cac gag cag cag    1440
Val Asp Gly Tyr Cys Tyr Asn Gly Ile Cys Gln Thr His Glu Gln Gln
465                 470                 475                 480 tgt gtc acg ctc tgg gga cca ggt gct aaa cct gcc cct ggg atc tgc    1488
Cys Val Thr Leu Trp Gly Pro Gly Ala Lys Pro Ala Pro Gly Ile Cys
                485                 490                 495 ttt gag aga gtc aat tct gca ggt gat cct tat ggc aac tgt ggc aaa    1536
Phe Glu Arg Val Asn Ser Ala Gly Asp Pro Tyr Gly Asn Cys Gly Lys
            500                 505                 510 gtc tcg aag agt tcc ttt gcc aaa tgc gag atg                        1569
Val Ser Lys Ser Ser Phe Ala Lys Cys Glu Met
        515                 520
```

<210> SEQ ID NO 24
<211> LENGTH: 523
<212> TYPE: PRT
<213> ORGANISM: Unknown Organism
<220> FEATURE:
<223> OTHER INFORMATION: Description of Unknown Organism: Clone:
      JM109(pMel-alpha-26N), human meltrin alpha

<400> SEQUENCE: 24

```
Gly Asp Leu Trp Ile Pro Val Lys Ser Phe Asp Ser Lys Asn His Pro
1               5                   10                  15

Glu Val Leu Asn Ile Arg Leu Gln Arg Glu Ser Lys Glu Leu Ile Ile
            20                  25                  30

Asn Leu Glu Arg Asn Glu Gly Leu Ile Ala Ser Ser Phe Thr Glu Thr
        35                  40                  45

His Tyr Leu Gln Asp Gly Thr Asp Val Ser Leu Ala Arg Asn Tyr Thr
    50                  55                  60

Gly His Cys Tyr Tyr His Gly His Val Arg Gly Tyr Ser Asp Ser Ala
65                  70                  75                  80

Val Ser Leu Ser Thr Cys Ser Gly Leu Arg Gly Leu Ile Gly Phe Glu
                85                  90                  95

Asn Glu Ser Tyr Val Leu Glu Pro Met Lys Ser Ala Thr Asn Arg Tyr
            100                 105                 110
```

```
Lys Leu Phe Pro Ala Lys Lys Leu Lys Ser Val Arg Gly Ser Cys Gly
            115                 120                 125

Ser His His Asn Thr Pro Asn Leu Ala Ala Lys Asn Val Phe Pro Pro
    130                 135                 140

Pro Ser Gln Thr Trp Ala Arg Arg His Lys Arg Glu Thr Leu Lys Ala
145                 150                 155                 160

Thr Lys Tyr Val Glu Leu Val Ile Val Ala Asp Asn Arg Glu Phe Gln
                165                 170                 175

Arg Gln Gly Lys Asp Leu Glu Lys Val Lys Gln Arg Leu Ile Glu Ile
            180                 185                 190

Ala Asn His Val Asp Lys Phe Tyr Arg Pro Leu Asn Ile Arg Ile Val
        195                 200                 205

Leu Val Gly Val Glu Val Trp Asn Asp Met Asp Lys Cys Ser Val Ser
    210                 215                 220

Gln Asp Pro Phe Thr Ser Leu His Glu Phe Leu Asp Trp Arg Lys Met
225                 230                 235                 240

Lys Leu Leu Pro Arg Lys Ser His Asp Asn Ala Gln Leu Val Ser Gly
                245                 250                 255

Val Tyr Phe Gln Gly Thr Thr Ile Gly Met Ala Pro Ile Met Ser Met
            260                 265                 270

Cys Thr Ala Asp Gln Ser Gly Gly Ile Val Met Asp His Ser Asp Asn
        275                 280                 285

Pro Leu Gly Ala Ala Val Thr Leu Ala His Glu Leu Gly His Asn Phe
    290                 295                 300

Gly Met Asn His Asp Thr Leu Asp Arg Gly Cys Ser Cys Gln Met Ala
305                 310                 315                 320

Val Glu Lys Gly Gly Cys Ile Met Asn Ala Ser Thr Gly Tyr Pro Phe
                325                 330                 335

Pro Met Val Phe Ser Ser Cys Ser Arg Lys Asp Leu Glu Thr Ser Leu
            340                 345                 350

Glu Lys Gly Met Gly Val Cys Leu Phe Asn Leu Pro Glu Val Arg Glu
        355                 360                 365

Ser Phe Gly Gly Gln Lys Cys Gly Asn Arg Phe Val Glu Glu Gly Glu
    370                 375                 380

Glu Cys Asp Cys Gly Glu Pro Glu Glu Cys Met Asn Arg Cys Cys Asn
385                 390                 395                 400

Ala Thr Thr Cys Thr Leu Lys Pro Asp Ala Val Cys Ala His Gly Leu
                405                 410                 415

Cys Cys Glu Asp Cys Gln Leu Lys Pro Ala Gly Thr Ala Cys Arg Asp
            420                 425                 430

Ser Ser Asn Ser Cys Asp Leu Pro Glu Phe Cys Thr Gly Ala Ser Pro
        435                 440                 445

His Cys Pro Ala Asn Val Tyr Leu His Asp Gly His Ser Cys Gln Asp
    450                 455                 460

Val Asp Gly Tyr Cys Tyr Asn Gly Ile Cys Gln Thr His Glu Gln Gln
465                 470                 475                 480

Cys Val Thr Leu Trp Gly Pro Gly Ala Lys Pro Ala Pro Gly Ile Cys
                485                 490                 495

Phe Glu Arg Val Asn Ser Ala Gly Asp Pro Tyr Gly Asn Cys Gly Lys
            500                 505                 510

Val Ser Lys Ser Ser Phe Ala Lys Cys Glu Met
        515                 520
```

-continued

```
<210> SEQ ID NO 25
<211> LENGTH: 2404
<212> TYPE: DNA
<213> ORGANISM: Unknown Organism
<220> FEATURE:
<223> OTHER INFORMATION: Description of Unknown Organism: Clone:
      JM109(pMel-beta-24C), human meltrin beta
<221> NAME/KEY: CDS
<222> LOCATION: (1)..(1017)

<400> SEQUENCE: 25 tgc tgc cac cag tgt aag ctg ttg gct cct ggg acc ctg tgc cgc gag        48
Cys Cys His Gln Cys Lys Leu Leu Ala Pro Gly Thr Leu Cys Arg Glu
 1               5                  10                  15 cag gcc agg cag tgt gac ctc ccg gag ttc tgt acg ggc aag tct ccc        96
Gln Ala Arg Gln Cys Asp Leu Pro Glu Phe Cys Thr Gly Lys Ser Pro
             20                  25                  30 cac tgc cct acc aac ttc tac cag atg gat ggt acc ccc tgt gag ggc       144
His Cys Pro Thr Asn Phe Tyr Gln Met Asp Gly Thr Pro Cys Glu Gly
         35                  40                  45 ggc cag gcc tac tgc tac aac ggc atg tgc ctc acc tac cag gag cag       192
Gly Gln Ala Tyr Cys Tyr Asn Gly Met Cys Leu Thr Tyr Gln Glu Gln
     50                  55                  60 tgc cag cag ctg tgg gga ccc gga gcc cga cct gcc cct gac ctc tgc       240
Cys Gln Gln Leu Trp Gly Pro Gly Ala Arg Pro Ala Pro Asp Leu Cys
 65                  70                  75                  80 ttc gag aag gtg aat gtg gca gga gac acc ttt gga aac tgt gga aag       288
Phe Glu Lys Val Asn Val Ala Gly Asp Thr Phe Gly Asn Cys Gly Lys
                 85                  90                  95 gac atg aat ggt gaa cac agg aag tgc aac atg aga gat gcg aag tgt       336
Asp Met Asn Gly Glu His Arg Lys Cys Asn Met Arg Asp Ala Lys Cys
            100                 105                 110 ggg aag atc cag tgt cag agc tct gag gcc cgg ccc ctg gag tcc aac       384
Gly Lys Ile Gln Cys Gln Ser Ser Glu Ala Arg Pro Leu Glu Ser Asn
        115                 120                 125 gcg gtg ccc att gac acc act atc atc atg aat ggg agg cag atc cag       432
Ala Val Pro Ile Asp Thr Thr Ile Ile Met Asn Gly Arg Gln Ile Gln
    130                 135                 140 tgc cgg ggc acc cac gtc tac cga ggt cct gag gag gag ggt gac atg       480
Cys Arg Gly Thr His Val Tyr Arg Gly Pro Glu Glu Glu Gly Asp Met
145                 150                 155                 160 ctg gac cca ggg ctg gtg atg act gga acc aag tgt ggc tac aac cat       528
Leu Asp Pro Gly Leu Val Met Thr Gly Thr Lys Cys Gly Tyr Asn His
                165                 170                 175 att tgc ctt gag ggg cag tgc agg aac acc tcc ttc ttt gaa act gaa       576
Ile Cys Leu Glu Gly Gln Cys Arg Asn Thr Ser Phe Phe Glu Thr Glu
            180                 185                 190 ggc tgt ggg aag aag tgc aat ggc cat ggg gtc tgt aac aac aac cag       624
Gly Cys Gly Lys Lys Cys Asn Gly His Gly Val Cys Asn Asn Asn Gln
        195                 200                 205 aac tgc cac tgc ctg ccg ggc tgg gcc ccg ccc ttc tgc aac aca ccg       672
Asn Cys His Cys Leu Pro Gly Trp Ala Pro Pro Phe Cys Asn Thr Pro
    210                 215                 220 ggc cac ggg ggc agt atc gac agt ggg cct atg ccc cct gag agt gtg       720
Gly His Gly Gly Ser Ile Asp Ser Gly Pro Met Pro Pro Glu Ser Val
225                 230                 235                 240 ggt cct gtg gta gct gga gtg ttg gtg gcc atc ttg gtg ctg gcg gtc       768
Gly Pro Val Val Ala Gly Val Leu Val Ala Ile Leu Val Leu Ala Val
                245                 250                 255 ctc atg ctg atg tac tac tgc tgc aga cag aac aac aaa cta ggc caa       816
Leu Met Leu Met Tyr Tyr Cys Cys Arg Gln Asn Asn Lys Leu Gly Gln
```

|     |     |
| --- | --- |
| ctc aag ccc tca gct ctc cct tcc aag ctg agg caa cag ttc agt tgt<br>Leu Lys Pro Ser Ala Leu Pro Ser Lys Leu Arg Gln Gln Phe Ser Cys<br>          275                 280                 285 | 864 |
| ccc ttc agg gtt tct cag aac agc ggg act ggt cat gcc aac cca act<br>Pro Phe Arg Val Ser Gln Asn Ser Gly Thr Gly His Ala Asn Pro Thr<br>      290                 295                 300 | 912 |
| ttc aag ccg gaa ttc cgg gcc ccc cac agc cca cac cac cat gac aag<br>Phe Lys Pro Glu Phe Arg Ala Pro His Ser Pro His His His Asp Lys<br>305                 310                 315                 320 | 960 |
| ggc cac caa ttc cac ggc cac acc ctc ctc cac tct ggg gac gac ccg<br>Gly His Gln Phe His Gly His Thr Leu Leu His Ser Gly Asp Asp Pro<br>                  325                 330                 335 | 1008 |
| gat cct cac tgagctgacc acaacagcca ctacaactgc agccactgga<br>Asp Pro His | 1057 |
| tccacggcca ccctgtcctc acccccaggg accacctgga tcctcacaga gccgagcact | 1117 |
| atagccaccg tgatggtgcc caccggttcc acggccaccg cctcctccac tctgggaaca | 1177 |
| gctcacaccc ccaaagtggt gaccaccatg gccactatgc ccacagccac tgcctccacg | 1237 |
| gttcccagct cgtccaccgt ggggaccacc cgcacccctg cagtgctccc cagcagcctg | 1297 |
| ccaaccttca gcgtgtccac tgtgtcctcc tcagtcctca ccaccctgag acccactggc | 1357 |
| ttccccagct cccacttctc tactccctgc ttctgcaggg catttggaca gtttttctcg | 1417 |
| cccggggaag tcatctacaa taagaccgac cgagccggct gccatttcta cgcagtgtgc | 1477 |
| aatcagcact gtgacattga ccgcttccag ggcgcctgtc ccacctcccc accgccagtg | 1537 |
| tcctccgccc cgctgtcctc gccctcccct gcccctggct gtgacaatgc catccctctc | 1597 |
| cggcaggtga atgagacctg gaccctggag aactgcacgg tggccaggtg cgtgggtgac | 1657 |
| aaccgtgtcg tcctgctgga cccaaagcct gtggccaacg tcacctgcgt gaacaagcac | 1717 |
| ctgcccatca aagtgtcgga cccgagccag ccctgtgact ccactatga gtgcgagtgc | 1777 |
| atctgcagca tgtggggcgg ctcccactat ccacctttg acggcacctc ttacaccttc | 1837 |
| cggggcaact gcacctatgt cctcatgaga gagatccatg cacgctttgg gaatctcagc | 1897 |
| ctctacctgg acaaccacta ctgcacggcc tctgccactg ccgctgccgc ccgctgcccc | 1957 |
| cgcgccctca gcatccacta caagtccatg gatatcgtcc tcactgtcac catggtgcat | 2017 |
| gggaaggagg agggcctgat cctgtttgac caaattccgg tgagcagcgg tttcagcaag | 2077 |
| aacggcgtgc ttgtgtctgt gctggggacc accaccatgc gtgtggacat tcctgccctg | 2137 |
| ggcgtgagcg tcaccttcaa tggccaagtc ttccaggccc ggctgcccta cagcctcttc | 2197 |
| cacaacaaca ccgagggcca gtgcggcacc tgcaccaaca accagaggga cgactgtctc | 2257 |
| cagcgggacg gaaccactgc cgccagttgc aaggacatgg ccaagacgtg gctggtcccc | 2317 |
| gacagcagaa aggatggctg ctgggccccg actggcacac cccccactgc cagccccgca | 2377 |
| gccccggtgt ctagcacacc caccccg | 2404 |

<210> SEQ ID NO 26
<211> LENGTH: 339
<212> TYPE: PRT
<213> ORGANISM: Unknown Organism
<220> FEATURE:
<223> OTHER INFORMATION: Description of Unknown Organism: Clone:
      JM109(pMel-beta-24C), human meltrin beta

<400> SEQUENCE: 26

Cys Cys His Gln Cys Lys Leu Leu Ala Pro Gly Thr Leu Cys Arg Glu

```
            1               5              10              15
        Gln Ala Arg Gln Cys Asp Leu Pro Glu Phe Cys Thr Gly Lys Ser Pro
                        20                  25                  30
        His Cys Pro Thr Asn Phe Tyr Gln Met Asp Gly Thr Pro Cys Glu Gly
                        35                  40                  45
        Gly Gln Ala Tyr Cys Tyr Asn Gly Met Cys Leu Thr Tyr Gln Glu Gln
                        50                  55                  60
        Cys Gln Gln Leu Trp Gly Pro Gly Ala Arg Pro Ala Pro Asp Leu Cys
         65                  70                  75                  80
        Phe Glu Lys Val Asn Val Ala Gly Asp Thr Phe Gly Asn Cys Gly Lys
                        85                  90                  95
        Asp Met Asn Gly Glu His Arg Lys Cys Asn Met Arg Asp Ala Lys Cys
                        100                 105                 110
        Gly Lys Ile Gln Cys Gln Ser Ser Glu Ala Arg Pro Leu Glu Ser Asn
                        115                 120                 125
        Ala Val Pro Ile Asp Thr Thr Ile Ile Met Asn Gly Arg Gln Ile Gln
                    130                 135                 140
        Cys Arg Gly Thr His Val Tyr Arg Gly Pro Glu Glu Glu Gly Asp Met
        145                 150                 155                 160
        Leu Asp Pro Gly Leu Val Met Thr Gly Thr Lys Cys Gly Tyr Asn His
                        165                 170                 175
        Ile Cys Leu Glu Gly Gln Cys Arg Asn Thr Ser Phe Phe Glu Thr Glu
                        180                 185                 190
        Gly Cys Gly Lys Lys Cys Asn Gly His Gly Val Cys Asn Asn Asn Gln
                        195                 200                 205
        Asn Cys His Cys Leu Pro Gly Trp Ala Pro Pro Phe Cys Asn Thr Pro
                    210                 215                 220
        Gly His Gly Gly Ser Ile Asp Ser Gly Pro Met Pro Pro Glu Ser Val
        225                 230                 235                 240
        Gly Pro Val Val Ala Gly Val Leu Val Ala Ile Leu Val Leu Ala Val
                        245                 250                 255
        Leu Met Leu Met Tyr Tyr Cys Cys Arg Gln Asn Asn Lys Leu Gly Gln
                        260                 265                 270
        Leu Lys Pro Ser Ala Leu Pro Ser Lys Leu Arg Gln Gln Phe Ser Cys
                        275                 280                 285
        Pro Phe Arg Val Ser Gln Asn Ser Gly Thr Gly His Ala Asn Pro Thr
                    290                 295                 300
        Phe Lys Pro Glu Phe Arg Ala Pro His Ser Pro His His Asp Lys
        305                 310                 315                 320
        Gly His Gln Phe His Gly His Thr Leu Leu His Ser Gly Asp Pro
                        325                 330                 335
        Asp Pro His

<210> SEQ ID NO 27
<211> LENGTH: 453
<212> TYPE: DNA
<213> ORGANISM: Unknown Organism
<220> FEATURE:
<223> OTHER INFORMATION: Description of Unknown Organism: Clone:
      JM109(pMel-beta-24N), human meltrin beta
<221> NAME/KEY: CDS
<222> LOCATION: (2)..(451)

<400> SEQUENCE: 27 c gga gct gcc act ggg cac ccc ttt ccc aaa gtg ttc aat gga tgc aac    49
  Gly Ala Ala Thr Gly His Pro Phe Pro Lys Val Phe Asn Gly Cys Asn
```

```
              1               5                  10                  15
agg agg gag ctg gac agg tat ctg cag tca ggt ggt gga atg tgt ctc       97
Arg Arg Glu Leu Asp Arg Tyr Leu Gln Ser Gly Gly Gly Met Cys Leu
            20                  25                  30 tcc aac atg cca gac acc agg atg ttg tat gga ggc cgg agg tgt ggg      145
Ser Asn Met Pro Asp Thr Arg Met Leu Tyr Gly Gly Arg Arg Cys Gly
        35                  40                  45 aac ggg tat ctg gaa gat ggg gaa gag tgt gac tgt gga gaa gaa gag      193
Asn Gly Tyr Leu Glu Asp Gly Glu Glu Cys Asp Cys Gly Glu Glu Glu
    50                  55                  60 gaa tgt aac aac ccc tgc tgc aat gcc tct aat tgt acc ctg agg ccg      241
Glu Cys Asn Asn Pro Cys Cys Asn Ala Ser Asn Cys Thr Leu Arg Pro
65                  70                  75                  80 ggg gcg gag tgt gct cac ggc tcc tgc tgc cac cag tgt aag ctg ttg      289
Gly Ala Glu Cys Ala His Gly Ser Cys Cys His Gln Cys Lys Leu Leu
                85                  90                  95 gct cct ggg acc ctg tgc cgc gag cag gcc agg cag tgt gac ctc ccg      337
Ala Pro Gly Thr Leu Cys Arg Glu Gln Ala Arg Gln Cys Asp Leu Pro
            100                 105                 110 gag ttc tgt acg ggc aag tct ccc cac tgc cct acc aac ttc tac cag      385
Glu Phe Cys Thr Gly Lys Ser Pro His Cys Pro Thr Asn Phe Tyr Gln
        115                 120                 125 atg gat ggt acc ccc tgt gag ggc ggc cag gcc tac tgc tac aac ggc      433
Met Asp Gly Thr Pro Cys Glu Gly Gly Gln Ala Tyr Cys Tyr Asn Gly
    130                 135                 140 atg tgc ctc acc tac cag ga                                           453
Met Cys Leu Thr Tyr Gln
145                 150

<210> SEQ ID NO 28
<211> LENGTH: 150
<212> TYPE: PRT
<213> ORGANISM: Unknown Organism
<220> FEATURE:
<223> OTHER INFORMATION: Description of Unknown Organism: Clone:
      JM109(pMel-beta-24N), human meltrin beta

<400> SEQUENCE: 28

Gly Ala Ala Thr Gly His Pro Phe Pro Lys Val Phe Asn Gly Cys Asn
1               5                   10                  15

Arg Arg Glu Leu Asp Arg Tyr Leu Gln Ser Gly Gly Gly Met Cys Leu
            20                  25                  30

Ser Asn Met Pro Asp Thr Arg Met Leu Tyr Gly Gly Arg Arg Cys Gly
        35                  40                  45

Asn Gly Tyr Leu Glu Asp Gly Glu Glu Cys Asp Cys Gly Glu Glu Glu
    50                  55                  60

Glu Cys Asn Asn Pro Cys Cys Asn Ala Ser Asn Cys Thr Leu Arg Pro
65                  70                  75                  80

Gly Ala Glu Cys Ala His Gly Ser Cys Cys His Gln Cys Lys Leu Leu
                85                  90                  95

Ala Pro Gly Thr Leu Cys Arg Glu Gln Ala Arg Gln Cys Asp Leu Pro
            100                 105                 110

Glu Phe Cys Thr Gly Lys Ser Pro His Cys Pro Thr Asn Phe Tyr Gln
        115                 120                 125

Met Asp Gly Thr Pro Cys Glu Gly Gly Gln Ala Tyr Cys Tyr Asn Gly
    130                 135                 140

Met Cys Leu Thr Tyr Gln
145                 150
```

<210> SEQ ID NO 29
<211> LENGTH: 20
<212> TYPE: DNA
<213> ORGANISM: Unknown Organism
<220> FEATURE:
<223> OTHER INFORMATION: Description of Unknown Organism: MA-1 Primer
      for PCR

<400> SEQUENCE: 29
acgatgggca ctcatgtcag                                               20

<210> SEQ ID NO 30
<211> LENGTH: 20
<212> TYPE: DNA
<213> ORGANISM: Unknown Organism
<220> FEATURE:
<223> OTHER INFORMATION: Description of Unknown Organism: MA-2 primer
      for PCR

<400> SEQUENCE: 30
catctcgcat ttggcaaagg                                               20

<210> SEQ ID NO 31
<211> LENGTH: 24
<212> TYPE: DNA
<213> ORGANISM: Unknown Organism
<220> FEATURE:
<223> OTHER INFORMATION: Description of Unknown Organism: lambda gt11
      forward primer for PCR

<400> SEQUENCE: 31
ggtggcgacg actcctggag cccg                                          24

<210> SEQ ID NO 32
<211> LENGTH: 24
<212> TYPE: DNA
<213> ORGANISM: Unknown Organism
<220> FEATURE:
<223> OTHER INFORMATION: Description of Unknown Organism: lambda gt11
      reverse primer for PCR

<400> SEQUENCE: 32
ttgacaccag accaactggt aatg                                          24

<210> SEQ ID NO 33
<211> LENGTH: 20
<212> TYPE: DNA
<213> ORGANISM: Unknown Organism
<220> FEATURE:
<223> OTHER INFORMATION: Description of Unknown Organism: Mel-alpha 5'S
      primer for PCR

<400> SEQUENCE: 33
cactgaacat tcggatcgtg                                               20

<210> SEQ ID NO 34
<211> LENGTH: 33
<212> TYPE: DNA
<213> ORGANISM: Unknown Organism
<220> FEATURE:
<223> OTHER INFORMATION: Description of Unknown Organism: lambda gt11
      forward-Eco primer for PCR

<400> SEQUENCE: 34
ccggaattcg gtggcgacga ctcctggagc ccg                                33

```
<210> SEQ ID NO 35
<211> LENGTH: 33
<212> TYPE: DNA
<213> ORGANISM: Unknown Organism
<220> FEATURE:
<223> OTHER INFORMATION: Description of Unknown Organism: lambda gt11
      Reverse-Eco Primer for PCR

<400> SEQUENCE: 35
ccggaattct tgacaccaga ccaactggta atg                              33

<210> SEQ ID NO 36
<211> LENGTH: 29
<212> TYPE: DNA
<213> ORGANISM: Unknown Organism
<220> FEATURE:
<223> OTHER INFORMATION: Description of Unknown Organism: MA-1-Eco
      primer for PCR

<400> SEQUENCE: 36
ccggaattca cgatgggcac tcatgtcag                                   29

<210> SEQ ID NO 37
<211> LENGTH: 29
<212> TYPE: DNA
<213> ORGANISM: Unknown Organism
<220> FEATURE:
<223> OTHER INFORMATION: Description of Unknown Organism: MA-2 Eco
      Primer for PCR

<400> SEQUENCE: 37
ccggaattcc atctcgcatt tggcaaagg                                   29

<210> SEQ ID NO 38
<211> LENGTH: 20
<212> TYPE: DNA
<213> ORGANISM: Unknown Organism
<220> FEATURE:
<223> OTHER INFORMATION: Description of Unknown Organism: S-hMel
      alpha-TM5' primer for PCR

<400> SEQUENCE: 38
gcacaaagtg tgcagatgga                                             20

<210> SEQ ID NO 39
<211> LENGTH: 19
<212> TYPE: DNA
<213> ORGANISM: Unknown Organism
<220> FEATURE:
<223> OTHER INFORMATION: Description of Unknown Organism: A-mMel
      alpha-3' primer for PCR
<221> NAME/KEY: Unsure
<222> LOCATION: 10
<223> OTHER INFORMATION: Nucleotide "n" is unknown

<400> SEQUENCE: 39
cagaggcttc tgaggaggn                                              19

<210> SEQ ID NO 40
<211> LENGTH: 6
<212> TYPE: PRT
<213> ORGANISM: Unknown organism
<220> FEATURE:
<223> OTHER INFORMATION: Description of unknown organism: a
      polypeptide

<400> SEQUENCE: 40

Glu Asp Cys Asp Cys Gly
```

```
<210> SEQ ID NO 41
<211> LENGTH: 6
<212> TYPE: PRT
<213> ORGANISM: Unknown organism
<220> FEATURE:
<223> OTHER INFORMATION: Description of unknown organism: a polypeptide

<400> SEQUENCE: 41

Glu Glu Cys Asp Cys Gly
 1               5

<210> SEQ ID NO 42
<211> LENGTH: 7
<212> TYPE: PRT
<213> ORGANISM: Unknown organism
<220> FEATURE:
<223> OTHER INFORMATION: Description of unknown organism: a polypeptide

<400> SEQUENCE: 42

Lys Cys Gly Lys Leu Ile Cys
 1               5

<210> SEQ ID NO 43
<211> LENGTH: 20
<212> TYPE: DNA
<213> ORGANISM: Unknown organism
<220> FEATURE:
<223> OTHER INFORMATION: Description of unknown organism: sense primer
      for PCR

<400> SEQUENCE: 43
cacgatgatg ggagagattg                                              20

<210> SEQ ID NO 44
<211> LENGTH: 21
<212> TYPE: DNA
<213> ORGANISM: Unknown organism
<220> FEATURE:
<223> OTHER INFORMATION: Description of unknown organism: antisense
      primer for PCR

<400> SEQUENCE: 44
ctccgtatcc tttagtctca c                                            21
```